US006680209B1

(12) United States Patent
Buechler et al.

(10) Patent No.: US 6,680,209 B1
(45) Date of Patent: Jan. 20, 2004

(54) HUMAN ANTIBODIES AS DIAGNOSTIC REAGENTS

(75) Inventors: Joe Buechler, Carlsbad, CA (US); Gunars Valkirs, Escondido, CA (US); Jeff Gray, Solana Beach, CA (US); Nils Lonberg, Woodside, CA (US)

(73) Assignees: Biosite, Incorporated, San Diego, CA (US); Medarex, Inc., Princeton, NJ (US)

(*) Notice: Subject to any disclaimer, the term of this patent is extended or adjusted under 35 U.S.C. 154(b) by 0 days.

(21) Appl. No.: 09/456,090

(22) Filed: Dec. 6, 1999

(51) Int. Cl.⁷ .............................................. G01N 33/543
(52) U.S. Cl. ...................... 436/518; 435/7.94; 435/962; 530/388.15
(58) Field of Search ................................ 435/7.94, 962; 530/388.15; 436/518

(56) References Cited

U.S. PATENT DOCUMENTS

| | | |
|---|---|---|
| 4,376,110 A | 3/1983 | David et al. |
| 4,486,530 A | 12/1984 | David et al. |
| 4,514,505 A * | 4/1985 | Canfield et al. ............ 436/500 |
| 5,173,418 A | 12/1992 | Molin et al. |
| 5,427,908 A | 6/1995 | Dower |
| 5,545,807 A | 8/1996 | Surani et al. |
| 5,565,332 A | 10/1996 | Hoogenboom et al. |
| 5,571,698 A | 11/1996 | Ladner et al. |
| 5,595,898 A | 1/1997 | Robinson et al. |
| 5,614,367 A * | 3/1997 | Kaluza et al. ................ 435/7.1 |
| 5,625,126 A | 4/1997 | Lonberg et al. |
| 5,658,727 A | 8/1997 | Barbas et al. |
| 5,667,988 A | 9/1997 | Barbas et al. |
| 5,766,905 A | 6/1998 | Studier et al. |
| 5,770,429 A | 6/1998 | Lonberg et al. |
| 5,789,208 A | 8/1998 | Sharon |
| 5,811,524 A | 9/1998 | Brams et al. |
| 5,914,241 A | 6/1999 | Valkirs |
| 5,939,807 A | 8/1999 | Patyk et al. |
| 6,057,098 A | 5/2000 | Buechler et al. ................ 435/6 |

FOREIGN PATENT DOCUMENTS

| | | |
|---|---|---|
| EP | 934 953 | 8/1999 |
| WO | WO 91/19818 | 2/1991 |
| WO | WO 92/06204 | 4/1992 |
| WO | WO 94/26787 | 11/1994 |
| WO | WO 96/33735 | 10/1996 |
| WO | WO 98/06704 | 2/1998 |
| WO | WO 98/47343 | 10/1998 |
| WO | WO 99/53049 | 10/1999 |

OTHER PUBLICATIONS

Rader et al., "Phage display of combinatorial antibody libraries," *Current Opinionin Biotech.* 8:503–508 (1997).
Cwirla et al., "Peptides on Phage: A Vast Library of Peptides for Identifying Ligands," *PNAS*, 87:6378–82 (1990).
Devlin et al., "Random Peptide Libraries: A Source of Specific Protein Binding Molecules," *Science*, 249:404–406 (1990).
Georgiou et al., "Display of Heterologous Proteins on the Surface of Microorganisms: From the Screening of Combinatorial Libraries to Live Recombinant Vaccines," *Nature Biotech.*, 15:29–34 (1997).
Kricka, L.J., "Human Anti–Animal Antibody Interferences in Immunological Assays," *Clinical Chemistry*, 45(7):942–956 (1999).
Kuijper et al., "Functional cloning vectors for use in directional cDNA cloning using cohesive ends produced with T4 DNA polymerase," *Gene*, 112(2):147–155 (1992).
McCafferty et al., "Selection and Rapid Purification of Murine Antibody Fragments That Bind a Transition–State Analog by Phage Display," *Applied Biochem. & Biotech.*, 47:157–173 (1994).
Scott et al., "Searching for Peptide Ligands With An Epitope Library," *Science*, 249:386–388 (1990).
Winter et al., "Making Antibodies by Phage Display Technology," *Annu. Rev. Immunol.*, 12:433–455 (1994).

* cited by examiner

*Primary Examiner*—David Saunders
(74) *Attorney, Agent, or Firm*—Townsend and Townsend and Crew LLP

(57) ABSTRACT

The invention provides methods of diagnosis using human antibodies. The methods are particularly useful for analyzing human samples containing HAMA or heterophilic antibodies. A human antibody can bind to an analyte in such samples without binding to HAMA or heterophilic antibodies present in the sample. The methods can be effected using a sandwhich format among others.

28 Claims, 9 Drawing Sheets

DNA SEQUENCES OF OLIGOS USED TO DELETE CDRI-CDR3 REGIONS OF 668-4

Kappa Chain

Framework 4 ... Stop Stop Stop Framework 1

TAT TTC CAG CTT GGT CCC TCT AGA GTT AAC GAT ATC AA CGT TTA T CTA A TCA GCA AGA GAT GGA GGC TTG

Heavy Chain

Freamework 4 ... Stop Stop Stop Framework 4

TGA GGT TCC TTG ACC CCA CTG CAG AGT ACT AGG CCT CT GAG CTA C TCA G TTA GGT GAT TGA GTA GCC AGT

* represents 19 base pairs at the 5'-end of the tetracycline promoter removed by HinDIII digestion

SEQUENCE LISTING

<160> NUMBER OF SEQ ID NOS: 110

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence:Oligo 188

<400> SEQUENCE: 1
ttacccctgt ggcaaaagcc gaagtgcagc tggtggagtc tgg                43

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence:Oligo 944

<400> SEQUENCE: 2
ttacccctgt ggcaaaagcc caggtgcagc tggtgcagtc tgg                43

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence:Oligo 948

<400> SEQUENCE: 3
ttacccctgt ggcaaaagcc caggtgcagc tggtggagtc tgg                43

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:Oligo 952

<400> SEQUENCE: 4
gatgggccct tggtggaggc                                              20

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence:Oligo 189

<400> SEQUENCE: 5
ctgcccaacc agccatggcc gaaattgtgc tcacccagtc tcc                    43

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence:Oligo 931

<400> SEQUENCE: 6
tcgctgccca accagccatg gccgtcatct ggatgaccca gtctcc                 46

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence:Oligo 932

<400> SEQUENCE: 7
tcgctgccca accagccatg gccaacatcc agatgaccca gtctcc                 46

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence:Oligo 933

<400> SEQUENCE: 8
tcgctgccca accagccatg gccgccatcc ggatgaccca gtctcc                 46

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence:Oligo 934

<400> SEQUENCE: 9
tcgctgccca accagccatg gccgccatcc agttgaccca gtctcc                 46

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence:Oligo 935

<400> SEQUENCE: 10
tcgctgccca accagccatg gccgaaatag tgatgacgca gtctcc                    46

<210> SEQ ID NO 11
<211> LENGTH: 46
<212> TYPE: DNA
<213> ORGANISM: Artificial Sequence
<220> FEATURE:
<223> OTHER INFORMATION: Description of Artificial Sequence:Oligo 936

<400> SEQUENCE: 11
tcgctgccca accagccatg gccgatgttg tgatgacaca gtctcc                    46

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence:Oligo 937

<400> SEQUENCE: 12
tcgctgccca accagccatg gccgaaattg tgttgacgca gtctcc                    46

<210> SEQ ID NO 13
<211> LENGTH: 46
<212> TYPE: DNA
<213> ORGANISM: Artificial Sequence
<220> FEATURE:
<223> OTHER INFORMATION: Description of Artificial Sequence:Oligo 955

<400> SEQUENCE: 13
tcgctgccca accagccatg gccgacatcc agatgatcca gtctcc                    46

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence:Oligo 956

<400> SEQUENCE: 14
tcgctgccca accagccatg gccgatattg tgatgaccca gactcc                    46

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:Oligo 973

<400> SEQUENCE: 15
cagcaggcac acaacagagg c                                               21

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence:Oligo 945

<400> SEQUENCE: 16 ttaccctgt ggcaaaagcc gaggtgcagc tgttggagtc tgg                        43

<210> SEQ ID NO 17

```
<211> LENGTH: 43
<212> TYPE: DNA
<213> ORGANISM: Artificial Sequence
<220> FEATURE:
<223> OTHER INFORMATION: Description of Artificial Sequence:Oligo 946

<400> SEQUENCE: 17
ttacccctgt ggcaaaagcc gaggtgcagc tggtgcagtc tgg                43

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence:Oligo 947

<400> SEQUENCE: 18
ttacccctgt ggcaaaagcc caggtgcagc tacagcagtg ggg                43

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:Oligo 953

<400> SEQUENCE: 19
gacagatggt gcagccacag t                                        21

<210> SEQ ID NO 20
<211> LENGTH: 75
<212> TYPE: DNA
<213> ORGANISM: Artificial Sequence
<220> FEATURE:
<223> OTHER INFORMATION: Description of Artificial Sequence:Oligo 864

<400> SEQUENCE: 20
atctggcaca tcatatggat aagtttcgtg tacaaaatgc cagacctaga ggaattttat    60
ttccagcttg gtccc                                               75

<210> SEQ ID NO 21
<211> LENGTH: 69
<212> TYPE: DNA
<213> ORGANISM: Artificial Sequence
<220> FEATURE:
<223> OTHER INFORMATION: Description of Artificial Sequence:Oligo 862

<400> SEQUENCE: 21
gtgatggtga tggtgatgga tcggagtacc aggttatcga gccctcgata ttgaggagac    60
ggtgactga                                                      69

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence:Primer 5

<400> SEQUENCE: 22
gcaactgttg ggaaggg                                             17

<210> SEQ ID NO 23
<211> LENGTH: 20
<212> TYPE: DNA
<213> ORGANISM: Artificial Sequence
```

```
<220> FEATURE:
<223> OTHER INFORMATION: Description of Artificial Sequence:Primer 197

<400> SEQUENCE: 23
tcgctgccca accagccatg                                                    20

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence:Primer 869

<400> SEQUENCE: 24
gggaccaagc tggaaataaa acgggctgtg gctgcaccat ctgtct                       46

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence:Primer 870

<400> SEQUENCE: 25
atctggcaca tcatatggat aagactctcc cctgttgaag ctctt                        45

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence:Primer 867

<400> SEQUENCE: 26
tcagtcaccg tctcctcagc ctccaccaag ggcccatc                                38

<210> SEQ ID NO 27
<211> LENGTH: 43
<212> TYPE: DNA
<213> ORGANISM: Artificial Sequence
<220> FEATURE:
<223> OTHER INFORMATION: Description of Artificial Sequence:Primer 876

<400> SEQUENCE: 27
gtgatggtga tggtgatgag atttgggctc tgctttcttg tcc                          43

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:Primer 885

<400> SEQUENCE: 28
taagagcggt aagagtgcca g                                                  21

<210> SEQ ID NO 29
<211> LENGTH: 69
<212> TYPE: DNA
<213> ORGANISM: Artificial Sequence
<220> FEATURE:
<223> OTHER INFORMATION: Description of Artificial Sequence:Primer 970

<400> SEQUENCE: 29
gtgataaact accgtaaagc ttatcgatga taagctgtca attagtgatg gtgatggtga        60
```

```
tgagatttg                                                                  69
```

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence:Decapeptide

<400> SEQUENCE: 30

```
Tyr Pro Tyr Asp Val Pro Asp Tyr Ala Ser
 1               5                  10
```

<210> SEQ ID NO 31
<211> LENGTH: 47
<212> TYPE: DNA
<213> ORGANISM: Artificial Sequence
<220> FEATURE:
<223> OTHER INFORMATION: Description of Artificial Sequence:Table 3
      Primer A

<400> SEQUENCE: 31

```
tcgctgccca accagccatg gccagtgcta aagaacttag atctcag                        47
```

<210> SEQ ID NO 32
<211> LENGTH: 86
<212> TYPE: DNA
<213> ORGANISM: Artificial Sequence
<220> FEATURE:
<223> OTHER INFORMATION: Description of Artificial Sequence:Table 3
      Primer B

<400> SEQUENCE: 32

```
gtgataaact accgcattaa agcttatcga tgataagctg tcaattagtg atggtgatgg          60
tgatgtgaat tctcagccct cttcaa                                              86
```

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:Table 3
      Primer C

<400> SEQUENCE: 33

```
gcaactctct actgtttctc c                                                   21
```

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:Table 3
      Primer D

<400> SEQUENCE: 34

```
gaggatgacg atgagcgc                                                       18
```

<210> SEQ ID NO 35
<211> LENGTH: 668
<212> TYPE: DNA
<213> ORGANISM: Homo sapiens
<220> FEATURE:
<223> OTHER INFORMATION: M1-1L

<400> SEQUENCE: 35

-continued

```
aaattgtgtt gacgcattcc agccaccctg tctttgtctc caggggaaag agccaccctc    60
tcctgcaggg ccagtcaggg tgttagcagc tacttagcct ggtaccaaca gaaacctggc   120
caggctccca ggctcctcat ctatgatgca tccaacaggg ccactggcat cccagccagg   180
ttcagtggca gtgggtctgg gacagacttc actctcacca tcagcagcct agagcctgaa   240
gattttgcag tttattactg tcagcagcgt agaactggcc tcggacgttc ggccaaggga   300
ccaaggtgga aatcaaacga actgtggctg caccatctgt cttcatcttc cgccatctg    360 atgagcagtt gaaatctgga actgcctctg ttgtgtgcct gctgaataac ttctatccca   420
gagaggccaa agtacagtgg aaggtggata acgccctcca atcgggtaac tcccaggaga   480
gtgtcacaga gcaggacagc aaggacagca cctacagcct cagcagcacc ctgacgctga   540
gcaaagcaga ctacgagaaa cacaaagtct acgcctgcga agtcacccat cagggcctga   600
gctcgcccgt cacaaagagc ttcaacaggg gagagtctta tccatatgat gtgccagatt   660
atgcgagc                                                           668
```

<210> SEQ ID NO 36
<211> LENGTH: 224
<212> TYPE: PRT
<213> ORGANISM: Homo sapiens
<220> FEATURE:
<223> OTHER INFORMATION: M1-1L

<400> SEQUENCE: 36

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Gly Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220
```

<210> SEQ ID NO 37
<211> LENGTH: 678

```
<212> TYPE: DNA
<213> ORGANISM: Homo sapiens
<220> FEATURE:
<221> NAME/KEY: CDS
<222> LOCATION: (1)..(678)
<223> OTHER INFORMATION: M1-3L

<400> SEQUENCE: 37 gaa ata gtg atg acg cag tct cca gcc acc ctg tct ttg tct cca ggg        48
Glu Ile Val Met Thr Gln Ser Pro Ala Thr Leu Ser Leu Ser Pro Gly
  1               5                  10                  15 gaa aga gcc acc ctc tcc tgc agg gcc agt cag agt gtt agc agc agc        96
Glu Arg Ala Thr Leu Ser Cys Arg Ala Ser Gln Ser Val Ser Ser Ser
             20                  25                  30 tac tta gcc tgg tac cag cag aaa cct ggc cag gct ccc agg ctc ctc       144
Tyr Leu Ala Trp Tyr Gln Gln Lys Pro Gly Gln Ala Pro Arg Leu Leu
         35                  40                  45 atc tat ggt gca tcc agc agg gcc act ggc atc cca gac agg ttc agt       192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc aga ctg gag       240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca cct       288
Pro Glu Asp Phe Ala Val Tyr Tyr Cys Gln Gln Tyr Gly Ser Ser Pro
                 85                  90                  95 cca ttc act ttc ggc cct ggg acc aaa gtg gat atc aaa cga act gtg       336
Pro Phe Thr Phe Gly Pro Gly Thr Lys Val Asp Ile Lys Arg Thr Val
            100                 105                 110 gct gca cca tct gtc ttc atc ttc ccg cca tct gat gag cag ttg aaa       384
Ala Ala Pro Ser Val Phe Ile Phe Pro Pro Ser Asp Glu Gln Leu Lys
        115                 120                 125 tct gga act gcc tct gtt gtg tgc ctg ctg aat aac ttc tat ccc aga       432
Ser Gly Thr Ala Ser Val Val Cys Leu Leu Asn Asn Phe Tyr Pro Arg
    130                 135                 140 gag gcc aaa gta cag tgg aag gtg gat aac gcc ctc caa tcg ggt aac       480
Glu Ala Lys Val Gln Trp Lys Val Asp Asn Ala Leu Gln Ser Gly Asn
145                 150                 155                 160 tcc cag gag agt gtc aca gag cag gac agc aag gac agc acc tac agc       528
Ser Gln Glu Ser Val Thr Glu Gln Asp Ser Lys Asp Ser Thr Tyr Ser
                165                 170                 175 ctc agc agc acc ctg acg ctg agc aaa gca gac tac gag aaa cac aaa       576
Leu Ser Ser Thr Leu Thr Leu Ser Lys Ala Asp Tyr Glu Lys His Lys
            180                 185                 190 gtc tac gcc tgc gaa gtc acc cat cag ggc ctg agc tcg ccc gtc aca       624
Val Tyr Ala Cys Glu Val Thr His Gln Gly Leu Ser Ser Pro Val Thr
        195                 200                 205 aag agc ttc aac agg gga gag tct tat cca tat gat gtg cca gat tat       672
Lys Ser Phe Asn Arg Gly Glu Ser Tyr Pro Tyr Asp Val Pro Asp Tyr
    210                 215                 220 gcg agc                                                               678
Ala Ser
225

<210> SEQ ID NO 38
<211> LENGTH: 226
<212> TYPE: PRT
<213> ORGANISM: Homo sapiens
<223> OTHER INFORMATION: M1-3L

<400> SEQUENCE: 38

Glu Ile Val Met Thr Gln Ser Pro Ala Thr Leu Ser Leu Ser Pro Gly
```

```
  1               5                    10                    15
Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Phe Thr Phe Gly Pro Gly Thr Lys Val Asp Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser Tyr Pro Tyr Asp Val Pro Asp Tyr
    210                 215                 220

Ala Ser
225

<210> SEQ ID NO 39
<211> LENGTH: 672
<212> TYPE: DNA
<213> ORGANISM: Homo sapiens
<220> FEATURE:
<221> NAME/KEY: CDS
<222> LOCATION: (1)..(672)
<223> OTHER INFORMATION: M1-4L

<400> SEQUENCE: 39 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
 1               5                  10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
             20                  25                  30 tac tta gcc tgg tac cag cag aaa cct ggc cag gct ccc agg ctc cac     144
Tyr Leu Ala Trp Tyr Gln Gln Lys Pro Gly Gln Ala Pro Arg Leu His
         35                  40                  45 atc tat ggt gca tcc aga agg gcc act ggc atc cca gac agg ttc agt     192
Ile Tyr Gly Ala Ser Arg Arg Ala Thr Gly Ile Pro Asp Arg Phe Ser
     50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
 65                  70                  75                  80 cct gaa gat ttt gca gtg tat tac tgt cag cag ttt ggt agc tca ttc     288
Pro Glu Asp Phe Ala Val Tyr Tyr Cys Gln Gln Phe Gly Ser Ser Phe
                 85                  90                  95
```

-continued

```
act ttc ggc cct ggg acc aaa gtg gat atc aaa cga act gtg gct gca         336
Thr Phe Gly Pro Gly Thr Lys Val Asp Ile Lys Arg Thr Val Ala Ala
            100                 105                 110 cca tct gtc ttc atc ttc ccg cca tct gat gag cag ttg aaa tct gga         384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc         432
Thr Ala Ser Val Val Cys Leu Leu Asn Asn Phe Tyr Pro Arg Glu Ala
130                 135                 140 aaa gta cag tgg aag gtg gat aac gcc ctc caa tcg ggt aac tcc cag         480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc         528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac         576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc         624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc         672
Phe Asn Arg Gly Glu Ser Tyr Pro Tyr Asp Val Pro Asp Tyr Ala Ser
    210                 215                 220
```

<210> SEQ ID NO 40
<211> LENGTH: 224
<212> TYPE: PRT
<213> ORGANISM: Homo sapiens
<223> OTHER INFORMATION: M1-4L

<400> SEQUENCE: 40

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu His
         35                  40                  45

Ile Tyr Gly Ala Ser Arg Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
                    195                 200                 205
Phe Asn Arg Gly Glu Ser Tyr Pro Tyr Asp Val Pro Asp Tyr Ala Ser
    210                 215                 220
```

<210> SEQ ID NO 41
<211> LENGTH: 678
<212> TYPE: DNA
<213> ORGANISM: Homo sapiens
<220> FEATURE:
<221> NAME/KEY: CDS
<222> LOCATION: (1)..(678)
<223> OTHER INFORMATION: M1-5L

<400> SEQUENCE: 41

```
gaa ata gtg atg acg cag tct cca ggc acc ctg tct ttg tct cca ggg        48
Glu Ile Val Met Thr Gln Ser Pro Gly Thr Leu Ser Leu Ser Pro Gly
  1               5                  10                  15 gaa aga gcc acc ctc tcc tgc agg gcc agt cag agt gtt agc agc agc        96
Glu Arg Ala Thr Leu Ser Cys Arg Ala Ser Gln Ser Val Ser Ser Ser
                 20                  25                  30 tac tta gcc tgg tac cag cag aaa cct ggc cag gct ccc agg ctc ctc       144
Tyr Leu Ala Trp Tyr Gln Gln Lys Pro Gly Gln Ala Pro Arg Leu Leu
             35                  40                  45 atc tat ggt gca tcc agc agg gcc act ggc atc cca gac agg ttc agt       192
Ile Tyr Gly Ala Ser Ser Arg Ala Thr Gly Ile Pro Asp Arg Phe Ser
         50                  55                  60 ggc agt ggg tct ggg aca gac ttc act ctc acc atc agc aga ctg gag       240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca cct       288
Pro Glu Asp Phe Ala Val Tyr Tyr Cys Gln Gln Tyr Gly Ser Ser Pro
                 85                  90                  95 ata ttc act ttc ggc cct ggg acc aaa gtg gat atc aaa cga act gtg       336
Ile Phe Thr Phe Gly Pro Gly Thr Lys Val Asp Ile Lys Arg Thr Val
            100                 105                 110 gct gca cca tct gtc ttc atc ttc ccg cca tct gat gag cag ttg aaa       384
Ala Ala Pro Ser Val Phe Ile Phe Pro Pro Ser Asp Glu Gln Leu Lys
        115                 120                 125 tct gga act gcc tct gtt gtg tgc ctg ctg aat aac ttc tat ccc aga       432
Ser Gly Thr Ala Ser Val Val Cys Leu Leu Asn Asn Phe Tyr Pro Arg
    130                 135                 140 gag gcc aaa gta cag tgg aag gtg gat aac gcc ctc caa tcg ggt aac       480
Glu Ala Lys Val Gln Trp Lys Val Asp Asn Ala Leu Gln Ser Gly Asn
145                 150                 155                 160 tcc cag gag agt gtc aca gag cag gac agc aag gac agc acc tac agc       528
Ser Gln Glu Ser Val Thr Glu Gln Asp Ser Lys Asp Ser Thr Tyr Ser
                165                 170                 175 ctc agc agc acc ctg acg ctg agc aaa gca gac tac gag aaa cac aaa       576
Leu Ser Ser Thr Leu Thr Leu Ser Lys Ala Asp Tyr Glu Lys His Lys
            180                 185                 190 gtc tac gcc tgc gaa gtc acc cat cag ggc ctg agc tcg ccc gtc aca       624
Val Tyr Ala Cys Glu Val Thr His Gln Gly Leu Ser Ser Pro Val Thr
        195                 200                 205 aag agc ttc aac agg gga gag tct tat cca tat gat gtg cca gat tat       672
Lys Ser Phe Asn Arg Gly Glu Ser Tyr Pro Tyr Asp Val Pro Asp Tyr
    210                 215                 220 gcg agc                                                                678
Ala Ser
225
```

<210> SEQ ID NO 42

-continued

```
<211> LENGTH: 226
<212> TYPE: PRT
<213> ORGANISM: Homo sapiens
<223> OTHER INFORMATION: M1-5L

<400> SEQUENCE: 42
```

| | | | | | | | | | | | | | | | |
|---|---|---|---|---|---|---|---|---|---|---|---|---|---|---|---|
| Glu | Ile | Val | Met | Thr | Gln | Ser | Pro | Gly | Thr | Leu | Ser | Leu | Ser | Pro | Gly |
| 1 | | | | 5 | | | | | 10 | | | | | 15 | |
| Glu | Arg | Ala | Thr | Leu | Ser | Cys | Arg | Ala | Ser | Gln | Ser | Val | Ser | Ser | Ser |
| | | | 20 | | | | | 25 | | | | | 30 | | |
| Tyr | Leu | Ala | Trp | Tyr | Gln | Gln | Lys | Pro | Gly | Gln | Ala | Pro | Arg | Leu | Leu |
| | | 35 | | | | | 40 | | | | | 45 | | | |
| Ile | Tyr | Gly | Ala | Ser | Ser | Arg | Ala | Thr | Gly | Ile | Pro | Asp | Arg | Phe | Ser |
| | 50 | | | | | 55 | | | | | 60 | | | | |
| Gly | Ser | Gly | Ser | Gly | Thr | Asp | Phe | Thr | Leu | Thr | Ile | Ser | Arg | Leu | Glu |
| 65 | | | | | 70 | | | | | 75 | | | | | 80 |
| Pro | Glu | Asp | Phe | Ala | Val | Tyr | Tyr | Cys | Gln | Gln | Tyr | Gly | Ser | Ser | Pro |
| | | | | 85 | | | | | 90 | | | | | 95 | |
| Ile | Phe | Thr | Phe | Gly | Pro | Gly | Thr | Lys | Val | Asp | Ile | Lys | Arg | Thr | Val |
| | | | 100 | | | | | 105 | | | | | 110 | | |
| Ala | Ala | Pro | Ser | Val | Phe | Ile | Phe | Pro | Pro | Ser | Asp | Glu | Gln | Leu | Lys |
| | | 115 | | | | | 120 | | | | | 125 | | | |
| Ser | Gly | Thr | Ala | Ser | Val | Val | Cys | Leu | Leu | Asn | Asn | Phe | Tyr | Pro | Arg |
| | 130 | | | | | 135 | | | | | 140 | | | | |
| Glu | Ala | Lys | Val | Gln | Trp | Lys | Val | Asp | Asn | Ala | Leu | Gln | Ser | Gly | Asn |
| 145 | | | | | 150 | | | | | 155 | | | | | 160 |
| Ser | Gln | Glu | Ser | Val | Thr | Glu | Gln | Asp | Ser | Lys | Asp | Ser | Thr | Tyr | Ser |
| | | | | 165 | | | | | 170 | | | | | 175 | |
| Leu | Ser | Ser | Thr | Leu | Thr | Leu | Ser | Lys | Ala | Asp | Tyr | Glu | Lys | His | Lys |
| | | | 180 | | | | | 185 | | | | | 190 | | |
| Val | Tyr | Ala | Cys | Glu | Val | Thr | His | Gln | Gly | Leu | Ser | Ser | Pro | Val | Thr |
| | | 195 | | | | | 200 | | | | | 205 | | | |
| Lys | Ser | Phe | Asn | Arg | Gly | Glu | Ser | Tyr | Pro | Tyr | Asp | Val | Pro | Asp | Tyr |
| | 210 | | | | | 215 | | | | | 220 | | | | |
| Ala | Ser | | | | | | | | | | | | | | |
| 225 | | | | | | | | | | | | | | | |

```
<210> SEQ ID NO 43
<211> LENGTH: 672
<212> TYPE: DNA
<213> ORGANISM: Homo sapiens
<220> FEATURE:
<221> NAME/KEY: CDS
<222> LOCATION: (1)..(672)
<223> OTHER INFORMATION: M1-8L

<400> SEQUENCE: 43
```

| gaa | ata | gtg | atg | acg | cag | tct | cca | ggc | acc | ctg | tct | ttg | tct | cca | ggg | 48 |
|---|---|---|---|---|---|---|---|---|---|---|---|---|---|---|---|---|
| Glu | Ile | Val | Met | Thr | Gln | Ser | Pro | Gly | Thr | Leu | Ser | Leu | Ser | Pro | Gly | |
| 1 | | | | 5 | | | | | 10 | | | | | 15 | | |
| gaa | aga | gcc | acc | ctc | tcc | tgc | agg | gcc | agt | cag | agt | gtt | agc | agc | acc | 96 |
| Glu | Arg | Ala | Thr | Leu | Ser | Cys | Arg | Ala | Ser | Gln | Ser | Val | Ser | Ser | Thr | |
| | | | 20 | | | | | 25 | | | | | 30 | | | |
| tac | tta | gcc | tgg | tac | cag | cag | aaa | cct | ggc | cag | gct | ccc | agg | ctc | ctc | 144 |
| Tyr | Leu | Ala | Trp | Tyr | Gln | Gln | Lys | Pro | Gly | Gln | Ala | Pro | Arg | Leu | Leu | |
| | | 35 | | | | | 40 | | | | | 45 | | | | |
| atc | tat | ggt | gca | tcc | agc | agg | gcc | act | ggc | atc | cca | gac | agg | ttc | agt | 192 |
| Ile | Tyr | Gly | Ala | Ser | Ser | Arg | Ala | Thr | Gly | Ile | Pro | Asp | Arg | Phe | Ser | |
| | 50 | | | | | 55 | | | | | 60 | | | | | |

-continued

```
ggc agt ggg tct ggg aca gac ttc act ctc acc atc agc aga ctg gag       240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat gtt agc tca ttc       288
Pro Glu Asp Phe Ala Val Tyr Tyr Cys Gln Gln Tyr Val Ser Ser Phe
                 85                  90                  95 act ttc ggc cct ggg acc aaa gtg gat atc aaa cga act gtg gct gca       336
Thr Phe Gly Pro Gly Thr Lys Val Asp Ile Lys Arg Thr Val Ala Ala
            100                 105                 110 cca tct gtc ttc atc ttc ccg cca tct gat gag cag ttg aaa tct gga       384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc       432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag       480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc       528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac       576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc       624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc       672
Phe Asn Arg Gly Glu Ser Tyr Pro Tyr Asp Val Pro Asp Tyr Ala Ser
    210                 215                 220

<210> SEQ ID NO 44
<211> LENGTH: 224
<212> TYPE: PRT
<213> ORGANISM: Homo sapiens
<223> OTHER INFORMATION: M1-8L

<400> SEQUENCE: 44

Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Val Ser Ser Phe
                 85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 45
<211> LENGTH: 672
<212> TYPE: DNA
<213> ORGANISM: Homo sapiens
<220> FEATURE:
<221> NAME/KEY: CDS
<222> LOCATION: (1)..(672)
<223> OTHER INFORMATION: M1-10L

<400> SEQUENCE: 45
```

| | |
|---|---|
| gat gtt gtg atg aca cag tct cca gcc acc ctg tct ttg tct cca ggg<br>Asp Val Val Met Thr Gln Ser Pro Ala Thr Leu Ser Leu Ser Pro Gly<br>1               5                   10                  15 | 48 |
| gaa aga gcc acc ctc tcc tgc agg gcc agt cag agt gtt agc agc tac<br>Glu Arg Ala Thr Leu Ser Cys Arg Ala Ser Gln Ser Val Ser Ser Tyr<br>            20                  25                  30 | 96 |
| tta gcc tgg tac caa cag aaa cct ggc cag gct ccc agg ctc ctc atc<br>Leu Ala Trp Tyr Gln Gln Lys Pro Gly Gln Ala Pro Arg Leu Leu Ile<br>        35                  40                  45 | 144 |
| tat gat gca tcc aac agg gcc act ggc atc cca gcc agg ttc agt ggc<br>Tyr Asp Ala Ser Asn Arg Ala Thr Gly Ile Pro Ala Arg Phe Ser Gly<br>    50                  55                  60 | 192 |
| agt ggg tct ggg aca gac ttc act ctc acc atc agc agc cta gag cct<br>Ser Gly Ser Gly Thr Asp Phe Thr Leu Thr Ile Ser Ser Leu Glu Pro<br>65                  70                  75                  80 | 240 |
| gaa gat ttt gca gtt tat tac tgt cag cag cgt agc aac tgg cct ccc<br>Glu Asp Phe Ala Val Tyr Tyr Cys Gln Gln Arg Ser Asn Trp Pro Pro<br>                85                  90                  95 | 288 |
| act ttc ggc gga ggg acc aag gtg gag atc aaa cga act gtg gct gca<br>Thr Phe Gly Gly Gly Thr Lys Val Glu Ile Lys Arg Thr Val Ala Ala<br>            100                 105                 110 | 336 |
| cca tct gtc ttc atc ttc ccg cca tct gat gag cag ttg aaa tct gga<br>Pro Ser Val Phe Ile Phe Pro Pro Ser Asp Glu Gln Leu Lys Ser Gly<br>        115                 120                 125 | 384 |
| act gcc tct gtt gtg tgc ctg ctg aat aac ttc tat ccc aga gag gcc<br>Thr Ala Ser Val Val Cys Leu Leu Asn Asn Phe Tyr Pro Arg Glu Ala<br>    130                 135                 140 | 432 |
| aaa gta cag tgg aag gtg gat aac gcc ctc caa tcg ggt aac tcc cag<br>Lys Val Gln Trp Lys Val Asp Asn Ala Leu Gln Ser Gly Asn Ser Gln<br>145                 150                 155                 160 | 480 |
| gag agt gtc aca gag cag gac agc aag gac agc acc tac agc ctc agc<br>Glu Ser Val Thr Glu Gln Asp Ser Lys Asp Ser Thr Tyr Ser Leu Ser<br>                165                 170                 175 | 528 |
| agc acc ctg acg ctg agc aaa gca gac tac gag aaa cac aaa gtc tac<br>Ser Thr Leu Thr Leu Ser Lys Ala Asp Tyr Glu Lys His Lys Val Tyr<br>            180                 185                 190 | 576 |
| gcc tgc gaa gtc acc cat cag ggc ctg agc tcg ccc gtc aca aag agc<br>Ala Cys Glu Val Thr His Gln Gly Leu Ser Ser Pro Val Thr Lys Ser<br>        195                 200                 205 | 624 |
| ttc aac agg gga gag tct tat cca tat gat gtg cca gat tat gcg agc<br>Phe Asn Arg Gly Glu Ser Tyr Pro Tyr Asp Val Pro Asp Tyr Ala Ser | 672 |

<210> SEQ ID NO 46
<211> LENGTH: 224
<212> TYPE: PRT
<213> ORGANISM: Homo sapiens
<223> OTHER INFORMATION: M1-10L

<400> SEQUENCE: 46

Asp Val Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 47
<211> LENGTH: 672
<212> TYPE: DNA
<213> ORGANISM: Homo sapiens
<220> FEATURE:
<221> NAME/KEY: CDS
<222> LOCATION: (1)..(672)
<223> OTHER INFORMATION: M1-21L

<400> SEQUENCE: 47 gcc atc cgg atg acc cag tct cca tcc ttc ctg tct gca tct gta gga      48
Ala Ile Arg Met Thr Gln Ser Pro Ser Phe Leu Ser Ala Ser Val Gly
1               5                   10                  15 gac aga gtc acc atc act tgc cgg gca agt cag agc att agc agc tat      96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt gtc     192
Tyr Ala Ala Ser Ser Leu Gln Ser Gly Val Pro Ser Arg Phe Ser Val -continued

```
           50                  55                  60
agt gga tct ggg aca gat ctc act ctc acc atc agc agt ctg caa cct       240
Ser Gly Ser Gly Thr Asp Leu Thr Leu Thr Ile Ser Ser Leu Gln Pro
 65                  70                  75                  80 gaa gat ttt gca act tat tac tgt cag tgt ggt tac agt aca cca ttc       288
Glu Asp Phe Ala Thr Tyr Tyr Cys Gln Cys Gly Tyr Ser Thr Pro Phe
                 85                  90                  95 act ttc ggc cct ggg acc aaa gtg gat atc aaa cga act gtg gct gca       336
Thr Phe Gly Pro Gly Thr Lys Val Asp Ile Lys Arg Thr Val Ala Ala
                100                 105                 110 cca tct gtc ttc atc ttc ccg cca tct gat gag cag ttg aaa tct gga       384
Pro Ser Val Phe Ile Phe Pro Pro Ser Asp Glu Gln Leu Lys Ser Gly
            115                 120                 125 act gcc tct gtt gtg tgc ctg ctg aat aac ttc tat ccc aga gag gcc       432
Thr Ala Ser Val Val Cys Leu Leu Asn Asn Phe Tyr Pro Arg Glu Ala
        130                 135                 140 aaa gta cag tgg aag gtg gat aac gcc ctc caa tcg ggt aac tcc cag       480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc       528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac       576
Ser Thr Leu Thr Leu Ser Lys Ala Asp Tyr Glu Lys His Lys Val Tyr
                180                 185                 190 gcc tgc gaa gtc acc cat cag ggc ctg agc tcg ccc gtc aca aag agc       624
Ala Cys Glu Val Thr His Gln Gly Leu Ser Ser Pro Val Thr Lys Ser
            195                 200                 205 ttc aac agg gga gag tct tat cca tat gat gtg cca gat tat gcg agc       672
Phe Asn Arg Gly Glu Ser Tyr Pro Tyr Asp Val Pro Asp Tyr Ala Ser
        210                 215                 220
```

<210> SEQ ID NO 48
<211> LENGTH: 224
<212> TYPE: PRT
<213> ORGANISM: Homo sapiens
<223> OTHER INFORMATION: M1-21L

<400> SEQUENCE: 48

```
Ala Ile Arg Met Thr Gln Ser Pro Ser Phe Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Val
        50                  55                  60

Ser Gly Ser Gly Thr Asp Leu Thr Leu Thr Ile Ser Ser Leu Gln Pro
 65                  70                  75                  80

Glu Asp Phe Ala Thr Tyr Tyr Cys Gln Cys Gly Tyr Ser Thr Pro Phe
                85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
```

-continued

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 49
<211> LENGTH: 678
<212> TYPE: DNA
<213> ORGANISM: Homo sapiens
<220> FEATURE:
<221> NAME/KEY: CDS
<222> LOCATION: (1)..(678)
<223> OTHER INFORMATION: M1-23L

<400> SEQUENCE: 49 gaa att gtg ttg acg cag tct cca ggc acc ctg tct ttg tct cca ggg        48
Glu Ile Val Leu Thr Gln Ser Pro Gly Thr Leu Ser Leu Ser Pro Gly
  1               5                  10                  15 gaa aga gcc acc ctc tcc tgc agg gcc agt cag agt gtt agc agc agc        96
Glu Arg Ala Thr Leu Ser Cys Arg Ala Ser Gln Ser Val Ser Ser Ser
             20                  25                  30 tac tta gcc tgg tac cag cag aaa cct ggc cag gct ccc agg ctc ctc       144
Tyr Leu Ala Trp Tyr Gln Gln Lys Pro Gly Gln Ala Pro Arg Leu Leu
         35                  40                  45 atc tat ggt gca tcc agc agg gcc act ggc atc cca gac agg ttc agt       192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc aga ctg gag       240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca cct       288
Pro Glu Asp Phe Ala Val Tyr Tyr Cys Gln Gln Tyr Gly Ser Ser Pro
                 85                  90                  95 ccg tac act ttt ggc cag ggg acc aag ctg gag atc aaa cga act gtg       336
Pro Tyr Thr Phe Gly Gln Gly Thr Lys Leu Glu Ile Lys Arg Thr Val
            100                 105                 110 gct gca cca tct gtc ttc atc ttc ccg cca tct gat gag cag ttg aaa       384
Ala Ala Pro Ser Val Phe Ile Phe Pro Pro Ser Asp Glu Gln Leu Lys
        115                 120                 125 tct gga act gcc tct gtt gtg tgc ctg ctg aat aac ttc tat ccc aga       432
Ser Gly Thr Ala Ser Val Val Cys Leu Leu Asn Asn Phe Tyr Pro Arg
    130                 135                 140 gag gcc aaa gta cag tgg agg gtg gat aac gcc ctc caa tcg ggt aac       480
Glu Ala Lys Val Gln Trp Arg Val Asp Asn Ala Leu Gln Ser Gly Asn
145                 150                 155                 160 tcc cag gag agt gtc aca gag cag gac agc aag gac agc acc tac agc       528
Ser Gln Glu Ser Val Thr Glu Gln Asp Ser Lys Asp Ser Thr Tyr Ser
                165                 170                 175 ctc agc agc acc ctg acg ctg agc aaa gca gac tac gag aaa cac aaa       576
Leu Ser Ser Thr Leu Thr Leu Ser Lys Ala Asp Tyr Glu Lys His Lys
            180                 185                 190 gtc tac gcc tgc gaa gtc acc cat cag ggc ctg agc tcg ccc gtc aca       624
Val Tyr Ala Cys Glu Val Thr His Gln Gly Leu Ser Ser Pro Val Thr
        195                 200                 205 aag agc ttc aac agg gga gag tct tat cca tat gat gtg cca gat tat       672
Lys Ser Phe Asn Arg Gly Glu Ser Tyr Pro Tyr Asp Val Pro Asp Tyr
```

```
    Lys Ser Phe Asn Arg Gly Glu Ser Tyr Pro Tyr Asp Val Pro Asp Tyr
        210                 215                 220 gcg agc                                                                  678
Ala Ser
225

<210> SEQ ID NO 50
<211> LENGTH: 226
<212> TYPE: PRT
<213> ORGANISM: Homo sapiens
<223> OTHER INFORMATION: M1-23L

<400> SEQUENCE: 50

Glu Ile Val Leu Thr Gln Ser Pro Gly Thr Leu Ser Leu Ser Pro Gly
    1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
    65                  70                  75                  80

Pro Glu Asp Phe Ala Val Tyr Tyr Cys Gln Gln Tyr Gly Ser Ser Pro
                    85                  90                  95

Pro Tyr Thr Phe Gly Gln Gly Thr Lys Leu Glu Ile Lys Arg Thr Val
                    100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
    130                 135                 140

Glu Ala Lys Val Gln Trp Arg Val Asp Asn Ala Leu Gln Ser Gly Asn
    145                 150                 155                 160

Ser Gln Glu Ser Val Thr Glu Gln Asp Ser Lys Asp Ser Thr Tyr Ser
                    165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Ser Tyr Pro Tyr Asp Val Pro Asp Tyr
        210                 215                 220

Ala Ser
225

<210> SEQ ID NO 51
<211> LENGTH: 672
<212> TYPE: DNA
<213> ORGANISM: Homo sapiens
<220> FEATURE:
<221> NAME/KEY: CDS
<222> LOCATION: (1)..(672)
<223> OTHER INFORMATION: M1-25L

<400> SEQUENCE: 51 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
```

-continued

```
                    20                  25                  30
tac tta gcc tgg tac cag cag aaa cct ggc cag gct ccc agg ctc ctc      144
Tyr Leu Ala Trp Tyr Gln Gln Lys Pro Gly Gln Ala Pro Arg Leu Leu
            35                  40                  45 atc tat ggt gca tcc agc agg gcc act ggc atc cca aac agg ttc agt      192
Ile Tyr Gly Ala Ser Ser Arg Ala Thr Gly Ile Pro Asn Arg Phe Ser
    50                  55                  60 ggc agt ggg tct ggg aca gac ttc act ctc acc atc agc aga ctg gag      240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca ttc      288
Pro Glu Asp Phe Ala Val Tyr Tyr Cys Gln Gln Tyr Gly Ser Ser Phe
                85                  90                  95 act ttc ggc cct ggg acc aaa gtg gat atc aaa cga act gtg gct gca      336
Thr Phe Gly Pro Gly Thr Lys Val Asp Ile Lys Arg Thr Val Ala Ala
            100                 105                 110 cca tct gtc ttc atc ttc ccg cca tct gat gag cag ttg aaa tct gga      384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc      432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag      480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc      528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac      576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc      624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc      672
Phe Asn Arg Gly Glu Ser Tyr Pro Tyr Asp Val Pro Asp Tyr Ala Ser
    210                 215                 220

<210> SEQ ID NO 52
<211> LENGTH: 224
<212> TYPE: PRT
<213> ORGANISM: Homo sapiens
<223> OTHER INFORMATION: M1-25L

<400> SEQUENCE: 52

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asn Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Thr Phe Gly Pro Gly Thr Lys Val Asp Ile Lys Arg Thr Val Ala Ala
            100                 105                 110
```

```
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 53
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M1-1H

<400> SEQUENCE: 53 cag gtg cag ctg gtg gag tct ggg gga ggc gtg gtc cag cct ggg aag      48
Gln Val Gln Leu Val Glu Ser Gly Gly Gly Val Val Gln Pro Gly Lys
  1               5                  10                  15 tcc ctg aga ctc tcc tgt gca gcg tct gaa ttc acc atc agt tac tat      96
Ser Leu Arg Leu Ser Cys Ala Ala Ser Glu Phe Thr Ile Ser Tyr Tyr
             20                  25                  30 ggc atg cac tgg gtc cgc cag gtt cca ggc aag ggg ctg gag tgg gtg     144
Gly Met His Trp Val Arg Gln Val Pro Gly Lys Gly Leu Glu Trp Val
         35                  40                  45 gca gct gtc tgg tat gat gaa agt act aca tat tct cca gac tcc gtg     192
Ala Ala Val Trp Tyr Asp Glu Ser Thr Thr Tyr Ser Pro Asp Ser Val
     50                  55                  60 aag ggc cga ttc acc atc tcc aga gac gat tcc aag aac acg ctg tat     240
Lys Gly Arg Phe Thr Ile Ser Arg Asp Asp Ser Lys Asn Thr Leu Tyr
 65                  70                  75                  80 ctg caa atg aac agc ctg aga gcc gag gac acg gct gtg tat tac tgt     288
Leu Gln Met Asn Ser Leu Arg Ala Glu Asp Thr Ala Val Tyr Tyr Cys
                 85                  90                  95 gcg aga gat agg gtg ggc ctc ttt gac tac tgg ggc cag gga acc ctg     336
Ala Arg Asp Arg Val Gly Leu Phe Asp Tyr Trp Gly Gln Gly Thr Leu
            100                 105                 110 gtc acc gtc tcc tca gcc tcc acc aag ggc cca tcg gtc ttc ccc ctg     384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc     432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca     480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc     528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc     576
```

```
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac    624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat    672
Thr Lys Val Asp Lys Lys Ala Glu Pro Lys Ser His His His His His
    210                 215                 220 cac                                                                 675
His
225

<210> SEQ ID NO 54
<211> LENGTH: 225
<212> TYPE: PRT
<213> ORGANISM: Homo sapiens
<223> OTHER INFORMATION: M1-1H

<400> SEQUENCE: 54

Gln Val Gln Leu Val Glu Ser Gly Gly Val Val Gln Pro Gly Lys
 1               5                  10                  15

Ser Leu Arg Leu Ser Cys Ala Ala Ser Glu Phe Thr Ile Ser Tyr Tyr
            20                  25                  30

Gly Met His Trp Val Arg Gln Val Pro Gly Lys Gly Leu Glu Trp Val
        35                  40                  45

Ala Ala Val Trp Tyr Asp Glu Ser Thr Thr Tyr Ser Pro Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 55
<211> LENGTH: 677
<212> TYPE: DNA
<213> ORGANISM: Homo sapiens
<220> FEATURE:
<221> NAME/KEY: CDS
<222> LOCATION: (3)..(677)
<223> OTHER INFORMATION: M1-3H
```

```
<400> SEQUENCE: 55 cc gat gtg cag ctg gtg cag tct ggg gga ggc gtg gtc cag cct ggg         47
   Asp Val Gln Leu Val Gln Ser Gly Gly Gly Val Val Gln Pro Gly
   1               5                   10                  15 agg tcc ctg aga ctc tcc tgt gca gcg tct gga ttc acc ttc agt tac         95
Arg Ser Leu Arg Leu Ser Cys Ala Ala Ser Gly Phe Thr Phe Ser Tyr
                20                  25                  30 tat ggc atg cac tgg gtc cgc cag gct cca ggc aag ggg ctg gag tgg        143
Tyr Gly Met His Trp Val Arg Gln Ala Pro Gly Lys Gly Leu Glu Trp
            35                  40                  45 gtg aca ctt ata acc tat gat gga gat aat aaa tac tat gca gac tcc        191
Val Thr Leu Ile Thr Tyr Asp Gly Asp Asn Lys Tyr Tyr Ala Asp Ser
        50                  55                  60 gtg aag ggc cga ttc acc atc tcc aga gac aat tcc aag aac acg ctg        239
Val Lys Gly Arg Phe Thr Ile Ser Arg Asp Asn Ser Lys Asn Thr Leu
65                  70                  75                  80 tat ctg caa atg aac agc ctg aga gcc gag gac acg gct gtg tat tac        287
Tyr Leu Gln Met Asn Ser Leu Arg Ala Glu Asp Thr Ala Val Tyr Tyr
                85                  90                  95 tgt gcg aga gac ggg atc ggg tac ttt gac tat tgg ggc cag gga acc        335
Cys Ala Arg Asp Gly Ile Gly Tyr Phe Asp Tyr Trp Gly Gln Gly Thr
            100                 105                 110 ctg gtc acc gtc tcc tca gcc tcc acc aag ggc cca tcg gtc ttc ccc        383
Leu Val Thr Val Ser Ser Ala Ser Thr Lys Gly Pro Ser Val Phe Pro
        115                 120                 125 ctg gca ccc tcc tcc aag agc acc tct ggg ggc aca gcg gcc ctg ggc        431
Leu Ala Pro Ser Ser Lys Ser Thr Ser Gly Gly Thr Ala Ala Leu Gly
    130                 135                 140 tgc ctg gtc aag gac tac ttc ccc gaa ccg gtg acg gtg tcg tgg aac        479
Cys Leu Val Lys Asp Tyr Phe Pro Glu Pro Val Thr Val Ser Trp Asn
145                 150                 155 tca ggc gcc ctg acc agc ggc gtg cac acc ttc ccg gct gtc cta cag        527
Ser Gly Ala Leu Thr Ser Gly Val His Thr Phe Pro Ala Val Leu Gln
                160                 165                 170                 175 tcc tca gga ctc tac tcc ctc agc agc gtg gtg acc gtg ccc tcc agc        575
Ser Ser Gly Leu Tyr Ser Leu Ser Ser Val Val Thr Val Pro Ser Ser
            180                 185                 190 agc ttg ggc acc cag acc tac atc tgc aac gtg aat cac aag ccc agc        623
Ser Leu Gly Thr Gln Thr Tyr Ile Cys Asn Val Asn His Lys Pro Ser
        195                 200                 205 aac acc aag gtg gac aag aaa gca gag ccc aaa tct cat cac cat cac        671
Asn Thr Lys Val Asp Lys Lys Ala Glu Pro Lys Ser His His His His
    210                 215                 220 cat cac                                                                 677
His His
    225

<210> SEQ ID NO 56
<211> LENGTH: 225
<212> TYPE: PRT
<213> ORGANISM: Homo sapiens
<223> OTHER INFORMATION: M1-3H

<400> SEQUENCE: 56

Asp Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45
```

```
Thr Leu Ile Thr Tyr Asp Gly Asp Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ile Gly Tyr Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Ala Glu Pro Lys Ser His His His His
    210                 215                 220

His
225

<210> SEQ ID NO 57
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M1-4H

<400> SEQUENCE: 57 cag gtg cag ctg gtg gag tct ggg gga ggc gtg gtc cag cct ggg aag     48
Gln Val Gln Leu Val Glu Ser Gly Gly Gly Val Val Gln Pro Gly Lys
  1               5                  10                  15 tcc ctg aga ctc tcc tgt gca gcg tct gga ttc acc ttc agt tac tat     96
Ser Leu Arg Leu Ser Cys Ala Ala Ser Gly Phe Thr Phe Ser Tyr Tyr
             20                  25                  30 ggc atg cac tgg gtc cgc cag gtt cca ggc aag ggg ctg gag tgg gtg    144
Gly Met His Trp Val Arg Gln Val Pro Gly Lys Gly Leu Glu Trp Val
         35                  40                  45 gca gct gtc tgg tat gat gga agt act aca tat tct cca gac tcc gtg    192
Ala Ala Val Trp Tyr Asp Gly Ser Thr Thr Tyr Ser Pro Asp Ser Val
     50                  55                  60 aag ggc cga ttc acc atc tcc aga gac gat tcc aag aac acg ctg tat    240
Lys Gly Arg Phe Thr Ile Ser Arg Asp Asp Ser Lys Asn Thr Leu Tyr
 65                  70                  75                  80 ctg caa atg aac agc ctg aga gcc gag gac acg gct gtg tat tac tgt    288
Leu Gln Met Asn Ser Leu Arg Ala Glu Asp Thr Ala Val Tyr Tyr Cys
                 85                  90                  95 gcg aga gat agg gtg ggc ctc ttt gac tac tgg ggc cag gga acc ctg    336
Ala Arg Asp Arg Val Gly Leu Phe Asp Tyr Trp Gly Gln Gly Thr Leu
                100                 105                 110 gtc acc gtc tcc tca gcc tcc acc aag ggc cca tcg gtc ttc ccc ctg    384
Val Thr Val Ser Ser Ala Ser Thr Lys Gly Pro Ser Val Phe Pro Leu
            115                 120                 125
```

-continued

```
                115                 120                 125
gca ccc tcc tcc aag agc acc tct ggg ggc aca gcg gcc ctg ggc tgc         432
Ala Pro Ser Ser Lys Ser Thr Ser Gly Gly Thr Ala Ala Leu Gly Cys
130                 135                 140 ctg gtc aag gac tac ttc ccc gaa ccg gtg acg gtg tcg tgg aac tca         480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc         528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc         576
Ser Gly Leu Tyr Ser Leu Ser Ser Val Val Thr Val Pro Ser Ser Ser
                180                 185                 190 ttg ggc acc cag acc tac atc tgc aac gtg aat cac aag ccc agc aac         624
Leu Gly Thr Gln Thr Tyr Ile Cys Asn Val Asn His Lys Pro Ser Asn
                195                 200                 205 acc aag gtg gac aag aaa gca ggg ccc aaa tct cat cac cat cac cat         672
Thr Lys Val Asp Lys Lys Ala Gly Pro Lys Ser His His His His His
210                 215                 220 cac                                                                     675
His
225
```

<210> SEQ ID NO 58
<211> LENGTH: 225
<212> TYPE: PRT
<213> ORGANISM: Homo sapiens
<223> OTHER INFORMATION: M1-4H

<400> SEQUENCE: 58

```
Gln Val Gln Leu Val Glu Ser Gly Gly Gly Val Val Gln Pro Gly Lys
 1               5                  10                  15

Ser Leu Arg Leu Ser Cys Ala Ala Ser Gly Phe Thr Phe Ser Tyr Tyr
                20                  25                  30

Gly Met His Trp Val Arg Gln Val Pro Gly Lys Gly Leu Glu Trp Val
            35                  40                  45

Ala Ala Val Trp Tyr Asp Gly Ser Thr Thr Tyr Ser Pro Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Ala Gly Pro Lys Ser His His His His His
```

His
225

<210> SEQ ID NO 59
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M1-5H

<400> SEQUENCE: 59

| cag | gtg | cag | ctg | gtg | gag | tct | ggg | gga | ggc | gtg | gtc | cag | cct | ggg | agg | 48 |
|---|---|---|---|---|---|---|---|---|---|---|---|---|---|---|---|---|
| Gln | Val | Gln | Leu | Val | Glu | Ser | Gly | Gly | Gly | Val | Val | Gln | Pro | Gly | Arg | |
| 1 | | | | 5 | | | | | 10 | | | | | 15 | | |

| tcc | ctg | aga | ctc | tcc | tgt | gca | gcg | tct | gga | ttt | acc | ttc | agt | tac | tat | 96 |
|---|---|---|---|---|---|---|---|---|---|---|---|---|---|---|---|---|
| Ser | Leu | Arg | Leu | Ser | Cys | Ala | Ala | Ser | Gly | Phe | Thr | Phe | Ser | Tyr | Tyr | |
| | | 20 | | | | | 25 | | | | | 30 | | | | |

| ggc | atg | cac | tgg | gtc | cgc | cag | gct | cca | ggc | aag | ggg | ctg | gag | tgg | gtg | 144 |
|---|---|---|---|---|---|---|---|---|---|---|---|---|---|---|---|---|
| Gly | Met | His | Trp | Val | Arg | Gln | Ala | Pro | Gly | Lys | Gly | Leu | Glu | Trp | Val | |
| | | 35 | | | | | 40 | | | | | 45 | | | | |

| aca | ctt | ata | acc | tat | gat | gga | gat | aat | aaa | tac | tat | gca | gac | tcc | gtg | 192 |
|---|---|---|---|---|---|---|---|---|---|---|---|---|---|---|---|---|
| Thr | Leu | Ile | Thr | Tyr | Asp | Gly | Asp | Asn | Lys | Tyr | Tyr | Ala | Asp | Ser | Val | |
| 50 | | | | | 55 | | | | | 60 | | | | | | |

| aag | ggc | cga | ttc | acc | atc | tcc | aga | gac | aat | tcc | aag | aac | acg | ctg | tat | 240 |
|---|---|---|---|---|---|---|---|---|---|---|---|---|---|---|---|---|
| Lys | Gly | Arg | Phe | Thr | Ile | Ser | Arg | Asp | Asn | Ser | Lys | Asn | Thr | Leu | Tyr | |
| 65 | | | | 70 | | | | | 75 | | | | | 80 | | |

| ctg | caa | atg | aac | agc | ctg | aga | gcc | gag | gac | acg | gct | gtg | tat | tac | tgt | 288 |
|---|---|---|---|---|---|---|---|---|---|---|---|---|---|---|---|---|
| Leu | Gln | Met | Asn | Ser | Leu | Arg | Ala | Glu | Asp | Thr | Ala | Val | Tyr | Tyr | Cys | |
| | | | 85 | | | | | 90 | | | | | 95 | | | |

| gcg | aga | gac | ggg | atc | ggg | tac | ttt | gac | tat | tgg | ggc | cag | gga | acc | ctg | 336 |
|---|---|---|---|---|---|---|---|---|---|---|---|---|---|---|---|---|
| Ala | Arg | Asp | Gly | Ile | Gly | Tyr | Phe | Asp | Tyr | Trp | Gly | Gln | Gly | Thr | Leu | |
| | | | 100 | | | | | 105 | | | | | 110 | | | |

| gtc | acc | gtc | tcc | tca | gcc | tcc | acc | aag | ggc | cca | tcg | gtc | ttc | ccc | ctg | 384 |
|---|---|---|---|---|---|---|---|---|---|---|---|---|---|---|---|---|
| Val | Thr | Val | Ser | Ser | Ala | Ser | Thr | Lys | Gly | Pro | Ser | Val | Phe | Pro | Leu | |
| | | 115 | | | | | 120 | | | | | 125 | | | | |

| gca | ccc | tcc | tcc | aag | agc | acc | tct | ggg | ggc | aca | gcg | gcc | ctg | ggc | tgc | 432 |
|---|---|---|---|---|---|---|---|---|---|---|---|---|---|---|---|---|
| Ala | Pro | Ser | Ser | Lys | Ser | Thr | Ser | Gly | Gly | Thr | Ala | Ala | Leu | Gly | Cys | |
| 130 | | | | | 135 | | | | | 140 | | | | | | |

| ctg | gtc | aag | gac | tac | ttc | ccc | gaa | ccg | gtg | acg | gtg | tcg | tgg | aac | tca | 480 |
|---|---|---|---|---|---|---|---|---|---|---|---|---|---|---|---|---|
| Leu | Val | Lys | Asp | Tyr | Phe | Pro | Glu | Pro | Val | Thr | Val | Ser | Trp | Asn | Ser | |
| 145 | | | | 150 | | | | | 155 | | | | | 160 | | |

| ggc | gcc | ctg | acc | agc | ggc | gtg | cac | acc | ttc | ccg | gct | gtc | cta | cag | tcc | 528 |
|---|---|---|---|---|---|---|---|---|---|---|---|---|---|---|---|---|
| Gly | Ala | Leu | Thr | Ser | Gly | Val | His | Thr | Phe | Pro | Ala | Val | Leu | Gln | Ser | |
| | | | 165 | | | | | 170 | | | | | 175 | | | |

| tca | gga | ctc | tac | tcc | ctc | agc | agc | gtg | gtg | acc | gtg | ccc | tcc | agc | agc | 576 |
|---|---|---|---|---|---|---|---|---|---|---|---|---|---|---|---|---|
| Ser | Gly | Leu | Tyr | Ser | Leu | Ser | Ser | Val | Val | Thr | Val | Pro | Ser | Ser | Ser | |
| | | | 180 | | | | | 185 | | | | | 190 | | | |

| ttg | ggc | acc | cag | acc | tac | atc | tgc | aac | gtg | aat | cac | aag | ccc | agc | aac | 624 |
|---|---|---|---|---|---|---|---|---|---|---|---|---|---|---|---|---|
| Leu | Gly | Thr | Gln | Thr | Tyr | Ile | Cys | Asn | Val | Asn | His | Lys | Pro | Ser | Asn | |
| | | 195 | | | | | 200 | | | | | 205 | | | | |

| acc | aag | gtg | gac | aag | aaa | gca | gag | ccc | aaa | tct | cat | cac | cat | cac | cat | 672 |
|---|---|---|---|---|---|---|---|---|---|---|---|---|---|---|---|---|
| Thr | Lys | Val | Asp | Lys | Lys | Ala | Glu | Pro | Lys | Ser | His | His | His | His | His | |
| 210 | | | | | 215 | | | | | 220 | | | | | | |

| cac | 675 |
|---|---|
| His | |
| 225 | |

<210> SEQ ID NO 60

```
<211> LENGTH: 225
<212> TYPE: PRT
<213> ORGANISM: Homo sapiens
<223> OTHER INFORMATION: M1-5H

<400> SEQUENCE: 60

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Tyr Tyr
             20                  25                  30

Gly Met His Trp Val Arg Gln Ala Pro Gly Lys Gly Leu Glu Trp Val
         35                  40                  45

Thr Leu Ile Thr Tyr Asp Gly Asp Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 61
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M1-8H

<400> SEQUENCE: 61 cag gtg cag ctg gtg cag tct ggg gga ggc gtg gtc cag cct ggg aag      48
Gln Val Gln Leu Val Gln Ser Gly Gly Gly Val Val Gln Pro Gly Lys
  1               5                  10                  15 tcc ctg aaa ctc tcc tgt gca gcg tct gga ttc acc ttc agt tac tat      96
Ser Leu Lys Leu Ser Cys Ala Ala Ser Gly Phe Thr Phe Ser Tyr Tyr
             20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
         35                  40                  45 gca gct gta tgg tat gat gga agt aac aca tac tct cca gac tcc gtg     192
Ala Ala Val Trp Tyr Asp Gly Ser Asn Thr Tyr Ser Pro Asp Ser Val
     50                  55                  60
```

-continued

```
aag ggc cga ttc acc atc tcc aga gac gat tcc aag aac acg gtg tat    240
Lys Gly Arg Phe Thr Ile Ser Arg Asp Asp Ser Lys Asn Thr Val Tyr
 65                  70                  75                  80 ctg caa atg aac agc ctg aga gcc gag gac acg gct gtg tat tac tgt    288
Leu Gln Met Asn Ser Leu Arg Ala Glu Asp Thr Ala Val Tyr Tyr Cys
                 85                  90                  95 gcg aga gat agg gtg ggc ctc ttt gac tac tgg ggc cag gga acc ctg    336
Ala Arg Asp Arg Val Gly Leu Phe Asp Tyr Trp Gly Gln Gly Thr Leu
            100                 105                 110 gtc acc gtc tcc tca gcc tcc acc aag ggc cca tcg gtc ttc ccc ctg    384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc    432
Ala Pro Ser Ser Lys Ser Thr Ser Gly Gly Thr Ala Ala Leu Gly Cys
130                 135                 140 ctg gtc aag gac tac ttc ccc gaa ccg gtg acg gtg tcg tgg aac tca    480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc    528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc    576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac    624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat    672
Thr Lys Val Asp Lys Lys Ala Glu Pro Lys Ser His His His His His
    210                 215                 220 cac                                                                675
His
225
```

<210> SEQ ID NO 62
<211> LENGTH: 225
<212> TYPE: PRT
<213> ORGANISM: Homo sapiens
<223> OTHER INFORMATION: M1-8H

<400> SEQUENCE: 62

```
Gln Val Gln Leu Val Gln Ser Gly Gly Gly Val Val Gln Pro Gly Lys
  1               5                  10                  15

Ser Leu Lys Leu Ser Cys Ala Ala Ser Gly Phe Thr Phe Ser Tyr Tyr
                 20                  25                  30

Gly Met His Trp Val Arg Gln Ala Pro Gly Lys Gly Leu Glu Trp Val
             35                  40                  45

Ala Ala Val Trp Tyr Asp Gly Ser Asn Thr Tyr Ser Pro Asp Ser Val
         50                  55                  60

Lys Gly Arg Phe Thr Ile Ser Arg Asp Asp Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
```

```
                130                 135                 140
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Ala Glu Pro Lys Ser His His His His
        210                 215                 220

His
225

<210> SEQ ID NO 63
<211> LENGTH: 708
<212> TYPE: DNA
<213> ORGANISM: Homo sapiens
<220> FEATURE:
<221> NAME/KEY: CDS
<222> LOCATION: (1)..(708)
<223> OTHER INFORMATION: M1-10H

<400> SEQUENCE: 63 cag gtg cag ctg gtg cag tct ggg gga ggc ttg gta cat cct ggg ggg     48
Gln Val Gln Leu Val Gln Ser Gly Gly Gly Leu Val His Pro Gly Gly
  1               5                  10                  15 tcc ctg aga ctc tcc tgt gaa ggc tct gga ttc atc ttc agg aac cat     96
Ser Leu Arg Leu Ser Cys Glu Gly Ser Gly Phe Ile Phe Arg Asn His
             20                  25                  30 cct ata cac tgg gtt cgc cag gct cca gga aaa ggt ctg gag tgg gta    144
Pro Ile His Trp Val Arg Gln Ala Pro Gly Lys Gly Leu Glu Trp Val
         35                  40                  45 tca gtt agt ggt att ggt ggt gac aca tac tat gca gac tcc gtg aag    192
Ser Val Ser Gly Ile Gly Gly Asp Thr Tyr Tyr Ala Asp Ser Val Lys
     50                  55                  60 ggc cga ttc tcc atc tcc aga gac aat gcc aag aac tcc ttg tat ctt    240
Gly Arg Phe Ser Ile Ser Arg Asp Asn Ala Lys Asn Ser Leu Tyr Leu
 65                  70                  75                  80 caa atg aac agc ctg aga gcc gag gac atg gct gtg tat tac tgt gca    288
Gln Met Asn Ser Leu Arg Ala Glu Asp Met Ala Val Tyr Tyr Cys Ala
                 85                  90                  95 aga gaa tat tac tat ggt tcg ggg agt tat cgc gtt gac tac tac tac    336
Arg Glu Tyr Tyr Tyr Gly Ser Gly Ser Tyr Arg Val Asp Tyr Tyr Tyr
            100                 105                 110 tac ggt atg gac gtc tgg ggc caa ggg acc acg gtc acc gtc tcc tca    384
Tyr Gly Met Asp Val Trp Gly Gln Gly Thr Thr Val Thr Val Ser Ser
        115                 120                 125 gcc tcc acc aag ggc cca tcg gtc ttc ccc ctg gca ccc tcc tcc aag    432
Ala Ser Thr Lys Gly Pro Ser Val Phe Pro Leu Ala Pro Ser Ser Lys
    130                 135                 140 agc acc tct ggg ggc aca gcg gcc ctg ggc tgc ctg gtc aag gac tac    480
Ser Thr Ser Gly Gly Thr Ala Ala Leu Gly Cys Leu Val Lys Asp Tyr
145                 150                 155                 160 ttc ccc gaa ccg gtg acg gtg tcg tgg aac tca ggc gcc ctg acc agc    528
Phe Pro Glu Pro Val Thr Val Ser Trp Asn Ser Gly Ala Leu Thr Ser
                165                 170                 175 ggc gtg cac acc ttc ccg gct gtc cta cag tcc tca gga ctc tac tcc    576
Gly Val His Thr Phe Pro Ala Val Leu Gln Ser Ser Gly Leu Tyr Ser
            180                 185                 190
```

-continued

```
ctc agc agc gtg gtg acc gtg ccc tcc agc agc ttg ggc acc cag acc      624
Leu Ser Ser Val Val Thr Val Pro Ser Ser Ser Leu Gly Thr Gln Thr
        195                 200                 205 tac atc tgc aac gtg aat cac aag ccc agc aac acc aag gtg gac aag      672
Tyr Ile Cys Asn Val Asn His Lys Pro Ser Asn Thr Lys Val Asp Lys
    210                 215                 220 aaa gca gag ccc aaa tct cat cac cat cac cat cac                      708
Lys Ala Glu Pro Lys Ser His His His His His His
225                 230                 235
```

<210> SEQ ID NO 64
<211> LENGTH: 236
<212> TYPE: PRT
<213> ORGANISM: Homo sapiens
<223> OTHER INFORMATION: M1-10H

<400> SEQUENCE: 64

```
Gln Val Gln Leu Val Gln Ser Gly Gly Gly Leu Val His Pro Gly Gly
  1               5                  10                  15

Ser Leu Arg Leu Ser Cys Glu Gly Ser Gly Phe Ile Phe Arg Asn His
             20                  25                  30

Pro Ile His Trp Val Arg Gln Ala Pro Gly Lys Gly Leu Glu Trp Val
         35                  40                  45

Ser Val Ser Gly Ile Gly Gly Asp Thr Tyr Tyr Ala Asp Ser Val Lys
     50                  55                  60

Gly Arg Phe Ser Ile Ser Arg Asp Asn Ala Lys Asn Ser Leu Tyr Leu
 65                  70                  75                  80

Gln Met Asn Ser Leu Arg Ala Glu Asp Met Ala Val Tyr Tyr Cys Ala
                 85                  90                  95

Arg Glu Tyr Tyr Tyr Gly Ser Gly Ser Tyr Arg Val Asp Tyr Tyr Tyr
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Ala Glu Pro Lys Ser His His His His His His
225                 230                 235
```

<210> SEQ ID NO 65
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M1-21H

<400> SEQUENCE: 65

-continued

```
cag gtg cag ctg gtg cag tct ggg gga ggc gtg gtc cag cct ggg aag      48
Gln Val Gln Leu Val Gln Ser Gly Gly Gly Val Val Gln Pro Gly Lys
 1               5                  10                  15 tcc ctg aga ctc tcc tgt gca gcg tct gga ttc acc ttc agt tac tat      96
Ser Leu Arg Leu Ser Cys Ala Ala Ser Gly Phe Thr Phe Ser Tyr Tyr
            20                  25                  30 ggc atg cac tgg gtc cgc cag gtt cca ggc aag ggg ctg gag tgg gtg     144
Gly Met His Trp Val Arg Gln Val Pro Gly Lys Gly Leu Glu Trp Val
        35                  40                  45 gca gct gtc tgg tat gat gga agt act aca tat tct cca gac tcc gtg     192
Ala Ala Val Trp Tyr Asp Gly Ser Thr Thr Tyr Ser Pro Asp Ser Val
 50                  55                  60 aag ggc cga ttc acc atc tcc aga gac gat tcc aag aac acg ctg tat     240
Lys Gly Arg Phe Thr Ile Ser Arg Asp Asp Ser Lys Asn Thr Leu Tyr
 65                  70                  75                  80 ctg caa atg agc agc ctg aga gcc gag gac acg gct gtg tat tac tgt     288
Leu Gln Met Ser Ser Leu Arg Ala Glu Asp Thr Ala Val Tyr Tyr Cys
                85                  90                  95 gcg aga gat agg gtg ggc ctc ttt gac tac tgg ggc cag gga acc ctg     336
Ala Arg Asp Arg Val Gly Leu Phe Asp Tyr Trp Gly Gln Gly Thr Leu
            100                 105                 110 gtc acc gtc tcc tca gcc tcc acc aag ggc cca tcg gtc ttc ccc ctg     384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc     432
Ala Pro Ser Ser Lys Ser Thr Ser Gly Gly Thr Ala Ala Leu Gly Cys
130                 135                 140 ctg gtc aag gac tac ttc ccc gaa ccg gtg acg gtg tcg tgg aac tca     480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc     528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc     576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac     624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat     672
Thr Lys Val Asp Lys Lys Ala Glu Pro Lys Ser His His His His His
    210                 215                 220 cac                                                                  675
His
225

<210> SEQ ID NO 66
<211> LENGTH: 225
<212> TYPE: PRT
<213> ORGANISM: Homo sapiens
<223> OTHER INFORMATION: M1-21H

<400> SEQUENCE: 66

Gln Val Gln Leu Val Gln Ser Gly Gly Gly Val Val Gln Pro Gly Lys
 1               5                  10                  15

Ser Leu Arg Leu Ser Cys Ala Ala Ser Gly Phe Thr Phe Ser Tyr Tyr
            20                  25                  30

Gly Met His Trp Val Arg Gln Val Pro Gly Lys Gly Leu Glu Trp Val
        35                  40                  45

Ala Ala Val Trp Tyr Asp Gly Ser Thr Thr Tyr Ser Pro Asp Ser Val
```

-continued

```
                  50                    55                   60
Lys Gly Arg Phe Thr Ile Ser Arg Asp Asp Ser Lys Asn Thr Leu Tyr
 65                  70                   75                   80

Leu Gln Met Ser Ser Leu Arg Ala Glu Asp Thr Ala Val Tyr Tyr Cys
                     85                  90                   95

Ala Arg Asp Arg Val Gly Leu Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225
```

<210> SEQ ID NO 67
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M1-23H

<400> SEQUENCE: 67

```
cag gtg cag ctg gtg cag tct ggg gga ggc gtg gtc cag cct ggg agg        48
Gln Val Gln Leu Val Gln Ser Gly Gly Gly Val Val Gln Pro Gly Arg
  1               5                  10                  15 tcc ctg aga ctc tcc tgt gca gcg tct gga ttc acc ttc agt aac tat        96
Ser Leu Arg Leu Ser Cys Ala Ala Ser Gly Phe Thr Phe Ser Asn Tyr
             20                  25                  30 ggc atg cac tgg gtc cgc cag gct cca ggc aag ggg ctg gag tgg gtg       144
Gly Met His Trp Val Arg Gln Ala Pro Gly Lys Gly Leu Glu Trp Val
         35                  40                  45 gca gct ata tgg tat gat gga agt aaa aca tac aat gca gac tcc gtg       192
Ala Ala Ile Trp Tyr Asp Gly Ser Lys Thr Tyr Asn Ala Asp Ser Val
     50                  55                  60 aag ggc cga ttc acc atc tcc aga gac aat tcc aag aac acg ctg tat       240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gct gtg tat tac tgt       288
Leu Gln Met Asn Ser Leu Arg Ala Glu Asp Thr Ala Val Tyr Tyr Cys
                     85                  90                  95 gcg aga gat ggg ata ggc tac ttt gac tac tgg ggc cag gga acc ctg       336
Ala Arg Asp Gly Ile Gly Tyr Phe Asp Tyr Trp Gly Gln Gly Thr Leu
                100                 105                 110 gtc acc gtc tcc tca gcc tcc acc aag ggc cca tcg gtc ttc ccc ctg       384
Val Thr Val Ser Ser Ala Ser Thr Lys Gly Pro Ser Val Phe Pro Leu
            115                 120                 125
```

-continued

```
gca ccc tcc tcc aag agc acc tct ggg gga aca gcg gcc ctg ggc tgc    432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca    480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc    528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc    576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac    624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat    672
Thr Lys Val Asp Lys Lys Ala Glu Pro Lys Ser His His His His His
    210                 215                 220 cac                                                                 675
His
225
```

<210> SEQ ID NO 68
<211> LENGTH: 225
<212> TYPE: PRT
<213> ORGANISM: Homo sapiens
<223> OTHER INFORMATION: M1-23H

<400> SEQUENCE: 68

```
Gln Val Gln Leu Val Gln Ser Gly Gly Gly Val Val Gln Pro Gly Arg
  1               5                  10                  15

Ser Leu Arg Leu Ser Cys Ala Ala Ser Gly Phe Thr Phe Ser Asn Tyr
                 20                  25                  30

Gly Met His Trp Val Arg Gln Ala Pro Gly Lys Gly Leu Glu Trp Val
             35                  40                  45

Ala Ala Ile Trp Tyr Asp Gly Ser Lys Thr Tyr Asn Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220
```

```
His
225

<210> SEQ ID NO 69
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M1-25H

<400> SEQUENCE: 69 cag gtg cag ctg gtg gag tct ggg gga ggc ttg gtc cag cct ggg ggg        48
Gln Val Gln Leu Val Glu Ser Gly Gly Gly Leu Val Gln Pro Gly Gly
 1               5                  10                  15 tcc ctg aga ctc tcc tgt gca gcg tct gga ttc acc ttc agt tac tat        96
Ser Leu Arg Leu Ser Cys Ala Ala Ser Gly Phe Thr Phe Ser Tyr Tyr
             20                  25                  30 ggc atg cac tgg gtc cgc cag gtt cca ggc aag ggg ctg gag tgg gtg       144
Gly Met His Trp Val Arg Gln Val Pro Gly Lys Gly Leu Glu Trp Val
         35                  40                  45 gca gct gtc tgg tat gat gga agt act aca tat cct cca gac tcc gtg       192
Ala Ala Val Trp Tyr Asp Gly Ser Thr Thr Tyr Pro Pro Asp Ser Val
     50                  55                  60 aag ggc cga ttc acc atc tcc aga gac gat tcc aag aac acg ctg tat       240
Lys Gly Arg Phe Thr Ile Ser Arg Asp Asp Ser Lys Asn Thr Leu Tyr
 65                  70                  75                  80 ctg caa atg aac agc ctg aga gcc gag gac acg gct gtt tat tac tgt       288
Leu Gln Met Asn Ser Leu Arg Ala Glu Asp Thr Ala Val Tyr Tyr Cys
                 85                  90                  95 gcg aga gat agg gtg ggc ctc ttt gac tac tgg ggc cag gga acc ctg       336
Ala Arg Asp Arg Val Gly Leu Phe Asp Tyr Trp Gly Gln Gly Thr Leu
            100                 105                 110 gtc acc gtc tcc tca gcc tcc acc aag ggc cca tcg gtc ttc ccc ctg       384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc       432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca       480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc       528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc       576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac       624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat       672
Thr Lys Val Asp Lys Lys Ala Glu Pro Lys Ser His His His His His
    210                 215                 220 cac                                                                    675
His
225

<210> SEQ ID NO 70
<211> LENGTH: 225
<212> TYPE: PRT
```

<213> ORGANISM: Homo sapiens
<223> OTHER INFORMATION: M1-25H

<400> SEQUENCE: 70

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Gly Met His Trp Val Arg Gln Val Pro Gly Lys Gly Leu Glu Trp Val
        35                  40                  45

Ala Ala Val Trp Tyr Asp Gly Ser Thr Thr Tyr Pro Pro Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 71
<211> LENGTH: 678
<212> TYPE: DNA
<213> ORGANISM: Homo sapiens
<220> FEATURE:
<221> NAME/KEY: CDS
<222> LOCATION: (1)..(678)
<223> OTHER INFORMATION: M2-11L

<400> SEQUENCE: 71 gaa ata gtg atg acg cag tct cca ggc acc ctg tct ttg tct cca ggg    48
Glu Ile Val Met Thr Gln Ser Pro Gly Thr Leu Ser Leu Ser Pro Gly
1               5                   10                  15 gaa aga gcc acc ctc tcc tgc agg gcc agt cag ggt gtt agc agc agc    96
Glu Arg Ala Thr Leu Ser Cys Arg Ala Ser Gln Gly Val Ser Ser Ser
            20                  25                  30 tac tta gcc tgg tac cag cag aaa cct ggc cag gct ccc agg ctc ctc   144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt   192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag   240

-continued

| | | |
|---|---|---|
| Gly Ser Gly Ser Gly Thr Asp Phe Thr Leu Thr Ile Ser Arg Leu Glu<br>65                            70                          75                          80 | |
| cct gaa gat ttt gca gtg tat tac tgt cag cag tat ggt agc tca cct<br>Pro Glu Asp Phe Ala Val Tyr Tyr Cys Gln Gln Tyr Gly Ser Ser Pro<br>                       85                       90                       95 | 288 |
| cca ttc act ttc ggc cct ggg acc aaa gtg gat atc aaa cga act gtg<br>Pro Phe Thr Phe Gly Pro Gly Thr Lys Val Asp Ile Lys Arg Thr Val<br>          100                      105                   110 | 336 |
| gct gca cca tct gtc ttc atc ttc ccg cca tct gat gag cag ttg aga<br>Ala Ala Pro Ser Val Phe Ile Phe Pro Pro Ser Asp Glu Gln Leu Arg<br>          115                     120                     125 | 384 |
| tct gga act gcc tct gtt gtg tgc ctg ctg aat aac ttc tat ccc aga<br>Ser Gly Thr Ala Ser Val Val Cys Leu Leu Asn Asn Phe Tyr Pro Arg<br>130                           135                     140 | 432 |
| gag gcc aaa gta cag tgg aag gtg gat aac gcc ctc caa tcg ggt aac<br>Glu Ala Lys Val Gln Trp Lys Val Asp Asn Ala Leu Gln Ser Gly Asn<br>145                           150                     155                   160 | 480 |
| tcc cag gag agt gtc aca gag cag gac agc aag gac agc acc tac agc<br>Ser Gln Glu Ser Val Thr Glu Gln Asp Ser Lys Asp Ser Thr Tyr Ser<br>                 165                     170                   175 | 528 |
| ctc agc agc acc ctg acg ctg agc aaa gca gac tac gag aaa cac aaa<br>Leu Ser Ser Thr Leu Thr Leu Ser Lys Ala Asp Tyr Glu Lys His Lys<br>          180                      185                   190 | 576 |
| gtc tac gcc tgc gaa gtc acc cat cag ggc ctg agc tcg ccc gtc aca<br>Val Tyr Ala Cys Glu Val Thr His Gln Gly Leu Ser Ser Pro Val Thr<br>               195                     200                   205 | 624 |
| aag agc ttc aac agg gga gag tct tat cca tat gat gtg cca gat tat<br>Lys Ser Phe Asn Arg Gly Glu Ser Tyr Pro Tyr Asp Val Pro Asp Tyr<br>210                           215                     220 | 672 |
| gcg agc<br>Ala Ser<br>225 | 678 |

<210> SEQ ID NO 72
<211> LENGTH: 226
<212> TYPE: PRT
<213> ORGANISM: Homo sapiens
<223> OTHER INFORMATION: M2-11L

<400> SEQUENCE: 72

Glu Ile Val Met Thr Gln Ser Pro Gly Thr Leu Ser Leu Ser Pro Gly
1                     5                       10                   15

Glu Arg Ala Thr Leu Ser Cys Arg Ala Ser Gln Gly Val Ser Ser Ser
               20                     25                     30

Tyr Leu Ala Trp Tyr Gln Gln Lys Pro Gly Gln Ala Pro Arg Leu Leu
         35                     40                     45

Ile Tyr Gly Ala Ser Ser Arg Ala Thr Gly Ile Pro Asp Arg Phe Ser
    50                     55                     60

Gly Ser Gly Ser Gly Thr Asp Phe Thr Leu Thr Ile Ser Arg Leu Glu
65                            70                          75                          80

Pro Glu Asp Phe Ala Val Tyr Tyr Cys Gln Gln Tyr Gly Ser Ser Pro
               85                     90                     95

Pro Phe Thr Phe Gly Pro Gly Thr Lys Val Asp Ile Lys Arg Thr Val
          100                      105                   110

Ala Ala Pro Ser Val Phe Ile Phe Pro Pro Ser Asp Glu Gln Leu Arg
          115                     120                     125

Ser Gly Thr Ala Ser Val Val Cys Leu Leu Asn Asn Phe Tyr Pro Arg
130                           135                     140

```
Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
            165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Ser Tyr Pro Tyr Asp Val Pro Asp Tyr
    210                 215                 220

Ala Ser
225

<210> SEQ ID NO 73
<211> LENGTH: 678
<212> TYPE: DNA
<213> ORGANISM: Homo sapiens
<220> FEATURE:
<221> NAME/KEY: CDS
<222> LOCATION: (1)..(678)
<223> OTHER INFORMATION: M2-12L

<400> SEQUENCE: 73 gaa ata gtg atg acg cag tct cca ggc acc ctg tct ttg tct cca ggg      48
Glu Ile Val Met Thr Gln Ser Pro Gly Thr Leu Ser Leu Ser Pro Gly
 1               5                  10                  15 gaa aga gcc acc ctc tcc tgc agg gcc agt cag ggt gtt agc agc agc      96
Glu Arg Ala Thr Leu Ser Cys Arg Ala Ser Gln Gly Val Ser Ser Ser
                20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
            35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
        50                  55                  60 ggc agt ggg tct ggg aca gac ttc act ctc acc atc agc agc cta gag     240
Gly Ser Gly Ser Gly Thr Asp Phe Thr Leu Thr Ile Ser Ser Leu Glu
 65                  70                  75                  80 cct gaa gat ttt gca gtg tat tac tgt cag cag tat ggt agc tca cct     288
Pro Glu Asp Phe Ala Val Tyr Tyr Cys Gln Gln Tyr Gly Ser Ser Pro
                85                  90                  95 ccg tac act ttt ggc cag ggg acc aag ctg gag atc aaa cga act gtg     336
Pro Tyr Thr Phe Gly Gln Gly Thr Lys Leu Glu Ile Lys Arg Thr Val
            100                 105                 110 gct gca cca tct gtc ttc atc ttc ccg cca tct gat gag cag ttg aaa     384
Ala Ala Pro Ser Val Phe Ile Phe Pro Pro Ser Asp Glu Gln Leu Lys
        115                 120                 125 tct gga act gcc tct gtt gtg tgc ctg ctg aat aac ttc tat ccc aga     432
Ser Gly Thr Ala Ser Val Val Cys Leu Leu Asn Asn Phe Tyr Pro Arg
130                 135                 140 gag gcc aaa gta cag tgg aag gtg gat aac gcc ctc caa tcg ggt aac     480
Glu Ala Lys Val Gln Trp Lys Val Asp Asn Ala Leu Gln Ser Gly Asn
145                 150                 155                 160 tcc cag gag agt gtc aca gag cag gac agc aag gac agc acc tac agc     528
Ser Gln Glu Ser Val Thr Glu Gln Asp Ser Lys Asp Ser Thr Tyr Ser
            165                 170                 175 ctc agc agc acc ctg acg ctg agc aaa gca gac tac gag aaa cac aaa     576
Leu Ser Ser Thr Leu Thr Leu Ser Lys Ala Asp Tyr Glu Lys His Lys
            180                 185                 190 gtc tac gcc tgc gaa gtc acc cat cag ggc ctg agc tcg ccc gtc aca     624
```

```
Val Tyr Ala Cys Glu Val Thr His Gln Gly Leu Ser Ser Pro Val Thr
            195                 200                 205 aag agc ttc aac agg gga gag tct tat cca tat gat gtg cca gat tat        672
Lys Ser Phe Asn Arg Gly Glu Ser Tyr Pro Tyr Asp Val Pro Asp Tyr
    210                 215                 220 gcg agc                                                                 678
Ala Ser
225
```

<210> SEQ ID NO 74
<211> LENGTH: 226
<212> TYPE: PRT
<213> ORGANISM: Homo sapiens
<223> OTHER INFORMATION: M2-12L

<400> SEQUENCE: 74

```
Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Gly Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Gly Ser Ser Pro
                85                  90                  95

Pro Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser Tyr Pro Tyr Asp Val Pro Asp Tyr
    210                 215                 220

Ala Ser
225
```

<210> SEQ ID NO 75
<211> LENGTH: 672
<212> TYPE: DNA
<213> ORGANISM: Homo sapiens
<220> FEATURE:
<221> NAME/KEY: CDS
<222> LOCATION: (1)..(672)
<223> OTHER INFORMATION: M2-16L

<400> SEQUENCE: 75

```
gaa ata gtg atg acg cag tct cca ggc acc ctg tct ttg tct cca ggg         48
Glu Ile Val Met Thr Gln Ser Pro Gly Thr Leu Ser Leu Ser Pro Gly
```

```
                 1               5                  10                 15
gaa aga gcc acc ctc tcc tgc agg gcc agt cag agt gtt agc agc agc        96
Glu Arg Ala Thr Leu Ser Cys Arg Ala Ser Gln Ser Val Ser Ser Ser
                20                  25                 30 tac tta gcc tgg tac cag cag aaa cct ggc cag gct ccc agg ctc ctc       144
Tyr Leu Ala Trp Tyr Gln Gln Lys Pro Gly Gln Ala Pro Arg Leu Leu
            35                  40                 45 atc tat ggt gca tcc agc agg gcc act ggc atc cca gac agg ttc agt       192
Ile Tyr Gly Ala Ser Ser Arg Ala Thr Gly Ile Pro Asp Arg Phe Ser
        50                  55                 60 gtc agt ggg tct ggg aca gac ttc act ctc acc atc agc aga ctg gag       240
Val Ser Gly Ser Gly Thr Asp Phe Thr Leu Thr Ile Ser Arg Leu Glu
    65                  70                 75                 80 cct gaa gat ttt gca gtg tat tac tgt cag cag tat ggt agc tca ttc       288
Pro Glu Asp Phe Ala Val Tyr Tyr Cys Gln Gln Tyr Gly Ser Ser Phe
                85                  90                 95 act ttc ggc cct ggg acc aaa gtg gat atc aaa cga act gtg gct gca       336
Thr Phe Gly Pro Gly Thr Lys Val Asp Ile Lys Arg Thr Val Ala Ala
            100                 105                110 cca tct gtc ttc atc ttc ccg cca tct gat gag cag ttg aaa tct gga       384
Pro Ser Val Phe Ile Phe Pro Pro Ser Asp Glu Gln Leu Lys Ser Gly
        115                 120                125 act gcc tct gtt gtg tgc ctg ctg aat aac ttc tat ccc aga gag gcc       432
Thr Ala Ser Val Val Cys Leu Leu Asn Asn Phe Tyr Pro Arg Glu Ala
    130                 135                140 aaa gta cag tgg aag gtg gat aac gcc ctc caa tcg ggt aac tcc cag       480
Lys Val Gln Trp Lys Val Asp Asn Ala Leu Gln Ser Gly Asn Ser Gln
145                 150                 155                160 gag agt gtc aca gag cag gac agc aag gac agc acc tac agc ctc agc       528
Glu Ser Val Thr Glu Gln Asp Ser Lys Asp Ser Thr Tyr Ser Leu Ser
                165                 170                175 agc acc ctg acg ctg agc aaa gca gac tac gag aaa cac aaa gtc tac       576
Ser Thr Leu Thr Leu Ser Lys Ala Asp Tyr Glu Lys His Lys Val Tyr
            180                 185                190 gcc tgc gaa gtc acc cat cag ggc ctg agc tcg ccc gtc aca aag agc       624
Ala Cys Glu Val Thr His Gln Gly Leu Ser Ser Pro Val Thr Lys Ser
        195                 200                205 ttc aac agg gga gag tct tat cca tat gat gtg cca gat tat gcg agc       672
Phe Asn Arg Gly Glu Ser Tyr Pro Tyr Asp Val Pro Asp Tyr Ala Ser
    210                 215                220
```

<210> SEQ ID NO 76
<211> LENGTH: 224
<212> TYPE: PRT
<213> ORGANISM: Homo sapiens
<223> OTHER INFORMATION: M2-16L

<400> SEQUENCE: 76

```
Glu Ile Val Met Thr Gln Ser Pro Gly Thr Leu Ser Leu Ser Pro Gly
1               5                  10                 15

Glu Arg Ala Thr Leu Ser Cys Arg Ala Ser Gln Ser Val Ser Ser Ser
                20                  25                 30

Tyr Leu Ala Trp Tyr Gln Gln Lys Pro Gly Gln Ala Pro Arg Leu Leu
            35                  40                 45

Ile Tyr Gly Ala Ser Ser Arg Ala Thr Gly Ile Pro Asp Arg Phe Ser
        50                  55                 60

Val Ser Gly Ser Gly Thr Asp Phe Thr Leu Thr Ile Ser Arg Leu Glu
    65                  70                 75                 80

Pro Glu Asp Phe Ala Val Tyr Tyr Cys Gln Gln Tyr Gly Ser Ser Phe
```

```
                    85                  90                  95
Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Ser Tyr Pro Tyr Asp Val Pro Asp Tyr Ala Ser
            210                 215                 220

<210> SEQ ID NO 77
<211> LENGTH: 672
<212> TYPE: DNA
<213> ORGANISM: Homo sapiens
<220> FEATURE:
<221> NAME/KEY: CDS
<222> LOCATION: (1)..(672)
<223> OTHER INFORMATION: M2-18L

<400> SEQUENCE: 77 gaa ata gtg atg acg cag tct cca ggc acc ctg tct ttg tct cca ggg     48
Glu Ile Val Met Thr Gln Ser Pro Gly Thr Leu Ser Leu Ser Pro Gly
  1               5                  10                  15 gaa aga gcc acc ctc tcc tgc agg gcc agt cag agt gtt agc agc acc     96
Glu Arg Ala Thr Leu Ser Cys Arg Ala Ser Gln Ser Val Ser Ser Thr
             20                  25                  30 tac tta gcc tgg tac cag cag aaa cct ggc cag gct ccc agg ctc ctc    144
Tyr Leu Ala Trp Tyr Gln Gln Lys Pro Gly Gln Ala Pro Arg Leu Leu
         35                  40                  45 atc tat ggt gca tcc agc agg gcc act ggc atc cca gac agg ttc agt    192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc aga ctg gag    240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat gtt agc tca ttc    288
Pro Glu Asp Phe Ala Val Tyr Tyr Cys Gln Gln Tyr Val Ser Ser Phe
                 85                  90                  95 act ttc ggc cct ggg acc aaa gtg gat atc aaa cga act gtg gct gca    336
Thr Phe Gly Pro Gly Thr Lys Val Asp Ile Lys Arg Thr Val Ala Ala
            100                 105                 110 cca tct gtc ttc atc ttc ccg cca tct gat gag cag ttg aaa tct gga    384
Pro Ser Val Phe Ile Phe Pro Pro Ser Asp Glu Gln Leu Lys Ser Gly
            115                 120                 125 act gcc tct gtt gtg tgc ctg ctg aat aac ttc tat ccc aga gag gcc    432
Thr Ala Ser Val Val Cys Leu Leu Asn Asn Phe Tyr Pro Arg Glu Ala
130                 135                 140 aaa gta cag tgg aag gtg gat aac gcc ctc caa tcg ggt aac tcc cag    480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc    528
```

```
           Glu Ser Val Thr Glu Gln Asp Ser Lys Asp Ser Thr Tyr Ser Leu Ser
                           165                 170                 175 agc acc ctg acg ctg agc aaa gca gac tac gag aaa cac aaa gtc tac          576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc          624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc          672
Phe Asn Arg Gly Glu Ser Tyr Pro Tyr Asp Val Pro Asp Tyr Ala Ser
    210                 215                 220
```

<210> SEQ ID NO 78
<211> LENGTH: 224
<212> TYPE: PRT
<213> ORGANISM: Homo sapiens
<223> OTHER INFORMATION: M2-18L

<400> SEQUENCE: 78

```
Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Val Ser Ser Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220
```

<210> SEQ ID NO 79
<211> LENGTH: 678
<212> TYPE: DNA
<213> ORGANISM: Homo sapiens
<220> FEATURE:
<221> NAME/KEY: CDS
<222> LOCATION: (1)..(678)
<223> OTHER INFORMATION: M2-20L

<400> SEQUENCE: 79

```
gaa ata gtg atg acg cag tct cca ggc acc ctg tct ttg tct cca ggg          48
```

```
Glu Ile Val Met Thr Gln Ser Pro Gly Thr Leu Ser Leu Ser Pro Gly
 1               5                  10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
             20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
         35                  40                  45 atc tac ggt gca tcc agg agg gcc act ggc atc cca gac agg ttc agt     192
Ile Tyr Gly Ala Ser Arg Arg Ala Thr Gly Ile Pro Asp Arg Phe Ser
     50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca ccc     288
Pro Glu Asp Phe Ala Val Tyr Tyr Cys Gln Gln Tyr Gly Ser Ser Pro
                 85                  90                  95 atg tac act ttt ggc cag ggg acc aag ctg gag atc aaa cga act gtg     336
Met Tyr Thr Phe Gly Gln Gly Thr Lys Leu Glu Ile Lys Arg Thr Val
            100                 105                 110 gct gca cca tct gtc ttc atc ttc ccg cca tct gat gag cag ttg aaa     384
Ala Ala Pro Ser Val Phe Ile Phe Pro Pro Ser Asp Glu Gln Leu Lys
        115                 120                 125 tct gga act gcc tct gtt gtg tgc ctg ctg aat aac ttc tat ccc aga     432
Ser Gly Thr Ala Ser Val Val Cys Leu Leu Asn Asn Phe Tyr Pro Arg
    130                 135                 140 gag gcc aaa gta cag tgg aag gtg gat aac gcc ctc caa tcg ggt aac     480
Glu Ala Lys Val Gln Trp Lys Val Asp Asn Ala Leu Gln Ser Gly Asn
145                 150                 155                 160 tcc cag gag agt gtc aca gag cag gac agc aag gac agc acc tac agc     528
Ser Gln Glu Ser Val Thr Glu Gln Asp Ser Lys Asp Ser Thr Tyr Ser
                165                 170                 175 ctc agc agc acc ctg acg ctg agc aaa gca gac tac gag aaa cac aaa     576
Leu Ser Ser Thr Leu Thr Leu Ser Lys Ala Asp Tyr Glu Lys His Lys
            180                 185                 190 gtc tac gcc tgc gaa gtc acc cat cag ggc ctg agc tcg ccc gtc aca     624
Val Tyr Ala Cys Glu Val Thr His Gln Gly Leu Ser Ser Pro Val Thr
        195                 200                 205 aag agc ttc aac agg gga gag tct tat cca tat gat gtg cca gat tat     672
Lys Ser Phe Asn Arg Gly Glu Ser Tyr Pro Tyr Asp Val Pro Asp Tyr
    210                 215                 220 gcg agc                                                              678
Ala Ser
225

<210> SEQ ID NO 80
<211> LENGTH: 226
<212> TYPE: PRT
<213> ORGANISM: Homo sapiens
<223> OTHER INFORMATION: M2-20L

<400> SEQUENCE: 80

Glu Ile Val Met Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Arg Arg Ala Thr Gly Ile Pro Asp Arg Phe Ser
     50                  55                  60
```

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Met Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Ser Tyr Pro Tyr Asp Val Pro Asp Tyr
    210                 215                 220

Ala Ser
225

<210> SEQ ID NO 81
<211> LENGTH: 672
<212> TYPE: DNA
<213> ORGANISM: Homo sapiens
<220> FEATURE:
<221> NAME/KEY: CDS
<222> LOCATION: (1)..(672)
<223> OTHER INFORMATION: M2-31L

<400> SEQUENCE: 81 gaa att gtg ttg acg cag tct cca gcc acc ctg tct ttg tct cca ggg        48
Glu Ile Val Leu Thr Gln Ser Pro Ala Thr Leu Ser Leu Ser Pro Gly
  1               5                  10                  15 gaa aga gcc acc ctc tcc tgc agg gcc agt cag agt gtt agc agc tac        96
Glu Arg Ala Thr Leu Ser Cys Arg Ala Ser Gln Ser Val Ser Ser Tyr
             20                  25                  30 tta gcc tgg tac caa cag aaa cct ggc cag gct ccc agg ctc ctc atc       144
Leu Ala Trp Tyr Gln Gln Lys Pro Gly Gln Ala Pro Arg Leu Leu Ile
         35                  40                  45 tat gat gca tcc aac agg gcc act ggc atc cca gcc agg ttc agt ggc       192
Tyr Asp Ala Ser Asn Arg Ala Thr Gly Ile Pro Ala Arg Phe Ser Gly
     50                  55                  60 agt ggg tct ggg aca gac ttc act ctc acc atc agc agc cta gag cct       240
Ser Gly Ser Gly Thr Asp Phe Thr Leu Thr Ile Ser Ser Leu Glu Pro
 65                  70                  75                  80 gaa gat ttt gca gtt tat tac tgt cag cag cgt acg aac tgg cct cgg       288
Glu Asp Phe Ala Val Tyr Tyr Cys Gln Gln Arg Thr Asn Trp Pro Arg
                 85                  90                  95 acg ttc ggc caa ggg acc aag gtg gaa atc aaa cga act gtg gct gca       336
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga       384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc       432
```

```
Thr Ala Ser Val Val Cys Leu Leu Asn Asn Phe Tyr Pro Arg Glu Ala
            130                 135                 140 aaa gta cag tgg aag gtg gat aac gcc ctc caa tcg ggt aac tcc cag        480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc        528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac        576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc        624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc        672
Phe Asn Arg Gly Glu Ser Tyr Pro Tyr Asp Val Pro Asp Tyr Ala Ser
    210                 215                 220

<210> SEQ ID NO 82
<211> LENGTH: 224
<212> TYPE: PRT
<213> ORGANISM: Homo sapiens
<223> OTHER INFORMATION: M2-31L

<400> SEQUENCE: 82

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
    210                 215                 220

<210> SEQ ID NO 83
<211> LENGTH: 672
<212> TYPE: DNA
<213> ORGANISM: Homo sapiens
```

```
<220> FEATURE:
<221> NAME/KEY: CDS
<222> LOCATION: (1)..(672)
<223> OTHER INFORMATION: M2-32L

<400> SEQUENCE: 83 gaa att gtg ttg acg cag tct cca gcc acc ctg tct ttg tct cca ggg      48
Glu Ile Val Leu Thr Gln Ser Pro Ala Thr Leu Ser Leu Ser Pro Gly
  1               5                  10                  15 gaa aga gcc acc ctc tcc tgc agg gcc agt cag agt gtt agc agc tac      96
Glu Arg Ala Thr Leu Ser Cys Arg Ala Ser Gln Ser Val Ser Ser Tyr
                 20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
             35                  40                  45 tat gat gca tcc aac agg gcc gct ggc atc cca gcc agg ttc agt ggc     192
Tyr Asp Ala Ser Asn Arg Ala Ala Gly Ile Pro Ala Arg Phe Ser Gly
 50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
 65                  70                  75                  80 gaa gat ttt gca gtt tat tac tgt cag caa cgt aac aac tgg cct ctc     288
Glu Asp Phe Ala Val Tyr Tyr Cys Gln Gln Arg Asn Asn Trp Pro Leu
                 85                  90                  95 act ttc ggc gga ggg acc aag gtg gag atc aaa cga act gtg gct gca     336
Thr Phe Gly Gly Gly Thr Lys Val Glu Ile Lys Arg Thr Val Ala Ala
                100                 105                 110 cca tct gtc ttc atc ttc ccg cca tct gat gag cag ttg aaa tct gga     384
Pro Ser Val Phe Ile Phe Pro Pro Ser Asp Glu Gln Leu Lys Ser Gly
            115                 120                 125 act gcc tct gtt gtg tgc ctg ctg aat aac ttc tat ccc aga gag gcc     432
Thr Ala Ser Val Val Cys Leu Leu Asn Asn Phe Tyr Pro Arg Glu Ala
130                 135                 140 aaa gta cag tgg aag gtg gat aac gcc ctc caa tcg ggt aac tcc cag     480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc     528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac     576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc     624
Ala Cys Glu Val Thr His Gln Gly Leu Ser Ser Pro Val Thr Lys Ser
        195                 200                 205 ttc aac agg gga gag tct tat cca tat gat gtg cca gat tat gcg agc     672
Phe Asn Arg Gly Glu Ser Tyr Pro Tyr Asp Val Pro Asp Tyr Ala Ser
    210                 215                 220

<210> SEQ ID NO 84
<211> LENGTH: 224
<212> TYPE: PRT
<213> ORGANISM: Homo sapiens
<223> OTHER INFORMATION: M2-32L

<400> SEQUENCE: 84

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
```

```
                       35                  40                  45
          Tyr Asp Ala Ser Asn Arg Ala Ala Gly Ile Pro Ala Arg Phe Ser Gly
               50                  55                  60

Ser Gly Ser Gly Thr Asp Phe Thr Leu Thr Ile Ser Ser Leu Glu Pro
           65                  70                  75                  80

Glu Asp Phe Ala Val Tyr Tyr Cys Gln Gln Arg Asn Asn Trp Pro Leu
                           85                  90                  95

Thr Phe Gly Gly Gly Thr Lys Val Glu Ile Lys Arg Thr Val Ala Ala
                      100                 105                 110

Pro Ser Val Phe Ile Phe Pro Pro Ser Asp Glu Gln Leu Lys Ser Gly
                      115                 120                 125

Thr Ala Ser Val Val Cys Leu Leu Asn Asn Phe Tyr Pro Arg Glu Ala
              130                 135                 140

Lys Val Gln Trp Lys Val Asp Asn Ala Leu Gln Ser Gly Asn Ser Gln
          145                 150                 155                 160

Glu Ser Val Thr Glu Gln Asp Ser Lys Asp Ser Thr Tyr Ser Leu Ser
                          165                 170                 175

Ser Thr Leu Thr Leu Ser Lys Ala Asp Tyr Glu Lys His Lys Val Tyr
                      180                 185                 190

Ala Cys Glu Val Thr His Gln Gly Leu Ser Ser Pro Val Thr Lys Ser
                   195                 200                 205

Phe Asn Arg Gly Glu Ser Tyr Pro Tyr Asp Val Pro Asp Tyr Ala Ser
              210                 215                 220

<210> SEQ ID NO 85
<211> LENGTH: 678
<212> TYPE: DNA
<213> ORGANISM: Homo sapiens
<220> FEATURE:
<221> NAME/KEY: CDS
<222> LOCATION: (1)..(678)
<223> OTHER INFORMATION: M2-33L

<400> SEQUENCE: 85 gaa att gtg ttg acg cag tct cca ggc acc ctg tct ttg tct cca ggg          48
Glu Ile Val Leu Thr Gln Ser Pro Gly Thr Leu Ser Leu Ser Pro Gly
  1               5                  10                  15 gaa aga gcc acc ctc tcc tgc agg gcc agt cag agt gtt agc agc agc          96
Glu Arg Ala Thr Leu Ser Cys Arg Ala Ser Gln Ser Val Ser Ser Ser
             20                  25                  30 tac tta gcc tgg tac cag cag aaa cct ggc cag gct ccc agg ctc ctc         144
Tyr Leu Ala Trp Tyr Gln Gln Lys Pro Gly Gln Ala Pro Arg Leu Leu
         35                  40                  45 atc tat ggt gca tcc agc agg gcc act ggc atc cca gac agg ttc agt         192
Ile Tyr Gly Ala Ser Ser Arg Ala Thr Gly Ile Pro Asp Arg Phe Ser
     50                  55                  60 ggc agt ggg tct ggg aca gac ttc act ctc acc atc agc aga ctg gag         240
Gly Ser Gly Ser Gly Thr Asp Phe Thr Leu Thr Ile Ser Arg Leu Glu
 65                  70                  75                  80 cct gaa gat ttt gca gtg tat tac tgt cag cag tat ggt agc tca cct         288
Pro Glu Asp Phe Ala Val Tyr Tyr Cys Gln Gln Tyr Gly Ser Ser Pro
                 85                  90                  95 ccg tac act ttt ggc cag ggg acc aag ctg gag atc aaa cga act gtg         336
Pro Tyr Thr Phe Gly Gln Gly Thr Lys Leu Glu Ile Lys Arg Thr Val
             100                 105                 110 gct gca cca tct gtc ttc atc ttc ccg cca tct gat gag cag ttg aaa         384
Ala Ala Pro Ser Val Phe Ile Phe Pro Pro Ser Asp Glu Gln Leu Lys
         115                 120                 125
```

```
tct gga act gcc tct gtt gtg tgc ctg ctg aat aac ttc tat ccc aga      432
Ser Gly Thr Ala Ser Val Val Cys Leu Leu Asn Asn Phe Tyr Pro Arg
    130                 135                 140 gag gcc aaa gta cag tgg aag gtg gat aac gcc ctc caa tcg ggt aac      480
Glu Ala Lys Val Gln Trp Lys Val Asp Asn Ala Leu Gln Ser Gly Asn
145                 150                 155                 160 tcc cag gag agt gtc aca gag cag gac agc aag gac agc acc tac agc      528
Ser Gln Glu Ser Val Thr Glu Gln Asp Ser Lys Asp Ser Thr Tyr Ser
                165                 170                 175 ctc agc agc acc ctg acg ctg agc aaa gca gac tac gag aaa cac aaa      576
Leu Ser Ser Thr Leu Thr Leu Ser Lys Ala Asp Tyr Glu Lys His Lys
                180                 185                 190 gtc tac gcc tgc gaa gtc acc cat cag ggc ctg agc tcg ccc gtc aca      624
Val Tyr Ala Cys Glu Val Thr His Gln Gly Leu Ser Ser Pro Val Thr
            195                 200                 205 aag agc ttc aac agg gga gag tct tat cca tat gat gtg cca gat tat      672
Lys Ser Phe Asn Arg Gly Glu Ser Tyr Pro Tyr Asp Val Pro Asp Tyr
        210                 215                 220 gcg agc                                                              678
Ala Ser
225
```

<210> SEQ ID NO 86
<211> LENGTH: 226
<212> TYPE: PRT
<213> ORGANISM: Homo sapiens
<223> OTHER INFORMATION: M2-33L

<400> SEQUENCE: 86

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Tyr Thr Phe Gly Gln Gly Thr Lys Leu Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
            195                 200                 205

Lys Ser Phe Asn Arg Gly Glu Ser Tyr Pro Tyr Asp Val Pro Asp Tyr
        210                 215                 220
```

-continued

Ala Ser
225

<210> SEQ ID NO 87
<211> LENGTH: 672
<212> TYPE: DNA
<213> ORGANISM: Homo sapiens
<220> FEATURE:
<221> NAME/KEY: CDS
<222> LOCATION: (1)..(672)
<223> OTHER INFORMATION: M2-34L

<400> SEQUENCE: 87

| gaa att gtg ttg acg cag tct cca gcc acc ctg tct ttg tct cca ggg | 48 |
|---|---|
| Glu Ile Val Leu Thr Gln Ser Pro Ala Thr Leu Ser Leu Ser Pro Gly | |
| 1               5                   10                  15 | |

| gaa aga gcc acc ctc tcc tgc agg gcc agt cag agt gtt agc agc tac | 96 |
|---|---|
| Glu Arg Ala Thr Leu Ser Cys Arg Ala Ser Gln Ser Val Ser Ser Tyr | |
|                 20                  25                  30 | |

| tta gcc tgg tac caa cag aaa cct ggc cag gct ccc agg ctc ctc atc | 144 |
|---|---|
| Leu Ala Trp Tyr Gln Gln Lys Pro Gly Gln Ala Pro Arg Leu Leu Ile | |
|         35                  40                  45 | |

| tat gat gca tcc aac agg gcc act ggc atc cca gcc agg ttc agt ggc | 192 |
|---|---|
| Tyr Asp Ala Ser Asn Arg Ala Thr Gly Ile Pro Ala Arg Phe Ser Gly | |
| 50                  55                  60 | |

| agt ggg tct ggg aca gac ttc act ctc acc atc agc agc cta gag cct | 240 |
|---|---|
| Ser Gly Ser Gly Thr Asp Phe Thr Leu Thr Ile Ser Ser Leu Glu Pro | |
| 65                  70                  75                  80 | |

| gaa gat ttt gca gtt tat tac tgt cag cag cgt acg aac tgg cct cgg | 288 |
|---|---|
| Glu Asp Phe Ala Val Tyr Tyr Cys Gln Gln Arg Thr Asn Trp Pro Arg | |
|                 85                  90                  95 | |

| acg ttc ggc caa ggg acc aag gtg gaa atc aaa cga act gtg gct gca | 336 |
|---|---|
| Thr Phe Gly Gln Gly Thr Lys Val Glu Ile Lys Arg Thr Val Ala Ala | |
|             100                 105                 110 | |

| cca tct gtc ttc atc ttc ccg cca tct gat gag cag ttg aaa tct gga | 384 |
|---|---|
| Pro Ser Val Phe Ile Phe Pro Pro Ser Asp Glu Gln Leu Lys Ser Gly | |
|         115                 120                 125 | |

| act gcc tct gtt gtg tgc ctg ctg aat aac ttc tat ccc aga gag gcc | 432 |
|---|---|
| Thr Ala Ser Val Val Cys Leu Leu Asn Asn Phe Tyr Pro Arg Glu Ala | |
| 130                 135                 140 | |

| aaa gta cag tgg aag gtg gat aac gcc ctc caa tcg ggt aac tcc cag | 480 |
|---|---|
| Lys Val Gln Trp Lys Val Asp Asn Ala Leu Gln Ser Gly Asn Ser Gln | |
| 145                 150                 155                 160 | |

| gag agt gtc aca gag cag gac agc aag gac agc acc tac agc ctc agc | 528 |
|---|---|
| Glu Ser Val Thr Glu Gln Asp Ser Lys Asp Ser Thr Tyr Ser Leu Ser | |
|                 165                 170                 175 | |

| agc acc ctg acg ctg agc aaa gca gac tac gag aaa cac aaa gtc tac | 576 |
|---|---|
| Ser Thr Leu Thr Leu Ser Lys Ala Asp Tyr Glu Lys His Lys Val Tyr | |
|             180                 185                 190 | |

| gcc tgc gaa gtc acc cat cag ggc ctg agc tcg ccc gtc aca aag agc | 624 |
|---|---|
| Ala Cys Glu Val Thr His Gln Gly Leu Ser Ser Pro Val Thr Lys Ser | |
|         195                 200                 205 | |

| ttc aac agg gga gag tct tat cca tat gat gtg cca gat tat gcg agc | 672 |
|---|---|
| Phe Asn Arg Gly Glu Ser Tyr Pro Tyr Asp Val Pro Asp Tyr Ala Ser | |
| 210                 215                 220 | |

<210> SEQ ID NO 88
<211> LENGTH: 224
<212> TYPE: PRT
<213> ORGANISM: Homo sapiens
<223> OTHER INFORMATION: M2-34L

<400> SEQUENCE: 88

-continued

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Ser Tyr Pro Tyr Asp Val Pro Asp Tyr Ala Ser
210                 215                 220
```

<210> SEQ ID NO 89
<211> LENGTH: 672
<212> TYPE: DNA
<213> ORGANISM: Homo sapiens
<220> FEATURE:
<221> NAME/KEY: CDS
<222> LOCATION: (1)..(672)
<223> OTHER INFORMATION: M2-35L

<400> SEQUENCE: 89

```
gaa att gtg ttg acg cag tct cca gcc acc ctg tct ttg tct cca ggg      48
Glu Ile Val Leu Thr Gln Ser Pro Ala Thr Leu Ser Leu Ser Pro Gly
 1               5                  10                  15 gaa aga gcc acc ctc tcc tgc agg gcc agt cag agt gtt agc agc tac      96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc     144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat tac tgt cag cag cgt acg aac tgg cct cgg     288
Glu Asp Phe Ala Val Tyr Tyr Cys Gln Gln Arg Thr Asn Trp Pro Arg
                85                  90                  95
```

```
acg ttc ggc caa ggg acc aag gtg gaa atc aaa cga act gtg gct gca    336
Thr Phe Gly Gln Gly Thr Lys Val Glu Ile Lys Arg Thr Val Ala Ala
        100                 105                 110 cca tct gtc ttc atc ttc ccg cca tct gat gag cag ttg aaa tct gga    384
Pro Ser Val Phe Ile Phe Pro Pro Ser Asp Glu Gln Leu Lys Ser Gly
            115                 120                 125 act gcc tct gtt gtg tgc ctg ctg aat aac ttc tat ccc aga gag gcc    432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag    480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc    528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac    576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc    624
Ala Cys Glu Val Thr His Gln Gly Leu Ser Ser Pro Val Thr Lys Ser
    195                 200                 205 ttc aac agg gga gag tct tat cca tat gat gtg cca gat tat gcg agc    672
Phe Asn Arg Gly Glu Ser Tyr Pro Tyr Asp Val Pro Asp Tyr Ala Ser
210                 215                 220
```

<210> SEQ ID NO 90
<211> LENGTH: 224
<212> TYPE: PRT
<213> ORGANISM: Homo sapiens
<223> OTHER INFORMATION: M2-35L

<400> SEQUENCE: 90

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Thr Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205
```

```
Phe Asn Arg Gly Glu Ser Tyr Pro Tyr Asp Val Pro Asp Tyr Ala Ser
        210                 215                 220

<210> SEQ ID NO 91
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M2-11H

<400> SEQUENCE: 91 cag gtg cag ctg gtg gag tct ggg gga ggc gtg gtc cag cct ggg agg       48
Gln Val Gln Leu Val Glu Ser Gly Gly Gly Val Val Gln Pro Gly Arg
  1               5                  10                  15 tcc ctg aga ctc tcc tgt gca gcg tct gga ttt acc ttc agt tac tat       96
Ser Leu Arg Leu Ser Cys Ala Ala Ser Gly Phe Thr Phe Ser Tyr Tyr
             20                  25                  30 ggc atg cac tgg gtc cgc cag gct cca ggc aag ggg ctg gag tgg gtg      144
Gly Met His Trp Val Arg Gln Ala Pro Gly Lys Gly Leu Glu Trp Val
         35                  40                  45 aca ctt ata acc tat gat gga gat aat aaa tac tat gca gac tcc gtg      192
Thr Leu Ile Thr Tyr Asp Gly Asp Asn Lys Tyr Tyr Ala Asp Ser Val
 50                  55                  60 aag ggc cga ttc acc atc tcc aga gac aat tcc aag aac acg ctg tat      240
Lys Gly Arg Phe Thr Ile Ser Arg Asp Asn Ser Lys Asn Thr Leu Tyr
 65                  70                  75                  80 ctg caa atg aac agc ctg aga gcc gag gac acg gct gtg tat tac tgt      288
Leu Gln Met Asn Ser Leu Arg Ala Glu Asp Thr Ala Val Tyr Tyr Cys
                 85                  90                  95 gcg aga gac ggg atc ggg tac ttt gac tat tgg ggc cag gga acc ctg      336
Ala Arg Asp Gly Ile Gly Tyr Phe Asp Tyr Trp Gly Gln Gly Thr Leu
            100                 105                 110 gtc acc gtc tcc tca gcc tcc acc aag ggc cca tcg gtc ttc ccc ctg      384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc      432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca      480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc      528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc      576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac      624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat      672
Thr Lys Val Asp Lys Lys Ala Glu Pro Lys Ser His His His His His
    210                 215                 220 cac                                                                   675
His
225

<210> SEQ ID NO 92
<211> LENGTH: 225
```

```
<212> TYPE: PRT
<213> ORGANISM: Homo sapiens
<223> OTHER INFORMATION: M2-11H

<400> SEQUENCE: 92

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Tyr Tyr
             20                  25                  30

Gly Met His Trp Val Arg Gln Ala Pro Gly Lys Gly Leu Glu Trp Val
         35                  40                  45

Thr Leu Ile Thr Tyr Asp Gly Asp Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 93
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M2-12H

<400> SEQUENCE: 93 gat gtg cag ctg gtg gag tct ggg gga ggc gtg gtc cat cct ggg agg    48
Asp Val Gln Leu Val Glu Ser Gly Gly Gly Val Val His Pro Gly Arg
  1               5                  10                  15 tcc ctg aga ctc tcc tgt gca gcg tct gga ttt acc ttc agt tac tat    96
Ser Leu Arg Leu Ser Cys Ala Ala Ser Gly Phe Thr Phe Ser Tyr Tyr
             20                  25                  30 ggc atg cac tgg gtc cgc cag gct cca ggc aag ggg ctg gaa tgg atg   144
Gly Met His Trp Val Arg Gln Ala Pro Gly Lys Gly Leu Glu Trp Met
         35                  40                  45 aca ctt ata tcc tat gat gga gat aat aaa tac tat gca gac tcc gtg   192
Thr Leu Ile Ser Tyr Asp Gly Asp Asn Lys Tyr Tyr Ala Asp Ser Val
     50                  55                  60
```

-continued

```
aag ggc cga ttc acc atc tcc aga gaa aat tcc aag aac acg ctg tat      240
Lys Gly Arg Phe Thr Ile Ser Arg Glu Asn Ser Lys Asn Thr Leu Tyr
 65                  70                  75                  80 ctg caa atg aac agt ctg aga gcc gag gac acg gct gtg tat tac tgt      288
Leu Gln Met Asn Ser Leu Arg Ala Glu Asp Thr Ala Val Tyr Tyr Cys
                 85                  90                  95 gcg aga gac ggg atc ggg tac ttt gac tat tgg ggc cag gga acc ctg      336
Ala Arg Asp Gly Ile Gly Tyr Phe Asp Tyr Trp Gly Gln Gly Thr Leu
            100                 105                 110 gtc acc gtc tcc tca gcc tcc acc aag ggc cca tcg gtc ttc ccc ctg      384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc      432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca      480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc      528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc      576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc agc      624
Leu Gly Thr Gln Thr Tyr Ile Cys Asn Val Asn His Lys Pro Ser Ser
        195                 200                 205 acc aag gtg gac aag aaa gca gag ccc aaa tct cat cac cat cac cat      672
Thr Lys Val Asp Lys Lys Ala Glu Pro Lys Ser His His His His His
    210                 215                 220 cac                                                                  675
His
225
```

<210> SEQ ID NO 94
<211> LENGTH: 225
<212> TYPE: PRT
<213> ORGANISM: Homo sapiens
<223> OTHER INFORMATION: M2-12H

<400> SEQUENCE: 94

```
Asp Val Gln Leu Val Glu Ser Gly Gly Val Val His Pro Gly Arg
 1               5                  10                  15

Ser Leu Arg Leu Ser Cys Ala Ala Ser Gly Phe Thr Phe Ser Tyr Tyr
                20                  25                  30

Gly Met His Trp Val Arg Gln Ala Pro Gly Lys Gly Leu Glu Trp Met
            35                  40                  45

Thr Leu Ile Ser Tyr Asp Gly Asp Asn Lys Tyr Tyr Ala Asp Ser Val
        50                  55                  60

Lys Gly Arg Phe Thr Ile Ser Arg Glu Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140
```

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Ser
        195                 200                 205

Thr Lys Val Asp Lys Lys Ala Glu Pro Lys Ser His His His His
    210                 215                 220

His
225

<210> SEQ ID NO 95
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M2-16H

<400> SEQUENCE: 95
```

| | | | | | | | | | | | | | | | | |
|---|---|---|---|---|---|---|---|---|---|---|---|---|---|---|---|---|
| cag | gtg | cag | ctg | gtg | cag | tct | ggg | gga | ggc | gtg | gtc | cag | cct | ggg | aag | 48 |
| Gln | Val | Gln | Leu | Val | Gln | Ser | Gly | Gly | Gly | Val | Val | Gln | Pro | Gly | Lys | |
| 1 | | | | 5 | | | | | 10 | | | | | 15 | | |
| tcc | ctg | aga | ctc | tcc | tgt | gca | gcg | tct | gga | ttc | agc | ttg | agt | tac | tat | 96 |
| Ser | Leu | Arg | Leu | Ser | Cys | Ala | Ala | Ser | Gly | Phe | Ser | Leu | Ser | Tyr | Tyr | |
| | | | 20 | | | | | 25 | | | | | 30 | | | |
| ggc | atg | cac | tgg | gtc | cgc | cag | gtt | cca | ggc | aag | ggg | ctg | gag | tgg | gtg | 144 |
| Gly | Met | His | Trp | Val | Arg | Gln | Val | Pro | Gly | Lys | Gly | Leu | Glu | Trp | Val | |
| | | 35 | | | | | 40 | | | | | 45 | | | | |
| gca | gct | gtc | tgg | tat | gat | gga | agt | act | aga | tat | tct | cca | gac | tcc | gtg | 192 |
| Ala | Ala | Val | Trp | Tyr | Asp | Gly | Ser | Thr | Arg | Tyr | Ser | Pro | Asp | Ser | Val | |
| | 50 | | | | | 55 | | | | | 60 | | | | | |
| aag | ggc | cga | ttc | acc | atc | tcc | aga | gac | gat | tcc | aag | aac | acg | ctg | tat | 240 |
| Lys | Gly | Arg | Phe | Thr | Ile | Ser | Arg | Asp | Asp | Ser | Lys | Asn | Thr | Leu | Tyr | |
| 65 | | | | | 70 | | | | | 75 | | | | | 80 | |
| ctg | caa | atg | aac | agc | ctg | aga | gcc | gag | gac | acg | gct | gtg | tat | tac | tgt | 288 |
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |
| gcg | aga | gat | agg | gtg | ggc | ctc | ttt | gac | tac | tgg | ggc | cag | gga | acc | ctg | 336 |
| Ala | Arg | Asp | Arg | Val | Gly | Leu | Phe | Asp | Tyr | Trp | Gly | Gln | Gly | Thr | Leu | |
| | | | 100 | | | | | 105 | | | | | 110 | | | |
| gtc | acc | gtc | tcc | tca | gcc | tcc | acc | aag | ggc | cca | tcg | gtc | ttc | ccc | ctg | 384 |
| Val | Thr | Val | Ser | Ser | Ala | Ser | Thr | Lys | Gly | Pro | Ser | Val | Phe | Pro | Leu | |
| | | 115 | | | | | 120 | | | | | 125 | | | | |
| gca | ccc | tcc | tcc | aag | agc | acc | tct | ggg | ggc | aca | gcg | gcc | ctg | ggc | tgc | 432 |
| Ala | Pro | Ser | Ser | Lys | Ser | Thr | Ser | Gly | Gly | Thr | Ala | Ala | Leu | Gly | Cys | |
| | 130 | | | | | 135 | | | | | 140 | | | | | |
| ctg | gtc | aag | gac | tac | ttc | ccc | gaa | ccg | gtg | acg | gtg | tcg | tgg | aac | tca | 480 |
| Leu | Val | Lys | Asp | Tyr | Phe | Pro | Glu | Pro | Val | Thr | Val | Ser | Trp | Asn | Ser | |
| 145 | | | | | 150 | | | | | 155 | | | | | 160 | |
| ggc | gcc | ctg | acc | agc | ggc | gtg | cac | acc | ttc | ccg | gct | gtc | cta | cag | tcc | 528 |
| Gly | Ala | Leu | Thr | Ser | Gly | Val | His | Thr | Phe | Pro | Ala | Val | Leu | Gln | Ser | |
| | | | | 165 | | | | | 170 | | | | | 175 | | |
| tca | gga | ctc | tac | tcc | ctc | agc | agc | gtg | gtg | acc | gtg | ccc | tcc | agc | agc | 576 |
| Ser | Gly | Leu | Tyr | Ser | Leu | Ser | Ser | Val | Val | Thr | Val | Pro | Ser | Ser | Ser | |
| | | | 180 | | | | | 185 | | | | | 190 | | | |

```
ttg ggc acc cag acc tac atc tgc aac gtg aat cac aag ccc agc aac      624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat      672
Thr Lys Val Asp Lys Lys Ala Glu Pro Lys Ser His His His His His
    210                 215                 220 cac                                                                  675
His
225
```

<210> SEQ ID NO 96
<211> LENGTH: 225
<212> TYPE: PRT
<213> ORGANISM: Homo sapiens
<223> OTHER INFORMATION: M2-16H

<400> SEQUENCE: 96

```
Gln Val Gln Leu Val Gln Ser Gly Gly Gly Val Val Gln Pro Gly Lys
  1               5                  10                  15

Ser Leu Arg Leu Ser Cys Ala Ala Ser Gly Phe Ser Leu Ser Tyr Tyr
             20                  25                  30

Gly Met His Trp Val Arg Gln Val Pro Gly Lys Gly Leu Glu Trp Val
         35                  40                  45

Ala Ala Val Trp Tyr Asp Gly Ser Thr Arg Tyr Ser Pro Asp Ser Val
     50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His His
    210                 215                 220

His
225
```

<210> SEQ ID NO 97
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M2-18H

<400> SEQUENCE: 97

```
cag gtg cag ctg gtg cag tct ggg gga ggc gtg gtc cag cct ggg aag       48
```

| | | | | | | | | | | | | | | | |
|---|---|---|---|---|---|---|---|---|---|---|---|---|---|---|---|
| | Gln | Val | Gln | Leu | Val | Gln | Ser | Gly | Gly | Val | Val | Gln | Pro | Gly | Lys |
| | 1 | | | | 5 | | | | | 10 | | | | | 15 |

| | | | | | | | | | | | | | | | | |
|---|---|---|---|---|---|---|---|---|---|---|---|---|---|---|---|---|
| tcc | ctg | aga | ctc | tcc | tgt | gca | gcg | tct | gga | ttc | agc | ttc | agt | tac | tat | 96 |
| Ser | Leu | Arg | Leu | Ser | Cys | Ala | Ala | Ser | Gly | Phe | Ser | Phe | Ser | Tyr | Tyr | |
| | | | 20 | | | | | 25 | | | | | 30 | | | |
| ggc | atg | cac | tgg | gtc | cgc | cag | gtt | cca | ggc | aag | ggg | ctg | gag | tgg | gtg | 144 |
| Gly | Met | His | Trp | Val | Arg | Gln | Val | Pro | Gly | Lys | Gly | Leu | Glu | Trp | Val | |
| | | 35 | | | | | 40 | | | | | 45 | | | | |
| gca | gct | gtc | tgg | tat | gat | gga | agt | act | aca | tat | tct | cca | gac | tcc | gtg | 192 |
| Ala | Ala | Val | Trp | Tyr | Asp | Gly | Ser | Thr | Thr | Tyr | Ser | Pro | Asp | Ser | Val | |
| 50 | | | | | 55 | | | | | 60 | | | | | | |
| aag | ggc | cga | ttc | acc | atc | tcc | aga | gac | gat | tcc | aag | aac | acg | ctg | tat | 240 |
| Lys | Gly | Arg | Phe | Thr | Ile | Ser | Arg | Asp | Asp | Ser | Lys | Asn | Thr | Leu | Tyr | |
| 65 | | | | | 70 | | | | | 75 | | | | | 80 | |
| ctg | caa | atg | aac | agc | ctg | aga | gcc | gag | gac | acg | gct | gtg | tat | tac | tgt | 288 |
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |
| gcg | aga | gat | agg | gtg | ggc | ctc | ttt | gac | tac | tgg | ggc | cag | gga | acc | ctg | 336 |
| Ala | Arg | Asp | Arg | Val | Gly | Leu | Phe | Asp | Tyr | Trp | Gly | Gln | Gly | Thr | Leu | |
| | | | 100 | | | | | 105 | | | | | 110 | | | |
| gtc | acc | gtc | tcc | tca | gcc | tcc | acc | aag | ggc | cca | tcg | gtc | ttc | ccc | ctg | 384 |
| Val | Thr | Val | Ser | Ser | Ala | Ser | Thr | Lys | Gly | Pro | Ser | Val | Phe | Pro | Leu | |
| | | 115 | | | | | 120 | | | | | 125 | | | | |
| gca | ccc | tcc | tcc | aag | agc | acc | tct | ggg | ggc | aca | gcg | gcc | ctg | ggc | tgc | 432 |
| Ala | Pro | Ser | Ser | Lys | Ser | Thr | Ser | Gly | Gly | Thr | Ala | Ala | Leu | Gly | Cys | |
| 130 | | | | | 135 | | | | | 140 | | | | | | |
| ctg | gtc | aag | gac | tac | ttc | ccc | gaa | ccg | gtg | acg | gtg | tcg | tgg | aac | tca | 480 |
| Leu | Val | Lys | Asp | Tyr | Phe | Pro | Glu | Pro | Val | Thr | Val | Ser | Trp | Asn | Ser | |
| 145 | | | | | 150 | | | | | 155 | | | | | 160 | |
| ggc | gcc | ctg | acc | agc | ggc | gtg | cac | acc | ttc | ccg | gct | gtc | cta | cag | tcc | 528 |
| Gly | Ala | Leu | Thr | Ser | Gly | Val | His | Thr | Phe | Pro | Ala | Val | Leu | Gln | Ser | |
| | | | | 165 | | | | | 170 | | | | | 175 | | |
| tca | gga | ctc | tac | tcc | ctc | agc | agc | gtg | gtg | acc | gtg | ccc | tcc | agc | agc | 576 |
| Ser | Gly | Leu | Tyr | Ser | Leu | Ser | Ser | Val | Val | Thr | Val | Pro | Ser | Ser | Ser | |
| | | | 180 | | | | | 185 | | | | | 190 | | | |
| ttg | ggc | acc | cag | acc | tac | atc | tgc | aac | gtg | aat | cac | aag | ccc | agc | aac | 624 |
| Leu | Gly | Thr | Gln | Thr | Tyr | Ile | Cys | Asn | Val | Asn | His | Lys | Pro | Ser | Asn | |
| | | 195 | | | | | 200 | | | | | 205 | | | | |
| acc | aag | gtg | gac | aag | aaa | gca | gag | ccc | aaa | tct | cat | cac | cat | cac | cat | 672 |
| Thr | Lys | Val | Asp | Lys | Lys | Ala | Glu | Pro | Lys | Ser | His | His | His | His | His | |
| 210 | | | | | 215 | | | | | 220 | | | | | | |

| | |
|---|---|
| cac | 675 |
| His | |
| 225 | |

<210> SEQ ID NO 98
<211> LENGTH: 225
<212> TYPE: PRT
<213> ORGANISM: Homo sapiens
<223> OTHER INFORMATION: M2-18H

<400> SEQUENCE: 98

| | | | | | | | | | | | | | | | |
|---|---|---|---|---|---|---|---|---|---|---|---|---|---|---|---|
| Gln | Val | Gln | Leu | Val | Gln | Ser | Gly | Gly | Gly | Val | Val | Gln | Pro | Gly | Lys |
| 1 | | | | 5 | | | | | 10 | | | | | 15 | |

| | | | | | | | | | | | | | | | |
|---|---|---|---|---|---|---|---|---|---|---|---|---|---|---|---|
| Ser | Leu | Arg | Leu | Ser | Cys | Ala | Ala | Ser | Gly | Phe | Ser | Phe | Ser | Tyr | Tyr |
| | | | 20 | | | | | 25 | | | | | 30 | | |

| | | | | | | | | | | | | | | | |
|---|---|---|---|---|---|---|---|---|---|---|---|---|---|---|---|
| Gly | Met | His | Trp | Val | Arg | Gln | Val | Pro | Gly | Lys | Gly | Leu | Glu | Trp | Val |
| | | 35 | | | | | 40 | | | | | 45 | | | |

| | | | | | | | | | | | | | | | |
|---|---|---|---|---|---|---|---|---|---|---|---|---|---|---|---|
| Ala | Ala | Val | Trp | Tyr | Asp | Gly | Ser | Thr | Thr | Tyr | Ser | Pro | Asp | Ser | Val |
| 50 | | | | | 55 | | | | | 60 | | | | | |

```
Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Val Gly Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 99
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M2-20H

<400> SEQUENCE: 99 cag gtg cag ctg gtg cag tct ggg gga ggc gtg gtc cag cct ggg agg    48
Gln Val Gln Leu Val Gln Ser Gly Gly Gly Val Val Gln Pro Gly Arg
 1               5                  10                  15 tcc ctg agg ctc tcc tgt gca gcc tct gga ttc act ttc agt tac tat    96
Ser Leu Arg Leu Ser Cys Ala Ala Ser Gly Phe Thr Phe Ser Tyr Tyr
             20                  25                  30 ggt atg cac tgg gtc cgc cag gct cca ggc aag ggg ctg gag tgg gtg   144
Gly Met His Trp Val Arg Gln Ala Pro Gly Lys Gly Leu Glu Trp Val
         35                  40                  45 tca ctt ata aca tat gat gga agg aat aaa tac tac gcc gac tcc gtg   192
Ser Leu Ile Thr Tyr Asp Gly Arg Asn Lys Tyr Tyr Ala Asp Ser Val
     50                  55                  60 aag ggc cga ttc acc atc tcc aga gag aat tcc aag aac acg ctg tat   240
Lys Gly Arg Phe Thr Ile Ser Arg Glu Asn Ser Lys Asn Thr Leu Tyr
 65                  70                  75                  80 ctg caa atg aac agc ctg aga act gag gac acg gct gag tat tac tgt   288
Leu Gln Met Asn Ser Leu Arg Thr Glu Asp Thr Ala Glu Tyr Tyr Cys
                 85                  90                  95 gcg aga gac ggg atc gga tac ttt gac tac tgg ggc cag gga atc ctg   336
Ala Arg Asp Gly Ile Gly Tyr Phe Asp Tyr Trp Gly Gln Gly Ile Leu
            100                 105                 110 gtc acc gtc tcc tca gcc tcc acc aag ggc cca tcg gtc ttc ccc ctg   384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc   432
```

```
Ala Pro Ser Ser Lys Ser Thr Ser Gly Gly Thr Ala Ala Leu Gly Cys
        130                 135                 140 ctg gtg aag gac tac ttc ccc gaa ccg gtg acg gtg tcg tgg aag tca       480
Leu Val Lys Asp Tyr Phe Pro Glu Pro Val Thr Val Ser Trp Lys Ser
145                 150                 155                 160 ggc gcc ctg acc agc ggc gtg cac acc ttc ccg gct gtc cta cag tcc       528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc       576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac       624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat       672
Thr Lys Val Asp Lys Lys Ala Glu Pro Lys Ser His His His His His
    210                 215                 220 cac                                                                    675
His
225

<210> SEQ ID NO 100
<211> LENGTH: 225
<212> TYPE: PRT
<213> ORGANISM: Homo sapiens
<223> OTHER INFORMATION: M2-20H

<400> SEQUENCE: 100

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ser Leu Ile Thr Tyr Asp Gly Arg Asn Lys Tyr Tyr Ala Asp Ser Val
    50                  55                  60

Lys Gly Arg Phe Thr Ile Ser Arg Glu Asn Ser Lys Asn Thr Leu Tyr
65                  70                  75                  80

Leu Gln Met Asn Ser Leu Arg Thr Glu Asp Thr Ala Glu Tyr Tyr Cys
                85                  90                  95

Ala Arg Asp Gly Ile Gly Tyr Phe Asp Tyr Trp Gly Gln Gly Ile Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Lys Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His His
    210                 215                 220

His
```

```
<210> SEQ ID NO 101
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M2-31H

<400> SEQUENCE: 101 cag gtg cag ctg gtg gag tct ggg gga gtc gtg gtc cag cct ggg agg        48
Gln Val Gln Leu Val Glu Ser Gly Gly Val Val Val Gln Pro Gly Arg
  1               5                  10                  15 tcc ctg aga ctc tcc tgt gca gcc tct gga ttc acg ttc agt tac tat        96
Ser Leu Arg Leu Ser Cys Ala Ala Ser Gly Phe Thr Phe Ser Tyr Tyr
             20                  25                  30 ggt ata cac tgg gtc cgc cag gtt cca ggc aag gga cta gag tgg gtg       144
Gly Ile His Trp Val Arg Gln Val Pro Gly Lys Gly Leu Glu Trp Val
         35                  40                  45 gca ctt ata tca tac gat gga agc aat aaa tac tac gca gac tcc gtg       192
Ala Leu Ile Ser Tyr Asp Gly Ser Asn Lys Tyr Tyr Ala Asp Ser Val
     50                  55                  60 aag ggc cga ttc acc atc tcc aga gac aat tcc aag aac act ctg tat       240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt       288
Leu Gln Met Asn Ser Leu Arg Ala Glu Asp Thr Ala Val Tyr Tyr Cys
                 85                  90                  95 gcg aga gac tgg atc ggg tac ttt gac tac tgg ggc cag gga acc ctg       336
Ala Arg Asp Trp Ile Gly Tyr Phe Asp Tyr Trp Gly Gln Gly Thr Leu
            100                 105                 110 gtc acc gtc tcc tca gcc tcc acc aag ggc cca tcg gtc ttc ccc ctg       384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc       432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca       480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc       528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc       576
Ser Gly Leu Tyr Ser Leu Ser Ser Val Val Thr Val Pro Ser Ser Ser
            180                 185                 190 ctg ggc acc cag acc tac atc tgc aac gtg aat cac aag ccc agc aac       624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat       672
Thr Lys Val Asp Lys Lys Ala Glu Pro Lys Ser His His His His His
    210                 215                 220 cac                                                                   675
His
225

<210> SEQ ID NO 102
<211> LENGTH: 225
<212> TYPE: PRT
<213> ORGANISM: Homo sapiens
```

<223> OTHER INFORMATION: M2-31H

<400> SEQUENCE: 102

```
Gln Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Tyr Tyr
             20                  25                  30

Gly Ile His Trp Val Arg Gln Val Pro Gly Lys Gly Leu Glu Trp Val
             35                  40                  45

Ala Leu Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Trp Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Ala Glu Pro Lys Ser His His His His
            210                 215                 220

His
225
```

<210> SEQ ID NO 103
<211> LENGTH: 708
<212> TYPE: DNA
<213> ORGANISM: Homo sapiens
<220> FEATURE:
<221> NAME/KEY: CDS
<222> LOCATION: (1)..(708)
<223> OTHER INFORMATION: M2-32H

<400> SEQUENCE: 103

```
cag gtg cag ctg gtg cag tct ggg gga ggc ttg gta cat cct ggg ggg      48
Gln Val Gln Leu Val Gln Ser Gly Gly Gly Leu Val His Pro Gly Gly
  1               5                  10                  15 tcc ctg aga ctc tcc tgt gaa ggc tct gga ttc atc ttc agg aac cat      96
Ser Leu Arg Leu Ser Cys Glu Gly Ser Gly Phe Ile Phe Arg Asn His
             20                  25                  30 cct ata cac tgg gtt cgc cag gct cca gga aaa ggt ctg gag tgg gta     144
Pro Ile His Trp Val Arg Gln Ala Pro Gly Lys Gly Leu Glu Trp Val
             35                  40                  45 tca gtt agt ggt att ggt ggt gac aca tac tat gca gac tcc gtg aag     192
Ser Val Ser Gly Ile Gly Gly Asp Thr Tyr Tyr Ala Asp Ser Val Lys
 50                  55                  60 ggc cga ttc tcc atc tcc aga gac aat gcc aag aac tcc ttg tat ctt     240
Gly Arg Phe Ser Ile Ser Arg Asp Asn Ala Lys Asn Ser Leu Tyr Leu
```

-continued

```
                65                  70                  75                  80
caa atg aac agc ctg aga gcc gag gac atg gct gtg tat tac tgt gca           288
Gln Met Asn Ser Leu Arg Ala Glu Asp Met Ala Val Tyr Tyr Cys Ala
                85                  90                  95 aga gaa tat tac tat ggt tcg ggg agt tat cgc gtt gac tac tac tac           336
Arg Glu Tyr Tyr Tyr Gly Ser Gly Ser Tyr Arg Val Asp Tyr Tyr Tyr
                100                 105                 110 tac ggt atg gac gtc tgg ggc caa ggg acc acg gtc acc gtc tcc tca           384
Tyr Gly Met Asp Val Trp Gly Gln Gly Thr Thr Val Thr Val Ser Ser
                115                 120                 125 gcc tcc acc aag ggc cca tcg gtc ttc ccc ctg gca ccc tcc tcc aag           432
Ala Ser Thr Lys Gly Pro Ser Val Phe Pro Leu Ala Pro Ser Ser Lys
        130                 135                 140 agc acc tct ggg ggc aca gcg gcc ctg ggc tgc ctg gtc aag gac tac           480
Ser Thr Ser Gly Gly Thr Ala Ala Leu Gly Cys Leu Val Lys Asp Tyr
145                 150                 155                 160 ttc ccc gaa ccg gtg acg gtg tcg tgg aac tca ggc gcc ctg acc agc           528
Phe Pro Glu Pro Val Thr Val Ser Trp Asn Ser Gly Ala Leu Thr Ser
                165                 170                 175 ggc gtg cac acc ttc ccg gct gtc cta cag tcc tca gga ctc tac tcc           576
Gly Val His Thr Phe Pro Ala Val Leu Gln Ser Ser Gly Leu Tyr Ser
                180                 185                 190 ctc agc agc gtg gtg acc gtg ccc tcc agc agc ttg ggc acc cag acc           624
Leu Ser Ser Val Val Thr Val Pro Ser Ser Ser Leu Gly Thr Gln Thr
                195                 200                 205 tac atc tgc aac gtg aat cac aag ccc agc aac acc aag gtg gac aag           672
Tyr Ile Cys Asn Val Asn His Lys Pro Ser Asn Thr Lys Val Asp Lys
        210                 215                 220 aaa gca gag ccc aaa tct cat cac cat cac cat cac                           708
Lys Ala Glu Pro Lys Ser His His His His His His
225                 230                 235
```

<210> SEQ ID NO 104
<211> LENGTH: 236
<212> TYPE: PRT
<213> ORGANISM: Homo sapiens
<223> OTHER INFORMATION: M2-32H

<400> SEQUENCE: 104

```
Gln Val Gln Leu Val Gln Ser Gly Gly Gly Leu Val His Pro Gly Gly
 1               5                  10                  15

Ser Leu Arg Leu Ser Cys Glu Gly Ser Gly Phe Ile Phe Arg Asn His
            20                  25                  30

Pro Ile His Trp Val Arg Gln Ala Pro Gly Lys Gly Leu Glu Trp Val
        35                  40                  45

Ser Val Ser Gly Ile Gly Gly Asp Thr Tyr Tyr Ala Asp Ser Val Lys
    50                  55                  60

Gly Arg Phe Ser Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Glu Tyr Tyr Tyr Gly Ser Gly Ser Tyr Arg Val Asp Tyr Tyr Tyr
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
```

```
145                 150                 155                 160
Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Ala Glu Pro Lys Ser His His His His His His
225                 230                 235
```

<210> SEQ ID NO 105
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M2-33H

<400> SEQUENCE: 105

```
cag gtg cag ctg gtg cag tct ggg gga ggc gtg gtc cag cct ggg agg        48
Gln Val Gln Leu Val Gln Ser Gly Gly Gly Val Val Gln Pro Gly Arg
  1               5                  10                  15 tcc ctg aga ctc tcc tgt gca gcg tct gga ttt acc ttc agt tac tat        96
Ser Leu Arg Leu Ser Cys Ala Ala Ser Gly Phe Thr Phe Ser Tyr Tyr
             20                  25                  30 ggc atg cac tgg gtc cgc cag gct cca ggc aag ggg ctg gaa tgg atg       144
Gly Met His Trp Val Arg Gln Ala Pro Gly Lys Gly Leu Glu Trp Met
         35                  40                  45 aca ctt ata acc tat gat gga gat aat aaa tac tat gca gac tcc gtg       192
Thr Leu Ile Thr Tyr Asp Gly Asp Asn Lys Tyr Tyr Ala Asp Ser Val
     50                  55                  60 aag ggc cga ttc acc atc tcc aga gac aat tcc aag aac acg ctg tat       240
Lys Gly Arg Phe Thr Ile Ser Arg Asp Asn Ser Lys Asn Thr Leu Tyr
 65                  70                  75                  80 ctg caa atg aac agt ctg aga gcc gag gac acg gct gtg tat tac tgt       288
Leu Gln Met Asn Ser Leu Arg Ala Glu Asp Thr Ala Val Tyr Tyr Cys
                 85                  90                  95 gcg aga gac ggg atc ggg tac ttt gac tat tgg ggc cag gga acc ctg       336
Ala Arg Asp Gly Ile Gly Tyr Phe Asp Tyr Trp Gly Gln Gly Thr Leu
            100                 105                 110 gtc acc gtc tcc tca gcc tcc acc aag ggc cca tcg gtc ttc ccc ctg       384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc       432
Ala Pro Ser Ser Lys Ser Thr Ser Gly Gly Thr Ala Ala Leu Gly Cys
    130                 135                 140 ctg gtc aag gac tac ttc ccc gaa ccg gtg acg gtg tcg tgg aac tca       480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc       528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc       576
Ser Gly Leu Tyr Ser Leu Ser Ser Val Val Thr Val Pro Ser Ser Ser
            180                 185                 190 ttg ggc acc cag acc tac atc tgc aac gtg aat cac aag ccc agc aac       624
Leu Gly Thr Gln Thr Tyr Ile Cys Asn Val Asn His Lys Pro Ser Asn
        195                 200                 205
```

```
                   195                 200                 205
acc aag gtg gac aag aaa gca gag ccc aaa tct cat cac cat cac cat      672
Thr Lys Val Asp Lys Lys Ala Glu Pro Lys Ser His His His His His
        210                 215                 220 cac                                                                   675
His
225

<210> SEQ ID NO 106
<211> LENGTH: 225
<212> TYPE: PRT
<213> ORGANISM: Homo sapiens
<223> OTHER INFORMATION: M2-33H

<400> SEQUENCE: 106

Gln Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Met
        35                  40                  45

Thr Leu Ile Thr Tyr Asp Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Gly Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His His
    210                 215                 220

His
225

<210> SEQ ID NO 107
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M2-34H

<400> SEQUENCE: 107 cag gtg cag ctg gtg gag tct ggg gga ggc gtg gtc cag cct ggg agg       48
Gln Val Gln Leu Val Glu Ser Gly Gly Gly Val Val Gln Pro Gly Arg
```

```
                1               5                   10                  15
        tcc ctg aga ctc tcc tgt gca gcc tct gga ttc acg ttc agt tac tat        96
        Ser Leu Arg Leu Ser Cys Ala Ala Ser Gly Phe Thr Phe Ser Tyr Tyr
                        20                  25                  30 ggt ata cac tgg gtc cgc cag gtt cca ggc aag gga cta gag tgg gtg       144
        Gly Ile His Trp Val Arg Gln Val Pro Gly Lys Gly Leu Glu Trp Val
                    35                  40                  45 gta ctt ata tca tac gat gga agc aat aaa tac tac gca gac tcc gtg       192
        Val Leu Ile Ser Tyr Asp Gly Ser Asn Lys Tyr Tyr Ala Asp Ser Val
            50                  55                  60 aag ggc cga ttc acc atc tcc aga gac aat tcc aag aac act ctg tat       240
        Lys Gly Arg Phe Thr Ile Ser Arg Asp Asn Ser Lys Asn Thr Leu Tyr
        65                  70                  75                  80 ctg caa atg aac agc ctg aga gct gag gac acg gct gtg tat tac tgt       288
        Leu Gln Met Asn Ser Leu Arg Ala Glu Asp Thr Ala Val Tyr Tyr Cys
                        85                  90                  95 gcg aga gac tgg atc ggg tac ttt gac tac tgg ggc cag gga acc ctg       336
        Ala Arg Asp Trp Ile Gly Tyr Phe Asp Tyr Trp Gly Gln Gly Thr Leu
                    100                 105                 110 gtc acc gtc tcc tca gcc tcc acc aag ggc cca tcg gtc ttc ccc ctg       384
        Val Thr Val Ser Ser Ala Ser Thr Lys Gly Pro Ser Val Phe Pro Leu
            115                 120                 125 gca ccc tcc tcc aag agc acc tct ggg ggc aca gcg gcc ctg ggc tgc       432
        Ala Pro Ser Ser Lys Ser Thr Ser Gly Gly Thr Ala Ala Leu Gly Cys
        130                 135                 140 ctg gtc aag gac tac ttc ccc gaa ccg gtg acg gtg tcg tgg aac tca       480
        Leu Val Lys Asp Tyr Phe Pro Glu Pro Val Thr Val Ser Trp Asn Ser
        145                 150                 155                 160 ggc gcc ctg acc agc ggc gtg cac acc ttc ccg gct gtc cta cag tcc       528
        Gly Ala Leu Thr Ser Gly Val His Thr Phe Pro Ala Val Leu Gln Ser
                        165                 170                 175 tca gga ctc tac tcc ctc agc agc gtg gtg acc gtg ccc tcc agc agc       576
        Ser Gly Leu Tyr Ser Leu Ser Ser Val Val Thr Val Pro Ser Ser Ser
                    180                 185                 190 ctg ggc acc cag acc tac atc tgc aac gtg aat cac aag ccc agc aac       624
        Leu Gly Thr Gln Thr Tyr Ile Cys Asn Val Asn His Lys Pro Ser Asn
            195                 200                 205 acc aag gtg gac aag aaa gca gag ccc aaa tct cat cac cat cac cat       672
        Thr Lys Val Asp Lys Lys Ala Glu Pro Lys Ser His His His His His
        210                 215                 220 cac                                                                   675
        His
        225

<210> SEQ ID NO 108
<211> LENGTH: 225
<212> TYPE: PRT
<213> ORGANISM: Homo sapiens
<223> OTHER INFORMATION: M2-34H

<400> SEQUENCE: 108

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Tyr Tyr
                20                  25                  30

Gly Ile His Trp Val Arg Gln Val Pro Gly Lys Gly Leu Glu Trp Val
            35                  40                  45

Val Leu Ile Ser Tyr Asp Gly Ser Asn Lys Tyr Tyr Ala Asp Ser Val
        50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Asp Trp Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Ala Glu Pro Lys Ser His His His His
    210                 215                 220

His
225

<210> SEQ ID NO 109
<211> LENGTH: 675
<212> TYPE: DNA
<213> ORGANISM: Homo sapiens
<220> FEATURE:
<221> NAME/KEY: CDS
<222> LOCATION: (1)..(675)
<223> OTHER INFORMATION: M2-35H

<400> SEQUENCE: 109 cag gtg cag ctg gtg gag tct ggg gga ggc gtg gtc cag cct ggg agg     48
Gln Val Gln Leu Val Glu Ser Gly Gly Gly Val Val Gln Pro Gly Arg
  1               5                  10                  15 tcc ctg aga ctc tcc tgt gca gcc tct gga ttc acg atc agt tac tat     96
Ser Leu Arg Leu Ser Cys Ala Ala Ser Gly Phe Thr Ile Ser Tyr Tyr
             20                  25                  30 ggt ata cac tgg gtc cgc cag gtt cca ggc aag gga cta gag tgg gtg    144
Gly Ile His Trp Val Arg Gln Val Pro Gly Lys Gly Leu Glu Trp Val
         35                  40                  45 gaa ctt ata tca tac gat gga agc aat aaa tac tac gca gac tcc gtg    192
Glu Leu Ile Ser Tyr Asp Gly Ser Asn Lys Tyr Tyr Ala Asp Ser Val
     50                  55                  60 aag ggc cga ttc acc atc tcc aga gac aat tcc aag aac act ctg tat    240
Lys Gly Arg Phe Thr Ile Ser Arg Asp Asn Ser Lys Asn Thr Leu Tyr
 65                  70                  75                  80 ctg caa atg aac agc ctg aga gct gag gac acg gct gtg tat tac tgt    288
Leu Gln Met Asn Ser Leu Arg Ala Glu Asp Thr Ala Val Tyr Tyr Cys
             85                  90                  95 gcg aga gac tgg atc ggg tac ttt gac tac tgg ggc cag gga acc ctg    336
Ala Arg Asp Trp Ile Gly Tyr Phe Asp Tyr Trp Gly Gln Gly Thr Leu
            100                 105                 110 gtc acc gtc tcc tca gcc tcc acc aag ggc cca tcg gtc ttc ccc ctg    384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc tgc    432
Ala Pro Ser Ser Lys Ser Thr Ser Gly Gly Thr Ala Ala Leu Gly Cys
    130                 135                 140
```

```
                130                 135                 140
ctg gtc aag gac tac ttc ccc gaa ccg gtg acg gtg tcg tgg aac tca        480
Leu Val Lys Asp Tyr Phe Pro Glu Pro Val Thr Val Ser Trp Asn Ser
145                 150                 155                 160 ggc gcc ctg acc agc ggc gtg cac acc ttc ccg gct gtc cta cag tcc        528
Gly Ala Leu Thr Ser Gly Val His Thr Phe Pro Ala Val Leu Gln Ser
                165                 170                 175 tca gga ctc tac tcc ctc agc agc gtg gtg acc gtg ccc tcc agc agc        576
Ser Gly Leu Tyr Ser Leu Ser Ser Val Val Thr Val Pro Ser Ser Ser
            180                 185                 190 ctg ggc acc cag acc tac atc tgc aac gtg aat cac aag ccc agc aac        624
Leu Gly Thr Gln Thr Tyr Ile Cys Asn Val Asn His Lys Pro Ser Asn
        195                 200                 205 acc aag gtg gac aag aaa gca gag ccc aaa tct cat cac cat cac cat        672
Thr Lys Val Asp Lys Lys Ala Glu Pro Lys Ser His His His His His
    210                 215                 220 cac                                                                    675
His
225

<210> SEQ ID NO 110
<211> LENGTH: 225
<212> TYPE: PRT
<213> ORGANISM: Homo sapiens
<223> OTHER INFORMATION: M2-35H

<400> SEQUENCE: 110

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Ile Ser Tyr Tyr
            20                  25                  30

Gly Ile His Trp Val Arg Gln Val Pro Gly Lys Gly Leu Glu Trp Val
        35                  40                  45

Glu Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Ile Gly Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205
```

```
                                        -continued

Thr Lys Val Asp Lys Lys Ala Glu Pro Lys Ser His His His His
    210             215                 220

His
225
```

HUMAN ANTIBODIES AS DIAGNOSTIC REAGENTS

BACKGROUND

Although it has long been recognized that human antibodies are superior to mouse antibodies for therapeutic use, the reverse has been thought to be the case for in vitro diagnostics. The different perceived roles of human and mouse antibodies reflect differences in their properties and methods of preparation. The principal hitherto recognized advantages of human antibodies relative to mouse antibodies are lack of human anti-mouse (HAMA) response on administration to a patient, longer in vivo half-life, and better interaction with human complement. All of these advantages account for the superiority of human antibodies to mouse antibodies for therapeutic use, but none is relevant to use of antibodies as reagents for in vitro diagnostics.

One of the principal advantages of mouse antibodies relative to human antibodies is ease of isolation. Despite improvements in methods for producing human antibodies in recent years, it has still generally been considered to have been a simpler matter to produce a mouse antibody than a human antibody, particularly when the desired antibody is sparsely represented in the total repertoire of antibodies that must be screened. Another advantage of mouse antibodies is that the mouse antibody constant region can be detected using a labelled anti-mouse antibody, typically prepared from another species, such as a goat, as a detection moiety. Such an antibody binds specifically to a mouse antibodies without binding to human antibodies present in the sample. Use of a secondary labelling moiety provides a useful format for detecting analytes in a human tissue sample. A comparable format cannot be used for human antibodies because an antibody against a human constant region would generate false positives by reacting with human antibodies in the sample. Because of their simplicity of isolation and compatibility with detection using a secondary labelling moiety, and because properties such as generation of a HAMA response, in vivo half life and complement activation are irrelevant for in vitro diagnostic purposes, mouse antibodies have been used for in vitro diagnostics to the virtual or total exclusion of human antibodies.

Although mouse antibodies are now in widespread use as diagnostic reagents, some problems have arisen when such antibodies are used to detect an analyte in a human sample. In some human samples, false positive or negative results are obtained due to the presence of HAMA or heterophilic antibodies in the sample. HAMA antibodies may be present in a human sample due to prior treatment of the patient from whom the sample was obtained with a mouse antibody (unrelated to the mouse antibody being used in diagnosis) or by environmental exposure to mouse antigens. Heterophilic antibodies are present in some patients as a response to certain pathogenic infections, such as Epstein Barr virus. Either HAMA or heterophilic antibodies in a sample can bind to a mouse antibody being used as a diagnostic reagent thereby generating a false positive signal. In sandwich assay formats, HAMA or heterophilic antibodies can form a bridge between immoblized and solution antibodies to generate a false positive, as in other formats. Alternatively, in a sandwich assay format, some HAMA or heterophilic antibodies may bind to the immobilized antibody without binding to the solution antibody (or vice versa) thereby preventing immobilized antibody and solution antibody from bridging to each other through an analyte and thus generating a false negative. In consequence, a significant number of assays performed on human clinical samples using mouse antibodies as the diagnostic reagent generate inaccurate results.

U.S. patent application Ser. No. 09/453,234, filed Dec. 1, 1999, U.S. Ser. No. 60/157,415, filed Oct. 2, 1999, PCT 98/06704, filed, Apr. 3, 1998, U.S. Ser. No. 08/835,159, filed Apr. 4, 1997 (now abandoned) and U.S. Ser. No. 08/832, 985, filed Apr. 4, 1997 (now U.S. Pat. No. 6,057,098) are directed to related subject matter, and each is incorporated by reference in its entirety for all purposes.

SUMMARY OF THE INVENTION

The invention provides methods of detecting an analyte in a human sample containing human antibodies that specifically bind to antibodies from a nonhuman species. Such methods entail contacting the sample with a human antibody. The human antibody specifically binds to the analyte without specifically binding to the human antibodies that specifically bind to antibodies from a nonhuman species (e.g., HAMA or heterophilic antibodies present in the sample). Binding between the human antibody and the analyte is then detected. In some methods, the sample is contacted with a first human antibody that is immobilized on a support and a second human antibody in solution wherein the first and second human antibodies bind to different epitopes on the analyte; and the detecting step detects binding between the first and/or second human antibody to the analyte. In such methods, the second antibody is typically labelled. In some methods, the sample is contacted with a first population of human antibodies immobilized to a support and a second population of human antibodies in solution, wherein members from the first and second populations bind to different epitopes on the analyte.

Human antibodies used in such methods typically have affinities of at least $10^8$ M$^{-1}$, $10^9$ M$^{-1}$, $10^{10}$ M$^{-1}$, $10^{11}$M$^{-1}$, $10^{12}$ M$^{-1}$ for the analyte. Some human antibodies used in the methods are produced by expression of a recombinant construct in *E. coli*. Some such antibodies have immunoreactivities of at least 90%.

The invention further provides methods of detecting an analyte in a sample Such methods entail contacting the sample with a first human antibody immobilized to a solid phase, and a second human antibody in solution, wherein the first and second antibodies bind to different epitopes of the analyte if present in the sample. Binding of the analyte to the first and/or second antibodies is then detected. Binding indicates presence of the analyte in the sample. In such methods, the second antibody is typically labelled and the detecting detects binding of second antibody to the analyte. In some methods, the sample is contacted with a first population of human antibodies immobilized to a support and a second population of human antibodies in solution, wherein members from the first and second populations bind to different epitopes on the analyte in some methods, the binding of the first and/or second human antibodies to the analyte reaches equilibrium within an hour.

A. Nonessential DNA sequence later deleted.
B. Lac promoter and ribosome binding site.
C. Pectate lyase signal sequence.

D. Kappa chain variable region.

E. Kappa chain constant region.

F. DNA sequence separating kappa and heavy chain, includes ribosome binding site for heavy chain.

G. Alkaline phosphatase signal sequence.

H. Heavy chain variable region.

I. Heavy chain constant region including 5 amino acids of the hinge region.

J. Decapeptide DNA sequence.

K. Pseudo gene VIII sequence with amber stop codon at 5' end.

L. Nonessential DNA sequence that was later deleted.

FIG. 2: Oligonucleotides used in vector construction.

Figure 3:
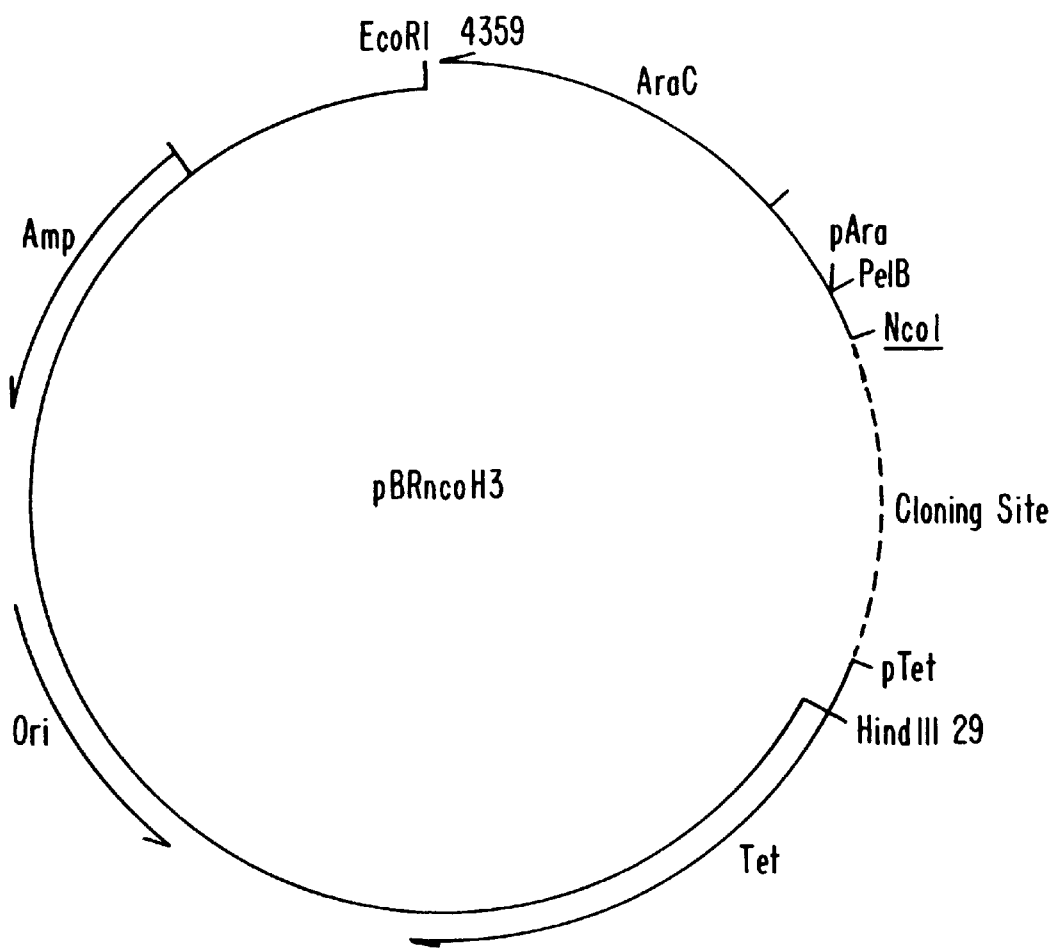

FIG. 3: Map of the vector pBRncoH3.

Figure 4A:
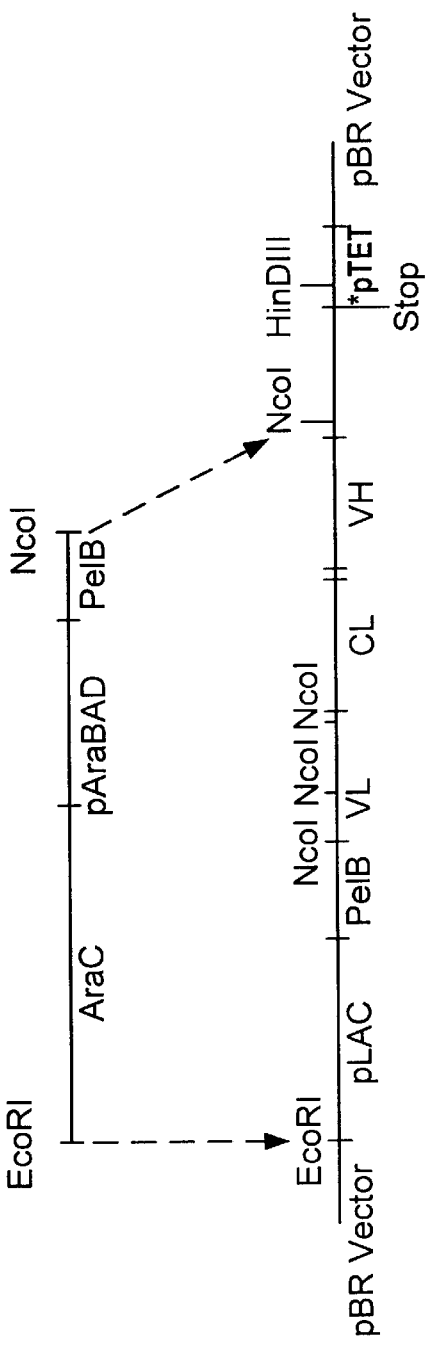
Figure 4B:
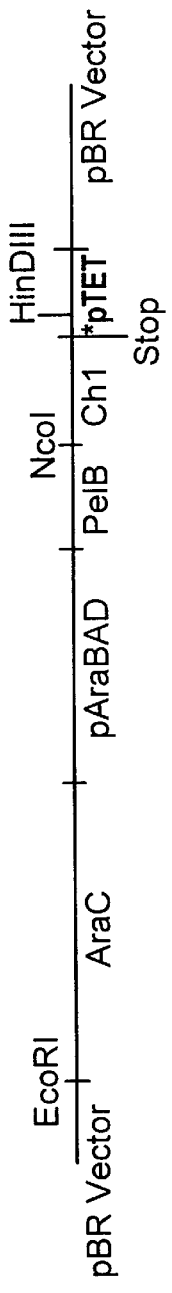

FIG. 4: Insertion of araC into pBR-based vector (FIG. 4A) and the resulting vector pBRnco (FIG. 4B).

Figure 5:
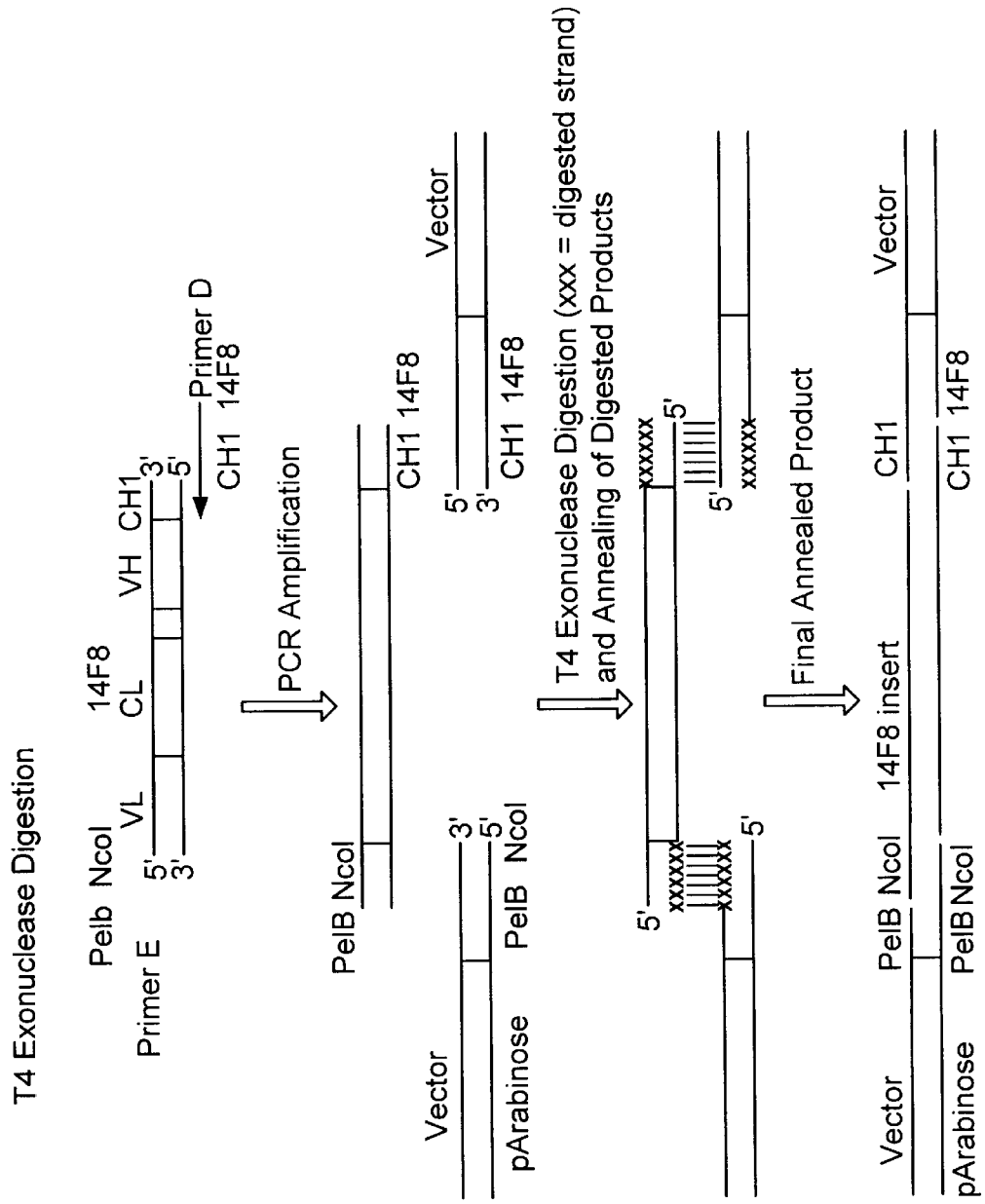

FIG. 5: Subcloning of a DNA segment encoding a Fab by T4 exonuclease digestion.

Figure 6:
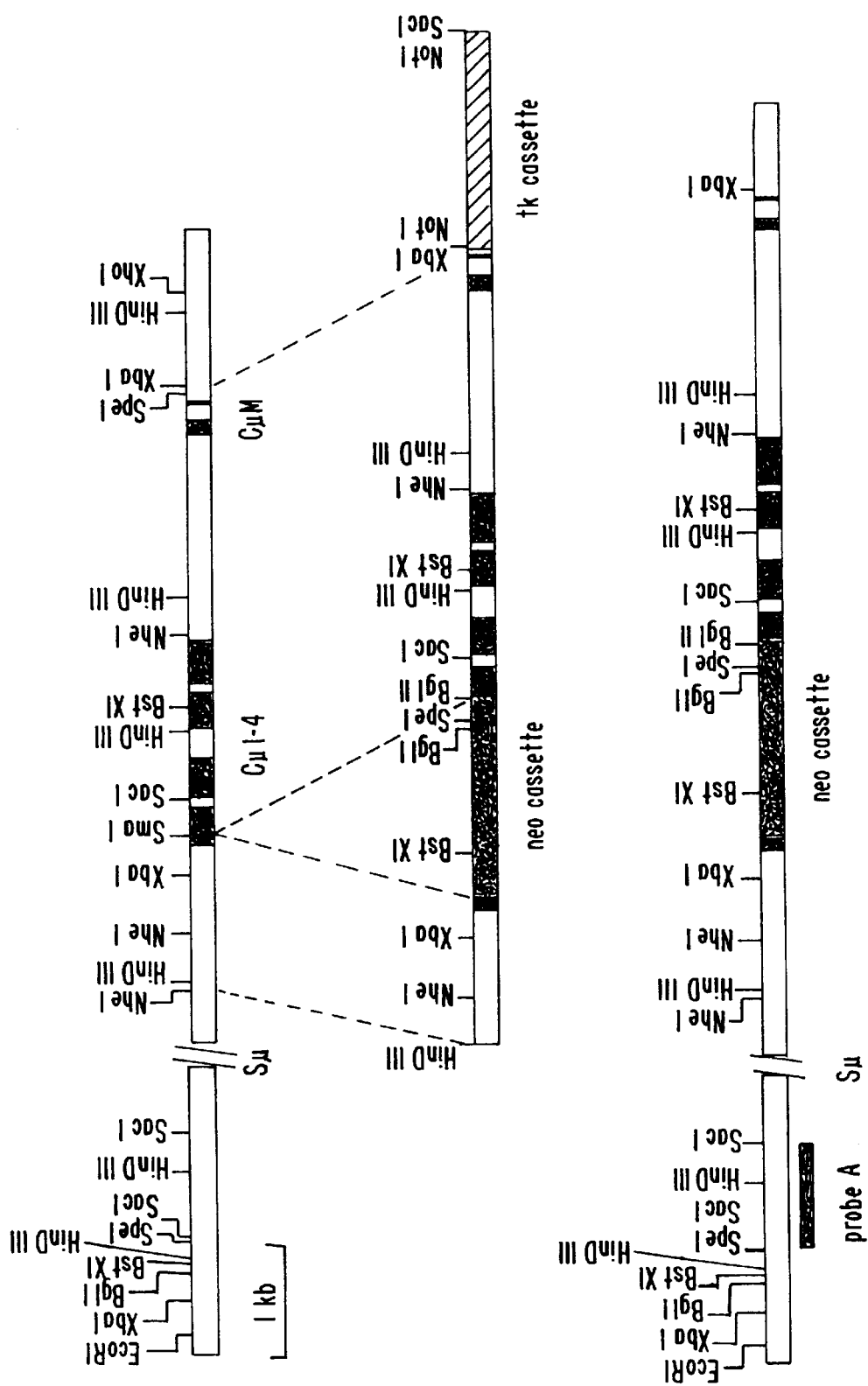

FIG. 6 Targeted insertion of a neo cassette into the SmaI site of the mu1 exon. A. Schematic diagram of the genomic structure of the mu locus. The filled boxes represent the mu exons. B. Schematic diagram of the CmuD targeting vector. The dotted lines denote those genomic mu sequences included in the construct. Plasmid sequences are not shown. C. Schematic diagram of the targeted mu locus in which the neo cassette has been inserted into mu1. The box at the right shows those RFLP's diagnostic of homologous recombination between the targeting construct and the mus locus. The FGLP's were detected by Southern blot hybridization using probe A, the 915 SaI fragment shown in C.

Figure 7:
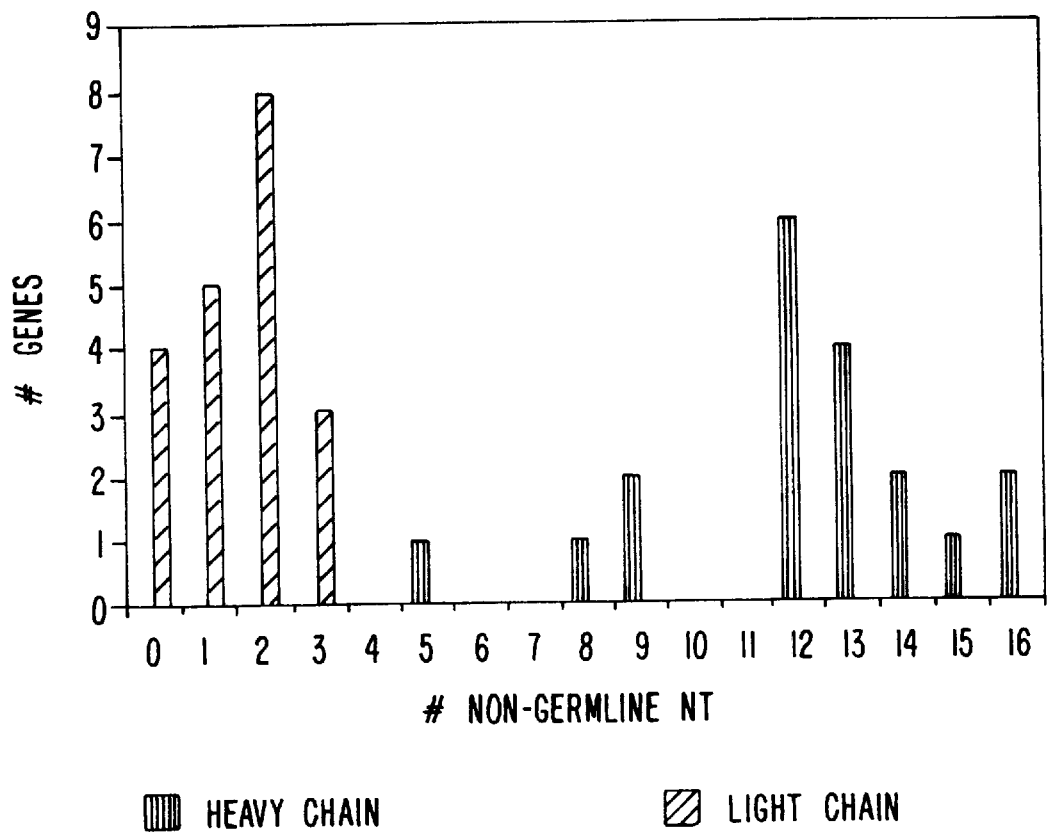

FIG. 7 Nongermline encoded nucleotides in heavy and light chain V genes. Heavy chain V genes were found to be heavily somatically mutated. Light chain V genes comprised fewer non-germline encoded nucleotides.

Figure 8:
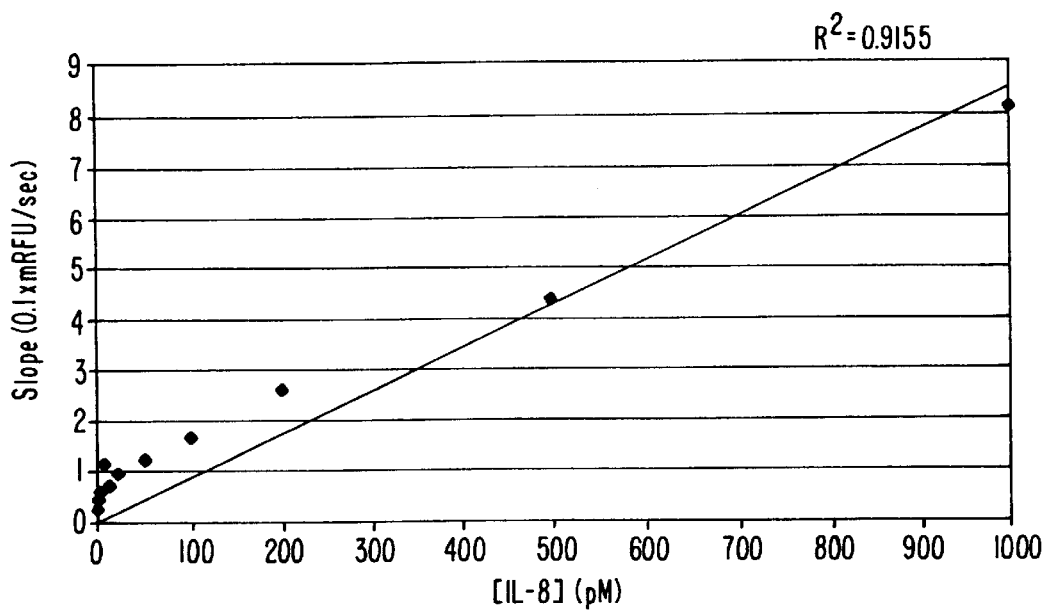

FIG. 8: Calibration curve for different concentrations of IL-8 detected using polyclonal mouse antibodies in sandwich assay.

Figure 9:
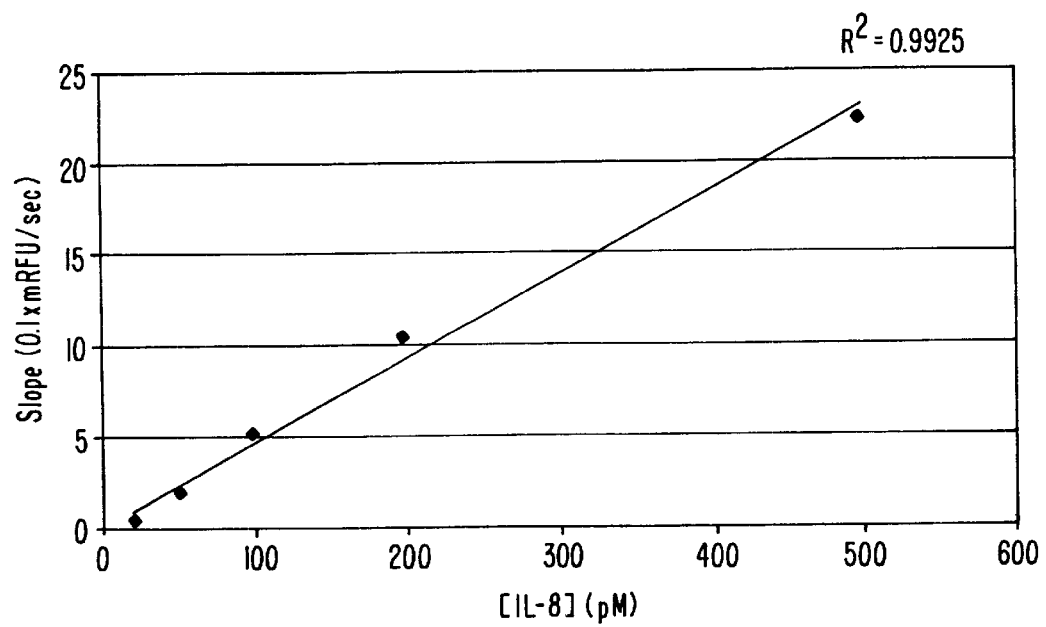

FIG. 9: Calibration curve for different concentrations of IL-8 detected using polyclonal human antibodies in sandwich assay.

Figure 10:
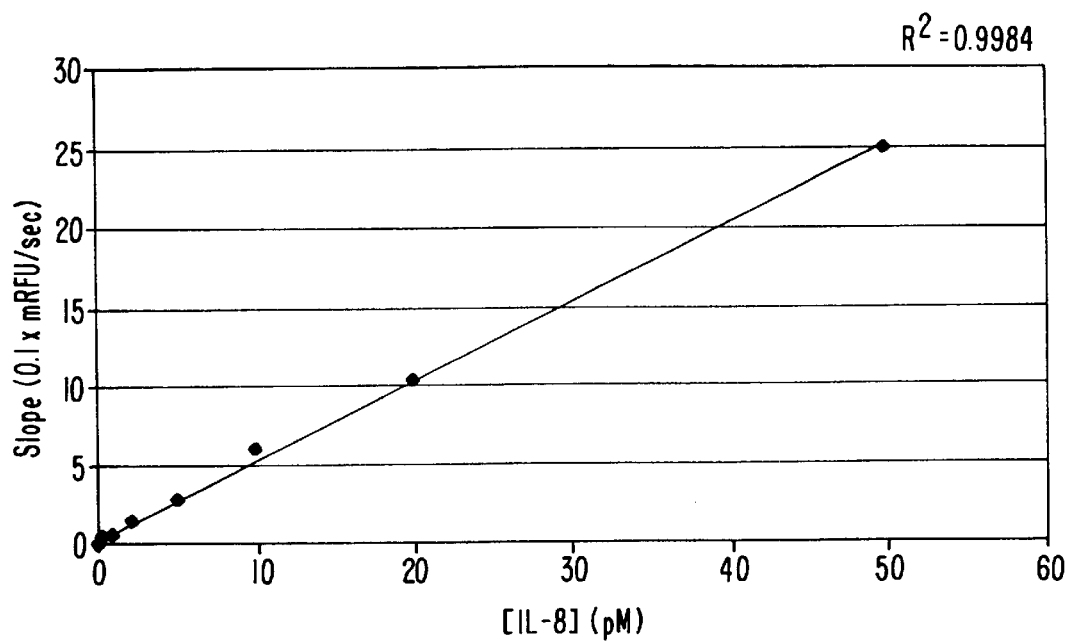

FIG. 10: Calibration curve for different concentrations of IL-8 detected using two monoclonal human antibodies in a sandwich assay.

DEFINITIONS

Specific binding between an antibody or other binding agent and an antigen means a binding affinity of at least $10^6$ $M^{-1}$. Preferred binding agents bind with affinities of at least about $10^7$ $M^{-1}$, and preferably $10^8$ $M^{-1}$ to $10^9$ $M^{-1}$, $10^{10}$ $M^{-1}$, $10^{11}$ $M^{-1}$, or $10^{12}$ $M^{-1}$. The term epitope means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The basic antibody structural unit is known to comprise a tetramer. Each tetramer is composed of two identical pairs of polypeptide chains, each pair having one "light" (about 25 kDa) and one "heavy" chain (about 50–70 Kda). The amino-terminal portion of each chain includes a variable region of about 100 to 110 or more amino acids primarily responsible for antigen recognition. The carboxyl-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, Fundamental Immunology (Paul, W., ed., 2nd ed. Raven Press, N.Y., 1989, 4th edition (1999), Paul William E., ed. Raven Press, N.Y., (incorporated by reference in its entirety for all purposes). The genes encoding variable regions of heavy and light immunoglobulin chains are referred to as $V_H$ and $V_L$ respectively. Although the amino acid sequence of an immunoglobulin chain is not exactly the same as would be predicted from the $V_H$ or $V_L$ gene that encoded it due to somatic mutations (see FIG. 7), there is sufficient similarity between predicted and actual sequences of immunoglobulins that the actual sequence is characteristic and allows recognition of a corresponding $V_H$ or $V_L$ gene. The term constant region is used to refer to both full-length natural constant regions and segments thereof, such as $C_H1$, hinge, $C_H2$ and $C_H3$ or fragments thereof. Typically, segments of light and heavy chain constant regions in antibodies have sufficient length to contribute to interchain bonding between heavy and light chain.

The variable regions of each light/heavy chain pair form the antibody binding site. Thus, an intact antibody has two binding sites. Except in bifunctional or bispecific antibodies, the two binding sites are the same. The chains all exhibit the same general structure of four relatively conserved framework regions (FR) joined by three hypervariable regions, also called complementarily determining regions or CDRs. The CDRs from the two chains of each pair are aligned by the framework regions, enabling binding to a specific epitope. CDR and FR residues are delineated according to the standard sequence definition of Kabat, et al., supra. An alternative structural definition has been proposed by Chothia, et al., *J. Mol. Biol.* 196:901–917 (1987); *Nature* 342:878–883 (1989); and *J. Mol. Biol.* 186:651–663 (1989).

The term antibody is used to mean whole antibodies and binding fragments thereof. Binding fragments include single chain fragments, Fv fragments and Fab fragments. The term Fab fragment is sometimes used in the art to mean the binding fragment resulting from papain cleavage of an intact antibody. The terms Fab' and F(ab')2 are sometimes used in the art to refer to binding fragments of intact antibodies generated by pepsin cleavage. Here, Fab is used to refer generically to double chain binding fragments of intact antibodies having at least substantially complete light and heavy chain variable domains sufficient for antigen-specific bindings, and parts of the light and heavy chain constant regions sufficient to maintain association of the light and heavy chains. Usually, Fab fragments are formed by complexing a full-length or substantially full-length light chain with a heavy chain comprising the variable domain and at least the $C_H1$ domain of the constant region.

An isolated species or population of species means an object species (e.g., binding polypeptides of the invention) that is the predominant species present (i.e., on a molar basis it is more abundant than other species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods). A target is any molecule for which it is desired to isolate partners with specific binding affinity for the target.

Targets of interest include antibodies, including anti-idiotypic antibodies and autoantibodies present in autoimmune diseases, such as diabetes, multiple sclerosis and rheumatoid arthritis. Other targets of interest are growth factor receptors (e.g., FGFR, PDGFR, EFG, NGFR, and VEGF) and their ligands. Other targets are G-protein receptors and include substance K receptor, the angiotensin receptor, the α- and β-adrenergic receptors, the serotonin receptors, and PAF receptor. See, e.g., Gilman, *Ann. Rev. Biochem.* 56:625–649 (1987). Other targets include ion channels (e.g., calcium, sodium, potassium channels), muscarinic receptors, acetylcholine receptors, GABA receptors, glutamate receptors, and dopamine receptors (see Harpold, U.S. Pat. No. 5,401,629 and U.S. Pat. No. 5,436,128). Other targets are adhesion proteins such as integrins, selecting, and immunoglobulin superfamily members (see Springer, *Nature* 346:425–433 (1990). Osborn, *Cell* 62:3 (1990); Hynes, *Cell* 69:11 (1992)). Other targets are cytokines, such as interleukins IL-1 through IL-13, tumor necrosis factors α & β, interferons α, β and γ, tumor growth factor Beta (TGF-β), colony stimulating factor (CSF) and granulocyte monocyte colony stimulating factor (GM-CSF). See Human Cytokines: Handbook for Basic & Clinical Research (Aggrawal et al. eds., Blackwell Scientific, Boston, Mass. 1991). Other targets are hormones, enzymes, and intracellular and intercellular messengers, such as, adenyl cyclase, guanyl cyclase, and phospholipase C. Drugs are also targets of interest. Target molecules can be human, mammalian or bacterial. Other targets are antigens, such as proteins, glycoproteins and carbohydrates from microbial pathogens, both viral and bacterial, and tumors. Still other targets are described in U.S. Pat. No. 4,366,241. Some agents screened by the target merely bind to a target. Other agents agonize or antagonize the target.

Display library members having full-length polypeptide coding sequences have coding sequences the same length as that of the coding sequences originally inserted into a display vector before propagation of the vector.

The term phage is used to refer to both phage containing infective genomes and phage containing defective genomes that can be packaged only with a helper phage. Such phage are sometimes referred to as phagemids.

The term "human antibody" includes antibodies having variable and constant regions (if present) derived from human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such has a mouse, have been grafted onto human framework sequences (i.e., humanized antibodies).

A rearranged heavy chain or light chain immunoglobulin locus has a V segment positioned immediately adjacent to a D-J or J segment in a conformation encoding essentially a complete $V_H$ or $V_L$ domain, respectively. A rearranged immunoglobulin gene locus can be identified by comparison to germline DNA; the rearranged locus having at least one recombined heptamer/nonamer homology element. Conversely, an unrearranged or germline configuration refers to a configuration in which the V segment is not recombined so as to be immediately adjacent to a D or J segment.

"Isotype switching" refers to the phenomenon by which the class, or isotype, of an antibody changes from one Ig class to one of the other Ig classes.

"Nonswitched isotype" refers to the isotypic class of heavy chain that is produced when no isotype switching has taken place; the $C_H$ gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ (δ-associated deletion). Alternative non-classical switching mechanisms, such as intertransgene and/or interchromosomal recombination, among others, may occur and effectuate isotype switching.

The term "switch sequence" refers to those DNA sequences responsible for switch recombination. A "switch donor" sequence, typically a μ switch region, are 5' (i.e., upstream) of the construct region to be deleted during the switch recombination. The "switch acceptor" region are between the construct region to be deleted and the replacement constant region (e.g., γ, ε, etc.). As there is no specific site where recombination always occurs, the final gene sequence is not typically predictable from the construct.

Competition is determined by an assay in which the antibody under test inhibits specific binding of a reference antibody to a given target. Numerous types of competitive binding assays are known for example: (see Harlow and Lane, *Antibodies, A Laboratory Manual*, Cold Spring Harbor Press (1988)). Typically, such an assay involves the use of purified target, an unlabelled test antibody and a labeled reference antibody. Competitive inhibition is measured by determining the amount of label bound to targetin the presence of the test antibody. Usually the test antibody is present in excess. Antibodies identified by competition assay (competing antibodies) include antibodies binding to the same epitope as a reference antibody and antibodies binding to an adjacent epitope sufficiently proximal to the epitope bound by the reference antibody for steric hindrance to occur. When a competing antibody is present in excess, it will inhibit specific binding of a reference antibody to the target by 50%.

DETAILED DESCRIPTION

I. General

The present invention provides methods of diagnosis using human antibodies as the diagnostic reagent(s). The methods are premised, in part, on the insight that use of human antibodies avoids substantial distortions in measured analyte concentrations due to HAMA and/or heterophilic antibodies present in some human samples. Data showing the extent of such distortions and how they are overcome by the use of human antibodies are provided in Example 28.

Inefficiencies and limitations of prior methods of generating human antibodies relative to mouse antibodies are overcome by the disclosure of new methods for producing indefinite numbers of human antibodies having extraordinarily high binding affinities and multiple epitope specificities. Examples of the affinities of human antibodies produced by these methods are described in Example 21. Evidence that the antibodies bind to a number of different epitopes is provided by Example 27. The use of high affinities antibodies as diagnotic reagents is desirable because it allows washing to be conducted at higher stringency and consequently results in a higher signal to noise ratio. Use of antibodies binding to different epitopes is advantageous sandwhich detection formats. Using the methods disclosed in U.S. Ser. No. 60/157415, filed Oct. 2, 1999 and reproduced in the present application, high affinity human antibodies, optionally binding to different epitopes, can be generated with comparable facility to that of mouse antibodies generated by Milstein-Kohler technology.

A further advantage of human antibodies for diagnostic assays disclosed by the present application is the result that human antibodies produced by recombinant expression in bacteria, such as *E. coli*, fold to produce antibody specifically immunoreactive with antigen at high efficiency, greater than that which is typical for mouse antibodies. Examples of the extent of immunoreactivity of human antibodies expressed in *E. coli* are provided in Table 4. Use of antibodies with high immunoreactive is advantageous in increasing the signal to noise ratio in a diagnostic assay.

II. Production of Human Antibodies

A. General

Methods for producing human antibodies are described in copending application U.S. Ser. No. 60/157415, filed Oct. 2, 1999. These methods include the trioma technology of Ostberg et al. (1983), *Hybridoma* 2:361–367 and Engelman et al., U.S. Pat. No. 4,634,666, phage display methods and nonhuman transgenic mice expressing genes of the human immune system. Preferred methods are reproduced below. The methods typically work by immunizing a nonhuman transgenic animal having human immunoglobulin genes. The animal expresses a diverse range of human antibodies that bind to the antigen. Nucleic acids encoding the antibody chain components of such antibodies are then cloned from the animal into a display vector. Typically, separate populations of nucleic acids encoding heavy and light chain sequences are cloned, and the separate populations then recombined on insertion into the vector, such that any given copy of the vector receives a random combination of a heavy and light chains. The vector is designed to express antibody chains so that they can be assembled and displayed on the outersurface of a display package containing the vector. For example, antibody chains can be expressed as fusion proteins with a phage coat protein from the outersurface of the phage. Thereafter, display packages can be screened for display of antibodies binding to a target.

In some methods, display packages are subject to a prescreening step. In such methods, the display package encode a tag expressed as a fusion protein with an antibody chain displayed from the package. Display packages are prescreened for binding to a receptor to the tag. It is believed that the prescreening serves to enrich for display packages displaying multiple copies of an antibody chain linked to the tag, and that it is this subset of display packages that binds to target in the subsequent screening step. However, practice of the invention is not dependent on whether this mechanism is correct.

After prescreening with receptor (if any) and screening with target, display packages binding to the target are isolated, and optionally, subject to further rounds screening to target, with each such round optionally being preceded by prescreening to receptor. Display packages are typically amplified between rounds of screening to target but not between prescreening and screening steps. After one or a few rounds of screening to target, the remaining display packages are highly enriched for high affinity binders to the target. For example, as shown in Example 13, it is possible to isolate large numbers of different antibodies having affinities in excess of $10^9$ or $10^{10}$ $M^{-1}$. Furthermore, the conditions of screening can be controlled to select antibodies having affinity in excess of a chosen threshold.

In some methods, nucleic acids encoding human antibody chains are subcloned en masse from display vectors surviving selection to an expression vector. Typically, a nucleic acid encoding both heavy and light chains of an antibody displayed from a display package is subcloned to an expression vector thereby preserving the same combinations of heavy and light chains in expression vectors as were present in the display packages surviving selection. The expression vector can be designed to express inserted antibody chains as Fab fragments, intact antibodies or other fragments. Cloning en masse of nucleic acids encoding antibody chains into an expression vector and subsequent expression of the vector in host cells results in a polyclonal population of intact human antibodies or fragments thereof. Such a population contains a diverse mixture of different antibody types, the majority of which types show very high affinity for the same target, albeit usually to different epitopes within the target.

It is believed that the success of the invention in providing virtually unlimited numbers of unusually high affinity human antibodies to any desired target (see Example 21) results, in part, from the combination of display and transgenic animal approaches. Display methods provide a means for screening vast numbers of antibodies for desired properties. However, the random association of light and heavy chains that occurs on cloning into a display vector results in unnatural combinations of heavy and light chains that may be nonfunctional. When heavy and light chains are cloned from a natural human, the number of permutations of heavy and light chains is very high, and probably a very large proportion of these are nonnaturally occurring and not capable of high affinity binding. Thus, high affinity antibodies constitute a very small proportion of such libraries and are difficult to isolate. Nonhuman transgenic animals with human immunoglobulin genes typically do not include the full complement of human immunoglobulin genes present in a natural human. It is believed that the more limited complement of human immunoglobulin genes present in such animals results in a reduced proportion of unnatural random permutations of heavy and light chains incapable of high affinity binding. Thus, when the vast power of display selection is applied free of the burden of very large numbers of unnatural combinations inherent in previous methods, indefinitely large numbers of human immunoglobulins having very high affinities result.

Somatic mutation and affinity maturation of antibody genes allows for the evolutionary selection of variant sequences based on binding affinity. However, this process differs from evolutionary natural selection of individuals from sexually reproducing species because there is no mechanism to allow for the combination of separately selected beneficial mutations. The absence of recombination between individual B cells requires that beneficial mutations be selected for sequentially. Theoretically, combinatorial libraries allow for such combinations (at least in the case where the two mutations are on heavy and light chains respectively). However, combinatorial libraries derived from natural sources include such a wide diversity of different heavy/light chain pairs that the majority of the clones are not derived from the same B cell bone marrow precursor cell. Such pairings are less likely to form stable antibody molecules that recognize the target antigen. Transgenic animals that comprise B cell populations derived from a smaller number of bone marrow precursors may be particularly useful for generating libraries that include novel, somatically mutated, heavy/light chain pairs in which each chain is derived from descendants of the same original pre-B cell.

Although the above mechanism is believed to explain the results achieved using the invention, practice of the invention is not dependent on the correctness of this belief.

B. Transgenic Animals with Human Immune Systems

The transgenic animals used in the invention bear a heterologous human immune system and typically a knocked out endogenous immune systems. Mice are a preferred species of nonhuman animal. Such transgenic mice sometimes referred to as HuMAb mice contain a human immunoglobulin gene miniloci that encodes unrearranged human heavy ($\mu$ and $\gamma$) and $\kappa$ light chain immunoglobulin sequences, together with targeted mutations that inactivate the endogenous $\mu$ and $\kappa$ chain loci (Lonberg et al. (1994) *Nature* 368(6474): 856–859 and U.S. Pat. No. 5,770,429). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal (Lonberg et al. (1994), supra; reviewed in Lonberg, N. (1994) *Handbook of Experimental Pharmacology* 113:49–101; Lonberg and Huszar,. (1995) *Intern. Rev. Immunol*. Vol. 13: 65–93, and Harding and Lonberg (1995) *Ann. N.Y. Acad. Sci* 764:536–546); Taylor, L. et al. (1992) *Nucleic Acids Research* 20:6287–6295; Chen, J. et al. (1993) *International Immunology* 5: 647–656; Tuaillon et al. (1993) *Proc. Natl. Acad. Sci USA* 90:3720–3724; Choi et al. (1993) *Nature Genetics* 4:117–123; Chen, J. et al. (1993) EMBO J. 12: 821–830; Tuaillon et al. (1994) *J. Immunol*. 152:2912–2920; Lonberg et al., (1994) *Nature* 368(6474): 856–859; Lonberg, N. (1994) *Handbook of Experimental Pharmacology* 113:49–101; Taylor, L. et al. (1994) *International Immunology* 6: 579–591; Lonberg, N. and Huszar, D. (1995) Intern. Rev. Immunol. Vol. 13: 65–93; Harding, F. and Lonberg, N. (1995) *Ann. N.Y. Acad. Sci* 764:536–546; Fishwild, D. et al. (1996) *Nature Biotechnology* 14:845–851; U.S. Pat. Nos. 5,625,126 and 5,770,429 U.S. Pat. No. 5,545,807, U.S. Pat. No. 5,939,598, WO 98/24884, WO 94/25585, WO 93/1227, WO 92/22645, WO 92/03918, the disclosures of all of which are hereby incorporated by reference in their entity.

Some transgenic non-human animals are capable of producing multiple isotypes of human monoclonal antibodies to an antigen (e.g., IgG, IgA and/or IgE) by undergoing V-D-J recombination and isotype switching. Isotype switching may occur by, e.g., classical or non-classical isotype switching.

Transgenic non-human animal are designed so that human immunoglobulin transgenes contained within the transgenic animal function correctly throughout the pathway of B-cell development. In some mice, correct function of a heterologous heavy chain transgene includes isotype switching. Accordingly, the transgenes of the invention are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

In transgenic animals in which the endogenous immunoglobulin loci of the transgenic animals are functionally disrupted, the transgene need not activate allelic exclusion. Further, in transgenic animals in which the transgene comprises a functionally rearranged heavy and/or light chain immunoglobulin gene, the second criteria of functional gene rearrangement is unnecessary, at least for transgenes that are already rearranged.

Some transgenic non-human animals used to generate the human monoclonal antibodies contain rearranged, unrearranged or a combination of rearranged and unrearranged heterologous immunoglobulin heavy and light chain transgenes in the germline of the transgenic animal. In addition, the heavy chain transgene can contain functional isotype switch sequences, which are capable of supporting isotype switching of a heterologous transgene encoding multiple CH genes in the B-cells of the transgenic animal. Such switch sequences can be those which occur naturally in the germline immunoglobulin locus from the species that serves as the source of the transgene CH genes, or such switch sequences can be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences can be isolated and cloned by conventional cloning methods, or can be synthesized de novo from overlapping synthetic oligonucleotides designed on the basis of published sequence information relating to immunoglobulin switch region sequences (Mills et al., *Nucl. Acids Res*. 15:7305–7316 (1991); Sideras et al., *Intl. Immunol*. 1:631–642 (1989) incorporated by reference). Typically, functionally rearranged heterologous heavy and light chain immunoglobulin transgenes are found in a significant fraction of the B-cells of the above transgenic animal (at least 10 percent).

The transgenes used to generate the transgenic animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species other than the transgenic non-human animal, typically the human species.

Typically transgenes are constructed so that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to antigen. Such transgenes typically comprise a substantial portion of the C, D, and J segments as well as a subset of the V gene segments.

In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences can be incorporated into the transgene from the same or a related species of the non-human animal used in the invention. For example, human immunoglobulin gene segments can be combined in a transgene with a rodent immunoglobulin enhancer sequence for use in a transgenic mouse. Alternatively, synthetic regulatory sequences can be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. The transgene can comprise a minilocus.

Some transgenic animals used to generate human antibodies contain at least one, typically 2–10, and sometimes 25–50 or more copies of the transgene described in Example 37 of U.S. Pat. No. 5,770,429, or the transgene described in Example 24 (e.g., HCo12), at least one copy of a light chain transgene described in Examples 38 of U.S. Pat. No. 5,770,429, two copies of the Cmu deletion described in Example 23, and two copies of the Jkappa deletion described in Example 9 of U.S. Pat. No. 5,770,429, each incorporated by reference in its entirety for all purposes.

Some transgenic animals exhibit immunoglobulin production with a significant repertoire. Thus, for example, animals in which the endogenous Ig genes Save been inactivated, the total immunoglobulin levels range from about 0.1 to 10 mg/ml of serum, preferably 0.5 to 5 mg/ml. The immunoglobulins expressed by the transgenic mice typically recognize about one-half or more of highly antigenic proteins, e.g., staphylococcus protein A.

The transgenic nonhuman animals can be immunized with a purified or enriched preparation of antigen and/or cells expressing antigen. The animals produce B cells that undergo class-switching via intratransgene switch recombination (cis-switching) and express immunoglobulins reactive with the antigen with which they are immunized. The immunoglobulins can be human sequence antibodies, in which the heavy and light chain polypeptides are encoded by human transgene sequences, which can include sequences derived by somatic mutation and V region recombinatorial joints, as well as germline-encoded sequences. These human sequence immunoglobulins can be referred to as being substantially identical to a polypeptide sequence encoded by a human $V_L$ or $V_H$ gene segment and a human JL or JL segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies frequently have some variable region sequences (and less frequently constant region sequences) which are not encoded by human V, D, or J gene segments as found in the human transgene(s) in the germline of the mice. Typically, such non-germline sequences (or individual nucleotide positions) cluster in or near CDRs, or in regions where somatic mutations are known to cluster.

The human sequence antibodies which bind to the predetermined antigen can result from isotype switching, such that human antibodies comprising a human sequence γ chain (such as γ1, γ2, γ3, or γ4) and a human sequence light chain (such as kappa or lamda) are produced. Such isotype-switched human sequence antibodies often contain one or more somatic mutation(s), typically in the variable region and often in or within about 10 residues of a CDR) as a result of affinity maturation and selection of B cells by antigen, particularly subsequent to secondary (or subsequent) antigen challenge. FIG. 7 shows the frequency of somatic mutations in various immunoglobulins of the invention.

HuMAb transgenic animals can be immunized intraperitoneally (IP) with antigen in complete Freund's adjuvant, followed by IP immunizations with antigen in incomplete Freund's adjuvant every two weeks or month for a few months. Adjuvants other than Freund's are also effective. In addition, whole cells in the absence of adjuvant are found to be highly immunogenic. The immune response can be monitored over the course of the immunization protocol with plasma samples being obtained by retroorbital bleeds. Mice can be boosted intravenously with antigen 3 days before sacrifice and removal of the spleen. 2–3 fusions for each immunization are typically performed.

Nucleic acids encoding at least the variable regions of heavy and light chains can be cloned from either immunized or naive transgenic animals. Nucleic acids can be cloned as genomic or cDNA from lymphatic cells of such animals. The spleen is a preferred source of such cells. No immortalization of such cells is required prior to cloning of immunoglobulin sequences. Usually, mRNA is isolated and amplified by reverse transcription with polydT primers. The cDNA is then amplified using primers to conserved regions of human immunoglobulins. Although populations of light and heavy chains can be amplified separately from each, the light chains within the light chain population are amplified en masse as are the heavy chains within the heavy chain population. Typically, the amplified population of light chains comprises at least 100, 1000, 10,000, 100,000 or 1,000,000 different light chains. Likewise, the amplified population of heavy chains comprises at least 100, 1000, 10,000, 100,000 or 1,000,000 different heavy chains.

C. Display Libraries 1. Display Packages

A display package, sometimes referred to as a replicable genetic package, is a screenable unit comprising a polypeptide to be screened linked to a nucleic acid encoding the polypeptide. The nucleic acid should be replicable either in vivo (e.g., as a vector) or in vitro (e.g., by PCR, transcription and translation). In vivo replication can be autonomous (as for a cell), with the assistance of host factors (as for a virus) or with the assistance of both host and helper virus (as for a phagemid). Cells, spores or viruses are examples of display packages. The replicable genetic package can be eukaryotic or prokaryotic. A display library is formed by introducing nucleic acids encoding exogenous polypeptides to be displayed into the genome of the display package to form a fusion protein with an endogenous protein that is normally expressed from the outer surface of the display package. Expression of the fusion protein, transport to the outer surface and assembly results in display of exogenous polypeptides from the outer surface of the genetic package.

A further type of display package comprises a polypeptide bound to a nucleic acid encoding the polypeptide. Such an arrangement can be achieved in several ways. U.S. Pat. No. 5,733,731 describe a method in which a plasmid is engineered to expression a fusion protein comprising a DNA binding polypeptide and a polypeptide to be screened. After expression the fusion protein binds to the vector encoding it though the DNA binding polypeptide component. Vectors displaying fusion proteins are screened for binding to a target, and vectors recovered for further rounds of screening or characterization. In another method, polypeptides are screened as components of display package comprising a polypeptide being screened, and mRNA encoding the polypeptide, and a ribosome holding together the mRNA and polypeptide (see Hanes & Pluckthun, *PNAS* 94, 4937–4942 (1997); Hanes et al., *PNAS* 95, 14130–14135 (1998); Hanes et al, *FEBS Let.* 450, 105–110 (1999); U.S. Pat. No. 5,922,545). mRNA of selected complexes is amplified by reverse transcription and PCR and in vitro transcription, and subject to further screening linked to a ribosome and protein translated from the mRNA. In another method, RNA is fused to a polypeptide encoded by the RNA for screening (Roberts & Szostak, *PNAS* 94, 12297–12302 (1997), Nemoto et al., *FEBS Letters* 414, 405–408 (1997). RNA from complexes surviving screening is amplified by reverse transcription PCR and in vitro transcription.

The genetic packages most frequently used for display libraries are bacteriophage, particularly filamentous phage, and especially phage M13, Fd and F1. Most work has inserted libraries encoding polypeptides to be displayed into either gIII or gVIII of these phage forming a fusion protein. See, e.g., Dower, WO 91/19818; Devlin, WO 91/18989; MacCafferty, WO 92/01047 (gene III); Huse, WO 92/06204; Kang, WO 92/18619 (gene VIII). Such a fusion protein comprises a signal sequence, usually from a secreted protein other than the phage coat protein, a polypeptide to be displayed and either the gene III or gene VIII protein or a fragment thereof. Exogenous coding sequences are often inserted at or near the N-terminus of gene III or gene VIII although other insertion sites are possible. Some filamentous phage vectors have been engineered to produce a second copy of either gene III or gene VIII. In such vectors, exogenous sequences are inserted into only one of the two copies. Expression of the other copy effectively dilutes the proportion of fusion protein incorporated into phage particles and can be advantageous in reducing selection against polypeptides deleterious to phage growth. In another variation, exogenous polypeptide sequences are cloned into phagemid vectors which encode a phage coat protein and phage packaging sequences but which are not capable of replication. Phagemids are transfected into cells and packaged by infection with helper phage. Use of phagemid system also has the effect of diluting fusion proteins formed from coat protein and displayed polypeptide with wild type copies of coat protein expressed from the helper phage. See, e.g., Garrard, WO 92/09690.

Eukaryotic viruses can be used to display polypeptides in an analogous manner. For example, display of human heregulin fused to gp70 of Moloney murine leukemia virus has been reported by Han, et al., *Proc. Natl. Acad. Sci. USA* 92:9747–9751 (1995). Spores can also be used as display packages. In this case, polypeptides are displayed from the outer surface of the spore. For example, spores from *B. subtilis* have been reported to be suitable. Sequences of coat proteins of these spores are provided by Donovan, et al., *J. Mol. Biol.* 196:1–10 (1987). Cells can also be used as display packages. Polypeptides to be displayed are inserted into a gene encoding a cell protein that is expressed on the cells surface. Bacterial cells including *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli* are preferred. Details of outer surface proteins are discussed by Ladner, et al., U.S. Pat. No. 5,571,698, and Georgiou, et al., *Nature Biotechnology* 15:29–34 (1997) and references cited therein. For example, the lamB protein of *E. coli* is suitable.

2. Displayed Antibodies

Antibody chains can be displayed in single or double chain form. Single chain antibody libraries can comprise the heavy or light chain of an antibody alone or the variable domain thereof. However, more typically, the members of single-chain antibody libraries are formed from a fusion of heavy and light chain variable domains separated by a peptide spacer within a single contiguous protein. See e.g., Ladner, et al., WO 88/06630; McCafferty, et al., WO 92/01047. Double-chain antibodies are formed by noncovalent association of heavy and light chains or binding fragments thereof. Double chain antibodies can also form by association of two single chain antibodies, each single chain antibody comprising a heavy chain variable domain, a linker and a light chain variable domain. In such antibodies, known as diabodies, the heavy chain of one single-chain antibody binds to the light chain of the other and vice versa, thus forming two identical antigen binding sites (see Hollinger et al., *Proc. Natl. Acad. Sci. USA* 90, 6444–6448 (1993) and Carter & Merchan, *Curr. Op. Biotech.* 8, 449–454 (1997). Thus, phage displaying single chain antibodies can form diabodies by association of two single chain antibodies as a diabody.

The diversity of antibody libraries can arise from obtaining antibody-encoding sequences from a natural source, such as a nonclonal population of immunized or unimmunized B cells. Alternatively, or additionally, diversity can be introduced by artificial mutagenesis of nucleic acids encoding antibody chains before or after introduction into a display vector. Such mutagenesis can occur in the course of PCR or can be induced before or after PCR.

Nucleic acids encoding antibody chains to be displayed optionally flanked by spacers are inserted into the genome of a display package as discussed above by standard recombinant DNA techniques (see generally, Sambrook, et al., Molecular Cloning, A Laboratory Manual, 2d ed., Cold Spring Harbor Laboratory Press, Cold Spring Harbor, N.Y., 1989, incorporated by reference herein). The nucleic acids are ultimately expressed as antibody chains (with or without spacer or framework residues). In phage, bacterial and spore vectors, antibody chains are fused to all or part of the an outer surface protein of the replicable package. Libraries often have sizes of about $10^3$, $10^4$, $10^6$, $10^7$, $10^8$ or more members.

Double-chain antibody display libraries represent a species of the display libraries discussed above. Production of such libraries is described by, e.g., Dower, U.S. Pat. No. 5,427,908; U.S. Pat. No. 5,580,717, Huse WO 92/06204; Huse, in Antibody Engineering, (Freeman 1992), Ch. 5; Kang, WO 92/18619; Winter, WO 92/20791; McCafferty, WO 92/01047; Hoogenboom WO 93/06213; Winter, et al., *Annu. Rev. Immunol.* 12:433–455 (1994); Hoogenboom, et al., *Immunological Reviews* 130:41–68 (1992); Soderlind, et al., *Immunological Reviews* 130:109–124 (1992). For example, in double-chain antibody phage display libraries, one antibody chain is fused to a phage coat protein, as is the case in single chain libraries. The partner antibody chain is complexed with the first antibody chain, but the partner is not directly linked to a phage coat protein. Either the heavy or light chain can be the chain fused to the coat protein. Whichever chain is not fused to the coat protein is the partner chain. This arrangement is typically achieved by incorporating nucleic acid segments encoding one antibody chain gene into either gIII or gVIII of a phage display vector to form a fusion protein comprising a signal sequence, an antibody chain, and a phage coat protein. Nucleic acid segments encoding the partner antibody chain can be inserted into the same vector as those encoding the first antibody chain. Optionally, heavy and light chains can be inserted into the same display vector linked to the same promoter and transcribed as a polycistronic message. Alternatively, nucleic acids encoding the partner antibody chain can be inserted into a separate vector (which may or may not be a phage vector). In this case, the two vectors are expressed in the same cell (see WO 92/20791). The sequences encoding the partner chain are inserted such that the partner chain is linked to a signal sequence, but is not fused to a phage coat protein. Both antibody chains are expressed and exported to the periplasm of the cell where they assemble and are incorporated into phage particles.

Typically, only the variable region of human light and heavy chains are cloned from a nonhuman transgenic animal. In such instances, the display vector can be designed to express heavy and light chain constant regions or fragments thereof in-frame with heavy and light chain variable regions expressed from inserted sequences. Typically, the constant regions are naturally occurring human constant regions; a few conservative substitutions can be tolerated but are not preferred. In a Fab fragment, the heavy chain constant region usually comprises a $C_H1$ region, and optionally, part or all of a hinge region, and the light chain constant region is an intact light chain constant region, such as $C_\kappa$ or $C_\lambda$. Choice of constant region isotype depends in part on whether complement-dependent cytotoxy is ultimately required. For example, human isotypes IgG1 and IgG4 support such cytotoxicity whereas IgG2 and IgG3 do not. Alternatively, the display vector can provide nonhuman constant regions. In such situations, typically, only the variable regions of antibody chains are subsequently subcloned from display vectors and human constant regions are provided by an expression vector in frame with inserted antibody sequences.

In a further variation, both constant and variable regions can be cloned from the transgenic animal. For example, heavy chain variable regions can be cloned linked to the $C_H1$ constant region and light chain variable regions linked to an intact light chain constant region for expression of Fab fragments. In this situation, display vectors need not encode constant regions.

Antibody encoding sequences can be obtained from lymphatic cells of a nonhuman transgenic animal. Typically, the cells have been immunized, in which case immunization can be performed in vivo before harvesting cells, or in vitro after harvesting cells, or both. Spleen cells of an immunized animal are a preferred source material. Immunization can be performed with any type of antigen. Antigens are often human proteins.

Rearranged immunoglobulin genes can be cloned from genomic DNA or mRNA. For the latter, mRNA is extracted from the cells and cDNA is prepared using reverse transcriptase and poly dT oligonucleotide primers. Primers for cloning antibody encoding sequences are discussed by Larrick, et al., *Bio/Technology* 7:934 (1989), Danielsson & Borrebaceick, in Antibody Engineering: A Practical Guide (Freeman, N.Y., 1992), p. 89 and Huse, id. at Ch. 5.

Repertoires of antibody fragments have been constructed by combining amplified $V_H$ and $V_L$ sequences together in several ways. Light and heavy chains can be inserted into different vectors and the vectors combined in vitro (Hogrefe, et al., *Gene* 128:119–126 (1993)) or in vivo (Waterhouse, et al., *Nucl. Acids. Res.* :2265–66 (1993)). Alternatively, the light and heavy chains can be cloned sequentially into the same vector (Barbas, et al., *Proc. Natl. Acad. Sci. USA* 88: 7987–82 (1991)) or assembled together by PCR and then inserted into a vector (Clackson, et al., *Nature* 352:624–28 (1991)). Repertoires of heavy chains can be also be combined with a single light chain or vice versa. Hoogenboom, et al., *J. Mol. Biol.* 227: 381–88 (1992).

Typically, segments encoding heavy and light antibody chains are subcloned from separate populations of heavy and light chains resulting in random association of a pair of heavy and light chains from the populations in each vector. Thus, modified vectors typically contain combinations of heavy and light chain variable region not found in naturally occurring antibodies. Some of these combinations typically survive the selection process and also exist in the polyclonal libraries described below.

Figure 1:
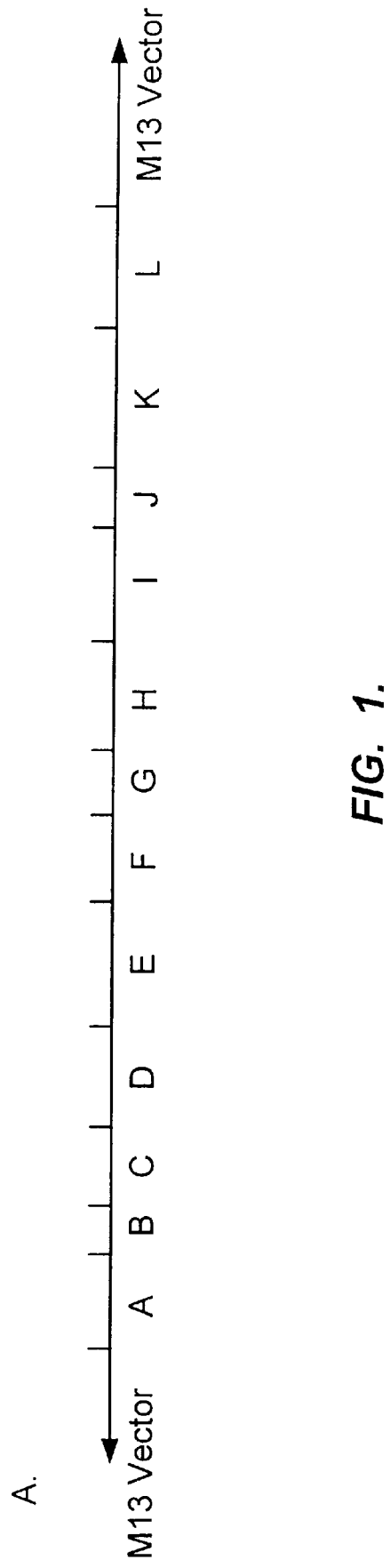
FIG. 1: shows a vector obtained from Ixsys, Inc. and described in Huse, WO 92/06204, which provides the starting material for producing phage display vectors. The following abbreviations are used.

Some exemplary vectors and procedures for cloning populations of heavy chain and light chain encoding sequences have been described by Huse, WO 92/06204. Diverse populations of sequences encoding $H_C$ polypeptides are cloned into M13IX30 and sequences encoding $L_C$ polypeptides are cloned into M13IX11. The populations are inserted between the XhoI-SeeI or StuI restriction enzyme sites in M13IX30 and between the SacI-XbaI or EcoRV sites in M13IX11 (FIGS. 1A and B of Huse, respectively). Both vectors contain two pairs of MluI-HindIII restriction enzyme sites (FIGS. 1A and B of Huse) for joining together the $H_C$ and $L_C$ encoding sequences and their associated vector sequences. The two pairs are symmetrically orientated about the cloning site so that only the vector proteins containing the sequences to be expressed are exactly combined into a single vector.

Others exemplary vectors and procedures for cloning antibody chains into filamentous phage are described in the present Examples.

D. Enrichment for Polyvalent Display Members

1. Theory of the Method

That a display library should preferably be enriched for members displaying multiple copies of a polypeptide is a finding apparently at variance with some early reports in the field. See, e.g., Cwirla et al., supra. Most work on display libraries has been done by inserting nucleic acid libraries into pIII or pVIII of filamentous phage. Because pIII is present in 4 or 5 copies per phage and pVIII is present in several hundred copies per phage, some early reports assumed that foreign polypeptides would be displayed in corresponding numbers per phage. However, more recent work has made clear that the actual number of copies of polypeptide displayed per phage is well below theoretical expectations, perhaps due to proteolytic cleavage of polypeptides. Winter, et al., *Ann. Rev. Immunol.* 12:433–55 (1994). Further, vector systems used for phage display often encode two copies of a phage coat protein, one of which is a wild type protein and the other of which forms a fusion protein with exogenous polypeptides to be displayed. Both copies are expressed and the wild type coat protein effectively dilutes the representation of the fusion protein in the phage coat.

A typical ratio of displayed Fabs per phage, when Fabs are expressed from pVIII of a filamentous phage is about 0.2. The probability, Pr(y), of y Fabs being expressed on a phage particle if the average frequency of expression per phage is n is given by the Poisson probability distribution $$Pr(y)=e^{-n}n^y/y!$$

For a frequency of 0.2 Fabs per phage, the probabilities for the expression of 0, 1, 2, and 3 Fabs per phage are 0.82, 0.16, 0.016, and 0.0011. The proportion of phage particle displaying two or more Fabs is therefore only 0.017.

The low representation of members displaying more than one Fab fragment in a phage display library can be related to the result that only a small percentage of such library members are capable of surviving affinity selection to immobilized binding partners. A library was constructed in which all members encoded the same Fab fragment which was known to have a high binding affinity for a particular target. It was found that even under the mildest separation conditions for removal of free from bound phage, it was not possible to bind more than about 0.004 of the total phage. This proportion is the same order of magnitude as the proportion of phage displaying at least two Fab fragments, suggesting that phage must display at least two Fab fragments to bind to immobilized target. Probably shear forces dissociate phage displaying only a single Fab fragment from the solid phase. Therefore, at least two binding events are necessary for a phage-Fab library member to be bound to immobilized target with sufficient avidity to enable separation of the bound from the free phage. It is expected that similar constraints apply in other forms of display library.

Therefore, a preferred strategy of the present invention is to enrich for library members binding to a receptor fused to displayed antibody chains before the library is contacted with a screening target. It is believed that the prescreening enriches for library members displaying at least two copies of a tag and therefore at least two copies of an antibody chain linked to the tag. Library members lacking two or more antibody chains, which are incapable of surviving affinity selection via binding through displayed antibody chain to any immobilized screening target, but which nevertheless can survive affinity selection by formation of multiple nonspecific bonds to such a target or its support, are thus substantially eliminated before screening of the library to the target is performed.

2. Tags and Receptors

The above strategy is effected by the use of paired tags and receptors. A tag can any peptide sequence that is common to different members of the library, heterologous to the display package, and fused to a polypeptide displayed from the display package. For example, a tag can be a synthetic peptide sequence, a constant region of an antibody. In some methods, single chain antibodies are displayed in which only the light or heavy chain variable region but not both varies between members. In such situations, among others, the variable region that is the same in different members can be used as a tag. Suitable tag-receptor combinations include epitope and antibody; for example, many high affinity hexapeptide ligands are known for the anti-dynorphin mAb 32.39, (see Barrett et al., *Neuropeptides* 6:113–120 (1985) and Cull et al., *Proc. Nat'l Acad. Sci. USA* 89:1865–1869 (1992)) and a variety of short peptides are known to bind the MAb 3E7 (Schatz, *Biotechnology* 11:1138–43 (1993)). Another combination of tag and antibody is described by Blanar & Rutter, *Science* 256:1014–1018 (1992).

Another example of a tag-receptor pair is the FLAG™ system (Kodak). The FLAG™ molecular tag consists of an eight amino acid FLAG peptide marker that is linked to the target binding moiety. A 24 base pair segment containing a FLAG coding sequence can be inserted adjacent to a nucleotide sequence that codes for the displayed polypeptide. The FLAG peptide includes an enterokinase recognition site that corresponds to the carboxyl-terminal five amino acids. Capture moieties suitable for use with the FLAG peptide marker include antibodies Anti-FLAG M1, M2 and M5, which are commercially available.

Still other combinations of peptides and antibodies can be identified by conventional phage display methods. Further suitable combinations of peptide sequence and receptor include polyhistidine and metal chelate ligands containing $Ni^{2+}$ immobilized on agarose (see Hochuli in Genetic Engineering: Principles and Methods (ed. J K Setlow, Plenum Press, N.Y.), Ch. 18, pp. 87–96 and maltose binding protein (Maina, et al., *Gene* 74:365–373 (1988)).

Receptors are often labeled with biotin allowing the receptors to be immobilized to an avidin-coated support. Biotin labeling can be performed using the biotinylating enzyme, BirA (see, e.g., Schatz, *Biotechnology* 11:1138–43 (1993)).

A nucleic acid sequence encoding a tag is inserted into a display vector in such a manner that the tag is expressed as part of the fusion protein containing the polypeptide to be displayed and an outer surface protein of the display package. The relative ordering of these components is not critical provided that the tag and polypeptide to be displayed are both exposed on the outer surface of the package. For example, the tag can be placed between the outer surface protein and the displayed polypeptide or at or near the exposed end of the fusion protein.

In display packages displaying Fabs, a tag can be fused to either the heavy or the light Fab chain, irrespective which chain is linked to a phage coat protein. Optionally, two different tags can used one fused to each of the heavy and light chains. One tag is usually positioned between the phage coat protein and antibody chain linked thereto, and the other tag is positioned at either the N- or C-terminus of the partner chain.

3. Selection of Polyvalent Library Members Members

Selection of polyvalent library members is performed by contacting the library with the receptor for the tag component of library members. Usually, the library is contacted with the receptor immobilized to a solid phase and binding of library members through their tag to the receptor is allowed to reach equilibrium. The complexed receptor and library members are then brought out of solution by addition of a solid phase to which the receptor bears affinity (e.g., an avidin-labeled solid phase can be used to immobilize biotin-labeled receptors). Alternatively, the library can be contacted with receptor in solution and the receptor subsequently immobilized. The concentration of receptor should usually be at or above the Kd of the tag/receptor during solution phase binding so that most displayed tags bind to a receptor at equilibrium. When the receptor-library members are contacted with the solid phase only the library members linked to receptor through at least two displayed tags remain bound to the solid phase following separation of the solid phase from library members in solution. Library members linked to receptor through a single tag are presumably sheared from the solid phase during separation and washing of the solid phase. After removal of unbound library members, bound library members can be dissociated from the receptor and solid phase by a change in ionic strength or pH, or addition of a substance that competes with the tag for binding to the receptor. For example, binding of metal chelate ligands immobilized on agarose and containing $Ni^{2+}$ to a hexahistidine sequence is easily reversed by adding imidazole to the solution to compete for binding of the metal chelate ligand. Antibody-peptide binding can often be dissociated by raising the pH to 10.5 or higher.

The average number of polypeptides per library member selected by this method is affected by a number of factors. Decreasing the concentration of receptor during solution-phase binding has the effect of increasing the average number of polypeptides in selected library members. An increase in the stringency of the washing conditions also increases the average number of polypeptides per selected library member. The physical relationship between library members and the solid phase can also be manipulated to increase the average number of polypeptides per library member. For example, if discrete particles are used as the solid phase, decreasing the size of the particles increases the steric constraints of binding and should require a higher density of polypeptides displayed per library member.

For Fab libraries having two tags, one linked to each antibody chain, two similar rounds of selection can be performed, with the products of one round becoming the starting materials for the second round. The first round of selection is performed with a receptor to the first tag, and the second round with a receptor to the second tag. Selecting for both tags enriches for library members displaying two copies of both heavy and light antibody chains (i.e., two Fab fragments).

Although the theory underlying the above methods of polyvalent enrichment is believed to be correct, the practice of the invention is in no way dependent on the correctness of this theory. Prescreening a display library for members binding to a tag, followed by screening those members for binding to a target results in a higher degree of enrichment for members with affinity for a target than if the method is performed without the prescreening step. Thus, the method can be practiced as described, and achieve the desired result of highly enriched libraries without any understanding of the underlying mechanism.

4. Selection for Affinity to Target

Library members displaying antibody chains, with or without prescreening to a tag receptor, are screened for binding to a target. The target can be any molecule of interest for which it is desired to identify binding partners. The target should lack specific binding affinity for the tag(s) (if used), because in this step it is the displayed polypeptides being screened, and not the tags that bind to the target. The screening procedure at this step is closely analogous to the prescreening step except that the affinity reagent is a target of interest rather than a receptor to a tag. The enriched library members are contacted with the target which is usually labeled (e.g., with biotin) in such a manner that allows its immobilization. Binding is allowed to proceed to equilibrium and then target is brought out of solution by contacting with the solid phase in a process known as panning (Parmley & Smith, Gene 73:305–318 (1988)). Library members that remain bound to the solid phase throughout the selection process do so by virtue of polyvalent bonds between them and immobilized target molecules. Unbound library members are washed away from the solid phase. In some methods, library members are screened by binding to cells displaying a receptor of interest. Thereafter, the entire cell population can be recovered by centrifugation or fractions bound to phage can be isolated by labelling with a phage specific antibody and separating labelled phage bound to cells using magnetic beads or FACS™.

Usually, library members are subject to amplification before performing a subsequent round of screening. Often, bound library members can be amplified without dissociating them from the support. For example, gene VIII phage library members immobilized to beads, can be amplified by immersing the beads in a culture of *E. coli*. Likewise, bacterial display libraries can be amplified by adding growth media to bound library members. Alternatively, bound library members can be dissociated from the solid phase (e.g., by change of ionic strength or pH) before performing subsequent selection, amplification or propagation.

After affinity selection, bound library members are now enriched for antibody chains having specific affinity for the target of interest (and for polyvalent display members if a prescreening step has been performed). After subsequent amplification, to produce a secondary library, the secondary library remains enriched for display of polypeptides having specific affinity for the target, but, as a result of amplification, is no longer enriched for polyvalent display of polypeptides. Thus, a second cycle of polyvalent enrichment can then be performed, followed by a second cycle of affinity enrichment to the screening target. Further cycles of affinity enrichment to the screening target, optionally, alternating with amplification and enrichment for polyvalent display can then be performed, until a desired degree of enrichment has been achieved.

In a variation, affinity screening to a target is performed in competition with a compound that resembles but is not identical to the target. Such screening preferentially selects for library members that bind to a target epitope not present on the compound. In a further variation, bound library members can be dissociated from the solid phase in competition with a compound having known crossreactivity with a target for an antigen. Library members having the same or similar binding specificity as the known compound relative to the target are preferentially eluted. Library members with affinity for the target through an epitope distinct from that recognized by the compound remain bound to the solid phase.

Discrimination in selecting between antibody chains of different monovalent affinities for the target is affected by the valency of library members and the concentration of target during the solution phase binding. Assuming a minimum of i labeled target molecules must be bound to a library member to immobilize it on a solid phase, then the probability of immobilization can be calculated for a library member displaying n polypeptides. From the law of mass action, the bound/total antibody chain fraction, F, is $K[\text{targ}]/(1+K[\text{targ}])$, where [targ] is the total target concentration in solution. Thus, the probability that i or more displayed antibody chains per library member are bound by the labeled target is given by the binomial probability distribution:

$$\sum_{n}^{y=i} (n!/[y!(n-y)!]F^{y}(1-F)^{n-y}$$

As the probability is a function of K and [target], multivalent display members each having a monovalent affinity, K, for the target can be selected by varying the concentration of target. The probabilities of solid-phase immobilization for i=1, 2, or 3, with library members exhibiting monovalent affinities of $0.1/[\text{Ag}]$, $1/[\text{Ag}]$, and $10/[\text{Ag}]$, and displaying n polypeptides per member are:

| n | K = 0.1/[targ] | K = 1/[targ] | K = 10/[targ] |
|---|---|---|---|
| | Probability of Immobilization (i = 1) | | |
| 1 | 0.09 | 0.5 | 0.91 |
| 2 | 0.17 | 0.75 | 0.99 |
| 3 | 0.25 | 0.875 | |
| 4 | 0.32 | 0.94 | |
| 5 | 0.38 | 0.97 | |
| 6 | 0.44 | 0.98 | |
| 7 | 0.49 | 0.99 | |
| 8 | 0.53 | | |
| 9 | 0.58 | | |
| 10 | 0.61 | | |

-continued

| n | K = 0.1/[targ] | K = 1/[targ] | K = 10/[targ] |
|---|---|---|---|
| 20 | 0.85 | | |
| 50 | 0.99 | | |
| Probability of Immobilization (i = 2) | | | |
| 2 | 0.008 | 0.25 | 0.83 |
| 3 | 0.023 | 0.50 | 0.977 |
| 4 | 0.043 | 0.69 | 0.997 |
| 5 | 0.069 | 0.81 | |
| 6 | 0.097 | 0.89 | |
| 7 | 0.128 | 0.94 | |
| 8 | 0.160 | 0.965 | |
| 9 | 0.194 | 0.98 | |
| 20 | 0.55 | | |
| 50 | 0.95 | | |
| Probability of Immobilization (i = 3) | | | |
| 3 | 0.00075 | 0.125 | 0.75 |
| 4 | 0.0028 | 0.31 | 0.96 |
| 5 | 0.0065 | 0.50 | 0.99 |
| 6 | 0.012 | 0.66 | |
| 7 | 0.02 | 0.77 | |
| 8 | 0.03 | 0.855 | |
| 9 | 0.0415 | 0.91 | |
| 10 | 0.055 | 0.945 | |
| 12 | 0.089 | 0.98 | |
| 14 | 0.128 | 0.99 | |
| 20 | 0.27 | | |
| 50 | 0.84 | | |

The above tables show that the discrimination between immobilizing polypeptides of different monovalent binding affinities is affected by the valency of library members (n) and by the concentration of target for the solution binding phase. Discrimination is maximized when n (number of polypeptides displayed per phage) is equal to i (minimum valency required for solid phase binding). Discrimination is also increased by lowering the concentration of target during the solution phase binding. Usually, the target concentration is around the Kd of the polypeptides sought to be isolated. Target concentration of $10^{-8}$–$10^{-10}$ M are typical.

Enriched libraries produced by the above methods are characterized by a high proportion of members encoding polypeptides having specific affinity for the target. For example, at least 10, 25, 50, 75, 80, 90, 95, or 99% of members encode polypeptides having specific affinity for the target. In some libraries, at least 10, 25, 50, 75, 80, 90, 95, or 99% of members have affinities of at least $10^8$ $M^{-1}$, $10^9$ $M^{-1}$ or $10^{10}$ $M^{-1}$. In libraries of double chain antibodies, a pair of segments encoding heavy and light chains of an antibody is considered a library member. The exact percentage of members having affinity for the target depends whether the library has been amplified following selection, because amplification increases the representation of genetic deletions. However, among members with full-length polypeptide coding sequences, the proportion encoding polypeptides with specific affinity for the target is very high (e.g., at 50, 75, 80, 90, 95 or 99% having affinity of $10^8$ $M^{-1}$, $10^9$ $M^{-1}$ or $10^{10}$ $M^{-1}$. Not all the library members that encode an antibody chain with specific affinity for the target necessarily display the antibody chain. For example, in a library in which 95% of members with full-length coding sequences encode antibody chains with specific affinity for the target, usually fewer than half actually display the antibody chain. Usually, such libraries have at least 4, 10, 20, 50, 100, 1000, 10,000 or 100,000 different coding sequences. Usually, the representation of any one such coding sequences is no more than 50%, 25% or 10% of the total coding sequences in the library.

F. Subcloning Antibody Chains into an Expression Vector

Screening of display library members typically results in a subpopulation of library members having specific affinity for a target. There are a number of options at this point. In some methods, clonal isolates of library members are obtained, and these isolates used directly. In other methods, clonal isolates of library member are obtained, and DNA encoding antibody chains amplified from each isolate. Typically, heavy and light chains are amplified as components of the same DNA molecule before transfer to an expression vector, such that combinations of heavy and light chain existing in the display vector are preserved in the expression vector. For displayed antibody chains that include both human variable regions and human constant regions, typically nucleic acids encoding both the variable region and constant region are subcloned. In other methods, nucleic acids encoding antibody chains are amplified and subcloned en masse from a pool of library members into multiple copies of an expression vector without clonal isolation of individual members.

The subcloning process is now described in detail for transfer of a mixed population of nucleic acids from a display vector to an expression vector. Essentially the same process can be used on nucleic acids obtained from a clonal isolate of an individual display vector.

Nucleic acids encoding antibody chains to be subcloned can be excised by restriction digestion of flanking sequences or can be amplified by PCR using primers to sites flanking the coding sequences. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila, et al., *Nucleic Acids Res.* 19:967 (1991); Eckert, et al., *PCR Methods and Applications* 1:17 (1991); PCR (eds. McPherson et al., IRL Press, Oxford). PCR primers can contain a marker sequence that allows positive selection of amplified fragments when introduced into an expression vector. PCR primers can also contain restriction sites to allow cloning into an expression vector, although this is not necessary. For Fab libraries, if heavy and light chains are inserted adjacent or proximate to each other in a display vector, the two chains can be amplified or excised together. For some Fab libraries, only the variable domains of antibody chain(s) are excised or amplified. If the heavy or light chains of a Fab library are excised or amplified separately, they can subsequently be inserted into the same or different expression vectors.

Having excised or amplified fragments encoding displayed antibody chains, the fragments are usually size-purified on an agarose gel or sucrose gradient. Typically, the fragments run as a single sharp full-length band with a smear at lower molecular corresponding to various deleted forms of coding sequence. The band corresponding to full-length coding sequences is removed from the gel or gradient and these sequences are used in subsequent steps.

The next step is to join the nucleic acids encoding full-length coding sequences to an expression vector thereby creating a population of modified forms of the expression vector bearing different inserts. This can be done by conventional ligation of cleaved expression vector with a mixture of inserts cleaved to have compatible ends. Alternatively, the use of restriction enzymes on insert DNA can be avoided. This method of cloning is beneficial because naturally encoded restriction enzyme sites may be present within insert sequences, thus, causing destruction of the sequence when treated with a restriction enzyme. For cloning without restricting, a mixed population of inserts and linearized vector sequences are treated briefly with a 3' to 5' exonuclease such as T4 DNA polymerase or exonuclease III. See Sambrook, et al., Molecular Cloning, A Laboratory Manual (2nd Ed., CSHP, New York 1989). The protruding 5' termini of the insert generated by digestion are complementary to single-stranded overhangs generated by digestion of the vector. The overhangs are annealed, and the re-annealed vector transfected into recipient host cells. The same result can be accomplished using 5' to 3' exonucleases rather than a 3' to 5' exonuclease.

Preferably, ligation of inserts to expression vector is performed under conditions that allow selection against re-annealed vector and uncut vector. A number of vectors containing conditional lethal genes that allow selection against re-annealed vector under nonpermissive conditions are known. See, e.g., Conley & Saunders, *Mol. Gen. Genet.* 194:211–218 (1984). These vectors effectively allow positive selection for vectors having received inserts. Selection can also be accomplished by cleaving an expression vector in such a way that a portion of a positive selection marker (e.g., antibiotic resistance) is deleted. The missing portion is then supplied by full-length inserts. The portion can be introduced at the 3' end of polypeptide coding sequences in the display vector, or can be included in a primer used for amplification of the insert. An exemplary selection scheme, in which inserts supply a portion of a tetracycline-resistance gene promoter deleted by HindIII cleavage of a pBR-derivative vector, is described in Example 14.

The choice of expression vector depends on the intended host cells in which the vector is to be expressed. Typically, the vector includes a promoter and other regulatory sequences in operable linkage to the inserted coding sequences that ensure the expression of the latter. Use of an inducible promoter is advantageous to prevent expression of inserted sequences except under inducing conditions. Inducible promoters include arabinose, lacZ, metallothionein promoter or a heat shock promoter. Cultures of transformed organisms can be expanded under noninducing conditions without biasing the population for coding sequences whose expression products are better tolerated by the host cells. The vector may also provide a secretion signal sequence position to form a fusion protein with polypeptides encoded by inserted sequences, although often inserted polypeptides are linked to a signal sequences before inclusion in the vector. Vectors to be used to receive sequences encoding antibody light and heavy chain variable domains sometimes encode constant regions or parts thereof that can be expressed as fusion proteins with inserted chains thereby leading to production of intact antibodies or fragments thereof. Typically, such constant regions are human. Conservative mutations although not preferred can be tolerated. For example, if display packages display a heavy chain variable region linked to a $C_H1$ constant region and a light chain variable region linked to an intact light chain constant region, and the complete antibody chains are transferred from the display vector to the expression vector, then the expression vector can be designed to encode human heavy chain constant region hinge, $C_H2$ and $C_H3$ regions in-frame with the $C_H1$ region of the inserted heavy chain nucleic acid thereby resulting in expression of an intact antibody. Of course, many minor variations are possible as to precisely which segment of the human heavy chain constant region is supplied by the display package and which by the expression vector. For example, the display package can be designed to include a $C_H1$ region, and some or all of the hinge region. In this case, the expression vector is designed to supply the residual portion of the hinge region (if any) and the $C_H2$ and $C_H3$ regions for expression of intact antibodies.

*E. coli* is one prokaryotic host useful particularly for cloning the polynucleotides of the present invention. Other microbial hosts suitable for use include bacilli, such as *Bacillus subtilis*, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation.

Other microbes, such as yeast, are also used for expression. Saccharomyces is a preferred host, with suitable vectors having expression control sequences, such as promoters, including 3-phosphoglycerate kinase or other glycolytic enzymes, and an origin of replication, termination sequences and the like as desired. Insect cells in combination with baculovirus vectors can also be used.

Mammalian tissue cell culture can also be used to express and produce the polypeptides of the present invention (see Winnacker, From Genes to Clones (VCH Publishers, N.Y., N.Y., 1987). A number of suitable host cell lines capable of secreting intact immunoglobulins have been developed including the CHO cell lines, various Cos cell lines, HeLa cells, myeloma cell lines, transformed B-cells and hybridomas. Expression vectors for these cells can include expression control sequences, such as an origin of replication, a promoter, and an enhancer (Queen, et al., *Immunol. Rev.* 89:49–68 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, or cytomegalovirus.

Methods for introducing vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra).

Once expressed, collections of antibodies are purified from culture media and host cells. Usually, antibody chains are expressed with signal sequences and are thus released to the culture media. However, if antibody chains are not naturally secreted by host cells, the antibody chains can be released by treatment with mild detergent. Antibody chains can then be purified by conventional methods including ammonium sulfate precipitation, affinity chromatography to immobilized target, column chromatography, gel electrophoresis and the like (see generally Scopes, Protein Purification (Springer-Verlag, N.Y., 1982)).

The above methods result in novel libraries of nucleic acid sequences encoding antibody chains having specific affinity for a chosen target. The libraries of nucleic acids typically have at least 5, 10, 20, 50, 100, 1000, $10^4$ or $10^5$ different members. Usually, no single member constitutes more than 25 or 50% of the total sequences in the library. Typically, at least 25, 50%, 75, 90, 95, 99 or 99.9% of library members encode antibody chains with specific affinity for the target molecules. In the case of double chain antibody libraries, a pair of nucleic acid segments encoding heavy and light chains respectively is considered a library member. The nucleic acid libraries can exist in free form, as components of any vector or transfected as a component of a vector into host cells.

The nucleic acid libraries can be expressed to generate polyclonal libraries of antibodies having specific affinity for a target. The composition of such libraries is determined from the composition of the nucleotide libraries. Thus, such libraries typically have at least 5, 10, 20, 50, 100, 1000, $10^4$ or $10^5$ members with different amino acid composition. Usually, no single member constitutes more than 25 or 50% of the total polypeptides in the library. The percentage of antibody chains in an antibody chain library having specific affinity for a target is typically lower than the percentage of corresponding nucleic acids encoding the antibody chains. The difference is due to the fact that not all polypeptides fold into a structure appropriate for binding despite having the appropriate primary amino acid sequence to support appropriate folding. In some libraries, at least 25, 50, 75, 90, 95, 99 or 99.9% of antibody chains have specific affinity to the target molecules. Again, in libraries of multi-chain antibodies, each antibody (such as a Fab or intact antibody) is considered a library member. The different antibody chains differ from each other in terms of fine binding specificity and affinity for the target. Some such libraries comprise members binding to different epitopes on the same antigen. Some such libraries comprises at least two members that bind to the same antigen without competing with each other.

Polyclonal libraries of human antibodies resulting from the above methods are distinguished from natural populations of human antibodies both by the high percentages of high affinity binders in the present libraries, and in that the present libraries typically do not show the same diversity of antibodies present in natural populations. The reduced diversity in the present libraries is due to the nonhuman transgenic animals that provide the source materials not including all human immunoglobulin genes. For example, some polyclonal antibody libraries are free of antibodies having lambda light chains. Some polyclonal antibody libraries of the invention have antibody heavy chains encoded by fewer than 10, 20, 30 or 40 $V_H$ genes. Some polyclonal antibody libraries of the invention have antibody light chains encoded by fewer than 10, 20, 30 or 40 $V_L$ genes.

III. Diagnostic Uses

1. Characteristics of Human Antibodies for Use as Diagnostic Reagents

Human antibodies for use in diagnostic methods of the invention are preferably produced using the methods described above. The methods result in virtually unlimited numbers of human antibodies of any epitope binding specificity and very high binding affinity to any desired antigen. In general, the higher the binding affinity of an antibody for its target, the more stringent wash conditions can be performed in an immunoassay to remove nonspecifically bound material without removing target antigen. Accordingly, human antibodies useed in the above assays usually have binding affinities of at least $10^8$, $10^9$, $10^{10}$, $10^{11}$ or $10^{12}$ $M^{-1}$. Further, it is desirable that antibodies used as diagnostic reagents have a sufficient on-rate to reach equilibrium under standard conditions such as those described in Example 28 in at least 12 hours, preferably at least five hours and more preferably at least one hour.

Human antibodies used in the claimed methods preferably have a high immunoreactivity, that is, percentages of antibodies molecules that are correctly folded so that they can specifically bind their target antigen. Such can be achieved by expression of sequences encoding the antibodies in *E. coli* as described above. Such expression usually results in immunoreactivity of at least 80%, 90%, 95% or 99% (see Table 4).

Some methods of the invention employ polyclonal preparations of human antibodies as diagnostic reagents, and other methods employ monoclonal isolates. The use of polyclonal mixtures has a number of advantages with respect to compositions made of one monoclonal antibody. By binding to multiple sites on a target, polyclonal antibodies or other polypeptides can generate a stronger signal (for diagnostics) than a monoclonal that binds to a single site. Further, a polyclonal preparation can bind to numerous variants of a prototypical target sequence (e.g., allelic variants, species variants, strain variants, drug-induced escape variants) whereas a monoclonal antibody may bind only to the prototypical sequence or a narrower range of variants thereto. However, monoclonal antibodies are advantageous for detecting a single antigen in the presence or potential presence of closely related antigens.

In methods employing polyclonal human antibodies prepared in accordance with the methods described above, the preparation typically contains an assortment of antibodies with different epitope specificities to the intended target antigen. Such can be verified by the methods described in Example 26. In some methods employing monoclonal antibodies, it is desirable to have two antibodies of different epitope binding specificities. A difference in epitope binding specificities can be determined by a competition assay.

2. Samples and Target

Although human antibodies can be used as diagnostic reagents for any kind of sample, they are most useful as diagnostic reagents for human samples. Samples can be obtained from any tissue or body fluid of a patient. Preferred sources of samples include, whole blood, plasma, semen, saliva, tears, urine, fecal material, sweat, buccal, skin and hair. Samples can also be obtained from biopsies of internal organs or from cancers. Samples can be obtained from clinical patients for diagnosis or research or can be obtained from undiseased individuals, as controls or for basic research.

The methods can be used for detecting any type of target antigen. Exemplary target antigens including bacterial, fungal and viral pathogens that cause human disease, such as. IV, Hepatitis (A, B, & C), Influenza, Herpes, Giardia, Malaria, Leishmania, *Staphylococcus Aureus, Pseudomonas aeruginosa*. Other target antigens are human proteins whose expression levels or compositions have been correlated with human disease or other phenotype. Examples of such antigens include adhesion proteins, hormones, growth factors, cellular receptors, autoantigens, autoantibodies, and amyloid deposits. Other targets of interest include tumor cell antigens, such as carcinoembryonic antigen. Other antigens of interest are class I and class II MHC antigens.

3. HAMA and Heterophilic Antibodies

At least some human samples contain human antibodies that specifically bind to antibodies from a different species. Some such human antibodies bind to the isotype of antibodies from a nonhuman species, and other human antibodies bind to the idiotype of antibodies from a nonhuman species. Such human antibodies can arise by a variety of mechanisms. For example, administration of a mouse antibody (such as FDA-approved OKT3) to a human patient typically generates a human antimouse response. A similar response can be generated by environmental exposure to mouse antigens. Human antibodies that specifically bind to antibodies from other species, such as rabbit or bovine, can likewise be generated by environmental exposure to antigens from rabbit or bovine. Further, exposure of humans to certain viruses, particularly Epstein Barr virus, the agent responsible for infectious mononucleosis generates a class of antibodies termed heterophilic antibodies that bind to antibodies from nonhuman species.

The frequency of human antibodies reactive with antibodies from nonhuman species in human patient samples has been the subject of varying reports. For example, estimates of frequency of human anti-mouse IgG vary from 0.72% to 80% in different studies, and estimates of human anti-rabbit IgG have varied from 0.09% to 5% (see Kricka et al., *Clinical Chemistry* 45, 942–956 (1999)). Regardless of the precise frequency, there is clearly a significant risk that any human sample contains human antibodies reactive with antibodies from some nonhuman animal. Therefore, use of an antibody from a nonhuman species as a diagnostic reagent runs a risk of generating inaccurate results. Inaccuracies can be reduced but not eliminated by using chimeric antibodies. Some inaccuracies remain due to the presence of human antibodies binding to the idiotype of the chimeric antibodies. The inaccuracies are however eliminated by the use of human antibodies as diagnostic reagents. There are no antibodies present in a typical human sample that bind to fully human antibodies.

4. Formats for Diagnostic Assays

Human antibodies can be used to detect a given target in a variety of standard assay formats. Such formats include immunoprecipitation, Western blotting, ELISA, radioimmunoassay, and immunometric assays. See Harlow & Lane, *Antibodies, A Laboratory Manual* (CSHP NY, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876.

Immunometric or sandwich assays are a preferred format (see U.S. Pat. No. 4,376,110, 4,486,530, 5,914,241, and 5,965,375). Such assays use one antibody or population of antibodies immobilized to a solid phase, and another antibody or population of antibodies in solution. Typically, the solution antibody or population of antibodies is labelled. If an antibody population is used, the population typically contains antibodies binding to different epitope specificities within the target antigen. Accordingly, the same population can be used for both solid phase and solution antibody. If monoclonal antibodies are used, first and second monoclonal antibodies having different binding specificities are used for the solid and solution phase. Solid phase and solution antibodies can be contacted with target antigen in either order or simultaneously. If the solid phase antibody is contacted first, the assay is referred to as being a forward assay. Conversely, if the solution antibody is contacted first, the assay is referred to as being a reverse assay. If target is contacted with both antibodies simultaneously, the assay is referred to as a simultaneous assay. After contacting the target with antibody, a sample is incubated for a period that usually varies from about 10 min to about 24 hr and is usually about 1 hr. A wash step is then performed to remove components of the sample not specifically bound to the antibody(ies) being used as a diagnostic reagent. When solid phase and solution antibodies are bound in separate steps, a wash can be performed after either or both binding steps. After washing, binding is quantified, typically by detecting label linked to the solid phase through binding of labelled solution antibody. Usually for a given pair of antibodies or populations of antibodies and given reaction conditions, a calibration curve is prepared from samples containing known concentrations of target antigen. Concentrations of antigen in samples being tested are then read by interpolation from the calibration curve. Analyte can be measured either from the amount of labelled solution antibody bound at equilibrium or by kinetic measurements of bound labelled solution antibody at a series of time points before equilibrium is reached. The slope of such a curve is a measure of the concentration of target in a sample Suitable detectable labels for use in the above methods include any moiety that is detectable by spectroscopic, photochemical, biochemical, immunochemical, electrical, optical, chemical, or other means. For example, suitable labels include biotin for staining with labeled streptavidin conjugate, fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horseradish peroxidase, alkaline phosphatase and others commonly used in an ELISA), and colorimetric labels such as colloidal gold or colored glass or plastic (e.g., polystyrene, polypropylene, latex beads). Patents that described the use of such labels include U.S. Pat. Nos. 3,817,837; 3,850,752; 3,939,350; 3,996,345; 4,277,437; 4,275,149; and 4,366,241. See also Handbook of Fluorescent Probes and Research Chemicals (6th Ed., Molecular Probes, Inc., Eugene Oreg.). Radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Suitable supports for use in the above methods include, for example, nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX.™. (Amersham Pharmacia Biotech, Piscataway N.J., and the like. Immobilization can be by absorption or by covalent attachment. Optionally, antibodies can be joined to a linker molecule, such as biotin for attachment to a surface bound linker, such as avidin.

Although the invention has been described in detail for purposes of clarity of understanding, it will be obvious that certain modifications may be practiced within the scope of the appended claims. All publications and patent documents cited in this application are hereby incorporated by reference in their entirety for all purposes to the same extent as if each were so individually denoted. A cell lines producing 7F11 (HB-12443, Dec. 5, 1997) has been deposited at the American Type Culture Collection, Rockville, Md. under the Budapest Treaty on the dates indicated and given the accession numbers indicated. The deposits will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

EXAMPLE 1

Purification of RNA from Mouse Spleens

Mice having 3 different sets of human heavy chain genes were used to make the antibody phage libraries to interleukin 8. Production of mice is described in Examples 23 and 24. The mice were immunized with interleukin 8 (Example 19). Mice were immunized with 25 microgram of antigen at 0.713 mg/ml. In a first procedure, mice were immunized once a month beginning with CFA followed by IFA until a high human gamma titer was reached (ca 6500) after a further six weeks, mice were boosted ip on days -7, -6, -5, and sacrificed 5 days later. In an alternative procedure, mice were immunized every two weeks beginning with CFA and followed by IFA. After a high human gamma titer was reached, mice were boosted on days -3, and -2 and sacrificed two days later.

The spleens were harvested in a laminar flow hood and transferred to a petri dish, trimming off and discarding fat and connective tissue. The spleen was, working quickly, macerated with the plunger from a sterile 5 cc syringe in the presence of 1.0 ml of solution D (25.0 g guanidine thiocyanate (Roche Molecular Biochemicals, Indianapolis, Ind.), 29.3 ml sterile water, 1.76 ml 0.75 M sodium citrate (pH 7.0), 2.64 ml 10% sarkosyl (Fisher Scientific, Pittsburgh, Pa.), 0.36 ml 2-mercaptoethanol (Fisher Scientific, Pittsburgh, Pa.)). The spleen suspension was pulled through an 18-gauge needle until viscous and all cells were lysed, then transferred to a microcentrifuge tube. The petri dish was washed with 100 µl of solution D to recover any remaining spleen, and this was transferred to the tube. The suspension was then pulled through a 22-gauge needle an additional 5–10 times. The sample was divided evenly between two microcentrifuge tubes and the following added in order, with mixing by inversion after each addition: 100 µl 2 M sodium acetate (pH 4.0), 1.0 ml water-saturated phenol (Fisher Scientific, Pittsburgh, Pa.), 200 µl chloroform/isoamyl alcohol 49:1 (Fisher Scientific, Pittsburgh, Pa.). The solution was vortexed for 10 seconds and incubated on ice for 15 min. Following centrifugation at 14 krpm for 20 min at 2–8° C., the aqueous phase was transferred to a fresh tube. An equal volume of water saturated phenol/chloroform/isoamyl alcohol (50:49:1) was added, and the tube was vortexed for ten seconds. After a 15 min incubation on ice, the sample was centrifuged for 20 min at 2–8° C., and the aqueous phase was transferred to a fresh tube and precipitated with an equal volume of isopropanol at −20° C. for a minimum of 30 min. Following centrifugation at 14,000 rpm for 20 min at 4° C., the supernatant was aspirated away, the tubes briefly spun and all traces of liquid removed. The RNA pellets were each dissolved in 300 µl of solution D, combined, and precipitated with an equal volume of isopropanol at −20° C. for a minimum of 30 min. The sample was centrifuged 14,000 rpm for 20 min at 4° C., the supernatant aspirated as before, and the sample rinsed with 100 µl of ice-cold 70% ethanol. The sample was again centrifuged 14,000 rpm for 20 min at 4° C., the 70% ethanol solution aspirated, and the RNA pellet dried in vacuo. The pellet was resuspended in 100 µl of sterile distilled water. The concentration was determined by $A_{260}$ using an absorbance of 1.0 for a concentration of 40 µg/ml. The RNA was stored at −80° C.

EXAMPLE 2

Preparation of Complementary DNA (cDNA)

The total RNA purified as described above was used directly as template for cDNA. RNA (50 µg) was diluted to 100 µL with sterile water, and 10 µL–130 ng/µL oligo dT12 (synthesized on Applied Biosystems Model 392 DNA synthesizer at Biosite Diagnostics) was added. The sample was heated for 10 min at 70° C., then cooled on ice. 40 µL 5×first strand buffer was added (Gibco/BRL, Gaithersburg, Md.), 20 µL 0.1 M dithiothreitol (Gibco/BRL, Gaithersburg, Md.), 10 µL 20 mM deoxynucleoside triphosphates (dNTP's, Roche Molecular Biochemicals, Indianapolis, Ind.), and 10 µL water on ice. The sample was then incubated at 37° C. for 2 min. 10 µL reverse transcriptase (Superscript™ II, Gibco/BRL, Gaithersburg, Md.) was added and incubation was continued at 37° C. for 1 hr. The cDNA products were used directly for polymerase chain reaction (PCR).

EXAMPLE 3

Amplification of Human Antibody Sequence cDNA by PCR

The cDNA of four mice having the genotype HCo7 was amplified using 3–5' oligonucleotides and 1–3' oligonucleotide for heavy chain sequences (Table A), and 10–5' oligonucleotides and 1–3' oligonucleotide for the kappa chain sequences (Table B). The cDNA of one mouse having the genotype HCo12 was amplified using 5–5' oligonucleotides and 1–3' oligonucleotide for heavy chain sequences (Table C), and the oligonucleotides shown in Table B for the kappa chain sequences. The cDNA of two mice having the genotype HCo7/Co12 was amplified using the oligonucleotide sequences shown in Tables A and C for the heavy chain sequences and oligonucleotides shown in Table B for the kappa chain sequences. The 5' primers were made so that a 20 nucleotide sequence complementary to the M13 uracil template was synthesized on the 5' side of each primer. This sequence is different between the H and L chain primers, corresponding to 20 nucleotides on the 3' side of the pelB signal sequence for L chain primers and the alkaline phosphatase signal sequence for H chain primers. The constant region nucleotide sequences required only one 3' primer each to the H chains and the kappa L chains (Tables A and B). Amplification by PCR was performed separately for each pair of 5' and 3' primers. A 50 µL reaction was performed for each primer pair with 50 pmol of 5' primer, 50 pmol of 3' primer, 0.25 µL Taq DNA Polymerase (5 units/µL, Roche Molecular Biochemicals, Indianapolis, Ind.), 3 µL cDNA (described in Example 2), 5 µL 2 mM dNTP's, 5 µL 10×Taq DNA polymerase buffer with MgCl$_2$ (Roche Molecular Biochemicals, Indianapolis, Ind.), and H$_2$O to 50 µL. Amplification was done using a GeneAmp® 9600 thermal cycler (Perkin Elmer, Foster City, Calif.) with the following program: 94° C. for 1 min; 30 cycles of 94° C. for 20 sec, 55° C. for 30 sec, and 72° C. for 30 sec; 72° C. for 6 min; 4° C.

Table A. Heavy chain oligonucleotides used to amplify cDNA for Hco7 mice. Oligonucleotides 188 (SEQ ID NO:1), 944 (SEQ ID NO:2) and 948 (SEQ ID NO: 3) are 5' primers and oligonucleotide 952 (SEQ ID NO:4) is the 3' primer.

TABLE A

Heavy chain oligonucleotides used to amplify cDNA for Hco7 mice. Oligonucleotides 188 (SEQ ID NO: 1), 944 (SEQ ID NO: 2) and 948 (SEQ ID NO: 3) are 5' primers and oligonucleotide 952 (SEQ ID NO: 4) is the 3' primer.

| OLIGO # | 5' TO 3' SEQUENCE |
|---|---|
| 188 | TT ACC CCT GTG GCA AAA GCC GAA GTG CAG CTG GTG GAG TCT GG |
| 944 | TT ACC CCT GTG GCA AAA GCC CAG GTG CAG CTG GTG CAG TCT GG |
| 948 | TT ACC CCT GTG GCA AAA GCC CAG GTG CAG CTG GTG GAG TCT GG |
| 952 | GA TGG GCC CTT GGT GGA GGC |

Table B. Kappa chain oligonucleotides used to amplify cDNA from Hco7 mice, Hco12 mice, and Hco7/Co12 mice. Oligonucleotide 973 (SEQ ID NO:15) is the 3' primer and the rest are 5' primers.

TABLE B

Kappa chain oligonucleotides used to amplify cDNA from Hco7 mice, Hco12 mice, and Hco7/Co12 mice. Oligonucleotide 973 (SEQ ID NO: 15) is the 3' primer and the rest are 5' primers.

| OLIGO # | 5' TO 3' SEQUENCE |
|---|---|
| 189 | CT GCC CAA CCA GCC ATG GCC GAA ATT GTG CTC ACC CAG TCT CC |
| 931 | TC GCT GCC CAA CCA GCC ATG GCC GTC ATC TGG ATG ACC CAG TCT CC |
| 932 | TC GCT GCC CAA CCA GCC ATG GCC AAC ATC CAG ATG ACC CAG TCT CC |
| 933 | TC GCT GCC CAA CCA GCC ATG GCC GCC ATC CGG ATG ACC CAG TCT CC |
| 934 | TC GCT GCC CAA CCA GCC ATG GCC GCC ATC CAG TTG ACC CAG TCT CC |
| 935 | TC GCT GCC CAA CCA GCC ATG GCC GAA ATA GTG ATG ACG CAG TCT CC |
| 936 | TC GCT GCC CAA CCA GCC ATG GCC GAT GTT GTG ATG ACA CAG TCT CC |
| 937 | TC GCT GCC CAA CCA GCC ATG GCC GAA ATT GTG TTG ACG CAG TCT CC |
| 955 | TC GCT GCC CAA CCA GCC ATG GCC GAC ATC CAG ATG ATC CAG TCT CC |
| 956 | TC GCT GCC CAA CCA GCC ATG GCC GAT ATT GTG ATG ACC CAG ACT CC |
| 973 | CAG CAG GCA CAC AAC AGA GGC |

Table C. Heavy chain oligonucleotides used to amplify cDNA for Hco12 mice. Oligonucleotides 944, 945, 946, 947 and 948 (SEQ ID NOS:2, 16, 17, 18, and 3 respectively) are 5' primers and oligonucleotide 952 (SEQ ID NO:4) is the 3' primer. The sequences of 944, 948 and 952 (SEQ ID NOS: 2, 3, and 4 respectively) are shown in Table A.

TABLE C

Heavy chain oligonucleotides used to amplify cDNA for Hco12 mice. Oligonucleotides 944, 945, 946, 947 and 948 (SEQ ID NOS: 2, 16, 17, 18, and 3 respectively) are 5' primers and oligonucleotide 952 (SEQ ID NO: 4) is the 3' primer. The sequences of 944, 948 and 952 (SEQ ID NOS: 2, 3, and 4 respectively) are shown in Table A.

| OLIGO # | 5' TO 3' SEQUENCE |
|---|---|
| 945 | TT ACC CCT GTG GCA AAA GCC GAG GTG CAG CTG TTG GAG TCT GG |
| 946 | TT ACC CCT GTG GCA AAA GCC GAG GTG CAG CTG GTG CAG TCT GG |
| 947 | TT ACC CCT GTG GCA AAA GCC CAG GTG CAG CTA CAG CAG TGG GG |

The dsDNA products of the PCR process were then subjected to asymmetric PCR using only 3' primer to generate substantially only the anti-sense strand of the target genes. Oligonucleotide 953 was used as the 3' primer for kappa chain asymmetric PCR (Table D) and oligonucleotide 952 was used as the 3' primer for heavy chain asymmetric PCR (Table A). For each spleen, two asymmetric reactions were run for the kappa chain PCR products to primer 189, 931, 932, 933, 934, 936, 955, and 956, (SEQ ID NOS: 5, 6, 7, 8, 9, 11, 13 and 14 respectively), four asymmetric reactions were run for the kappa chain PCR product to primer 935 (SEQ ID NO:10), and eight asymmetric reactions were run for the kappa chain PCR product to primer 937 (SEQ ID NO:12). The number of asymmetric reactions used for each heavy chain PCR product was dependent on the mouse genotype. For Co7 mice, eight asymmetric reactions were run for each PCR product. For Co12 mice, eight asymmetric reactions were run for the PCR product from primer 944 (SEQ ID NO:2), and four asymmetric reactions were run for the PCR products from the other primers. For Co7/Co12 mice, six asymmetric reactions were run for the PCR products from primers 944 and 948 (SEQ ID NOS: 2 and 3), and three asymmetric reactions were run for the PCR products from the other primers. Each reaction described above is 100 µL total volume with 200 pmol of 3' primer, 2 µL of ds-DNA product, 0.5 µL Taq DNA Polymerase, 10 µL 2 mM dNTP's, 10 µL 10×Taq DNA polymerase buffer with $MgCl_2$, and $H_2O$ to 100 µL. Heavy chain reactions were amplified using the thermal profile described above, while kappa chain reactions were amplified with the same thermal profile but 25 cycles were used instead of 30 cycles.

TABLE D

Oligonucleotide sequences used for asymmetric PCR of kappa chains.

| OLIGO # | 5' TO 3' SEQUENCE |
|---|---|
| 953 | GAC AGA TGG TGC AGC CAC AGT (SEQ ID NO:19) |

EXAMPLE 4

Purification of ss-DNA by High Performance Liquid Chromatography and Kinasing ss-DNA The H chain ss-PCR products and the L chain ss-PCR products were separately pooled and ethanol precipitated by adding 2.5 volumes ethanol and 0.2 volumes 7.5 M ammonium acetate and incubating at −20° C. for at least 30 min. The DNA was pelleted by centrifuging at 15,000 rpm for 15 min at 2–8° C. The supernatant was carefully aspirated, and the tubes were briefly spun a 2nd time. The last drop of supernatant was removed with a pipet. The DNA was dried in vacuo for 10 min on medium heat. The H chain products were dissolved in 210 µL water and the L chain products were dissolved separately in 210 µL water. The ss-DNA was purified by high performance liquid chromatography (HPLC) using a Hewlett Packard 1090 HPLC and a Gen-Pak™ FAX anion exchange column (Millipore Corp., Milford, Mass.). The gradient used to purify the ss-DNA is shown in Table 1, and the oven temperature was at 60° C. Absorbance was monitored at 260 nm. The ss-DNA eluted from the HPLC was collected in 0.5 min fractions. Fractions containing ss-DNA were pooled, ethanol precipitated, pelleted and dried as described above. The dried DNA pellets were resuspended in 200 µL sterile water.

TABLE 1

HPLC gradient for purification of ss-DNA

| Time (min) | % A | % B | % C | Flow (mL/min) |
|---|---|---|---|---|
| 0 | 70 | 30 | 0 | 0.75 |
| 2 | 40 | 60 | 0 | 0.75 |
| 17 | 15 | 85 | 0 | 0.75 |
| 18 | 0 | 100 | 0 | 0.75 |
| 23 | 0 | 100 | 0 | 0.75 |
| 24 | 0 | 0 | 100 | 0.75 |
| 28 | 0 | 0 | 100 | 0.75 |
| 29 | 0 | 100 | 0 | 0.75 |
| 34 | 0 | 100 | 0 | 0.75 |
| 35 | 70 | 30 | 0 | 0.75 |

Buffer A is 25 mM Tris, 1 mM EDTA, pH 8.0
Buffer B is 25 mM Tris, 1 mM EDTA, 1M NaCl, pH 8.0
Buffer C is 40 mm phosphoric acid The ss-DNA was kinased on the 5' end in preparation for mutagenesis (Example 7). 24 µL 10×kinase buffer (United States Biochemical, Cleveland, Ohio), 10.4 µL 10 mM adenosine-5'-triphosphate (Boehringer Mannheim, Indianapolis, Ind.), and 2 µL polynucleotide kinase (30 units/µL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of equilibrated phenol (pH>8.0, United States Biochemical, Cleveland, Ohio)-chloroform-isoamyl alcohol (50:49:1) and one extraction with chloroform:isoamyl alcohol (49:1). After the extractions, the DNA was ethanol precipitated and pelleted as described above. The DNA pellets were dried, then dissolved in 50 µL sterile water. The concentration was determined by measuring the absorbance of an aliquot of the DNA at 260 nm using 33 µg/mL for an absorbance of 1.0. Samples were stored at −20° C.

EXAMPLE 5

Construction of Antibody Phage Display Vector Having Human Antibody Constant Region Sequences The antibody phage display vector for cloning antibodies was derived from an M13 vector supplied by Ixsys, designated 668-4. The vector 668-4 contained the DNA sequences encoding the heavy and light chains of a mouse monoclonal Fab fragment inserted into a vector described by Huse, WO 92/06024. The vector had a Lac promoter, a pelB signal sequence fused to the 5' side of the L chain variable region of the mouse antibody, the entire kappa chain of the mouse antibody, an alkaline phosphatase signal sequence at the 5' end of the H chain variable region of the mouse antibody, the entire variable region and the first constant region of the H chain, and 5 codons of the hinge region of an IgG1 H chain. A decapeptide sequence was at the 3' end of the H chain hinge region and an amber stop codon separated the decapeptide sequence from the pseudo-gene VIII sequence. The amber stop allowed expression of H chain fusion proteins with the gene VIII protein in *E. coli* suppressor strains such as XL1 blue (Stratagene, San Diego, Calif.), but not in nonsuppressor cell strains such as MK30 (Boehringer Mannheim, Indianapolis, Ind.) (see FIG. 1).

To make the first derivative cloning vector, deletions were made in the variable regions of the H chain and the L chain by oligonucleotide directed mutagenesis of a uracil template (Kunkel, *Proc. Natl. Acad. Sci. USA* 82:488 (1985); Kunkel, et al., *Methods. Enzymol.* 154:367 (1987)). These mutations deleted the region of each chain from the 5' end of CDR1 to the 3' end of CDR3, and the mutations added a DNA sequence where protein translation would stop (see FIG. 2 for mutagenesis oligonucleotides). This prevented the expression of H or L chain constant regions in clones without an insert, thereby allowing plaques to be screened for the presence of insert. The resulting cloning vector was called BS11.

Many changes were made to BS11 to generate the cloning vector used in the present screening methods. The amber stop codon between the heavy chain and the pseudo gene VIII sequence was removed so that every heavy chain was expressed as a fusion protein with the gene VIII protein. This increased the copy number of the antibodies on the phage relative to BS11. A HindIII restriction enzyme site in the sequence between the 3' end of the L chain and the 5' end of the alkaline phosphatase signal sequence was deleted so antibodies could be subcloned into a pBR322 derivative (Example 14). The interchain cysteine residues at the carboxyl-terminus of the L and H chains were changed to serine residues. This increased the level of expression of the antibodies and the copy number of the antibodies on the phage without affecting antibody stability. Nonessential DNA sequences on the 5' side of the lac promoter and on the 3' side of the pseudo gene VIII sequence were deleted to reduce the size of the M13 vector and the potential for rearrangement. A transcriptional stop DNA sequence was added to the vector at the L chain cloning site to replace the translational stop so that phage with only heavy chain proteins on their surface, which might be nonspecifically in panning, could not be made. Finally, DNA sequences for protein tags were added to different vectors to allow enrichment for polyvalent phage by metal chelate chromatography (polyhistidine sequence) or by affinity purification using a decapeptide tag and a magnetic latex having an immobilized antibody that binds the decapeptide tag. BS45 had a polyhistidine sequence between the end of the heavy chain constant region and the pseudo-gene VIII sequence, and a decapeptide sequence at the 3' end of the kappa chain constant region.

The mouse heavy and kappa constant region sequences were deleted from BS45 by oligonucleotide directed mutagenesis. Oligonucleotide 864 was used to delete the mouse kappa chain and oligonucleotide 862 was used to delete the mouse heavy chain.

Oligonucleotide 864 (SEQ ID NO:20)

5' ATC TGG CAC ATC ATA TGG ATA AGT TTC GTG TAC AAA ATG CCA GAC CTA GAG GAA TTT TAT TTC CAG CTT GGT CCC

Oligonucleotide 862 (SEQ ID NO:21)

5' GTG ATG GTG ATG GTG ATG GAT CGG AGT ACC AGG TTA TCG AGC CCT CGA TAT TGA GGA GAC GGT GAC TGA

Deletion of both constant region sequences was determined by amplifying the DNA sequence containing both constant regions by PCR using oligonucleotides 5 and 197, followed by sizing the PCR products on DNA agarose gel. The PCR was accomplished as described in Example 3 for the double-stranded DNA, except 1 µL of phage was template instead of cDNA. Phage with the desired deletion had a shorter PCR product than one deletion or no deletion. Uracil template was made from one phage stock having both deletions, as described in Example 6. This template, BS50, was used to insert the human constant region sequences for the kappa chain and IgG1.

Primer 5 (SEQ ID NO:22)

5' GCA ACT GTT GGG AAG GG

Primer 197 (SEQ ID NO:23)

5' TC GCT GCC CAA CCA GCC ATG

The human constant region DNA sequences were amplified from human spleen cDNA (Clontech, Palo Alto, Calif.). Oligonucleotides 869 and 870 were used to amplify the kappa constant region sequence, and oligonucleotides 867 and 876 were used to amplify the IgG1 constant region sequence and the codons for 6 amino acids of the hinge region (Kabat et al., Sequences of Proteins of Immunological Interest, 1991).

5' PCR primer (869)—GGG ACC AAG CTG GAA ATA AAA CGG GCT GTG GCT GCA CCA TCT GTC T (SEQ ID NO:24)

3' PCR primer (870)—ATC TGG CAC ATC ATA TGG ATA AGA CTC TCC CCT GTT GAA GCT CTT (SEQ ID NO:25)

5' PCR primer (867)—TCA GTC ACC GTC TCC TCA GCC TCC ACC AAG GGC CCA TC (SEQ ID NO:26)

3' PCR primer (876)—GTG ATG GTG ATG GTG ATG AGA TTT GGG CTC TGC TTT CTT GTC C (SEQ ID NO:27)

PCR (1–50 µL reaction for each chain) was performed using Expand high-fidelity PCR system (Roche Molecular Biochemicals, Indianapolis, Ind.). Each 50 µL reaction contained 50 pmol of 5' primer, 50 pmol of 3' primer, 0.35 units of Expand DNA polymerase, 5 µL 2 mM dNTP's, 5 µL 10×Expand reaction buffer, 1 µL cDNA as template, and water to 50 µL. The reaction was carried out in a Perkin-Elmer thermal cycler (Model 9600) using the following thermal profile for the kappa chain: one cycle of denaturation at 94° C. (1 min); ten cycles of denaturation (15 sec, 94° C.), annealing (30 sec, 55° C.), elongation (60 sec, 72° C.); fifteen cycles of denaturation (15 sec, 94° C.), annealing (30 sec, 55° C.), elongation (80 sec plus 20 sec for each additional cycle, 72° C.); elongation (6 min, 72° C.); soak (4° C., indefinitely). The thermal profile used for the heavy chain reaction had twenty cycles instead of fifteen in the second part of the thermal profile.

The dsDNA products of the PCR process were then subjected to asymmetric PCR using only 3' primer to generate substantially only the anti-sense strand of the human constant region genes, as described in Example 3. Five reactions were done for the kappa chain and ten reactions were done for the heavy chain (100 µL per reaction). The thermal profile for both constant region genes is the same as that described in Example 3, including the heavy chain asymmetric PCR was done with 30 cycles and the kappa chain asymmetric PCR was done with 25 cycles. The single stranded DNA was purified by HPLC as described in Example 4. The HPLC purified kappa chain DNA was dissolved in 55 µL of water and the HPLC purified heavy chain was dissolved in 100 µL of water. The DNA was quantified by absorbance at 260 nm, as described in Example 4, then the DNA was kinased as described in Example 4 except added 6 µL 10×kinase buffer, 2.6 µL 10 mM ATP, and 0.5 µL of polynucleotide kinase to 50 µL of kappa chain DNA. Twice those volumes of kinase reagents were added to 100 µL of heavy chain DNA.

The kinased DNA was used to mutate BS50 without purifying the DNA by extractions. The mutagenesis was performed on a 2 µg scale by mixing the following in a 0.2 mL PCR reaction tube: 8 µl of (250 ng/µl) BS50 uracil template, 8 µl of 10×annealing buffer (200 mM Tris pH 7.0, 20 mM $MgCl_2$, 500 mM NaCl), 2.85 µl of kinased single-stranded heavy chain insert (94 ng/µl), 6.6 µl of kinased single-stranded kappa chain insert (43.5 ng/µl), and sterile water to 80 µl. DNA was annealed in a GeneAmp® 9600 thermal cycler using the following thermal profile: 20 sec at 94° C., 85° C. for 60 sec, 85° C. to 55° C. ramp over 30 min, hold 55° C. for 15 min. The DNA was transferred to ice after the program finished. The extension/ligation was carried out by adding 8 µl of 10×synthesis buffer (5 mM each dNTP, 10 mM ATP, 100 mM Tris pH 7.4, 50 mM $MgCl_2$, 20 mM DTT), 8 µl T4 DNA ligase (1 U/µl, Roche Molecular Biochemicals, Indianapolis, Ind.), 8 µl diluted T7 DNA polymerase (1 U/µl, New England BioLabs, Beverly, Mass.) and incubating at 37° C. for 30 min. The reaction was stopped with 296 µl of mutagenesis stop buffer (10 mM Tris pH 8.0, 10 mM EDTA). The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 µl of sterile water. 1 µl mutagenesis DNA was (500 ng) was transferred into 40 µl electrocompetent *E. coli* DH12S (Gibco/BRL, Gaithersburg, Md.) using the electroporation conditions in Example 8. The transformed cells were mixed with 1.0 mL 2×YT broth (Sambrook, et al., supra) and transferred to a 15 mL sterile culture tube. Aliquots (10 µL of $10^{-3}$ and $10^{-4}$ dilutions) of the transformed cells were plated on 100 mm LB agar plates as described in Example 11. After 6 hr of growth at 37° C., 20 individual plaques were picked from a plate into 2.75 mL 2×YT and 0.25 ml overnight XL1 blue cells. The cultures were grown at 37° C., 300 rpm overnight to amplify the phage from the individual plaques. The phage samples were analyzed for insertion of both constant regions by PCR using oligonucleotides 197 and 5 (see above in BS50 analysis), followed by sizing of the PCR products by agarose gel electrophoresis. The sequence of two clones having what appeared to be two inserts by agarose gel electrophoresis was verified at MacConnell Research (San Diego, Calif.) by the dideoxy chain termination method using a Sequatherm sequencing kit (Epicenter Technologies, Madison, Wis.) and a LI-COR 4000L automated sequencer (LI-COR, Lincoln, Nev.). Oligonucleotide primers 885 and 5, that bind on the 3' side of the kappa chain and heavy chain respectively, were used. Both clones had the correct sequence. The uracil template having human constant region sequences, called BS46, was prepared as described in Example 6.

Primer 885

5' TAA GAG CGG TAA GAG TGC CAG (SEQ ID NO:28)

EXAMPLE 6

Preparation of Uracil Templates Used in Generation of Spleen Antibody Phage Libraries 1 mL of *E. coli* CJ236 (BioRAD, Hercules, Calif.) overnight culture and 10 μL of a 1/100 dilution of vector phage stock was added to 50 ml 2×YT in a 250 mL baffled shake flask. The culture was grown at 37° C. for 6 hr. Approximately 40 mL of the culture was centrifuged at 12,000 rpm for 15 minutes at 4° C. The supernatant (30 mL) was transferred to a fresh centrifuge tube and incubated at room temperature for 15 minutes after the addition of 15 μl of 10 mg/ml RnaseA (Boehringer Mannheim, Indianapolis, Ind.). The phage were precipitated by the addition of 7.5 ml of 20% polyethylene glycol 8000 (Fisher Scientific, Pittsburgh, Pa.)/3.5M ammonium acetate (Sigma Chemical Co., St. Louis, Mo.) and incubation on ice for 30 min. The sample was centrifuged at 12,000 rpm for 15 min at 2–8° C. The supernatant was carefully discarded, and the tube was briefly spun to remove all traces of supernatant. The pellet was resuspended in 400 μl of high salt buffer (300 mM NaCl, 100 mM Tris pH 8.0, 1 mM EDTA), and transferred to a 1.5 mL tube. The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and ⅕ volume 7.5 M ammonium acetate and incubated 30 min at −20° C. The DNA was centrifuged at 14,000 rpm for 10 min at 4° C., the pellet washed once with cold 70% ethanol, and dried in vacuo. The uracil template DNA was dissolved in 100 μl sterile water and the concentration determined by $A_{260}$ using an absorbance of 1.0 for a concentration of 40 μg/ml. The template was diluted to 250 ng/μl with sterile water, aliquoted, and stored at −20° C.

EXAMPLE 7

Mutagenesis of Uracil Template with ss-DNA and Electroporation Into *E. coli* to Generate Antibody Phage Libraries Antibody phage-display libraries were generated by simultaneously introducing single-stranded heavy and light chain genes onto a phage-display vector uracil template. A typical mutagenesis was performed on a 2 μg scale by mixing the following in a 0.2 mL PCR reaction tube: 8 μl of (250 ng/μl) BS46 uracil template (examples 5 and 6), 8 μl of 10×annealing buffer (200 mM Tris pH 7.0, 20 mM $MgCl_2$, 500 mM NaCl), 3.33 μl of kinased single-stranded heavy chain insert (100 ng/μl), 3.1 μl of kinased single-stranded light chain insert (100 ng/ml), and sterile water to 80 μl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 μl of 10×synthesis buffer (5 mM each dNTP, 10 mM ATP, 100 mM Tris pH 7.4, 50 mM $MgCl_2$, 20 mM DTT), 8 μl T4 DNA ligase (1 U/μl), 8 μl diluted T7 DNA polymerase (1 U/μl) and incubating at 37° C. for 30 min. The reaction was stopped with 300 μl of mutagenesis stop buffer (10 mM Tris pH 8.0, 10 mM EDTA). The mutagenesis DNA was extracted once with equilibrated phenol (pH>8): chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 μl of sterile water. 1 μl mutagenesis DNA was (500 ng) was transferred into 40 μl electrocompetent *E. coli* DH12S (Gibco/BRL, Gaithersburg, Md.) using the electroporation conditions in Example 8. The transformed cells were mixed with 0.4 mL 2×YT broth (Sambrook, et al., supra) and 0.6 mL overnight XL1 Blue cells, and transferred to 15 mL sterile culture tubes. The first round antibody phage samples were generated by plating the electroporated samples on 150 mm LB plates as described in Example 11. The plates were incubated at 37° C. for 4 hr, then 20° C. overnight. The first round antibody phage was eluted from the 150 mm plates by pipeting 10 mL 2YT media onto the lawn and gently shaking the plate at room temperature for 20 min. The phage were transferred to 15 mL disposable sterile centrifuge tubes with plug seal cap and the debris from the LB plate was pelleted by centrifuging for 15 min at 3500 rpm. The $1^{st}$ round antibody phage was then transferred to a new tube.

The efficiency of the electroporation was measured by plating 10 μl of $10^{-3}$ and $10^{-4}$ dilutions of the cultures on LB agar plates (see Example 11). These plates were incubated overnight at 37° C. The efficiency was determined by multiplying the number of plaques on the $10^{-3}$ dilution plate by $10^5$ or multiplying the number of plaques on the $10^{-4}$ dilution plate by $10^6$.

EXAMPLE 8

Transformation of *E. coli* by Electroporation

The electrocompetent *E. coli* cells were thawed on ice. DNA was mixed with 20–40 μL electrocompetant cells by gently pipetting the cells up and down 2–3 times, being careful not to introduce air-bubble. The cells were transferred to a Gene Pulser cuvette (0.2 cm gap, BioRAD, Hercules, Calif.) that had been cooled on ice, again being careful not to introduce an air-bubble in the transfer. The cuvette was placed in the *E. coli* Pulser (BioRAD, Hercules, Calif.) and electroporated with the voltage set at 1.88 kV according to the manufacturer's recommendation. The transformed sample was immediately diluted to 1 ml with 2×YT broth or 1 ml of a mixture of 400 μL 2×YT/600 μL overnight XL1 Blue cells and processed as procedures dictate.

EXAMPLE 9

Preparation of Biotinylated Interleukin 8 (IL8)

IL8 was dialyzed against a minimum of 100 volumes of 20 mM borate, 150 mM NaCl, pH 8 (BBS) at 2–8° C. for at least 4 hr. The buffer was changed at least once prior to biotinylation. IL8 was reacted with biotin-XX-NHS ester (Molecular Probes, Eugene, Oreg., stock solution at 40 mM in dimethylformamide) at a final concentration of 1 mM for 1 hr at room temperature. After 1 hr, the IL8 was extensively dialyzed into BBS to remove unreacted small molecules.

EXAMPLE 10

Preparation of Avidin Magnetic Latex

The magnetic latex (superparamagnetic microparticles, 0.96 μm, Estapor, 10% solids, Bangs Laboratories, Carmel, Ind.) was thoroughly resuspended and 2 ml aliquoted into a 15 ml conical tube. The magnetic latex was suspended in 12 ml distilled water and separated from the solution for 10 min using a magnet. While still in the magnet, the liquid was carefully removed with a 10 mL sterile pipet. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture vortexed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM TRIS, 1.50 mM NaCl, 20 mg/mL BSA, 0.1% Tween 20 (Fisher Scientific, Pittsburgh, Pa.), pH 7.5). The avidin magnetic latex needed for a panning experiment (200 μl/sample) was added to a sterile 15 ml centrifuge tube and brought to 10 ml with panning buffer. The tube was placed on the magnet for 10 min to separate the latex. The solution was carefully removed with a 10 mL sterile pipet as described above. The magnetic latex was resuspended in 10 mL of panning buffer to begin the second wash. The magnetic latex was washed a total of 3 times with panning buffer. After the final wash, the latex was resuspended in panning buffer to the initial aliquot volume.

EXAMPLE 11

Plating M13 Phage or Cells Transformed with Antibody Phage-display Vector Mutagenesis Reaction The phage samples were added to 200 μL of an overnight culture of *E. coli* XL1-Blue when plating on 100 mm LB agar plates or to 600 μL of overnight cells when plating on 150 mm plates in sterile 15 ml culture tubes. The electroporated phage samples were in 1 mL 2×YT/overnight XL1 cells, as described in Example 8, prior to plating on 150 mm plates. After adding LB top agar (3 mL for 100 mm plates or 9 mL for 150 mm plates, top agar stored at 55° C., Appendix A1, Molecular Cloning, A Laboratory Manual, (1989) Sambrook. J), the mixture was evenly distributed on an LB agar plate that had been pre-warmed (37° C.–55° C.) to remove any excess moisture on the agar surface. The plates were cooled at room temperature until the top agar solidified. The plates were inverted and incubated at 37° C. as indicated.

EXAMPLE 12

Develop Nitrocellulose Filters with Alkaline Phosphatase (AP) Conjugates

After overnight incubation of the nitrocellulose filters on LB agar plates, the filters were carefully removed from the plates with membrane forceps and incubated for 2 hr in block (1% bovine serum albumin (from 30% BSA, Bayer, Kankakee, Ill.), 10 mM Tris, 150 mM NaCl, 1 mM $MgCl_2$, 0.1 mM $ZnCl_2$, 0.1% polyvinyl alcohol (80% hydrolyzed, Aldrich Chemical Co., Milwaukee, Wis.), pH 8.0).

After 2 hr, the filters were incubated with goat anti-human kappa AP (Southern Biotechnology Associates, Inc, Birmingham, Ala.) for 2–4 hr. The AP conjugate was diluted into block at a final concentration of 1 μg/mL. Filters were washed 3 times with 40 mM TRIS, 150 mM NaCl, 0.05% Tween 20, pH 7.5 (TBST) (Fisher Chemical, Pittsburgh, Pa.) for 5 min each. After the final wash, the filters were developed in a solution containing 0.2 M 2-amino-2-methyl-1-propanol (JBL Scientific, San Luis Obispo, Calif.), 0.5 M TRIS, 0.33 mg/mL nitro blue tetrazolium (Fisher Scientific, Pittsburgh, Pa.) and 0.166 mg/mL 5-bromo-4-chloro-3-indolyl-phosphate, p-toluidine salt.

EXAMPLE 13

Enrichment of Polyclonal Phage to Human Interleukin-8 Using a Decapeptide Tag on the Kappa Chain The first round antibody phage was prepared as described in Example 7 using BS46 uracil template, which has a decapeptide tag for polyvalent enrichment fused to the kappa chain. Fourteen electroporations of mutagenesis DNA were done from 7 different spleens (2 electroporations from each spleen) yielding 14 different phage samples. Prior to functional panning, the antibody phage samples were enriched for polyvalent display using the decapeptide tag on the kappa chain and the 7F11 magnetic latex. Binding studies had previously shown that the decapeptide could be eluted from the monoclonal antibody 7F11 (see Example 17) at a relatively mild pH of 10.5–11. The 7F11 magnetic latex (2.9 mL) was equilibrated with panning buffer as described above for the avidin magnetic latex (Example 10). Each first round phage stock (1 mL) was aliquoted into a 15 mL tube. The 7F11 magnetic latex (200 μL per phage sample) was incubated with phage for 10 min at room temperature. After 10 min, 9 mL of panning buffer was added, and the magnetic latex was separated from unbound phage by placing the tubes in a magnet for 10 min. After 10 min in the magnet, the unbound phage was carefully removed with a 10 mL sterile pipet. The magnetic latex was then resuspended in 1 mL panning buffer and transferred to 1.5 mL tubes. The magnetic latex was separated from unbound phage by placing the tubes in a smaller magnet for 5 min, then the supernatant was carefully removed with a sterile pipet. The latexes were washed with 1 additional 1 mL panning buffer wash. Each latex was resuspended in 1 mL elution buffer (20 mM 3-(cyclohexylamino)propanesulfonic acid (United States Biochemical, Cleveland, Ohio), 150 mM NaCl, 20 mg/mL BSA, pH 10.5) and incubated at room temperature for 10 min. After 10 min, tubes were placed in the small magnet again for 5 min and the eluted phage was transferred to a new 1.5 mL tube. The phage samples were again placed in the magnet for 5 min to remove the last bit of latex that was transferred. Eluted phage was carefully removed into a new tube and 25 µL 3 M Tris, pH 6.8 was added to neutralize the phage. Panning with IL8-biotin was set up for each sample by mixing 900 µL 7F11/decapeptide enriched phage, 100 µL panning buffer, and 10 µL $10^{-7}$ M IL8-biotin and incubating overnight at 2–8° C.

The antibody phage samples were panned with avidin magnetic latex. The equilibrated avidin magnetic latex (see Example 11), 200 µL latex per sample, was incubated with the phage for 10 min at room temperature. After 10 min, approximately 9 mL of panning buffer was added to each phage sample, and the magnetic latex was washed as described above for the 7F11 magnetic latex. A total of one 9 mL and three 1 mL panning buffer washes were done. After the last wash, each latex was resuspended in 200 µL 2×YT, then the entire latex of each sample was plated on 150 mm LB plates to generate the 2nd round antibody phage. The 150 mm plates were incubated at 37° C. for 4 hr, then overnight at 20° C.

The resulting $2^{nd}$ round antibody phage samples were set up for the second round of functional panning in separate 15 mL disposable sterile centrifuge tubes with plug seal cap by mixing 900 µL panning buffer, 100 µL $2^{nd}$ round antibody phage, and 10 µL $10^{-7}$M interleukin-8-biotin. After overnight incubation at 2–8° C., the phage samples were panned with avidin magnetic latex as described above. Aliquots of one sample from each spleen were plated on 100 mm LB agar plates to determine the percentage of kappa positives (Example 12). The percentage of kappa positives for the 2nd round of panning was between 83–92% for 13 samples. One sample was discarded because it was 63% kappa positive.

The remaining thirteen samples were set up for a third round of functional panning as described above using 950 µL panning buffer, 50 µL $3^{rd}$ round antibody phage, and 10 µL $10^{-6}$M interleukin-8-biotin. After incubation for 1.5 hours at 2–8° C., the phage samples were panned with avidin magnetic latex, and nitrocellulose filters were placed on each phage sample, as described above. The percentage of kappa positives for the 4th round antibody phage samples was estimated to be greater than 80%.

The 4th round antibody phage samples were titered by plating 50 µL $10^{-8}$ dilutions on 100 mm LB plates. After 6 hr at 37° C., the number of plaques on each plate were counted, and the titers were calculated by multipying the number of plaques by $2 \times 10^9$. A pool of 13—4th round phage was made by mixing an equal number of phage from each phage stock so that high titer phage stocks would not bias the pool. The pooled antibody phage was set up in duplicate for a $4^{th}$ round of functional panning as described above using 950 µL panning buffer, 50 µL 4th round pooled-antibody phage. One sample (foreground) received 10 µL $10^{-6}$M interleukin-8-biotin and the other sample (background) did not receive interleukin-8-biotin and served as a blank to monitor non-specific binding of phage to the magnetic latex. After incubation for 1.5 hours at 2–8° C., the phage samples were panned with avidin magnetic latex as described above. The next day, the $5^{th}$ round antibody phage was eluted and the number of plaques was counted on the foreground and background plates. The foreground:background ratio was 58:1.

The $5^{th}$ round antibody phage was set up in triplicate as described above using 950 µL panning buffer, 50 µL 5th round antibody phage per sample with the experimental (foreground) tubes receiving 10 µL $10^{-7}$M interleukin-8-biotin or 10 µL $10^{-8}$M interleukin-8-biotin, respectively. The third tube did not receive any interleukin-8-biotin. This round of panning or affinity selection preferentially selects for antibodies of >$10^9$ affinity and >$10^{10}$ affinity by including the interleukin-8-biotin at a final concentration of $10^{-9}$ M and $10^{-10}$ M, respectively. After greater than 24 hours at 2–8° C., the phage samples were panned with avidin magnetic latex and processed as described above. The $6^{th}$ round antibody phage sample $10^{-9}$ M cut had a foreground:background ratio 1018:1 and the $10^{-10}$M cut had a foreground:background ratio 225:1.

An additional round of panning was done on the $6^{th}$ round $10^{-10}$ M cut antibody phage to increase the number of antibodies with affinity of $10^{10}$. The $6^{th}$ round phage were set up as described above using 975 µL panning buffer, 25 µL 6th round antibody phage per sample with the experimental (foreground) tube receiving 10 µL $10^{-8}$M interleukin-8-biotin. The blank did not receive any interleukin-8-biotin. After overnight incubation at 2–8° C., the phage samples were panned with avidin magnetic latex and processed as described above. The $7^{th}$ round antibody phage sample $10^{-10}$ M cut had a foreground:background ratio 276:1. The antibody phage populations were subcloned into the expression vector and electroporated as described in Example 15.

EXAMPLE 14

Construction of the pBR Expression Vector

An expression vector and a process for the subcloning of monoclonal and polyclonal antibody genes from a phage-display vector has been developed that is efficient, does not substantially bias the polyclonal population, and can select for vector containing an insert capable of restoring antibiotic resistance. The vector is a modified pBR322 plasmid, designated pBRncoH3, that contains an arabinose promoter, ampicillin resistance (beta-lactamase) gene, a partial tetracycline resistance gene, a pelB (pectate lyase) signal sequence, and NcoI and HindIII restriction sites. (FIG. 3). The pBRncoH3 vector can also be used to clone proteins other than Fabs with a signal sequence. A second vector, pBRnsiH3, has been developed for cloning proteins with or without signal sequences, identical to the vector described above except that the pelB signal sequence is deleted and the NcoI restriction site has been replaced with an NsiI site.

The araC regulatory gene (including the araBAD promoter) was amplified from *E. coli* K-12 strain NL31-001 (a gift from Dr. Nancy Lee at UCSB) by PCR (Example 3) using Taq DNA polymerase (Boehringer Mannheim, Indianapolis, Ind.) with primers A and B (Table 3). Primers A and B contain 20 base-pairs of the BS39 vector sequence at their 5'-ends complementary to the 5' side of the lac promoter and the 5' side of the pelB signal sequence, respectively. Primer A includes an EcoRI restriction site at its 5'-end used later for ligating the ara insert into the pBR vector. The araCparaBAD PCR product was verified by agarose gel electrophoresis and used as template for an asymmetric PCR reaction with primer 'B' in order to generate the anti-sense strand of the insert. The single-stranded product was run on agarose gel electrophoresis, excised, purified with GeneClean (Bio101, San Diego, Calif.), and resuspended in water as per manufacturers recommendations. The insert was kinased with T4 polynucleotide kinase for 45 min at 37° C. The T4 polynucleotide kinase was heat inactivated at 70° C. for 10 min and the insert extracted with an equal volume of phenol/chloroform, followed by chloroform. The DNA was precipitated with ethanol at –20° C.

for 30 min. The DNA was pelleted by centrifugation at 14 krpm for 15 min at 4° C., washed with ice-cold 70% ethanol, and dried in vacuo.

The insert was resuspended in water and the concentration determined by $A_{260}$ using an absorbance of 1.0 for a concentration of 40 µg/ml. The insert was cloned into the phage-display vector BS39 for sequence verification and to introduce the pelB signal sequence in frame with the arabinose promoter (the pelB signal sequence also contains a NcoI restriction site at its 3'-end used later for ligating the ara insert into the pBR vector). The cloning was accomplished by mixing 250 ng of BS39 uracil template (Example 5), 150 ng of kinased araCpBAD insert, and 1.0 µl of 10×annealing buffer in a final volume of 10 µl. The sample was heated to 70☐ C. for 2 min and cooled over 20 min to room temperature to allow the insert and vector to anneal. The insert and vector were ligated together by adding 1 µl of 10×synthesis buffer, 1 µl T4 DNA ligase (1U/µl), 1 µl T7 DNA polymerase (1 U/µl) and incubating at 37° C. for 30 min. The reaction was stopped with 90 µl of stop buffer (10 mM Tris pH 8.0, 10 mM EDTA) and 1 µl electroporated (Example 8) into electrocompetent E. coli strain, DH10B, (Life Technologies, Gaithersburg, Md.).

The transformed cells were diluted to 1.0 ml with 2×YT broth and 1 10 µl, 100 µl plated as described in Example 12. Following incubation overnight at 37° C., individual plaques were picked, amplified by PCR with primers A and B, and checked for full-length insert by agarose gel electrophoresis. Clones with full-length insert were sequenced with primers D, E, F, G (Table 3) and checked against the literature. An insert with the correct DNA sequence was amplified by PCR (Example 3) from BS39 with primers A and C (FIG. 4A) and the products run on agarose gel electrophoresis.

Full-length products were excised from the gel and purified as described previously and prepared for cloning by digestion with EcoRI and NcoI. A pBR lac-based expression vector that expressed a murine Fab was prepared to receive this insert by EcoRI and NcoI digestion. This digestion excised the lac promoter and the entire coding sequence up to the 5'-end of the heavy chain ($C_H1$) constant region (FIG. 4A).

The insert and vector were mixed (2:1 molar ratio) together with 1 µl 10 mM ATP, 1 µl (1U/µl) T4 DNA ligase, 1 µl 10×ligase buffer in a final volume of 10 µl and ligated overnight at 15° C. The ligation reaction was diluted to 20 µl, and 1 µl electroporated into electrocompetent E. coli strain, DH10B (Example 8), plated on LB tetracycline (10 µg/ml) plates and grown overnight at 37° C.

Clones were picked and grown overnight in 3 ml LB broth supplemented with tetracycline at 20 µg/ml. These clones were tested for the correct insert by PCR amplification (Example 3) with primers A and C, using 1 µl of overnight culture as template. Agarose gel electrophoresis of the PCR reactions demonstrated that all clones had the araCparaB insert. The vector (plasmid) was purified from each culture by Wizard miniprep columns (Promega, Madison, Wis.) following manufacturers recommendations. The new vector contained the araC gene, the araB promoter, the pelB signal sequence, and essentially the entire $C_H1$ region of the heavy chain (FIG. 4B).

The vector was tested for expression by re-introducing the region of the Fab that was removed by EcoRI and NcoI digestion. The region was amplified by PCR, (Example 3) from a plasmid (20 ng) expressing 14F8 with primers H and I (Table 3). The primers, in addition to having sequence specific to 14F8, contain 20 base-pairs of vector sequence at their 5'-end corresponding to the 3'-end of the pelB signal sequence and the 5'-end of the $C_H1$ region for cloning purposes. The PCR products were run on agarose gel electrophoresis and full-length products excised from the gel and purified as described previously.

The vector was linearized with NcoI and together with the insert, prepared for cloning through the 3'→5' exonuclease activity of T4 DNA polymerase. The insert and NcoI digested vector were prepared for T4 exonuclease digestion by aliquoting 1.0 µg of each in separate tubes, adding 1.0 µl of 10×restriction endonuclease Buffer A (Boehringer Mannheim, Indianapolis, Ind.) and bringing the volume to 9.0 µl with water. The samples were digested for 5 min at 30° C. with 1 µl (1U/µl) of T4 DNA polymerase. The T4 DNA polymerase was heat inactivated by incubation at 70° C. for 15 min. The samples were cooled, briefly spun, and the digested insert (35 ng) and vector (100 ng) mixed together and the volume brought to 10 µl with 1 mM $MgCl_2$. The sample was heated to 70° C. for 2 min and cooled over 20 min to room temperature to allow the complementary 5' single-stranded overhangs of the insert and vector resulting from the exonuclease digestion to anneal together (FIG. 5). The annealed DNA (1.5 µl) was electroporated (Example 8) into 30 µl of electrocompetent E. coli strain DH10B.

The transformed cells were diluted to 1.0 ml with 2×YT broth and 1 µl, 10 µl, and 100 µl plated on LB agar plates supplemented with tetracycline (10 µg/ml) and grown overnight at 37° C. The following day, two clones were picked and grown overnight in 2×YT (10 µg/ml tetracycline) at 37° C. To test protein expression driven from the ara promoter, these cultures were diluted 1/50 in 2×YT(tet) and grown to $OD_{600}=1.0$ at which point they were each split into two cultures, one of which was induced by the addition of arabinose to a final concentration of 0.2% (W/V). The cultures were grown overnight at room temperature, and assayed for Fab production by ELISA. Both of the induced cultures were producing approximately 20 µg/ml Fab. There was no detectable Fab in the uninduced cultures.

Initial efforts to clone polyclonal populations of Fab were hindered by backgrounds of undigested vector ranging from 3–13%. This undigested vector resulted in loss of Fab expressing clones due to the selective advantage non-expressing clones have over Fab expressing clones. A variety of means were tried to eliminate undigested vector from the vector preparations with only partial success; examples including: digesting the vector overnight 37° C. with NcoI, extracting, and redigesting the preparation a second time; including spermidine in the NcoI digest; including single-stranded binding protein (United States Biochemical, Cleveland, Ohio) in the NcoI digest; preparative gel electrophoresis. It was then noted that there is a HindIII restriction site in pBR, 19 base-pairs from the 5'-end of the tetracycline promoter. A vector missing these 19 base-pairs is incapable of supporting growth in the presence of tetracycline, eliminating background due to undigested vector.

The ara-based expression vector was modified to make it tetracycline sensitive in the absence of insert. This was done by digesting the pBRnco vector with NcoI and HindIII (Boehringer Mannheim, Indianapolis, Ind.), which removed the entire antibody gene cassette and a portion of the tet promoter (FIG. 4B). The region excised by NcoI/HindIII digestion was replaced with a stuffer fragment of unrelated DNA by ligation as described above. The ligation reaction was diluted to 20 µl, and 1 µl electroporated (Example 8) into electrocompetent E. coli strain DH10B, plated on LB ampicillin (100 µg/ml) and incubated at 37° C.

After overnight incubation, transformants were picked and grown overnight in LB broth supplemented with ampicillin (100 µg/ml). The vector (plasmid) was purified from each culture by Wizard miniprep columns following manufacturers recommendations. This modified vector, pBRncoH3, is tet sensitive, but still retains ampicillin resistance for growing preparations of the vector.

The antibody gene inserts were amplified by PCR with primers I and J (Table 3) as described in Example 3; primer J containing the 19 base-pairs of the tet promoter removed by HindIII digestion, in addition to 20 base-pairs of vector sequence 3' to the HindIII site for annealing. This modified vector was digested with NcoI/HindIII and, together with the insert, exonuclease digested and annealed as described previously. The tet resistance is restored only in clones that contain an insert capable of completing the tet promoter. The annealed Fab/vector (1 µl) was transformed (Example 8) into 30 µl of electrocompetent E. coli strain, DH10B.

The transformed cells were diluted to 1.0 ml with 2xYT broth and 10 µl of $10^{-2}$ and $10^{-3}$ dilutions plated on LB agar plates supplemented with tetracycline at 10 µg/ml to determine the size of the subcloned polyclonal population. This plating also provides and opportunity to pick individual clones from the polyclonal if necessary. The remaining cells were incubated at 37° C. for 1 hr and then diluted 1/100 into 30 ml 2xYT supplemented with 1% glycerol and 20 µg/ml tetracycline and grown overnight at 37° C. The overnight culture was diluted 1/100 into the same media and grown 8 hr at which time glycerol freezer stocks were made for long term storage at −80° C.

The new vector eliminates growth bias of clones containing vector only, as compared to clones with insert. This, together with the arabinose promoter which is completely repressed in the absence of arabinose, allows cultures of transformed organisms to be expanded without biasing the polyclonal antibody population for antibodies that are better tolerated by E. coli until induction.

A variant of this vector was also constructed to clone any protein with or without a signal sequence. The modified vector has the NcoI restriction site and all of the pelB signal-sequence removed. In its place a NsiI restriction site was incorporated such that upon NsiI digestion and then T4 digestion, there is single base added, in frame, to the araBAD promoter that becomes the adenosine residue (A) of the ATG initiation codon. The HindIII site and restoration of the tetracycline promoter with primer J (Table 3) remains the same as described for the pBRncoH3 vector. Additionally, the T4 exonuclease cloning process is identical to that described above, except that the 5' PCR primer used to amplify the insert contains 20 bp of vector sequence at its 5'-end corresponding to 3'-end of the araBAD promoter rather than the 3'-end of the PelB signal sequence.

Three PCR primers, K, L, and M (Table 3) were used for amplifying the araC regulatory gene (including the araBAD promoter). The 5'-primer, primer K, includes an EcoRI restriction site at its 5'-end for ligating the ara insert into the pBR vector. The 3'-end of the insert was amplified using two primers because a single primer would have been too large to synthesize. The inner 3'-primer (L) introduces the NsiI restriction site, in frame, with the araBAD promoter, with the outer 3' primer (M) introducing the HindIII restriction site that will be used for ligating the insert into the vector.

The PCR reaction was performed as in Example 3 on a 4×100 µl scale; the reactions containing 100 pmol of 5' primer (K), 1 pmol of the inner 3' primer (L), and 100 pmol of outer 3' primer (M), 10 µl 2 mM dNTPs, 0.5 µL Taq DNA Polymerase, 10 µl 10×Taq DNA polymerase buffer with MgCl$_2$, and H$_2$O to 100 µL. The araCparaBAD PCR product was precipitated and fractionated by agarose gel electrophoresis and full-length products excised from the gel, purified, resuspended in water, and prepared for cloning by digestion with EcoRI and HindIII as described earlier. The pBR vector (Life Technologies, Gaithersburg, Md.) was prepared to receive this insert by digestion with EcoRI and HindIII and purification by agarose gel electrophoresis as described above.

The insert and vector were mixed (2:1 molar ratio) together with 1 µl 10 mM ATP, 1 µl (1 U/µl) T4 DNA ligase, 1 µl 10×ligase buffer in a final volume of 10 µl and ligated overnight at 15° C. The ligation reaction was diluted to 20 µl, and 1 µl electroporated into electrocompetent E. coli strain, DH10B (Example 8), plated on LB tetracycline (10 µg/ml) plates and grown overnight at 37° C. Clones were picked and grown overnight in 3 ml LB broth supplemented with tetracycline.

These clones were tested for the correct insert by PCR amplification (Example 3) with primers K and M, using 1 µl of overnight culture as template. Agarose gel electrophoresis of the PCR reactions demonstrated that all clones had the araCparaB insert. The vector (plasmid) was purified from each culture by Wizard miniprep columns following manufacturers recommendations. The new vector, pBRnsi contained the araC gene, the araBAD promoter, and a NsiI restriction site.

The vector was tested for expression by introducing a murine Fab. The region was amplified by PCR (Example 3) from a plasmid (20 ng) containing a murine Fab with primers O and N (Table 3). The primers, in addition to having sequence specific to the Fab, contain 20 bp of vector sequence at their 5'-end corresponding to the 3'-end araBAD promoter and the 5'-end of the C$_H$1 region for cloning purposes. The pBRnsi vector was linearized with NsiI and HindIII. The vector and the PCR product were run on an agarose gel, and full-length products were excised from the gel and purified as described previously. The vector and insert were digested with T4 DNA polymerase and annealed as described earlier. The annealed DNA (1 µl) was electroporated (Example 8) into 30 µl of electrocompetent E. coli strain DH10B. The transformed cells were diluted to 1.0 ml with 2xYT broth and 1 µl, 10 µl, and 100 µl plated on LB agar plates supplemented with tetracycline (10 µg/ml) and grown overnight at 37° C.

Nitrocellulose lifts were placed on the placed on the surface of the agar plates for 1 min and processed as described (Section 12.24, Molecular Cloning, A laboratory Manual, (1989) Sambrook. J.). The filters were developed with goat anti-kappa-AP, and a positive (kappa expressing) clone was picked and grown overnight in 2xYT (10 µg/ml tetracycline) at 37° C. The vector (plasmid) was purified from the culture by Wizard miniprep columns (Promega, Madison, Wis.) following manufacturers recommendations. The Fab region was excised by NcoI/HindIII digestion and replaced with a stuffer fragment of unrelated DNA by ligation as described above. The ligation reaction was diluted to 20 µl, and 1 µl electroporated (Example 8) into electrocompetent E. coli strain DH10B, plated on LB ampicillin (100 µg/ml) and incubated at 37° C. After overnight incubation, transformants were picked and grown overnight in LB broth supplemented with ampicillin (100 µg/ml). The vector (plasmid) was purified from each culture by Wizard miniprep columns following manufacturers recommendations. This modified vector, pBRnsiH3, is tet sensitive, but still retains ampicillin resistance for growing preparations of the vector.

EXAMPLE 15

Subcloning Polyclonal Fab Populations into Expression Vectors and Electroporation into *Escherichia coli*

The polyclonal IL8 antibody phage form both the $10^9$ and $10^{10}$ affinity cuts (see Example 13) were diluted 1/30 in 2×YT and 1 μl used as template for PCR amplification of the antibody gene inserts with primers 197 (Example 5) and 970 (see below). PCR (3–100 μL reactions) was performed using a high-fidelity PCR system, Expand (Roche Molecular Biochemicals, Indianapolis, Ind.) to minimize errors incorporated into the DNA product. Each 100 μl reaction contained 100 pmol of 5' primer 197, 100 pmol of 3' primer 970, 0.7 units of Expand DNA polymerase, 10 μl 2 mM dNTPs, 10 μl 10×Expand reaction buffer, 1 μl diluted phage stock as template, and water to 100 μl. The reaction was carried out in a Perkin-Elmer thermal cycler (Model 9600) using the following thermal profile: one cycle of denaturation at 94° C. (1 min); ten cycles of denaturation (15 sec, 94° C.), annealing (30 sec, 55° C.), elongation (60 sec, 72° C.); fifteen cycles of denaturation (15 sec, 94° C.), annealing (30 sec, 55° C.), elongation (80 sec plus 20 sec for each additional cycle, 72° C.); elongation (6 min, 72° C.); soak (4° C., indefinitely). The PCR products were ethanol precipitated, pelleted and dried as described above. The DNA was dissolved in water and fractionated by agarose gel electrophoresis. Only full-length products were excised from the gel, purified, and resuspended in water as described earlier.

Primer 970—5' GT GAT AAA CTA CCG TA AAG CTT ATC GAT GAT AAG CTG TCA A TTA GTG ATG GTG ATG GTG ATG AGA TTT G (SEQ ID NO:29)

The insert and NcoI/HindIII digested pBRncoH3 vector were prepared for T4 exonuclease digestion by adding 1.0 μl of 10×Buffer A to 1.0 μg of DNA and bringing the final volume to 9 μl with water. The samples were digested for 4 min at 30° C. with 1 μl (1U/μl) of T4 DNA polymerase. The T4 DNA polymerase was heat inactivated by incubation at 70° C. for 10 min. The samples were cooled, briefly spun, and 100 ng of the digested antibody gene insert and 1 μl of 10×annealing buffer were mixed with 100 ng of digested vector in a 1.5 mL tube. The volume was brought to 10 μl with water, heated to 70° C. for 2 min and cooled over 20 min to room temperature to allow the insert and vector to anneal. The insert and vector were ligated together by adding 1 μl of 10×synthesis buffer, 1 μl T4 DNA ligase (1U/μl), 1 μl diluted T7 DNA polymerase (1U/μl) and incubating at 37° C. for 15 min.

The ligated DNA (1 μl) was diluted into 2 μL of water, then 1 μL of the diluted DNA was electroporated (Example 8) into 40 μl of electrocompetent *E. coli* strain, DH10B. The transformed cells were diluted to 1.0 ml with 2×YT broth and 10 μl of $10^{-1}$, $10^{-2}$ and $10^{-3}$ dilutions plated on LB agar plates supplemented with tetracycline at 10 μg/ml to determine the size of the subcloned polyclonal population. The $10^9$ affinity polyclonal had approximately 6000 different clones, and the $10^{10}$ affinity polyclonal had approximately 10,000 different clones. The remaining cells were incubated at 37° C., 300 rpm for 1 hr, and then the entire culture was transferred into 50 ml 2×YT supplemented with 1% glycerol and 20 μg/ml tetracycline and grown overnight at 37° C. The overnight culture was diluted 1/100 into the same media, grown 8 hr, and glycerol freezer stocks made for long term storage at −80° C.

Monoclonal antibodies were obtained by picking individual colonies off the LB agar plates supplemented with tetracycline used to measure the subcloning efficiency or from plates streaked with cells from the glycerol freezer stocks. The picks were incubated overnight at 37° C., 300 rpm in a shake flask containing 2×YT media and 10 μg/mL tetracyclin. Glycerol freezer stocks were made for each monoclonal for long term storage at −80° C. A total of 15 different colonies were picked off of the $10^9$ affinity cut and analyzed for binding to IL8. Of those 15 clones, two expressed a very low amount of antibody, one expressed antibody but did not bind IL8, two expressed functional antibody but the DNA sequence was ambiguous most likely due to sequence template quality, and one expressed functional protein but was not sequenced. Nine clones were sequenced as described in Example 22. A total of 21 different colonies were picked off of the $10^{10}$ affinity cut and analyzed for binding to IL8. Of those 21 clones, four expressed a very low amount of antibody, three expressed antibody but did not bind IL8, and four expressed functional protein but were not sequenced. Ten clones were sequenced as described in Example 22.

EXAMPLE 16

Expression of IL8 or Antibodies in Shake Flasks and Purification

A shake flask inoculum is generated overnight from a −80° C. cell bank or from a colony (Example 15) in an incubator shaker set at 37° C., 300 rpm. The cells are cultured in a defined medium described above. The inoculum is used to seed a 2 μL Tunair shake flask (Shelton Scientific, Shelton, Conn.) which is grown at 37° C., 300 rpm. Expression is induced by addition of L(+)-arabinose to 2 g/L during the logarithmic growth phase, following which, the flask is maintained at 23° C., 300 rpm. Following batch termination, the culture is passed through an M-110Y Microfluidizer (Microfluidics, Newton, Mass.) at 17000 psi.

Purification employs immobilized metal affinity chromatography. Chelating Sepharose FastFlow resin (Pharmacia, Piscataway, N.J.) is charged with 0.1 M $NiCl_2$ and equilibrated in 20 mM borate, 150 mM NaCl, 10 mM imidazole, 0.01% $NaN_3$, pH 8.0 buffer. A stock solution is used to bring the culture to 10 mM imidazole. The supernatant is then mixed with the resin and incubated for at least 1 hour in the incubator shaker set at room temperature, 150–200 rpm. IL8 or antibody is captured by means of the high affinity interaction between nickel and the hexahistidine tag on the protein. After the batch binding is complete, the resin is allowed to settle to the bottom of the bottle for at least 10 min. The culture is carefully poured out of the bottle, making sure that the resin is not lost. The remaining culture and resin mixture is poured into a chromatography column. After washing, the protein is eluted with 20 mM borate, 150 mM NaCl, 200 mM imidazole, 0.01% $NaN_3$, pH 8.0 buffer. If needed, the protein pool is concentrated in a Centriprep-10 concentrator (Amicon, Beverly, Mass.) at 3500 rpm. It is then dialyzed overnight into 20 mM borate, 150 mM NaCl, 0.01% $NaN_3$, pH 8.0 for storage, using 12–14,000 MWCO dialysis tubing.

IL8 was furthur purified by the following procedure. The protein was dialyzed exhaustively against 10 mM sodium phosphate, 150 mM sodium chloride, pH 7.35, and diluted 1:3 with 10 mM sodium phosphate, pH 7.35. This material was loaded onto a Q-Sepharose column (Amersham Pharmacia Biotech, Piscataway, N.J.) equilibrated in 10 mM sodium phosphate, 40 mM NaCl. The IL8 was contained in the flow through fraction. By SDS-polyacrylamide gel analysis, the IL8 was greater than 95% pure. The IL8 was brought to 120 mM NaCl and 0.01% $NaN_3$ and stored at −80° C.

EXAMPLE 17

Preparation of 7F11 Monoclonal Antibody
Synthesis of Acetylthiopropionic Acid To a stirred solution of 3-mercaptopropionic acid (7 ml, 0.08 moles) and imidazole (5.4 g, 0.08 moles) in tetrahydrofuran (THF, 700 ml) was added dropwise over 15 min, under argon, a solution of 1-acetylimidazole (9.6 g, 0.087 moles) in THF (100 ml). The solution was allowed to stir a further 3 hr at room temperature after which time the THF was removed in vacuo. The residue was treated with ice-cold water (18 ml) and the resulting solution acidified with ice-cold concentrated HCl (14.5 ml) to pH 1.5–2. The mixture was extracted with water (2×50 ml), dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44–45° C.

Decapeptide Derivatives

The decapeptide, YPYDVPDYAS, (SEQ ID NO:30), (Chiron Mimotopes Peptide Systems, San Diego, Calif.) was dissolved (0.3 g) in dry DMF (5.4 mL) in a round bottom flask under argon with moderate stirring. Imidazole (0.02 g) was added to the stirring solution. Separately, acetylthiopropionic acid (0.041 g) was dissolved in 0.55 mL of dry DMF in a round bottom flask with stirring and 0.056 g of 1,1'-carbonyldiimidazole (Aldrich Chemical Co., Milwaukee, Wis.) was added to the stirring solution. The flask was sealed under argon and stirred for at least 30 min at room temperature. This solution was added to the decapeptide solution and the reaction mixture was stirred for at least six hr at room temperature before the solvent was removed in vacuo. The residue in the flask was triturated twice using 10 mL of diethyl ether each time and the ether was decanted. Methylene chloride (20 mL) was added to the residue in the flask and the solid was scraped from the flask and filtered using a fine fritted Buchner funnel. The solid was washed with an additional 20 mL of methylene chloride and the Buchner funnel was dried under vacuum. In order to hydrolyze the derivative to generate a free thiol, it was dissolved in 70% DMF and 1 M potassium hydroxide was added to a final concentration of 0.2 M while mixing vigorously. The derivative solution was allowed to stand for 5 min at room temperature prior to neutralization of the solution by the addition of a solution containing 0.5 M potassium phosphate, 0.1 M borate, pH 7.0, to which concentrated hydrochloric acid has been added to a final concentration of 1 M. The thiol concentration of the hydrolyzed decapeptide derivative was determined by diluting 10 μL of the solution into 990 μL of a solution containing 0.25 mM 5,5'-dithiobis (2-nitrobenzoic acid) (DTNB, Aldrich Chemical Co., Milwaukee Wis.) and 0.2 M potassium borate, pH 8.0. The thiol concentration in mM units was equal to the A412(100/13.76).

Preparation of Conjugates of Decapeptide Derivative with Keyhole Limpet Hemocyanin and Bovine Serum Albumin Keyhole limpet hemocyanin (KLH, 6 ml of 14 mg/ml, Calbiochem, San Diego, Calif.) was reacted with sulfosuccinimidyl 4-(N-maleimidomethyl)cyclohexane-1-carboxylate (SULFO-SMCC) by adding 15 mg of SULFO-SMCC and maintaining the pH between 7 and 7.5 with 1N potassium hydroxide over a period of one hr at room temperature while stirring. The protein was separated from the unreacted SULFO-SMCC by gel filtration chromatography in 0.1 M potassium phosphate, 0.02 M potassium borate, and 0.15 M sodium chloride, pH 7.0, and 24 ml of KLH-maleimide was collected at a concentration of 3.1 mg/ml. The hydrolyzed decapeptide derivative was separately added to portions of the KLH-maleimide in substantial molar excess over the estimated maleimide amounts present and the solution was stirred for 4 hr at 4° C. and then each was dialyzed against 3 volumes of one liter of pyrogen-free phosphate-buffered saline, pH7.4, prior to immunization.

Bovine serum albumin (BSA, 3.5 ml of 20 mg/ml) was reacted with SMCC by adding a solution of 6.7 mg of SMCC in 0.3 ml acetonitrile and stirring the solution for one hr at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. The hydrolyzed decapeptide derivative was separately added to portions of the BSA-maleimide in substantial molar excess over the estimated maleimide amounts present and the solution was stirred for 4 hr at 4° C. The solutions were used to coat microtiter plates for the detection of antibodies that bound to the decapeptide derivative by standard techniques.

Production and Primary Selection of Monoclonal Antibodies

Immunization of Balb/c mice was performed according to the method of Liu, et al. *Clin Chem* 25:527–538 (1987). Fusions of spleen cells with SP2/0-Ag 14 myeloma cells, propagation of hybridomas, and cloning were performed by standard techniques. Selection of hybridomas for further cloning began with culture supernatant at the 96-well stage. A standard ELISA procedure was performed with a BSA conjugate of decapeptide derivative adsorbed to the ELISA plate. Typically, a single fusion was plated out in twenty plates and approximately 10–20 wells per plate were positive by the ELISA assay. At this stage, a secondary selection could be performed if antibodies to the SMCC part of the linking arm were to be eliminated from further consideration. An ELISA assay using BSA derivatized with SMCC but not linked to the decapeptide derivative identified which of the positive clones that bound the BSA conjugates were actually binding the SMCC-BSA. The antibodies specific for SMCC-BSA may be eliminated at this step. Monoclonal antibody 7F11, specific for the decapeptide derivative, was produced and selected by this process.

EXAMPLE 18

Preparation of 7F11 Magnetic Latex
MAG/CM-BSA

To 6 mL of 5% magnetic latex (MAG/CM, 740 μm 5.0%, Seradyn, Indianapolis, Ind.) was added 21 mL of water followed by 3 mL of 600 mM 2-(4-morpholino)-ethane sulfonic acid, pH 5.9 (MES, Fisher Scientific, Pittsburgh, Pa.). Homocysteine thiolactone hydrochloride (HCTL, 480 mg, Aldrich Chemical Co., Milwaukee, Wis.) and 1-(3-Dimethylaminopropyl)-3-ethylcarbodiimide (EDAC, 660 mg, Aldrich Chemical Co., Milwaukee, Wis.) were added in succession, and the reaction mixture was rocked at room temperature for 2 h. The derivatized magnetic latex was washed 3 times with 30 mL of water (with magnet as in Example 14) using probe sonication to resuspend the particles. The washed particles were resuspended in 30 mL of water. Three mL of a solution containing sodium hydroxide (2M) and EDTA (1 mM) was added to the magnetic latex-HCTL suspension, and the reaction proceeded at room temperature for 5 min. The pH was adjusted to 6.9 with 6.45 mL of 1 M hydrochloric acid in 500 mM sodium phosphate, 100 mM sodium borate. The hydrolyzed magnetic latex-HCTL was separated from the supernate with the aid of a magnet, and then resuspended in 33 mL of 50 mM sodium phosphate, 10 mM sodium borate, 0.1 mM EDTA, pH 7.0. The magnetic latex suspension was then added to 2 mL of 36 mg mL-1 BSA-SMCC (made as described in Example 21 with a 5-fold molar excess of SMCC over BSA), and the reaction mixture was rocked overnight at room temperature. N-Hydroxyethylmaleimide (NHEM, 0.42 mL of 500 mM, Organix Inc., Woburn, Mass.) was added to cap any remaining thiols for 30 min. After 30 min, the magnetic latex-BSA was washed twice with 30 mL of 50 mM potassium phosphate, 10 mM potassium borate, 150 mM sodium chloride, pH 7.0 (50/10/150) and twice with 30 mL of 10 mM potassium phosphate, 2 mM potassium borate, 200 mM sodium thiocyanate, pH 7.0 (10/2/200). The magnetic latex-BSA was resuspended in 30 mL of 10/2/200.

7F11-SH (1:5)

To a solution of 7F11 (3.8 mL of 5.85 mg mL$^{-1}$) was added 18 μL of SPDP (40 mM in acetonitrile). The reaction proceeded at room temperature for 90 min after which taurine (Aldrich Chemical Co., Milwaukee, Wis.) was added to a final concentration of 20 mM. Fifteen min later DTT was added to a final concentration of 2 mM, and the reduction reaction proceeded at room temperature for 30 min. The 7F11-SH was purified on G-50 (40 mL) that was eluted with 50/10/150 plus 0.1 mM EDTA. The pool of purified 7F11-SH was reserved for coupling to the MAG/CM-BSA-SMCC.

MAG/CM-BSA-7F11

SMCC (10 mg) was dissolved in 0.5 mL of dry dimethylformamide (Aldrich Chemical Co., Milwaukee, Wis.), and this solution was added to the magnetic latex-BSA suspension. The reaction proceeded at room temperature with gentle rocking for 2 h. Taurine was added to a final concentration of 20 mM. After 20 min the magnetic latex-BSA-SMCC was separated from the supernate with the aid of a magnet and then resuspended in 10/2/200 (20 mL) with probe sonication. The magnetic latex was purified on a column of Superflow-6 (240 mL, Sterogene Bioseparations Inc., Carlsbad, Calif.) that was eluted with 10/2/200. The buffer was removed, and to the magnetic latex cake was added 30 mL of 0.7 mg mL$^{-1}$ 7F11-SH. The reaction mixture was rocked overnight at room temperature. After 20 hr the reaction was quenched with mercaptoethanol (2 mM, Aldrich Chemical Co., Milwaukee, Wis.) followed by NHEM (6 mM). The MAG/CM-7F11 was washed with 10/2/200 followed by 50/10/150. The magnetic latex was then resuspended in 30 mL of 50/10/150.

EXAMPLE 19

Cloning of the Mature Human Interleukin-8 Antigen

PCR primers A and B (5' and 3' respectively, Table 3) were made corresponding to the coding sequence at the 5'-end of the mature human interleukin-8 antigen and the coding sequence at the 3'-end of human interleukin-8 (Genbank accession number M28130). The 5' primer contains 20 base pairs of vector sequence at its 5'-end corresponding to the 3'-end of the pBRncoH3 vector (Example 14). The 3' primer has six histidine codons inserted between the end of the coding sequence and the stop codon to assist in purification of the recombinant protein by metal-chelate chromatography. The 3' primer also has 19 base-pairs of tet promoter removed from the tet resistance gene in pBRncoH3 by HindIII digestion, and base-pairs of vector sequence 3' to the HindIII site at its 5' end (Example 14).

The PCR amplification of the mature interleukin-8 gene insert was done on a 3×100 μl reaction scale each containing 100 pmol of 5' primer (A), 100 pmol of 3' primer (B), 2.5 units of Expand polymerase, 10 μl 2 mM dNTPs, 10 μl 10×Expand reaction buffer, 1 μl of Clontech Quick-clone human liver cDNA (Clontech Laboratories, Palo Alto, Calif.) as template, and water to 100 μl. The reaction was carried out in a Perkin-Elmer thermal cycler as described in Example 18. The PCR products were precipitated and fractionated by agarose gel electrophoresis and full-length products excised from the gel, purified, and resuspended in water (Example 17). The insert and NcoI/HindIII digested pBRncoH3 vector were prepared for T4 exonuclease digestion by adding 1.0 μl of 10×Buffer A to 1.0 μg of DNA and bringing the final volume to 9 μl with water. The samples were digested for 4 minutes at 30° C. with 1 μl (1U/μl) of T4 DNA polymerase. The T4 DNA polymerase was heat inactivated by incubation at 70° C. for 10 minutes. The samples were cooled, briefly spun, and 15 ng of the digested insert added to 100 ng of digested pBRncoH3 vector in a fresh microfuge tube. After the addition of 1.0 μl of 10×annealing buffer, the volume was brought to 10μl with water. The mixture was heated to 70° C. for 2 minutes and cooled over 20 minutes to room temperature, allowing the insert and vector to anneal. The annealed DNA was diluted one to four with distilled water and electroporated (example 8) into 30μl of electrocompetent E. coli strain, DH10B. The transformed cells were diluted to 1.0 ml with 2×YT broth and 10 μl, 100 μl, 300 μl plated on LB agar plates supplemented with tetracycline (10 μg/ml) and grown overnight at 37° C. Colonies were picked and grown overnight in 2×YT (20 μg/ml tetracycline at 37° C. The following day glycerol freezer stocks were made for long term storage at −80° C. The sequence of these clones was verified at MacConnell Research (San Diego, Calif.) by the dideoxy chain termination method using a Sequatherm sequencing kit (Epicenter Technologies, Madison, Wis.), oligonucleotide primers C and D (Table 3) that bind on the 5' and 3' side of the insert in the pBR vector, respectively, and a LI-COR 4000L automated sequencer (LI-COR, Lincoln, Nev.).

Table 3. PCR and Sequencing Primer Sequences (SEQ ID NOS:31, 32, 33 and 34 respectively)

TABLE 3

PCR and Sequencing Primer Sequences
(SEQ ID NOS: 31, 32, 33 and 34 respectively)

A- 5' (TCGCTGCCCAACCAGCCATGGCCAGTGCTAAAGAACTTAGATCTCAG)
B- 5' (GTGATAAACTACCGCATTAAAGCTTATCGATGATAAGCTGTCAATTAGTGAT
GGTGATGGTGATGTGAATTCTCAGCCCTCTTCAA)
C- 5' (GCAACTCTCTACTGTTTCTCC)
D- 5' (GAGGATGACGATGAGCGC)

EXAMPLE 20

Estimation of Library Diversity

Upon the completion of library selection for a given target antigen, the library contains members encoding antibodies exhibiting an affinity determined by the criteria used during the selection process. Preferably, the selection process is repeated until the majority of the members in the library encode antibodies exhibiting the desired characteristics. Most preferably, the selection process is repeated until substantially all of the members of the library encode antibodies that exhibit the desired affinity for the target antigen. In order to estimate the number of different antibodies in the selected library, individual members are randomly chosen and sequenced to determine if their amino acid sequences are different. Antibodies exhibiting at least one amino acid difference in either the heavy or light chain variable domain (preferably in the CDRs) are considered different antibodies. A random sampling of the library in such a manner provides an estimate of the frequency antibody copies in the library. If ten antibodies are randomly sampled and each antibody amino acid sequence is distinct from the other sampled antibodies, then an estimate of 1/10 can be applied to the frequency that one might expect to observe for repeated antibodies in the library. A library with hundreds or thousands of total members will exhibit a probability distribution for the frequency of antibody copies that closely approximates the Poisson distribution, $Pr(y)=e^{-\eta}\eta^y/y!$, where the probability of a particular value y of the frequency is dependent only on the mean frequency $\eta$. If no antibody replicates are observed in a random sampling of ten antibodies, then an estimate for $\eta$ is 0.1 and the probability of not observing a copy of a library member when randomly sampling the library is estimated by $Pr(0)=e^{-0.1}=0.9$. Multiplying this probability by the total number of members in the library provides an estimate of the total number of different antibodies in the library.

EXAMPLE 21

Determination of Antibody Affinity for IL-8 Labeled with Biotin

The equilibrium binding constants of individual monoclonal antibodies were determined by analysis of the total and free antibody concentrations after a binding equilibrium was established in the presence of biotinylated IL-8 at $10^{-10}$ M in a 1% solution of bovine serum albumin buffered at pH 8.0. In all experiments the antibody was mixed with IL-8 and incubated overnight at room temperature before the biotin-labeled IL-8 was removed from the solution by adding superparamagnetic microparticles (0.96 $\mu$m, Bangs Laboratories, Carmel, Ind.) coated with NeutrAvidin™ (deglycosylated avidin, Pierce, Rockford, Ill.) incubating for 10 minutes, and separating the particles from the solution using a permanent magnet. The supernatant solution was removed from the microtiter wells containing the magnetic particles and the antibody concentration was determined. The concentration of total antibody added to the individual wells was determined by quantifying the antibody in a sample that was not mixed with IL-8. The concentration of immunoreactive antibody (the fraction of the antibody protein that was capable of binding to IL-8) was determined by incubating a large excess of biotin-labeled IL-8 with a known concentration of antibody for a sufficient time to reach equilibrium, removing the IL-8 using magnetic latex as described above, and quantifying the concentration of antibody left in the solution using the assay described below. The fraction of antibody that bound to the excess of IL-8 is the immunoreactive fraction and the fraction that did not bind to IL-8 is the non-immunoreactive fraction. When determining the concentration of total antibody in an equilibrium mixture, the antibody concentration is the amount of total antibody in the mixture determined from the assay described below multiplied by the immunoreactive fraction. Similarly, when calculating the free antibody in an equilibrium mixture after the removal of IL-8, the non-immunoreactive fraction of antibody is subtracted from the free antibody concentration determined by the assay described below. The bound fraction, B, is determined by subtracting the free immunoreactive antibody concentration in the mixture, F, from the total immunoreactive antibody concentration in the mixture. From the Law of Mass Action, $B/F=-KB+KT$ where T is the total antigen concentration. A plot of B/F vs. B yields a slope of $-K$ and a y-intercept of KT.

To determine the antibody concentrations in samples a sandwich assay was constructed using immobilized monoclonal antibody 7F11 to bind the decapeptide tag present a the C-terminus of the kappa chain and affinity-purified goat-anti-human kappa antibody conjugated to alkaline phosphatase (Southern Biotechnology Associates, Birmingham, Ala.) to bind the kappa chain of each human antibody. A purified antibody of known concentration with the same kappa chain construction as the assayed antibodies was used to calibrate the assay. The 7F11 antibody was labeled with biotin and immobilized on microtiter plates coated with streptavidin using standard methods. The assay was performed by adding 50 $\mu$l of sample from the equilibrium mixtures to each well and incubating for four hours at room temperature. The conjugate was added at a final concentration of approximately 0.125 $\mu$g/ml to each well and incubated overnight at room temperature. The wells were washed using an automatic plate washer with borate buffered saline containing 0.02% polyoxyethylene 20-sorbitan monolaurate at pH 8.2 and the ELISA Amplification System (Life Technologies, Gaithersburg, Md.) was employed to develop the assay. The absorbance at 490 nm was measured using a microtiter plate reader and the unknown antibody concentrations were determined from the standard curve.

TABLE 4

| Monoclonal Antibody | % Immunoreactive Protein | Affinity ($10^{10}$ $M^{-1}$) |
|---|---|---|
| M1-3 | 93 | 6.1 |
| M1-4 | 93 | 22 |
| M1-5 | 90 | 11 |
| M1-8 | 91 | 10 |
| M1-10 | 90 | 6.1 |
| M1-21 | 67 | 6.6 |
| M1-23 | 91 | 8.9 |
| M1-25 | 90 | 6.4 |
| M2-11 | 93 | 10 |
| M2-12 | 93 | 28 |
| M2-16 | 90 | 1.9 |
| M2-18 | 80 | 5.4 |
| M2-20 | 94 | 37 |
| M2-34 | 94 | 27 |

EXAMPLE 22

DNA Sequence Analysis of Random Clones

The glycerol freezer stocks (Example 15) corresponding to each monoclonal Fab to be analyzed were used to inoculate 50 ml cultures for plasmid isolation and subsequent DNA sequencing of the interleukin-8 insert. After overnight growth in 2×YT (10 µg/ml tetracycline) at 37° C., the recombinant plasmid was purified using a Qiagen Plasmid Midi kit (Qiagen, Valencia, Calif.) following manufacturer's recommendations. The sequence corresponding to the kappa and heavy chain variable and constant regions for each monoclonal was determined at MacConnell Research (San Diego, Calif.). The nomenclature used for antibodies is the same as that in Example 21. Sequencing was done by the dideoxy chain termination method using a Sequatherm sequencing kit (Epicenter Technologies, Madison, Wis.), oligonucleotide primers C and D (Table 3) that bind on the 5' and 3' side of the Fab cassette in the pBR vector, respectively, and a LI-COR 4000L automated sequencer (LI-COR, Lincoln, Nev.).

M1-1L (SEQ ID NO:35)
AAATTGTGTTGACGCATTCCAGCCAC-
CCTGTCTTTGTCTCCAGGGGAAAGAGC-
CACCCTCTCCTGCAGG GCCAGTCAGGGTGT-
TAGCAGCTACTTAGCCTGGTACCAACAGAAA
CCTGGCCAGGCTCCCAGGCTCCTC ATCTAT-
GATGCATCCAACAGGGCCACTGGCATC-
CCAGCCAGGTTCAGTG-
GCAGTGGGTCTGGGACAGAC
TTCACTCTCACCATCAGCAGCCTAGAGC-
CTGAAGATTTTGCAGTTTATTACTGT-
CAGCAGCGTAGAACT GGCCTCGGACGTTCG-
GCCAAGGGACCAAGGTGGAAATCAAACGAA
CTGTGGCTGCACCATCTGTCTTCA TCTTC-
CCGCCATCTGATGAGCAGTTGAAATCTG-
GAACTGCCTCTGTTGTGCCTGCT-
GAATAACTTCT
ATCCCAGAGAGGCCAAAGTACAGTG-
GAAGGTGGATAACGCCCTCCAATCGGG-
TAACTCCCAGGAGAGTG TCACAGAGCAGGA-
CAGCAAGGACAGCACCTACAGCCTCAGCAGC
ACCCTGACGCTGAGCAAAGCAGACT
ACGAGAAACACAAAGTCTACGCCTGC-
GAAGTCACCCATCAGGGCCTGAGCTCGC-
CCGTCACAAAGAGCT TCAACAGGG-
GAGAGTCTTATCCATATGATGTGCCAGATTAT
GCGAGC

M1-3L (SEQ ID NO:37)
GAAATAGTGATGACGCAGTCTCCAGC-
CACCCTGTCTTTGTCTCCAGGGGAAA-
GAGCCACCCTCTCCTGC AGGGCCAGTCA-
GAGTGTTAGCAGCAGCTACTTAGCCTGGTAC
CAGCAGAAACCTGGCCAGGCTCCCAGG CTC-
CTCATCTATGGTGCATCCAGCAGGGC-
CACTGGCATCCCAGACAGGTTCAGTG-
GCAGTGGGTCTGGG
ACAGACTTCACTCTCACCATCAGCA-
GACTGGAGCCTGA
AGATTTTGCAGTGTATTACTGTCAGCAGTAT
GGTAGCTCACCTCCATTCACTTTCGGC-
CCTGGGACCAAAGTGGATATCAAAC-
GAACTGTGGCTGCACCA TCTGTCTTCATCTTC-
CCGCCATCTGATGAGCAGTTGAAATCTGGAA
CTGCCTCTGTTGTGCCTGCTG AATAACTTC-
TATCCCAGAGAGGCCAAAGTACAGTG-
GAAGGTGGATAACGCCCTCCAATCGGG-
TAACTCC
CAGGAGAGTGTCACAGAGCAGGACAG-
CAAGGACAGCACCTACAGCCTCAGCAG-
CACCCTGACGCTGAGC AAAGCAGACTAC-
GAGAAACACAAAGTCTACGCCTGCGAAGTC
ACCCATCAGGGCCTGAGCTCGCCCGTC
ACAAAGAGCTTCAACAGGGGAGAGTCT-
TATCCATATGATGTGCCAGATTATGCGAGC

M1-4L (SEQ ID NO:39)
GAAATTGTGTTGACGCAGTCTCCAG-
GCACCCTGTCTTTGTCTCCAGGGGAAA-
GAGCCACCCTCTCCTGC AGGGCCAGTCA-
GAGTGTTAGCAGCAGCTACTTAGCCTGGTAC
CAGCAGAAACCTGGCCAGGCTCCCAGG CTC-
CACATCTATGGTGCATCCAGAAGGGC-
CACTGGCATCCCAGACAGGTTCAGTG-
GCAGTGGGTCTGGG
ACAGACTTCACTCTCACCATCAGCA-
GACTGGAGCCTGAAGATTTTGCAGTG-
TATTACTGTCAGCAGTTT GGTAGCTCAT-
TCACTTTCGGCCCTGGGACCAAAGTGGATAT
CAAACGAACTGTGGCTGCACCATCTGTC
TTCATCTTCCCGCCATCTGATGAGCAGT-
TGAAATCTGGAACTGCCTCTGTTGTGT-
GCCTGCTGAATAAC TTCTATCCCAGAGAGGC-
CAAAGTACAGTGGAAGGTGGATAACGCCCTC
CAATCGGGTAACTCCCAGGAG AGTGTCACA-
GAGCAGGACAGCAAGGACAGCACCTA-
CAGCCTCAGCAGCACCCTGACGCTGAG-
CAAAGCA
GACTACGAGAAACACAAAGTCTACGCCT-
GCGAAGTCACCCATCAGGGCCT-
GAGCTCGCCCGTCACAAAG AGCTTCAA-
CAGGGGAGAGTCTTATCCATATGATGTGCCAG
ATTATGCGAGC

M1-5L (SEQ ID NO:41)
GAAATAGTGATGACGCAGTCTCCAG-
GCACCCTGTCTTTGTCTCCAGGGGAAA-
GAGCCACCCTCTCCTGC AGGGCCAGTCA-
GAGTGTTAGCAGCAGCTACTTAGCCTGGTACC
AGCAGAAACCTGGCCAGGCTCCCAGG CTCCT-
CATCTATGGTGCATCCAGCAGGGC-
CACTGGCATCCCAGACAGGTTCAGTG-
GCAGTGGGTCTGGG
ACAGACTTCACTCTCACCATCAGCA-
GACTGGAGCCTGAAGATTTTGCAGTG-
TATTACTGTCAGCAGTAT GGTAGCTCAC-
CTATATTCACTTTCGGCCCTGGGACCAAAGTG
GATATCAAACGAACTGTGGCTGCACCA TCT-

GTCTTCATCTTCCCGCCATCTGATGAG-
CAGTTGAAATCTGGAACTGCCTCTGT-
TGTGTGCCTGCTG
AATAACTTCTATCCCAGAGAGGCCAAAG-
TACAGTGGAAGGTGGATAACGCCCTC-
CAATCGGGTAACTCC CAGGAGAGTGTCACA-
GAGCAGGACAGCAAGGACAGCACCTACAGC
CTCAGCAGCACCCTGACGCTGAGC AAAGCA-
GACTACGAGAAACACAAAGTCTACGCCT-
GCGAAGTCACCCATCAGGGCCT-
GAGCTCGCCCGTC
ACAAAGAGCTTCAACAGGGGAGAGTCT-
TATCCATATGATGTGCCAGATTATGCGAGC

M1-8L (SEQ ID NO:43)
GAAATAGTGATGACGCAGTCTCCAG-
GCACCCTGTCTTTGTCTCCAGGGGAAA-
GAGCCACCCTCTCCTGC AGGGCCAGTCA-
GAGTGTTAGCAGCACCTACTTAGCCTGGTAC
CAGCAGAAACCTGGCCAGGCTCCCAGG CTC-
CTCATCTATGGTGCATCCAGCAGGGC-
CACTGGCATCCAGACAGGTTCAGTG-
GCAGTGGGTCTGGG
ACAGACTTCACTCTCACCATCAGCA-
GACTGGAGCCTGAAGATTTTGCAGTG-
TATTACTGTCAGCAGTAT GTTAGCTCAT-
TCACTTTCGGCCCTGGGACCAAAGTGGATATC
AAACGAACTGTGGCTGCACCATCTGTC
TTCATCTTCCCGCCATCTGATGAGCAGT-
TGAAATCTGGAACTGCCTCTGTTGTGT-
GCCTGCTGAATAAC TTCTATCCCAGAGAGGC-
CAAAGTACAGTGGAAGGTGGATAACGCCCTC
CAATCGGGTAACTCCCAGGAG AGTGTCACA-
GAGCAGGACAGCAAGGACAGCACCTA-
CAGCCTCAGCAGCACCCTGACGCTGAG-
CAAAGCA
GACTACGAGAAACACAAAGTCTACGCCT-
GCGAAGTCACCCATCAGGGCCT-
GAGCTCGCCCGTCACAAAG AGCTTCAA-
CAGGGGAGAGTCTTATCCATATGATGTGCCAG
ATTATGCGAGC

M1-10L (SEQ ID NO:45)
GATGTTGTGATGACACAGTCTCCAGC-
CACCCTGTCTTTGTCTCCAGGGGAAA-
GAGCCACCCTCTCCTGC AGGGCCAGTCA-
GAGTGTTAGCAGCTACTTAGCCTGGTACCAA
CAGAAACCTGGCCAGGCTCCCAGGCTC
CTCATCTATGATGCATCCAACAGGGC-
CACTGGCATCCAGCCAGGTTCAGTG-
GCAGTGGGTCTGGGACA GACTTCACTCTCAC-
CATCAGCAGCCTAGAGCCTGAAGATTTTGCA
GTTTATTACTGTCAGCAGCGTAGC AACTGGC-
CTCCCACTTTCGGCGGAGGGACCAAG-
GTGGAGATCAAACGAACTGTGGCTGCAC-
CATCTGTC
TTCATCTTCCCGCCATCTGATGAGCAGT-
TGAAATCTGGAACTGCCTCTGTTGTGT-
GCCTGCTGAATAAC TTCTATCCCAGAGAGGC-
CAAAGTACAGTGGAAGGTGGATAACGCCCTC
CAATCGGGTAACTCCCAGGAG AGTGTCACA-
GAGCAGGACAGCAAGGACAGCACCTA-
CAGCCTCAGCAGCACCCTGACGCTGAG-
CAAAGCA
GACTACGAGAAACACAAAGTCTACGCCT-
GCGAAGTCACCCATCAGGGCCT-
GAGCTCGCCCGTCACAAAG AGCTTCAA-
CAGGGGAGAGTCTTATCCATATGATGTGCCAG
ATTATGCGAGC

M1-21L (SEQ ID NO:47)
GCCATCCGGATGACCCAGTCTCCATCCT-
TCCTGTCTGCATCTGTAGGAGACAGAGT-
CACCATCACTTGC CGGGCAAGTCAGAGCATT-
AGCAGCTATTTAAATTGGTATCAGCAGAAACC
AGGGAAAGCCCCTAAGCTC CTGATCTATGCTG-
CATCCAGTTTGCAAAGTGGGGTCCCAT-
CAAGGTTCAGTGTCAGTGGATCTGGGACA
GATCTCACTCTCACCATCAGCAGTCTG-
CAACCTGAAGATTTTGCAACTTATTACT-
GTCAGTGTGGTTAC AGTACACCAT-
TCACTTTCGGCCCTGGGACCAAAGTGGATA
TCAAACGAACTGTGGCTGCACCATCTGTC
TTCATCTTCCCGCCATCTGATGAGCAGT-
TGAAATCTGGAACTGCCTCTGTTGTGT-
GCCTGCTGAATAAC TTCTATCCCAGAGAGGC-
CAAAGTACAGTGGAAGGTGGATAACGCCCTC
CAATCGGGTAACTCCCAGGAG AGTGTCACA-
GAGCAGGACAGCAAGGACAGCACCTA-
CAGCCTCAGCAGCACCCTGACGCTGAG-
CAAAGCA
GACTACGAGAAACACAAAGTCTACGCCT-
GCGAAGTCACCCATCAGGGCCT-
GAGCTCGCCCGTCACAAAG AGCTTCAA-
CAGGGGAGAGTCTTATCCATATGATGTGCCAG
ATTATGCGAGC

M1-23L (SEQ ID NO:49)
GAAATTGTGTTGACGCAGTCTCCAG-
GCACCCTGTCTTTGTCTCCAGGGGAAA-
GAGCCACCCTCTCCTGC AGGGCCAGTCA-
GAGTGTTAGCAGCAGCTACTTAGCCTGGTAC
CAGCAGAAACCTGGCCAGGCTCCCAGG CTC-
CTCATCTATGGTGCATCCAGCAGGGC-
CACTGGCATCCAGACAGGTTCAGTG-
GCAGTGGGTCTGGG
ACAGACTTCACTCTCACCATCAGCA-
GACTGGAGCCTGAAGATTTTGCAGTG-
TATTACTGTCAGCAGTAT GGTAGCTCACCTC-
CGTACACTTTTGGCCAGGGGACCAAGCTGGA
GATCAAACGAACTGTGGCTGCACCA TCTGTCT-
TCATCTTCCCGCCATCTGATGAGCAGT-
TGAAATCTGGAACTGCCTCTGTTGTGT-
GCCTGCTG
AATAACTTCTATCCCAGAGAGGCCAAAG-
TACAGTGGAGGGTGGATAACGCCCTC-
CAATCGGGTAACTCC CAGGAGAGTGTCACA-
GAGCAGGACAGCAAGGACAGCACCTACAGCC
TCAGCAGCACCCTGACGCTGAGC AAAGCA-
GACTACGAGAAACACAAAGTCTACGCCT-
GCGAAGTCACCCATCAGGGCCT-
GAGCTCGCCCGTC
ACAAAGAGCTTCAACAGGGGAGAGTCT-
TATCCATATGATGTGCCAGATTATGCGAGC

M1-25L (SEQ ID NO:51)
GAAATTGTGTTGACGCAGTCTCCAG-
GCACCCTGTCTTTGTCTCCAGGGGAAA-
GAGCCACCCTCTCCTGC AGGGCCAGTCA-
GAGTGTTAGCAGCAGCTACTTAGCCTGGTAC
CAGCAGAAACCTGGCCAGGCTCCCAGG CTC-
CTCATCTATGGTGCATCCAGCAGGGC-
CACTGGCATCCAAACAGGTTCAGTG-
GCAGTGGGTCTGGG
ACAGACTTCACTCTCACCATCAGCA-
GACTGGAGCCTGAAGATTTTGCAGTG-
TATTACTGTCAGCAGTAT GGTAGCTCAT-
TCACTTTCGGCCCTGGGACCAAAGTGGATAT
CAAACGAACTGTGGCTGCACCATCTGTC

TTCATCTTCCCGCCATCTGATGAGCAGT-
TGAAATCTGGAACTGCCTCTGTTGTGT-
GCCTGCTGAATAAC TTCTATCCCAGAGAGGC-
CAAAGTACAGTGGAAGGTGGATAACGCCCTC
CAATCGGGTAACTCCCAGGAG AGTGTCACA-
GAGCAGGACAGCAAGGACAGCACCTA-
CAGCCTCAGCAGCACCCTGACGCTGAG-
CAAAGCA
GACTACGAGAAACACAAAGTCTACGCCT-
GCGAAGTCACCCATCAGGGCCT-
GAGCTCGCCCGTCACAAAG AGCTTCAA-
CAGGGGAGAGTCTTATCCATATGATGTGCCA
GATTATGCGAGC

M1-1H (SEQ ID NO:53)

CAGGTGCAGCTGGTGGAGTCTGGGGGAG-
GCGTGGTCCAGCCTGGGAAGTCCCT-
GAGACTCTCCTGTGCA GCGTCTGAATTCAC-
CATCAGTTACTATGGCATGCACTGGGTCCGCC
AGGTTCCAGGCAAGGGGCTGGAG TGGGTG-
GCAGCTGTCTGGTATGATGAAAGTACTA-
CATATTCTCCAGACTCCGTGAAGGGC-
CGATTCACC
ATCTCCAGAGACGATTCCAAGAA-
CACGCTGTATCTGCAAATGAACAGCCT-
GAGAGCCGAGGACACGGCT GTGTATTACTGT-
GCGAGAGATAGGGTGGGCCTCTTTGACTACT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTC
CTCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M1-3H (SEQ ID NO:55)

CCGATGTGCAGCTGGTGCAGTCTGGGG-
AGGCGTGGTCCAGCCTGGGAGGTCCCT-
GAGACTCTCCTGTG CAGCGTCTGGATTCACCT-
TCAGTTACTATGGCATGCACTGGGTCCGCCA
GGCTCCAGGCAAGGGGCTGG AGTGGGTGA-
CACTTATAACCTATGATG-
GAGATAATAAATACTATGCAGACTCCGT-
GAAGGGCCGATTCA
CCATCTCCAGAGACAATTCCAAGAA-
CACGCTGTATCTGCAAATGAACAGCCT-
GAGAGCCGAGGACACGG CTGTGTATTACTGT-
GCGAGAGACGGGATCGGGTACTTTGACTATTG
GGGCCAGGGAACCCTGGTCACCG TCTCCT-
CAGCCTCCACCAAGGGCCCATCGGTCT-
TCCCCCTGGCACCCTCCTCCAAGAGCAC-
CTCTGGGG
GCACAGCGGCCCTGGGCTGCCTGGT-
CAAGGACTACTTCCCCGAACCGGTGACG-
GTGTCGTGGAACTCAG GCGCCCTGACCAGCG-
GCGTGCACACCTTCCCGGCTGTCCTACAGTC
CTCAGGACTCTACTCCCTCAGCA GCGTGGT-
GACCGTGCCCTCCAGCAGCTTGGGCAC-
CCAGACCTACATCTGCAACGTGAATCA-
CAAGCCCA
GCAACACCAAGGTGGACAAGAAAGCA-
GAGCCCAAATCTCATCACCATCACCATCAC

M1-4H (SEQ ID NO:57)

CAGGTGCAGCTGGTGGAGTCTGGGGGAG-
GCGTGGTCCAGCCTGGGAAGTCCCT-
GAGACTCTCCTGTGCA GCGTCTGGATTCACCT-
TCAGTTACTATGGCATGCACTGGGTCCGCCA
GGTTCCAGGCAAGGGGCTGGAG TGGGTG-
GCAGCTGTCTGGTATGATGGAAGTACTA-
CATATTCTCCAGACTCCGTGAAGGGC-
CGATTCACC
ATCTCCAGAGACGATTCCAAGAA-
CACGCTGTATCTGCAAATGAACAGCCT-
GAGAGCCGAGGACACGGCT GTGTATTACTGT-
GCGAGAGATAGGGTGGGCCTCTTTGACTACT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTC
CTCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGGGC-
CCAAATCTCATCACCATCACCATCAC

M1-5H (SEQ ID NO:59)

CAGGTGCAGCTGGTGGAGTCTGGGGGAG-
GCGTGGTCCAGCCTGGGAGGTCCCT-
GAGACTCTCCTGTGCA GCGTCTGGATTACCT-
TCAGTTACTATGGCATGCACTGGGTCCGCCAG
GCTCCAGGCAAGGGGCTGGAG TGGGTGA-
CACTTATAACCTATGATG-
GAGATAATAAATACTATGCAGACTCCGT-
GAAGGGCCGATTCACC
ATCTCCAGAGACAATTCCAAGAA-
CACGCTGTATCTGCAAATGAACAGCCT-
GAGAGCCGAGGACACGGCT GTGTATTACTGT-
GCGAGAGACGGGATCGGGTACTTTGACTATT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTCC
TCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M1-8H (SEQ ID NO:61)

CAGGTGCAGCTGGTGCAGTCTGGGGGAG-
GCGTGGTCCAGCCTGGGAAGTCCCT-
GAAACTCTCCTGTGCA GCGTCTGGATTCACCT-
TCAGTTACTATGGCATGCACTGGGTCCGCCA
GGCTCCAGGCAAGGGGCTGGAG TGGGTG-
GCAGCTGTATGGTATGATGGAAGTAACA-
CATACTCTCCAGACTCCGTGAAGGGC-
CGATTCACC
ATCTCCAGAGACGATTCCAAGAACACG-
GTGTATCTGCAAATGAACAGCCT-
GAGAGCCGAGGACACGGCT GTGTATTACTGT-
GCGAGAGATAGGGTGGGCCTCTTTGACTACT

GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTC
CTCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M1-10H (SEQ ID NO:63)
CAGGTGCAGCTGGTGCAGTCTGGGGGAG-
GCTTGGTACATCCTGGGGGGTCCCT-
GAGACTCTCCTGTGAA GGCTCTGGATTCATCT-
TCAGGAACCATCCTATACACTGGGTTCGCCA
GGCTCCAGGAAAAGGTCTGGAG TGGGTAT-
CAGTTAGTGGTATTGGTGGTGACACAT-
ACTATGCAGACTCCGTGAAGGGCCGAT-
TCTCCATC
TCCAGAGACAATGCCAAGAACTCCTTG-
TATCTTCAAATGAACAGCCTGAGAGC-
CGAGGACATGGCTGTG TATTACTGTGCAA-
GAGAATATTACTATGGTTCGGGGAGTTATCGC
GTTGACTACTACTACTACGGTATG
GACGTCTGGGGCCAAGGGACCACGGT-
CACCGTCTCCTCAGCCTCCACCAAGGGC-
CCATCGGTCTTCCCC CTGGCACCCTCCTCCAA-
GAGCACCTCTGGGGGCACAGCGGCCCTGGGC
TGCCTGGTCAAGGACTACTTC CCCGAACCG-
GTGACGGTGTCGTGGAACTCAGGCGC-
CCTGACCAGCGGCGTGCACACCTTCCCG-
GCTGTC
CTACAGTCCTCAGGACTCTACTCCCT-
CAGCAGCGTGGTGACCGTGCCCTCCAG-
CAGCTTGGGCACCCAG ACCTACATCTG-
CAACGTGAATCACAAGCCCAGCAACACCAA
GGTGGACAAGAAAGCAGAGCCCAAATCT CAT-
CACCATCACCATCAC

M1-2H (SEQ ID NO:65)
CAGGTGCAGCTGGTGCAGTCTGGGGGAG-
GCGTGGTCCAGCCTGGGAAGTCCCT-
GAGACTCTCCTGTGCA GCGTCTGGATTCACCT-
TCAGTTACTATGGCATGCACTGGGTCCGCCA
GGTTCCAGGCAAGGGGCTGGAG TGGGTG-
GCAGCTGTCTGGTATGATGGAAGTACTA-
CATATTCTCCAGACTCCGTGAAGGGC-
CGATTCACC
ATCTCCAGAGACGATTCCAAGAA-
CACGCTGTATCTGCAAATGAGCAGCCT-
GAGAGCCGAGGACACGGCT GTGTATTACTGT-
GCGAGAGATAGGGTGGGCCTCTTTGACTACT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTCC
TCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M1-23H (SEQ ID NO:67)
CAGGTGCAGCTGGTGCAGTCTGGGGGAG-
GCGTGGTCCAGCCTGGGAGGTCCCT-
GAGACTCTCCTGTGCA GCGTCTGGATTCACCT-
TCAGTAACTATGGCATGCACTGGGTCCGCCA
GGCTCCAGGCAAGGGGCTGGAG TGGGTG-
GCAGCTATATGGTATGATGGAAGTAAAA-
CATACAATGCAGACTCCGTGAAGGGC-
CGATTCACC
ATCTCCAGAGACAATTCCAAGAA-
CACGCTGTATCTGCAAATGAACAGCCT-
GAGAGCCGAGGACACGGCT GTGTATTACTGT-
GCGAGAGATGGGATAGGCTACTTTGACTACT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTC
CTCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M1-25H (SEQ ID NO:69)
CAGGTGCAGCTGGTGGAGTCTGGGGGAG-
GCTTGGTCCAGCCTGGGGGGTCCCT-
GAGACTCTCCTGTGCA GCGTCTGGATTCACCT-
TCAGTTACTATGGCATGCACTGGGTCCGCCA
GGTTCCAGGCAAGGGGCTGGAG TGGGTG-
GCAGCTGTCTGGTATGATGGAAGTACTA-
CATATCCTCCAGACTCCGTGAAGGGC-
CGATTCACC
ATCTCCAGAGACGATTCCAAGAA-
CACGCTGTATCTGCAAATGAACAGCCT-
GAGAGCCGAGGACACGGCT GTTTATTACTGT-
GCGAGAGATAGGGTGGGCCTCTTTGACTACTG
GGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTC
CTCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M2-11L (SEQ ID NO:71)
GAAATAGTGATGACGCAGTCTCCAG-
GCACCCTGTCTTTGTCTCCAGGGGAAA-
GAGCCACCCTCTCCTGC AGGGCCAGT-
CAGGGTGTTAGCAGCAGCTACTTAGCCTGGTA
CCAGCAGAAACCTGGCCAGGCTCCCAGG CTC-
CTCATCTATGGTGCATCCAGCAGGGC-
CACTGGCATCCCAGACAGGTTCAGTG-
GCAGTGGGTCTGGG
ACAGACTTCACTCTCACCATCAGCA-
GACTGGAGCCTGAAGATTTTGCAGTG-

TATTACTGTCAGCAGTAT GGTAGCTCACCTC-
CATTCACTTTCGGCCCTGGGACCAAAGTGGAT
ATCAAACGAACTGTGGCTGCACCA TCTGTCT-
TCATCTTCCCGCCATCTGATGAGCAGT-
TGAGATCTGGAACTGCCTCTGTTGTGT-
GCCTGCTG
AATAACTTCTATCCCAGAGAGGCCAAAG-
TACAGTGGAAGGTGGATAACGCCCTC-
CAATCGGGTAACTCC CAGGAGAGTGTCACA-
GAGCAGGACAGCAAGGACAGCACCTACAGC
CTCAGCAGCACCCTGACGCTGAGC AAAGCA-
GACTACGAGAAACACAAAGTCTACGCCT-
GCGAAGTCACCCATCAGGGCCT-
GAGCTCGCCCGTC
ACAAAGAGCTTCAACAGGGGAGAGTCT-
TATCCATATGATGTGCCAGATTATGCGAGC

M2-12L (SEQ ID NO:73)

GAAATAGTGATGACGCAGTCTCCAG-
GCACCCTGTCTTTGTCTCCAGGGGAAA-
GAGCCACCCTCTCCTGC AGGGCCAGT-
CAGGGTGTTAGCAGCAGCTACTTAGCCTGGT
ACCAGCAGAAACCTGGCCAGGCTCCCAGG
CTCCTCATCTATGGTGCATCCAG-
CAGGGCCACTGGCATCCCAGACAGGT-
TCAGTGGCAGTGGGTCTGGG ACAGACT-
TCACTCTCACCATCAGCAGCCTAGAGCCTGA
AGATTTTGCAGTGTATTACTGTCAGCAGTAT
GGTAGCTCACCTCCGTACACTTTTGGC-
CAGGGGACCAAGCTGGAGATCAAAC-
GAACTGTGGCTGCACCA TCTGTCTTCATCTTC-
CCGCCATCTGATGAGCAGTTGAAATCTGGAA
CTGCCTCTGTTGTGCCTGCTG AATAACTTC-
TATCCCAGAGAGGCCAAAGTACAGTG-
GAAGGTGGATAACGCCCTCCAATCGGG-
TAACTCC
CAGGAGAGTGTCACAGAGCAGGACAG-
CAAGGACAGCACCTACAGCCTCAGCAG-
CACCCTGACGCTGAGC AAAGCAGACTAC-
GAGAAACACAAAGTCTACGCCTGCGAAGTCA
CCCATCAGGGCCTGAGCTCGCCCGTC ACAAA-
GAGCTTCAACAGGGGAGAGTCTTATC-
CATATGATGTGCCAGATTATGCGAGC

M2-16L (SEQ ID NO:75)

GAAATAGTGATGACGCAGTCTCCAG-
GCACCCTGTCTTTGTCTCCAGGGGAAA-
GAGCCACCCTCTCCTGC AGGGCCAGTCA-
GAGTGTTAGCAGCAGCTACTTAGCCTGGTACC
AGCAGAAACCTGGCCAGGCTCCCAGG CTCCT-
CATCTATGGTGCATCCAGCAGGGC-
CACTGGCATCCCAGACAGGTTCAGTGT-
CAGTGGGTCTGGG
ACAGACTTCACTCTCACCATCAGCA-
GACTGGAGCCTGAAGATTTTGCAGTG-
TATTACTGTCAGCAGTAT GGTAGCTCAT-
TCACTTTCGGCCCTGGGACCAAAGTGGATATC
AAACGAACTGTGGCTGCACCATCTGTC
TTCATCTTCCCGCCATCTGATGAGCAGT-
TGAAATCTGGAACTGCCTCTGTTGTGT-
GCCTGCTGAATAAC TTCTATCCCAGAGAGGC-
CAAAGTACAGTGGAAGGTGGATAACGCCCTC
CAATCGGGTAACTCCCAGGAG AGTGTCACA-
GAGCAGGACAGCAAGGACAGCACCTA-
CAGCCTCAGCAGCACCCTGACGCTGAG-
CAAAGCA
GACTACGAGAAACACAAAGTCTACGCCT-
GCGAAGTCACCCATCAGGGCCT-
GAGCTCGCCCGTCACAAAG AGCTTCAA-
CAGGGGAGAGTCTTATCCATATGATGTGCCAG
ATTATGCGAGC

M2-18L (SEQ ID NO:77)

GAAATAGTGATGACGCAGTCTCCAG-
GCACCCTGTCTTTGTCTCCAGGGGAAA-
GAGCCACCCTCTCCTGC AGGGCCAGTCA-
GAGTGTTAGCAGCACCTACTTAGCCTGGTAC
CAGCAGAAACCTGGCCAGGCTCCCAGG CTC-
CTCATCTATGGTGCATCCAGCAGGGC-
CACTGGCATCCCAGACAGGTTCAGTG-
GCAGTGGGTCTGGG
ACAGACTTCACTCTCACCATCAGCA-
GACTGGCCTGAAGATTTTGCAGTG-
TATTACTGTCAGCAGTAT GTTAGCTCAT-
TCACTTTCGGCCCTGGGACCAAAGTGGATAT
CAAACGAACTGTGGCTGCACCATCTGTC
TTCATCTTCCCGCCATCTGATGAGCAGT-
TGAAATCTGGAACTGCCTCTGTTGTGT-
GCCTGCTGAATAAC TTCTATCCCAGAGAGGC-
CAAAGTACAGTGGAAGGTGGATAACGCCCTC
CAATCGGGTAACTCCCAGGAG AGTGTCACA-
GAGCAGGACAGCAAGGACAGCACCTA-
CAGCCTCAGCAGCACCCTGACGCTGAG-
CAAAGCA
GACTACGAGAAACACAAAGTCTACGCCT-
GCGAAGTCACCCATCAGGGCCT-
GAGCTCGCCCGTCACAAAG AGCTTCAA-
CAGGGGAGAGTCTTATCCATATGATGTGCCA
GATTATGCGAGC

M2-20L (SEQ ID NO:79)

GAAATAGTGATGACGCAGTCTCCAG-
GCACCCTGTCTTTGTCTCCAGGGGAAA-
GAGCCACCCTCTCCTGC AGGGCCAGTCA-
GAGTGTTAGCAGCAGCTACTTAGCCTGGTAC
CAGCAGAAACCTGGCCAGGCTCCCAGG CTC-
CTCATCTACGGTGCATCCAGGAGGGC-
CACTGGCATCCCAGACAGGTTCAGTG-
GCAGTGGGTCTGGG
ACAGACTTCACTCTCACCATCAGCA-
GACTGGAGCCTGAAGATTTTGCAGTG-
TATTACTGTCAGCAGTAT GGTAGCTCACCCAT-
GTACACTTTTGGCCAGGGGACCAAGCTGGAG
ATCAAACGAACTGTGGCTGCACCA TCTGTCT-
TCATCTTCCCGCCATCTGATGAGCAGT-
TGAAATCTGGAACTGCCTCTGTTGTGT-
GCCTGCTG
AATAACTTCTATCCCAGAGAGGCCAAAG-
TACAGTGGAAGGTGGATAACGCCCTC-
CAATCGGGTAACTCC CAGGAGAGTGTCACA-
GAGCAGGACAGCAAGGACAGCACCTACAGC
CTCAGCAGCACCCTGACGCTGAGC AAAGCA-
GACTACGAGAAACACAAAGTCTACGCCT-
GCGAAGTCACCCATCAGGGCCT-
GAGCTCGCCCGTC
ACAAAGAGCTTCAACAGGGGAGAGTCT-
TATCCATATGATGTGCCAGATTATGCGAGC

M2-31L (SEQ ID NO:81)

GAAATTGTGTTGACGCAGTCTCCAGC-
CACCCTGTCTTTGTCTCCAGGGGAAA-
GAGCCACCCTCTCCTGC AGGGCCAGTCA-
GAGTGTTAGCAGCTACTTAGCCTGGTACCAA
CAGAAACCTGGCCAGGCTCCCAGGCTC
CTCATCTATGATGCATCCAACAGGGC-
CACTGGCATCCCAGCCAGGTTCAGTG-
GCAGTGGGTCTGGGACA GACTTCACTCTCAC-
CATCAGCAGCCTAGAGCCTGAAGATTTTGCA
GTTATTACTGTCAGCAGCGTACG AACTGGC-

CTCGGACGTTCGGCCAAGGGACCAAG-
GTGGAAATCAAACGAACTGTGGCTGCAC-
CATCTGTC
TTCATCTTCCCGCCATCTGATGAGCAGT-
TGAAATCTGGAACTGCCTCTGTTGTGT-
GCCTGCTGAATAAC TTCTATCCCAGAGAGGC-
CAAAGTACAGTGGAAGGTGGATAACGCCCTC
CAATCGGGTAACTCCCAGGAG AGTGTCACA-
GAGCAGGACAGCAAGGACAGCACCTA-
CAGCCTCAGCAGCACCCTGACGCTGAG-
CAAAGCA
GACTACGAGAAACACAAAGTCTACGCCT-
GCGAAGTCACCCATCAGGGCCT-
GAGCTCGCCCGTCACAAAG AGCTTCAA-
CAGGGGAGAGTCTTATCCATATGATGTGCCA
GATTATGCGAGC

M2-32L (SEQ ID NO:83)
GAAATTGTGTTGACGCAGTCTCCAGC-
CACCCTGTCTTTGTCTCCAGGGGAAA-
GAGCCACCCTCTCCTGC AGGGCCAGTCA-
GAGTGTTAGCAGCTACTTAGCCTGGTACCAA
CAGAAACCTGGCCAGGCTCCCAGGCTC
CTCATCTATGATGCATCCAACAGGGC-
CGCTGGCATCCCAGCCAGGTTCAGTG-
GCAGTGGGTCTGGGACA GACTTCACTCTCAC-
CATCAGCAGCCTAGAGCCTGAAGATTTTGCA
GTTTATTACTGTCAGCAACGTAAC AACTGGC-
CTCTCACTTTCGGCGGAGGGACCAAG-
GTGGAGATCAAACGAACTGTGGCTGCAC-
CATCTGTC
TTCATCTTCCCGCCATCTGATGAGCAGT-
TGAAATCTGGAACTGCCTCTGTTGTGT-
GCCTGCTGAATAAC TTCTATCCCAGAGAGGC-
CAAAGTACAGTGGAAGGTGGATAACGCCCT
CAATCGGGTAACTCCCAGGAG AGTGTCACA-
GAGCAGGACAGCAAGGACAGCACCTA-
CAGCCTCAGCAGCACCCTGACGCTGAG-
CAAAGCA
GACTACGAGAAACACAAAGTCTACGCCT-
GCGAAGTCACCCATCAGGGCCT-
GAGCTCGCCCGTCACAAAG AGCTTCAA-
CAGGGGAGAGTCTTATCCATATGATGTGCCA
GATTATGCGAGC

M2-33L (SEQ ID NO:85)
GAAATTGTGTTGACGCAGTCTCCAG-
GCACCCTGTCTTTGTCTCCAGGGGAAA-
GAGCCACCCTCTCCTGC AGGGCCAGTCA-
GAGTGTTAGCAGCAGCTACTTAGCCTGGTAC
AGCAGAAACCTGGCCAGGCTCCCAGG CTCCT-
CATCTATGGTGCATCCAGCAGGGC-
CACTGGCATCCCAGACAGGTTCAGTG-
GCAGTGGGTCTGGG
ACAGACTTCACTCTCACCATCAGCA-
GACTGGAGCCTGAAGATTTTGCAGTG-
TATTACTGTCAGCAGTAT GGTAGCTCACCTC-
CGTACACTTTTGGCCAGGGGACCAAGCTGGA
GATCAAACGAACTGTGGCTGCACCA TCTGTCT-
TCATCTTCCCGCCATCTGATGAGCAGT-
TGAAATCTGGAACTGCCTCTGTTGTGT-
GCCTGCTG
AATAACTTCTTCCCAGAGAGGCCAAAG-
TACAGTGGAAGGTGGATAACGCCCTC-
CAATCCGGGTAACTCC CAGGAGAGTGTCACA-
GAGCAGGACAGCAAGGACAGCACCTACAGC
CTCAGCAGCACCCTGACGCTGAGC AAAGCA-
GACTACGAGAAACACAAAGTCTACGCCT-
GCGAAGTCACCCATCAGGGCCT-
GAGCTCGCCCGTC
ACAAAGAGCTTCAACAGGGGAGAGTCT-
TATCCATATGATGTGCCAGATTATGCGAGC

M2-34L (SEQ ID NO:87)
GAAATTGTGTTGACGCAGTCTCCAGC-
CACCCTGTCTTTGTCTCCAGGGGAAA-
GAGCCACCCTCTCCTGC AGGGCCAGTCA-
GAGTGTTAGCAGCTACTTAGCCTGGTACCAA
CAGAAACCTGGCCAGGCTCCCAGGCTC
CTCATCTATGATGCATCCAACAGGGC-
CACTGGCATCCCAGCCAGGTTCAGTG-
GCAGTGGGTCTGGGACA GACTTCACTCTCAC-
CATCAGCAGCCTAGAGCCTGAAGATTTTGCA
GTTTATTACTGTCAGCAGCGTACG AACTGGC-
CTCGGACGTTCGGCCAAGGGACCAAG-
GTGGAAATCAAACGAACTGTGGCTGCAC-
CATCTGTC
TTCATCTTCCCGCCATCTGATGAGCAGT-
TGAAATCTGGAACTGCCTCTGTTGTGT-
GCCTGCTGAATAAC TTCTATCCCAGAGAGGC-
CAAAGTACAGTGGAAGGTGGATAACGCCCTC
CAATCGGGTAACTCCCAGGAG AGTGTCACA-
GAGCAGGACAGCAAGGACAGCACCTA-
CAGCCTCAGCAGCACCCTGACGCTGAG-
CAAAGCA
GACTACGAGAAACACAAAGTCTACGCCT-
GCGAAGTCACCCATCAGGGCCT-
GAGCTCGCCCGTCACAAAG AGCTTCAA-
CAGGGGAGAGTCTTATCCATATGATGTGCCAG
ATTATGCGAGC

M2-35L (SEQ ID NO:89)
GAAATTGTGTTGACGCAGTCTCCAGC-
CACCCTGTCTTTGTCTCCAGGGGAAA-
GAGCCACCCTCTCCTGC AGGGCCAGTCA-
GAGTGTTAGCAGCTACTTAGCCTGGTACCAA
CAGAAACCTGGCCAGGCTCCCAGGCTC
CTCATCTATGATGCATCCAACAGGGC-
CACTGGCATCCCAGCCAGGTTCAGTG-
GCAGTGGGTCTGGGACA GACTTCACTCTCAC-
CATCAGCAGCCTAGAGCCTGAAGATTTTGCA
GTTTATTACTGTCAGCAGCGTACG AACTGGC-
CTCGGACGTTCGGCCAAGGGACCAAG-
GTGGAAATCAAACGAACTGTGGCTGCAC-
CATCTGTC
TTCATCTTCCCGCCATCTGATGAGCAGT-
TGAAATCTGGAACTGCCTCTGTTGTGT-
GCCTGCTGAATAAC TTCTATCCCAGAGAGGC-
CAAAGTACAGTGGAAGGTGGATAACGCCCTC
CAATCGGGTAACTCCCAGGAG AGTGTCACA-
GAGCAGGACAGCAAGGACAGCACCTA-
CAGCCTCAGCAGCACCCTGACGCTGAG-
CAAAGCA
GACTACGAGAAACACAAAGTCTACGCCT-
GCGAAGTCACCCATCAGGGCCT-
GAGCTCGCCCGTCACAAAG AGCTTCAA-
CAGGGGAGAGTCTTATCCATATGATGTGCCAG
ATTATGCGAGC

M2-35L (SEQ ID NO:91)
CAGGTGCAGCTGGTGGAGTCTGGGGGAG-
GCGTGGTCCAGCCTGGGAGGTCCCT-
GAGACTCTCCTGTGCA GCGTCTGGATTTACCT-
TCAGTTACTATGGCATGCACTGGGTCCGCCAG
GCTCCAGGCAAGGGGCTGGAG TGGGTGA-
CACTTATAACCTATGATG-
AGATAATAAATACTATGCAGACTCCGT-
GAAGGGCCGATTCACC
ATCTCCAGAGACAATTCCAAGAA-

CACGCTGTATCTGCAAATGAACAGCCT-
GAGAGCCGAGGACACGGCT GTGTATTACTGT-
GCGAGAGACGGGATCGGGTACTTTGACTATT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTC
CTCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M2-12H (SEQ ID NO:93)

GATGTGCAGCTGGTGGAGTCTGGGGGAG-
GCGTGGTCCATCCTGGGAGGTCCCT-
GAGACTCTCCTGTGCA GCGTCTGGATTTACCT-
TCAGTTACTATGGCATGCACTGGGTCCGCCA
GGCTCCAGGCAAGGGGCTGGAA TGGATGA-
CACTTATATCCTATGATG-
GAGATAATAAATACTATGCAGACTCCGT-
GAAGGGCCGATTCACC
ATCTCCAGAGAAATTCCAAGAA-
CACGCTGTATCTGCAAATGAACAGTCT-
GAGAGCCGAGGACACGGCT GTGTATTACTGT-
GCGAGAGACGGGATCGGGTACTTTGACTATT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTC
CTCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AGCACCAAGGTGGACAAGAAAGCAGAGC-
CCAAATCTCATCACCATCACCATCAC

M2-16H (SEQ ID NO:95)

CAGGTGCAGCTGGTGCAGTCTGGGGGAG-
GCGTGGTCCAGCCTGGGAAGTCCCT-
GAGACTCTCCTGTGCA GCGTCTGGATTCAGCT-
TGAGTTACTATGGCATGCACTGGGTCCGCCAG
GTTCCAGGCAAGGGGCTGGAG TGGGTG-
GCAGCTGTCTGGTATGATGGAAGTACTA-
GATATTCTCCAGACTCCGTGAAGGGC-
CGATTCACC
ATCTCCAGAGACGATTCCAAGAA-
CACGCTGTATCTGCAAATGAACAGCCT-
GAGAGCCGAGGACACGGCT GTGTATTACTGT-
GCGAGAGATAGGGTGGGCCTCTTTGACTACT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTC
CTCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M2-18H (SEQ ID NO:97)

CAGGTGCAGCTGGTGCAGTCTGGGGGAG-
GCGTGGTCCAGCCTGGGAAGTCCCT-
GAGACTCTCCTGTGCA GCGTCTGGATTCAGCT-
TCAGTTACTATGGCATGCACTGGGTCCGCCAG
GTTCCAGGCAAGGGGCTGGAG TGGGTG-
GCAGCTGTCTGGTATGATGGAAGTACTA-
CATATTCTCCAGACTCCGTGAAGGGC-
CGATTCACC
ATCTCCAGAGACGATTCCAAGAA-
CACGCTGTATCTGCAAATGAACAGCCT-
GAGAGCCGAGGACACGGCT GTGTATTACTGT-
GCGAGAGATAGGGTGGGCCTCTTTGACTACT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTC
CTCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M2-20H (SEQ ID NO:99)

CAGGTGCAGCTGGTGCAGTCTGGGGGAG-
GCGTGGTCCAGCCTGGGAGGTCCTGAG-
GCTCTCCTGTGCA GCCTCTGGAT-
TCACTTTCAGTTACTATGGTATGCACTGGGTC
CGCCAGGCTCCAGGCAAGGGGCTGGAG
TGGGTGTCACTTATAACATATGATG-
GAAGGAATAAATACTACGCCGACTCCGT-
GAAGGGCCGATTCACC ATCTCCAGAGAGAAT-
TCCAAGAACACGCTGTATCTGCAAATGAACA
GCCTGAGAACTGAGGACACGGCT GAGTAT-
TACTGTGCGAGAGACGGGATCG-
GATACTTTGACTACTGGGGCCAGG-
GAATCCTGGTCACCGTC
TCCTCAGCCTCCACCAAGGGCCCATCG-
GTCTTCCCCCTGGCACCCTCCTCCAA-
GAGCACCTCTGGGGGC ACAGCGGC-
CCTGGGCTGCCTGGTGAAGGACTACTTCCCC
GAACCGGTGACGGTGTCGTGGAAGTCAGGC
GCCCTGACCAGCGGCGTGCACACCTTC-
CCGGCTGTCCTACAGTCCTCAGGACTC-
TACTCCCTCAGCAGC GTGGTGACCGTGC-
CCTCCAGCAGCTTGGGCACCCAGACCTACAT
CTGCAACGTGAATCACAAGCCCAGC AACAC-
CAAGGTGGACAAGAAAGCAGAGC-
CCAAATCTCATCACCATCACCATCAC

M2-31H (SEQ ID NO:101)

CAGGTGCAGCTGGTGGAGTCTGGGG-
GAGTCGTGGTCCAGCCTGGGAGGTCCCT-
GAGACTCTCCTGTGCA GCCTCTGGATTCACGT-
TCAGTTACTATGGTATACACTGGGTCCGCCAG
GTTCCAGGCAAGGGACTAGAG TGGGTG-
GCACTTATATCATACGATGGAAG-

CAATAAATACTACGCAGACTCCGT-
GAAGGGCCGATTCACC ATCTCCAGAGACAAT-
TCCAAGAACACTCTGTATCTGCAAATGAACA
GCCTGAGAGCTGAGGACACGGCT GTGTAT-
TACTGTGCGAGAGACTGGATCGGG-
TACTTTGACTACT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTCC
TCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M2-32H (SEQ ID NO:103)

CAGGTGCAGCTGGTGCAGTCTGGGGGAG-
GCTTGGTACATCCTGGGGGGTCCCT-
GAGACTCTCCTGTGAA GGCTCTGGATTCATCT-
TCAGGAACCATCCTATACACTGGGTTCGCCAG
GCTCCAGGAAAAGGTCTGGAG TGGGTAT-
CAGTTAGTGGTATTGGTGGTGACACAT-
ACTATGCAGACTCCGTGAAGGGCCGAT-
TCTCCATC
TCCAGAGACAATGCCAAGAACTCCTTG-
TATCTTCAAATGAACAGCCTGAGAGC-
CGAGGACATGGCTGTG TATTACTGTCAA-
GAGAATATTACTATGGTTCGGGGAGTTATCGC
GTTGACTACTACTACTACGGTATG
GACGTCTGGGGCCAAGGGACCACGGT-
CACCGTCTCCTCAGCCTCCACCAAGGGC-
CCATCGGTCTTCCC CTGGCACCCTCCTCCAA-
GAGCACCTCTGGGGGCACAGCGGCCCTGGGC
TGCCTGGTCAAGGACTACTTC CCCGAACCG-
GTGACGGTGTCGTGGAACTCAGGCGC-
CCTGACCAGCGGCGTGCACACCTTCCCG-
GCTGTC
CTACAGTCCTCAGGACTCTACTCCCT-
CAGCAGCGTGGTGACCGTGCCCTCCAG-
CAGCTTGGGCACCCAG ACCTACATCTG-
CAACGTGAATCACAAGCCCAGCAACACCAA
GGTGGACAAGAAAGCAGAGCCCAAATCT CAT-
CACCATCACCATCAC

M2-33H (SEQ ID NO:105)

CAGGTGCAGCTGGTGCAGTCTGGGGGAG-
GCGTGGTCCAGCCTGGGAGGTCCCT-
GAGACTCTCCTGTGCA GCGTCTGGATTTACCT-
TCAGTTACTATGGCATGCACTGGGTCCGCCAG
GCTCCAGGCAAGGGGCTGGAA TGGATGA-
CACTTATAACCTATGATG-
GAGATAATAAATACTATGCAGACTCCGT-
GAAGGGCCGATTCACC
ATCTCCAGAGACAATTCCAAGAA-
CACTCTGTATCTGCAAATGAACAGTCT-
GAGAGCCGAGGACACGGCT GTGTATTACTGT-
GCGAGAGACGGGATCGGGTACTTTGACTATTG
GGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTCC
TCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M2-34H (SEQ ID NO:107)

CAGGTGCAGCTGGTGGAGTCTGGGGGAG-
GCGTGGTCCAGCCTGGGAGGTCCCT-
GAGACTCTCCTGTGCA GCCTCTGGATTCACGT-
TCAGTTACTATGGTATACACTGGGTCCGCCAG
GTTCCAGGCAAGGGACTAGAG TGGGTGG-
TACTTATATCATACGATGGAAG-
CAATAAATACTACGCAGACTCCGT-
GAAGGGCCGATTCACC
ATCTCCAGAGACAATTCCAAGAA-
CACTCTGTATCTGCAAATGAACAGCCT-
GAGAGCTGAGGACACGGCT GTGTATTACTGT-
GCGAGAGACTGGATCGGGTACTTTGACTACT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTC
CTCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

M2-35H (SEQ ID NO:109)

CAGGTGCAGCTGGTGGAGTCTGGGGGAG-
GCGTGGTCCAGCCTGGGAGGTCCCT-
GAGACTCTCCTGTGCA GCCTCTGGATTCAC-
GATCAGTTACTATGGTATACACTGGGTCCGCC
AGGTTCCAGGCAAGGGACTAGAG TGGGTG-
GAACTTATATCATACGATGGAAG-
CAATAAATACTACGCAGACTCCGT-
GAAGGGCCGATTCACC
ATCTCCAGAGACAATTCCAAGAA-
CACTCTGTATCTGCAAATGAACAGCCT-
GAGAGCTGAGGACACGGCT GTGTATTACTGT-
GCGAGAGACTGGATCGGGTACTTTGACTACT
GGGGCCAGGGAACCCTGGTCACCGTC TCCT-
CAGCCTCCACCAAGGGCCCATCGGTCT-
TCCCCCTGGCACCCTCCTCCAAGAGCAC-
CTCTGGGGGC
ACAGCGGCCCTGGGCTGCCTGGTCAAG-
GACTACTTCCCCGAACCGGTGACGGT-
GTCGTGGAACTCAGGC GCCCTGACCAGCG-
GCGTGCACACCTTCCCGGCTGTCCTACAGTC
CTCAGGACTCTACTCCCTCAGCAGC GTGGT-
GACCGTGCCCTCCAGCAGCTTGGGCAC-
CCAGACCTACATCTGCAACGTGAATCA-
CAAGCCCAGC
AACACCAAGGTGGACAAGAAAGCAGAGC-
CCAAATCTCATCACCATCACCATCAC

```
Translated amino acid sequences of sequenced antibodies.
M1-H Heavy Chain Variable and CH1 Regions 10-9M Affinity Cut
(SEQ ID NOS: 64, 54, 66, 68, 70, 56, 58, 60, and 62
repectively)
              1                                              50
M1_10H   QVQLVQSGGG LVHPGGSLRL SCEGSGFIFR NHPIHWVRQA PGKGLEWVSV
 M1_1H   QVQLVESGGG VVQPGKSLRL SCAASEFTIS YYGMHWVRQV PGKGLEWVAA
M1_21H   QVQLVQSGGG VVQPGKSLRL SCAASGFTFS YYGMHWVRQV PGKGLEWVAA
M1_23H   QVQLVQSGGG VVQPGRSLRL SCAASGFTFS NYGMHWVRQA PGKGLEWVAA
M1_25H   QVQLVESGGG LVQPGGSLRL SCAASGFTFS YYGMHWVRQV PGKGLEWVAA
 M1_3H   DVQLVQSGGG VVQPGRSLRL SCAASGFTFS YYGMHWVRQA PGKGLEWVTL
 M1_4H   QVQLVESGGG VVQPGKSLRL SCAASGFTFS YYGMHWVRQV PGKGLEWVAA
 M1_5H   QVQLVESGGG VVQPGRSLRL SCAASGFTFS YYGMHWVRQA PGKGLEWVTL
 M1_8H   QVQLVQSGGG VVQPGKSLKL SCAASGFTFS YYGMHWVRQA PGKGLEWVAA
             51                                             100
M1_10H   SGIGGDTYY. ADSVKGRFSI SRDNAKNSLY LQMNSLRAED MAVYYCAREY
 M1_1H   VWYDESTTYS PDSVKGRFTI SRDDSKNTLY LQMNSLRAED TAVYYCARDR
M1_21H   VWYDGSTTYS PDSVKGRFTI SRDDSKNTLY LQMSSLRAED TAVYYCARDR
M1_23H   IWYDGSKTYN ADSVKGRFTI SRDNSKNTLY LQMNSLRAED TAVYYCARDG
M1_25H   VWYDGSTTYP PDSVKGRFTI SRDDSKNTLY LQMNSLRAED TAVYYCARDR
 M1_3H   ITYDGDNKYY ADSVKGRFTI SRDNSKNTLY LQMNSLRAED TAVYYCARDG
 M1_4H   VWYDGSTTYS PDSVKGRFTI SRDDSKNTLY LQMNSLRAED TAVYYCARDR
 M1_5H   ITYDGDNKYY ADSVKGRFTI SRDNSKNTLY LQMNSLRAED TAVYYCARDG
 M1_8H   VWYDGSNTYS PDSVKGRFTI SRDDSKNTVY LQMNSLRAED TAVYYCARDR
            101                                             150
M1_10H   YYGSGSYRVD YYYYGMDVWG QGTTVTVSSA STKGPSVFPL APSSKSTSGG
 M1_1H   VG........ ....LFDYWG QGTLVTVSSA STKGPSVFPL APSSKSTSGG
M1_21H   VG........ ....LFDYWG QGTLVTVSSA STKGPSVFPL APSSKSTSGG
M1_23H   IG........ ....YFDYWG QGTLVTVSSA STKGPSVFPL APSSKSTSGG
M1_25H   VG........ ....LFDYWG QGTLVTVSSA STKGPSVFPL APSSKSTSGG
 M1_3H   IG........ ....YFDYWG QGTLVTVSSA STKGPSVFPL APSSKSTSGG
 M1_4H   VG........ ....LFDYWG QGTLVTVSSA STKGPSVFPL APSSKSTSGG
 M1_5H   IG........ ....YFDYWG QGTLVTVSSA STKGPSVFPL APSSKSTSGG
 M1_8H   VG........ ....LFDYWG QGTLVTVSSA STKGPSVFPL APSSKSTSGG
            151                                             200
M1_10H   TAALGCLVKD YFPEPVTVSW NSGALTSGVH TFPAVLQSSG LYSLSSVVTV
 M1_1H   TAALGCLVKD YFPEPVTVSW NSGALTSGVH TFPAVLQSSG LYSLSSVVTV
M1_21H   TAALGCLVKD YFPEPVTVSW NSGALTSGVH TFPAVLQSSG LYSLSSVVTV
M1_23H   TAALGCLVKD YFPEPVTVSW NSGALTSGVH TFPAVLQSSG LYSLSSVVTV
M1_25H   TAALGCLVKD YFPEPVTVSW NSGALTSGVH TFPAVLQSSG LYSLSSVVTV
 M1_3H   TAALGCLVKD YFPEPVTVSW NSGALTSGVH TFPAVLQSSG LYSLSSVVTV
 M1_4H   TAALGCLVKD YFPEPVTVSW NSGALTSGVH TFPAVLQSSG LYSLSSVVTV
 M1_5H   TAALGCLVKD YFPEPVTVSW NSGALTSGVH TFPAVLQSSG LYSLSSVVTV
 M1_8H   TAALGCLVKD YFPEPVTVSW NSGALTSGVH TFPAVLQSSG LYSLSSVVTV
            201                        237
M1_10H   PSSSLGTQTY ICNVNHKPSN TKVDKKAEPK SHHHHHH
 M1_1H   PSSSLGTQTY ICNVNHKPSN TKVDKKAEPK SHHHHHH
M1_21H   PSSSLGTQTY ICNVNHKPSN TKVDKKAEPK SHHHHHH
M1_23H   PSSSLGTQTY ICNVNHKPSN TKVDKKAEPK SHHHHHH
M1_25H   PSSSLGTQTY ICNVNHKPSN TKVDKKAEPK SHHHHHH
 M1_3H   PSSSLGTQTY ICNVNHKPSN TKVDKKAEPK SHHHHHH
 M1_4H   PSSSLGTQTY ICNVNHKPSN TKVDKKAGPK SHHHHHH
 M1_5H   PSSSLGTQTY ICNVNHKPSN TKVDKKAEPK SHHHHHH
 M1_8H   PSSSLGTQTY ICNVNHKPSN TKVDKKAEPK SHHHHHH
M1-L Kappa Chain Variable and Constant Regions 10-9
Affinity Cut (SEQ ID NOS: 46, 36, 48, 50, 52, 38, 40, 42,
and 44 respectively)
              1                                              50
M1_10L   DVVMTQSPAT LSLSPGERAT LSCRASQSVS S.YLAWYQQK PGQAPRLLIY
 M1_1L   EIVLTQSPAT LSLSPGERAT LSCRASQGVS S.YLAWYQQK PGQAPRLLIY
M1_21L   AIRMTQSPSF LSASVGDRVT ITCRASQSIS S.YLNWYQQK PGKAPKLLIY
M1_23L   EIVLTQSPGT LSLSPGERAT LSCRASQSVS SSYAWYQQK  PGQAPRLLIY
M1_25L   EIVLTQSPGT LSLSPGERAT LSCRASQSVS SSYLAWYQQK PGQAPRLLIY
 M1_3L   EIVMTQSPAT LSLSPGERAT LSCRASQSVS SSYLAWYQQK PGQAPRLLIY
 M1_4L   EIVLTQSPGT LSLSPGERAT LSCRASQSVS SSYLAWYQQK PGQAPRLHIY
 M1_5L   EIVMTQSPGT LSLSPGERAT LSCRASQSVS SSYLAWYQQK PGQAPRLLIY
 M1_8L   EIVMTQSPGT LSLSPGERAT LSCRASQSVS STYLAWYQQK PGQAPRLLIY
             51                                             100
M1_10L   DASNRATGIP ARFSGSGSGT DFTLTISSLE PEDFAVYYCQ QRSNWP.PTF
 M1_1L   DASNRATGIP ARFSGSGSGT DFTLTISSLE PEDFAVYYCQ QRSNWP.RTF
M1_21L   AASSLQSGVP SRFSVSGSGT DLTLTISSLQ PEDFATYYCQ CGYSTP.FTF
M1_23L   GASSRATGIP DRFSGSGSGT DFTLTISRLE PEDFAVYYCQ QYGSSPPYTF
M1_25L   GASSRATGIP NRFSGSGSCT DFTLTISRLE PEDFAVYYCQ QYGSS..FTF
 M1_3L   GASSRATGIP DRFSGSGSGT DFTLTISRLE PEDFAVYYCQ QYGSSPPFTF
 M1_4L   GASRRATGIP DRFSGSGSGT DFTLTISRLE PEDFAVYYCQ QFGSS..FTF
 M1_5L   GASSRATGTP DRFSGSGSGT DFTLTISRLE PEDFAVYYCQ QYGSSPIFTF
 M1_8L   GASSRATGIP DRFSGSGSGT DFTLTTSRLE PEDFAVYYCQ QYVSS..FTF
            101                                             150
M1_10L   GGGTKVEIKR TVAAPSVFIF PPSDEQLKSG TASVVCLLNN FYPREAKVQW
```

```
M1_10L   GQGTKVEIKR TVAAPSVFIF PPSDEQLKSG TASVVCLLNN FYPREAKVQW
M1_1L    GPGTKVDIKR TVAAPSVFIF PPSDEQLKSG TASVVCLLNN FYPREAKVQW
M1_21L   GQGTKLEIKR TVAAPSVFIF PPSDEQLKSG TASVVCLLNN FYPREAKVQW
M1_23L   GPGTKVDIKR TVAAPSVFIF PPSDEQLKSG TASVVCLLNN FYPREAKVQW
M1_25L   GPGTKVDIKR TVAAPSVFIF PPSDEQLKSG TASVVCLLNN FYPREAKVQW
M1_3L    GPGTKVDIKR TVAAPSVFIF PPSDEQLKSG TASVVCLLNN FYPREAKVQW
M1_4L    GPGTKVDIKR TVAAPSVFIF PPSDEQLKSG TASVVCLLNN FYPREAKVQW
M1_5L    GPGTKVDIKR TVAAPSVFIF PPSDEQLKSG TASVVCLLNN FYPREAKVQW
M1_8L    GPGTKVDIKR TVAAPSVFIF PPSDEQLKSG TASVVCLLNN FYPREAKVQW
              151                                            200
M1_10L   KVDNALQSGN SQESVTEQDS KDSTYSLSST LTLSKADYEK HKVYACEVTH
M1_1L    KVDNALQSGN SQESVTEQDS KDSTYSLSST LTLSKADYEK HKVYACEVTH
M1_21L   KVDNALQSGN SQESVTEQDS KDSTYSLSST LTLSKADYEK RKVYACEVTH
M1_23L   RVDNALQSGN SQESVTEQDS KDSTYSLSST LTLSKADYEK HKVYACEVTH
M1_25L   KVDNALQSGN SQESVTEQDS KDSTYSLSST LTLSKADYEK HKVYACEVTH
M1_3L    KVDNALQSGN SQESVTEQDS KDSTYSLSST LTLSKADYEK HKVYACEVTH
M1_4L    KVDNALQSGN SQESVTEQDS KDSTYSLSST LTLSKADYEK HKVYACEVTH
M1_5L    KVDNALQSGN SQESVTEQDS KDSTYSLSST LTLSKADYEK HKVYACEVTH
M1_8L    KVDNALQSGN SQESVTEQDS KDSTYSLSST LTLSKADYEK HKVYACEVTH
              201          226
M1_10L   QGLSSPVTKS FNRGESYPYD VPDYAS
M1_1L    QGLSSPVTKS FNRGESYPYD VPDYAS
M1_21L   QGLSSPVTKS FNRGESYPYD VPDYAS
M1_23L   QGLSSPVTKS FNRGESYPYD VPDYAS
M1_25L   QGLSSPVTKS FNRGESYPYD VPDYAN
M1_3L    QGLSSPVTKS FNRGESYPYD VPDYAS
M1_4L    QGLSSPVTKS FNRGESYPYD VPDYAS
M1_5L    QGLSSPVTKS FNRGESYPYD VPDYAS
M1_8L    QGLSSPVTKS FNRGESYPYD VPDYAS
M2-H Heavy Chain VH-CH1 Sequence 10-10M Affinity Cut
(SEQ ID NOS: 92, 94, 96, 98, 100, 102, 104, 106, 108,
and 110 respectively)
              1                                              50
M2_11H   QVQLVESGGG VVQPGRSLRL SCAASGFTFS YYGMHWVRQA PGKGLEWVTL
M2_12H   DVQLVESGGG VVHPGRSLRL SCAASGFTFS YYGMHWVRQA PGKGLEWMTL
M2_16H   QVQLVQSGGG VVQPGKSLRL SCAASGFSLS YYGMHWVRQV PGKGLEWVAA
M2_18H   QVQLVQSGGG VVQPGKSLRL SCAASGFSFS YYGMHWVRQA PGKGLEWVAA
M2_20H   QVQLVQSGGG VVQPGRSLRL SCAASGFTFS YYGMHWVRQA PGKGLEWVSL
M2_31H   QVQLVESGGV VVQPGRSLRL SCAASGFTFS YYGIHWVRQV PGKGLEWVAL
M2_32H   QVQLVQSGGG LVHPGGSLRL SCEGSGFIFR NHPIHWVRQA PGKGLEWVSV
M2_33H   QVQLVQSGGG VVQPGRSLRL SCAASGFTFS YYGMHWVRQA PGKGLEWMTL
M2_34H   QVQLVESGGG VVQPGRSLRL SCAASGFTFS YYGIHWVRQV PGKGLEWVVL
M2_35H   QVQLVESGGG VVQPGRSLRL SCAASGFTIS YYGIHWVRQV PGKGLEWVEL
              51                                             100
M2_11H   ITYDGDNKYY ADSVKGRFTI SRDNSKNTLY LQMNSLRAED TAVYYCARDG
M2_12H   ISYDGDNKYY ADSVKGRFTI SRENSKNTLY LQMNSLRAED TAVYYCARDG
M2_16H   VWYDGSTRYS PDSVKGRFTI SRDDSKNTLY LQMNSLRAED TAVYYCARDR
M2_18H   VWYDGSTTYS PDSVKGRFTI SRDDSKNTLY LQMNSLRAED TAVYYCARDR
M2_20H   ITYDGRNKYY ADSVKGRFTI SRENSKNTLY LQMNSLRTED TAEYYCARDG
M2_31H   ISYDGSNKYY ADSVKGRFTI SRDNSKNTLY LQMNSLRAED TAVYYCARDW
M2_32H   SGIGG.DTYY ADSVKGRFSI SRDNAKNSLY LQMNSLRAED MAVYYCAREY
M2_33H   ITYDGDNKYY ADSVKGRFTI SRDNSKNTLY LQMNSLRAED TAVYYCARDG
M2_34H   ISYDGSNKYY ADSVKGRFTI SRDNSKNTLY LQMNSLRAED TAVYYCARDW
M2_35H   ISYDGSNKYY ADSVKGRFTI SRDNSKNTLY LQMNSLRAED TAVYYCARDW
              101                                            150
M2_11H   IG........ ....YFDYWG QGTLVTVSSA STKGPSVFPL APSSKSTSGG
M2_12H   IG........ ....YFDYWG QGTLVTVSSA STKGPSVFPL APSSKSTSGG
M2_16H   VG........ ....LFDYWG QGTLVTVSSA STKGPSVFPL APSSKSTSGG
M2_18H   VG........ ....LFDYWG QGTLVTVSSA STKGPSVFPL APSSKSTSGG
M2_20H   IG........ ....YFDYWG QGILVTVSSA STKGPSVFPL APSSKSTSGG
M2_31H   IG........ ....YFDYWG QGTLVTVSSA STKGPSVFPL APSSKSTSGG
M2_32H   YYGSGSYRVD YYYYGMDVWG QGTTVTVSSA STKGPSVFPL APSSKSTSGG
M2_33H   IG........ ....YFDYWG QGTLVTVSSA STKGPSVFPL APSSKSTSGG
M2_34H   IG........ ....YFDYWG QGTLVTVSSA STKGPSVFPL APSSKSTSGG
M2_35H   IG........ ....YFDYWG QGTLVTVSSA STKGPSVFPL APSSKSTSGG
              151                                            200
M2_11H   TAALGCLVKD YFPEPVTVSW NSGALTSGVH TFPAVLQSSG LYSLSSVVTV
M2_12H   TAALGCLVKD YFPEPVTVSW NSGALTSGVH TFPAVLQSSG LYSLSSVVTV
M2_16H   TAALGCLVKD YFPEPVTVSW NSGALTSGVH TFPAVLQSSG LYSLSSVVTV
M2_18H   TAALGCLVKD YFPEPVTVSW NSGALTSGVH TFPAVLQSSG LYSLSSVVTV
M2_20H   TAALGCLVKD YFPEPVTVSW KSGALTSGVH TFPAVLQSSG LYSLSSVVTV
M2_31H   TAALGCLVKD YFPEPVTVSW NSGALTSGVH TFPAVLQSSG LYSLSSVVTV
M2_32H   TAALGCLVKD YFPEPVTVSW NSGALTSGVH TFPAVLQSSG LYSLSSVVTV
M2_33H   TAALGCLVKD YFPEPVTVSW NSGALTSGVH TFPAVLQSSG LYSLSSVVTV
M2_34H   TAALGCLVKD YFPEPVTVSW NSGALTSGVH TFPAVLQSSG LYSLSSVVTV
M2_35H   TAALGCLVKD YFPEPVTVSW NSGALTSGVH TFPAVLQSSG LYSLSSVVTV
              201                      237
M2_11H   PSSSLGTQTY ICNVNHKPSN TKVDKKAEPK SHHHHHH
M2_12H   PSSSLGTQTY ICNVNHKPSS TKVDKKAEPK SHHHHHH
M2_16H   PSSSLGTQTY ICNVNHKPSN TKVDKKAEPK SHHHHHH
```

```
                        -continued
M2_18H  PSSSLGTQTY ICNVNHKPSN TKVDKKAEPK SHHHHHH
M2_20H  PSSSLGTQTY ICNVNHKPSN TKVDKKAEPK SHHHHHH
M2_31H  PSSSLGTQTY ICNVNHKPSN TKVDKKAEPK SHHHHHH
M2_32H  PSSSLGTQTY ICNVNHKPSN TKVDKKAEPK SHHHHHH
M2_33H  PSSSLGTQTY ICNVNHKPSN TKVDKKAEPK SHHHHHH
M2_34H  PSSSLGTQTY ICNVNHKPSN TKVDKKAEPK SHHHHHH
M2_35H  PSSSLGTQTY ICNVNHKPSN TKVDKKAEPK SHHHHHH
M2-L Kappa Chain VKCK 10-10M Affinity Cut
(Thu Sep 23) (SEQ ID NOS: 72, 74, 76, 78, 80, 82, 84,
86, 88, and 90 respectively)
            1                                              50
M2_11L  EIVMTQSPGT LSLSPGERAT LSCRASQGVS SSYLAWYQQK PGQAPRLLIY
M2_12L  EIVMTQSPGT LSLSPGERAT LSCRASQGVS SSYLAWYQQK PGQAPRLLIY
M2_16L  EIVMTQSPGT LSLSPGERAT LSCRASQSVS SSYLAWYQQK PGQAPRLLIY
M2_18L  EIVMTQSPGT LSLSPGERAT LSCRASQSVS STYLAWYQQK PGQAPRLLIY
M2_20L  EIVMTQSPGT LSLSPGERAT LSCRASQSVS SSYLAWYQQK PGQAPRLLIY
M2_31L  EIVLTQSPAT LSLSPGERAT LSCRASQSVS S.YLAWYQQK PGQAPRLLIY
M2_32L  EIVLTQSPAT LSLSPGERAT LSCRASQSVS S.YLAWYQQK PGQAPRLLIY
M2_33L  EIVLTQSPGT LSLSPGERAT LSCRASQSVS SSYLAWYQQK PGQAPRLLIY
M2_34L  EIVLTQSPAT LSLSPGERAT LSCRASQSVS S.YLAWYQQK PGQAPRLLIY
M2_35L  EIVLTQSPAT LSLSPGERAT LSCRASQSVS S.YLAWYQQK PGQAPRLLIY
            51                                             100
M2_11L  GASSRATGIP DRFSGSGSGT DFTLTISRLE PEDFAVYYCQ QYGSSPPFTF
M2_12L  GASSRATGIP DRFSGSGSGT DFTLTISSLE PEDFAVYYCQ QYGSSPPYTF
M2_16L  GASSRATGIP DRFSVSGSGT DFTLTISRLE PEDFAVYYCQ QYGSS..FTF
M2_18L  GASSRATGTP DRFSGSGSGT DFTLTISRLE PEDFAVYYCQ QYVSS..FTF
M2_20L  GASRRATGIP DRFSGSGSGT DFTLTISRLE PEDFAVYYCQ QYGSSPMYTF
M2_31L  DASNRATGIP ARFSGSGSGT DFTLTISSLE PEDFAVYYCQ QRTNWP.RTF
M2_32L  DASNRAAGIP ARFSGSGSGT DFTLTISSLE PEDFAVYYCQ QRNNWP.LTF
M2_33L  GASSRATGIP DRFSGSGSGT DFTLTISRLE PEDFAVYYCQ QYGSSPPYTF
M2_34L  DASNRATGIP ARFSGSGSGT DFTLTTSSLE PEDFAVYYCQ QRTNWP.RTF
M2_35L  DASNRATGIP ARFSGSGSGT DFTLTISSLE PEDFAVYYCQ QRTNWP.RTF
            101                                            150
M2_11L  GPGTKVDIKR TVAAPSVFIF PPSDEQLRSG TASVVCLLNN FYPREAKVQW
M2_12L  GQGTKLEIKR TVAAPSVFIF PPSDEQLKSG TASVVCLLNN FYPREAKVQW
M2_16L  GPGTKVDIKR TVAAPSVFIF PPSDEQLKSG TASVVCLLNN FYPREAKVQW
M2_18L  GPGTKVDIKR TVAAPSVFIF PPSDEQLKSG TASVVCLLNN FYPREAKVQW
M2_20L  GQGTKLEIKR TVAAPSVFIF PPSDEQLKSG TASVVCLLNN FYPREAKVQW
M2_31L  GQGTKVEIKR TVAAPSVFIF PPSDEQLKSG TASVVCLLNN FYPREAKVQW
M2_32L  GGGTKVEIKR TVAAPSVFIF PPSDEQLKSG TASVVCLLNN FYPREAKVQW
M2_33L  GQGTKLEIKR TVAAPSVFIF PPSDEQLKSG TASVVCLLNN FYPREAKVQW
M2_34L  GQGTKVEIKR TVAAPSVFIF PPSDEQLKSG TASVVCLLNN FYPREAKVQW
M2_35L  GQGTKVEIKR TVAAPSVFIF PPSDEQLKSG TASVVCLLNN FYPREAKVQW
            151                                            200
M2_11L  KVDNALQSGN SQESVTEQDS KDSTYSLSST LTLSKADYEK HKVYACEVTH
M2_12L  KVDNALQSGN SQESVTEQDS KDSTYSLSST LTLSKADYEK HKVYACEVTH
M2_16L  KVDNALQSGN SQESVTEQDS KDSTYSLSST LTLSKADYEK HKVYACEVTH
M2_18L  KVDNALQSGN SQESVTEQDS KDSTYSLSST LTLSKADYEK HKVYACEVTH
M2_20L  KVDNALQSGN SQESVTEQDS KDSTYSLSST LTLSKADYEK HKVYACEVTH
M2_31L  KVDNALQSGN SQESVTEQDS KDSTYSLSST LTLSKADYEK HKVYACEVTH
M2_32L  KVDNALQSGN SQESVTEQDS KDSTYSLSST LTLSKADYEK HKVYACEVTH
M2_33L  KVDNALQSGN SQESVTEQDS KDSTYSLSST LTLSKADYEK HKVYACEVTH
M2_34L  KVDNALQSGN SQESVTEQDS KDSTYSLSST LTLSKADYEK HKVYACEVTH
M2_35L  KVDNALQSGN SQESVTEQDS KDSTYSLSST LTLSKADYEK HKVYACEVTH
            201              226
M2_11L  QGLSSPVTKS FNRGESYPYD VPDYAS
M2_12L  QGLSSPVTKS FNRGESYPYD VPDYAS
M2_16L  QGLSSPVTKS FNRGESYPYD VPDYAS
M2_18L  QGLSSPVTKS FNRGESYPYD VPDYAS
M2_20L  QGLSSPVTKS FNRGESYPYD VPDYAS
M2_31L  QGLSSPVTKS FNRGESYPYD VPDYAS
M2_32L  QGLSSPVTKS FNRGESYPYD VPDYAS
M2_33L  QGLSSPVTKS FNRGESYPYD VPDYAS
M2_34L  QGLSSPVTKS FNRGESYPYD VPDYAS
M2_35L  QGLSSPVTKS FNRGESYPYD VPDYAS
```

EXAMPLE 23

Growth of *E. coli* Cultures and Purification of Recombinant Antibodies and Antigens A shake flask inoculum is generated overnight from a −70° C. cell bank in an Innova 4330 incubator shaker (New Brunswick Scientific, Edison, N.J.) set at 37° C., 300 rpm. The inoculum is used to seed a 20 μL fermenter (Applikon, Foster City, Calif.) containing defined culture medium (Pack, et al., *Bio/Technology* 11:1271–1277 (1993)) supplemented with 3 μg/L L-leucine, 3 μg/L L-isoleucine, 12 μg/L casein digest (Difco, Detroit, Mich.), 12.5 μg/L glycerol and 10 mg/ml tetracycline. The temperature, pH and dissolved oxygen in the fermenter are controlled at 26° C., 6.0–6.8 and 25% saturation, respectively. Foam is controlled by addition of polypropylene glycol (Dow, Midland, Mich.). Glycerol is added to the fermenter in a fed-batch mode. Fab expression is induced by addition of L(+)-arabinose (Sigma, St. Louis, Mo.) to 2 μg/L during the late logarithmic growth phase. Cell density is measured by optical density at 600 nm in an UV-1201 spectrophotometer (Shimadzu, Columbia, Md.). Final Fab concentrations are typically 100–500 mg/L. Following run termination and adjustment of pH to 6.0, the culture is passed twice through an M-210B-EH Microfluidizer (Microfluidics, Newton, Mass.) at 17000 psi. The high pressure homogenization of the cells releases the Fab into the culture supernatant.

The first step in purification is expanded bed immobilized metal affinity chromatography (EB-IMAC). Streamline Chelating resin (Pharmacia, Piscataway, N.J.) is charged with 0.1 M NiCl$_2$. It is then expanded and equilibrated in 50 mM acetate, 200 mM NaCl, 10 mM imidazole, 0.01% NaN$_3$, pH 6.0 buffer flowing in the upward direction. A stock solution is used to bring the culture homogenate to 10 mM imidazole, following which, it is diluted two-fold or higher in equilibration buffer to reduce the wet solids content to less than 5% by weight. It is then loaded onto the Streamline column flowing in the upward direction at a superficial velocity of 300 cm/hr. The cell debris passes through unhindered, but the Fab is captured by means of the high affinity interaction between nickel and the hexahistidine tag on the Fab heavy chain. After washing, the expanded bed is converted to a packed bed and the Fab is eluted with 20 mM borate, 150 mM NaCl, 200 mM imidazole, 0.01% NaN$_3$, pH 8.0 buffer flowing in the downward direction. The second step in purification uses ion-exchange chromatography (IEC). Q Sepharose FastFlow resin (Pharmacia, Piscataway, N.J.) is equilibrated in 20 mM borate, 37.5 mM NaCl, 0.01% NaN$_3$, pH 8.0. The Fab elution pool from the EB-IMAC step is diluted four-fold in 20 mM borate, 0.01% NaN$_3$, pH 8.0 and loaded onto the IEC column. After washing, the Fab is eluted with a 37.5–200 mM NaCl salt gradient. The elution fractions are evaluated for purity using an Xcell II SDS-PAGE system (Novex, San Diego, Calif.) prior to pooling. Finally, the Fab pool is concentrated and diafiltered into 20 mM borate, 150 mM NaCl, 0.01% NaN$_3$, pH 8.0 buffer for storage. This is achieved in a Sartocon Slice system fitted with a 10,000 MWCO cassette (Sartorius, Bohemia, N.Y.). The final purification yields are typically 50%. The concentration of the purified Fab is measured by UV absorbance at 280 nm, assuming an absorbance of 1.6 for a 1 mg/mL solution.

EXAMPLE 24

Generation of Cmu Targeted Mice

The following example describes the making of mice with disrupted, and thus non-functional, imnmunoglobulin genes.
Construction of a CMD Targeting Vector To disrupt the mouse immunoglobulin gene, a vector containing a fragment of a murine Ig heavy chain locus is transfected into a mouse embryonic cell. The mouse Ig heavy chain sequence "targets" the vector to the mouse immunoglobulin gene locus. The following describes construction of this immunoglobulin gene "targeting" vector.

The plasmid pICEmu contains an EcoRI/XhoI fragment of the murine Ig heavy chain locus, spanning the mu gene, that was obtained from a Balb/C genomic lambda phage library (Marcu et al. Cell 22: 187, 1980). This genomic fragment was subcloned into the XhoI/EcoRI sites of the plasmid pICEMI9H (Marsh et al; Gene 32, 481–485, 1984). The heavy chain sequences included in pICEmu extend downstream of the EcoRI site located just 3' of the mu intronic enhancer, to the XhoI site located approximately 1 kb downstream of the last transmembrane exon of the mu gene; however, much of the mu switch repeat region has been deleted by passage in E. coli.

The targeting vector was constructed as follows (See FIG. 6). A 1.3 kb HindIII/SmaI fragment was excised from pICEmu and subcloned into HindIII/SmaI digested pBluescript (Stratagene, La Jolla, Calif.). This pICEmu fragment extends from the HindIII site located approximately 1 kb 5' of Cmu1 to the SmaI site located within Cmu1. The resulting plasmid was digested with SmaI/SpeI and the approximately 4 kb SmaI/XbaI fragment from pICEmu, extending from the Sma I site in Cmu1 3' to the XbaI site located just downstream of the last Cmu exon, was inserted.

The resulting plasmid, pTAR1, was linearized at the SmaI site, and a neo expression cassette inserted. This cassette consists of the neo gene under the transcriptional control of the mouse phosphoglycerate kinase (pgk) promoter (XbaI/TaqI fragment; Adra et al. (1987) Gene 60: 65–74) and containing the pgk polyadenylation site (PvuII/HindIII fragment; Boer et al. (1990) Biochemical Genetics 28: 299–308). This cassette was obtained from the plasmid pKJ1 (described by Tybulewicz et al. (1991) Cell 65: 1153–1163) from which the neo cassette was excised as an EcoRI/HindIII fragment and subcloned into EcoRI/HindIII digested pGEM-7Zf (+) to generate pGEM-7 (KJ1). The neo cassette was excised from pGEM-7 (KJ1) by EcoRI/SalI digestion, blunt ended and subcloned into the SmaI site of the plasmid pTAR1, in the opposite orientation of the genomic Cmu sequences.

The resulting plasmid was linearized with Not I, and a herpes simplex virus thymidine kinase (tk) cassette was inserted to allow for enrichment of ES clones (mouse embryo-derived stem cells) bearing homologous recombinants, as described by Mansour et al. (1988) Nature 336: 348–352. This cassette consists of the coding sequences of the tk gene bracketed by the mouse pgk promoter and polyadenylation site, as described by Tybulewicz et al. (1991) Cell 65: 1153–1163. The resulting CMD targeting vector contains a total of approximately 5.3 kb of homology to the heavy chain locus and is designed to generate a mutant mu gene into which has been inserted a neo expression cassette in the unique SmaI site of the first Cmu exon. The targeting vector was linearized with PvuI, which cuts within plasmid sequences, prior to electroporation into ES cells.
Generation and Analysis of Targeted ES Cells.

The vector containing the murine Ig heavy chain gene fragment is then inserted into a mouse embryonic stem cell (an ES cell). The following describes the construction of this immunoglobulin gene-containing vector "targeted" ES cell and analysis of the ES cells' DNA after the vector has been inserted (i.e., transfected) into the cell.

AB-1 ES cells (McMahon, A. P. and Bradley, A., (1990) Cell 62: 1073–1085) were grown on mitotically inactive SNL76/7 cell feeder layers (ibid.) essentially as described (Robertson, E. J. (1987) in Teratocarcinomas and Embryonic Stem Cells: a Practical Approach (E. J. Robertson, ed.) Oxford: IRL Press, p. 71–112). The linearized CMD targeting vector was electroporated into AB-1 cells by the methods described Hasty et al. (Hasty, P. R. et al. (1991) Nature 350: 243–246). Electroporated cells were plated into 100 mm dishes at a density of 1–2×10$^6$ cells/dish. After 24 hours, G418 (200 micrograms/ml of active component) and FIAU (5×10$^{-7}$ M) were added to the medium, and drug-resistant clones were allowed to develop over 8–9 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described Laird et al. (Laird, P. W. et al., (1991) *Nucleic Acids Res.* 19: 4293). Isolated genomic DNA was digested with SpeI and probed with a 915 bp SacI fragment, probe A (FIG. 6), which hybridizes to a sequence between the mu intronic enhancer and the mu switch region. Probe A detects a 9.9 kb SpeI fragment from the wild type locus, and a diagnostic 7.6 kb band from a mu locus which has homologously recombined with the CMD targeting vector (the neo expression cassette contains a SpeI site). Of 1132 G418 and FIAU resistant clones screened by Southern blot analysis, 3 displayed the 7.6 kb Spe I band indicative of homologous recombination at the mu locus. These 3 clones were further digested with the enzymes BglI, BstXI, and EcoRI to verify that the vector integrated homologously into the mu gene. When hybridized with probe A, Southern blots of wild type DNA digested with BglI, BstXI, or EcoRI produce fragments of 15.7, 7.3, and 12.5 kb, respectively, whereas the presence of a targeted mu allele is indicated by fragments of 7.7, 6.6, and 14.3 kb, respectively. All 3 positive clones detected by the SpeI digest showed the expected BglI, BstXI, and EcoRI restriction fragments diagnostic of insertion of the neo cassette into the Cmu1 exon.

Generation of Mice Bearing the Mutated Mu Gene

The three targeted ES clones, designated number 264, 272, and 408, were thawed and injected into C57BL/6J blastocysts as described by Bradley (Bradley, A. (1987) in Teratocarcinomas and Embryonic Stem Cells: a Practical Approach. (E. J. Robertson, ed.) Oxford: IRL Press, p. 113–151). Injected blastocysts were transferred into the uteri of pseudopregnant females to generate chimeric mice representing a mixture of cells derived from the input ES cells and the host blastocyst. The extent of ES cell contribution to the chimera can be visually estimated by the amount of agouti coat coloration, derived from the ES cell line, on the black C57BL/6J background. Clones 272 and 408 produced only low percentage chimeras (i.e. low percentage of agouti pigmentation) but clone 264 produced high percentage male chimeras. These chimeras were bred with C57BL/6J females and agouti offspring were generated, indicative of germline transmission of the ES cell genome. Screening for the targeted mu gene was carried out by Southern blot analysis of BglI digested DNA from tail biopsies (as described above for analysis of ES cell DNA). Approximately 50% of the agouti offspring showed a hybridizing BglI band of 7.7 kb in addition to the wild type band of 15.7 kb, demonstrating a germline transmission of the targeted mu gene.

Analysis of Transgenic Mice for Functional Inactivation of Mu Gene.

To determine whether the insertion of the neo cassette (including the Ig heavy chain sequence) into Cmu1 has inactivated the Ig heavy chain gene, a clone 264 chimera was bred with a mouse homozygous for the JHD mutation, which inactivates heavy chain expression as a result of deletion of the JH gene segments (Chen et al, (1993) Immunol. 5: 647–656). Four agouti offspring were generated. Serum was obtained from these animals at the age of 1 month and assayed by ELISA for the presence of murine IgM. Two of the four offspring were completely lacking IgM (Table 2). Genotyping of the four animals by Southern blot analysis of DNA from tail biopsies by BglI digestion and hybridization with probe A (FIG. 6), and by StuI digestion and hybridization with a 475 bp EcoRI/StuI fragment (ibid.) demonstrated that the animals which fail to express serum IgM are those in which one allele of the heavy chain locus carries the JHD mutation, the other allele the Cmu1 mutation. Mice heterozygous for the JHD mutation display wild type levels of serum Ig. These data demonstrate that the Cmu1 mutation inactivates expression of the mu gene.

TABLE 2

Level of serum IgM, detected by ELISA, for mice carrying both the CMD and JHD mutations (CMD/JHD), for mice heterozygous for the JHD mutation (+/JHD), for wild type (129 Sv × C57BL/6J)F1 mice (+/+), and for B cell deficient mice homozygous for the JHD mutation (JHD/JHD).

| Mouse | Serum IgM (micrograms/ml) | Ig H chain genotype |
|---|---|---|
| 42 | <0.002 | CMD/JHD |
| 43 | 196 | +/JHD |
| 44 | <0.002 | CMD/JHD |
| 45 | 174 | +/JHD |
| 129 × BL6 F1 | 153 | +/+ |
| JHD | <0.002 | JHD/JHD |

EXAMPLE 25

Generation of HCo12 Transgenic Mice

The following describes the generation of transgenic mice containing human immunoglobulin heavy chain gene sequence that can generate human immunoglobulins. Because these mice cannot make endogenous (i.e., mouse) immunoglobulins, upon challenge with antigen, e.g., a human polypeptide, only human sequence immunoglobulins are made by the transgenic mouse.

The HCo12 Human Heavy Chain Transgene.

The HCo12 transgene was generated by coinjection of the 80 kb insert of pHC2 (Taylor et al., 1994, Int. Immunol., 6: 579–591) and the 25 kb insert of pVx6. The plasmid pVx6 was constructed as described below. An 8.5 kb HindIII/SalI DNA fragment, comprising the germline human VH1–18 (DP-14) gene together with approximately 2.5 kb of 5' flanking, and 5 kb of 3' flanking genomic sequence was subcloned into the plasmid vector pSP72 (Promega, Madison, Wis.) to generate the plasmid p343.7.16. A 7 kb BamHI/HindIII DNA fragment, comprising the germline human VH5–51 (DP-73) gene together with approximately 5 kb of 5' flanking and 1 kb of 3' flanking genomic sequence, was cloned into the pBR322 based plasmid cloning vector pGP1f (Taylor et al. 1992, Nucleic Acids Res. 20: 6287–6295), to generate the plasmid p251f.

A new cloning vector derived from pGP1f, pGP1k (Seq. ID #1), was digested with EcoRV/BamHI, and ligated to a 10 kb EcoRV/BamHI DNA fragment, comprising the germline human VH3–23 (DP47) gene together with approximately 4 kb of 5' flanking and 5 kb of 3' flanking genomic sequence. The resulting plasmid, p112.2RR.7, was digested with BamHI/SalI and ligated with the 7 kb purified BamHI/SalI insert of p251f. The resulting plasmid, pVx4, was digested with XhoI and ligated with the 8.5 kb XhoI/SalI insert of p343.7.16.

A plasmid clone was obtained with the $V_H1$–18 gene in the same orientation as the other two V genes. This clone, designated pVx6, was then digested with NotI and the purified 26 kb insert coinjected—together with the purified 80 kb NotI insert of pHC2 at a 1:1 molar ratio—into the pronuclei of one-half day (C57BL/6J × DBA/2J)F2 embryos as described by Hogan et al. (B. Hogan et al., Manipulating the Mouse Embryo, A Laboratory Manual, 2nd edition, 1994, Cold Spring Harbor Laboratory Press, Plainview N.Y.).

Three independent lines of transgenic mice comprising sequences from both Vx6 and HC2 were established from mice that developed from the injected embryos. These lines of transgenic mice are designated (HCo12)14881, (HCo12)

15083, and (HCo12)15087. Each of the three lines were then bred with mice comprising the CMD mutation described in Example 23, the JKD mutation (Chen et al. 1993, EMBO J. 12: 811–820), and the (KCo5)9272 transgene (Fishwild et al. 1996, *Nature* Biotechnology 14: 845–851). The resulting mice express human heavy and kappa light chain transgenes (and produce human sequence heavy and kappa light chain antibodies) in a background homozygous for disruption of the endogenous mouse heavy and kappa light chain loci.

Two different strains of mice were used to generate hybridomas and monoclonal antibodies reactive to human IL-8. Strain ((CMD)++; (JKD)++; (HCo7)11952+/++; (KCo5)9272+/++), and strain ((CMD)++; (JKD)++; (HCo12)15087+/++; (KCo5)9272+/++). Each of these strains are homozygous for disruptions of the endogenous heavy chain (CMD) and kappa light chain (JKD) loci. Both strains also comprise a human kappa light chain transgene (HCo7), with individual animals either hemizygous or homozygous for insertion #11952. The two strains differ in the human heavy chain transgene used. Mice were hemizygous or homozygous for either the HCo7 or the HCo12 transgene. The CMD mutation is described above in Example 23, above. The generation of(HCo12)15087 mice is described above. The JKD mutation (Chen et al. 1993, EMBO J. 12: 811–820) and the (KCo5)9272 (Fishwild et al. 1996, *Nature Biotechnology* 14: 845–851) and (HCo7) 11952 mice, are described in U.S. Pat. No. 5,770,429 (Lonberg & Kay, Jun. 23, 1998).

EXAMPLE 26

Preparation of Biotinylated Antibodies

Purified antibodies were dialyzed against a minimum of 100 volumes of phosphate buffered saline (PBS), pH 7.4, for at least 4 hours. Antibodies were diluted to a final concentration of 2 mg/ml in PBS. A stock solution containing 40 mM of biotin-XX-NHS ester (Molecular Probes, Eugene, Oreg.) was prepared in dimethylsulfoxide. The biotin-XX-NHS solution was added to antibodies at a final concentration of 0.4 mM and reacted for 90 minutes at room temperature. Aminoethanesulfonic acid was added to a final concentration of 20 mM and incubated for five minutes to quench remaining reactive groups. The biotinylated antibodies were dialyzed extensively to remove small molecules containing biotin from the antibodies.

Preparation of Alkaline Phosphatase-antibody Conjugates

Alkaline phosphatase (AP, Calzyme Laboratories, San Luis Obispo, Calif.) was placed into dialysis using a minimum of 100 volumes of column buffer (50 mM potassium phosphate, 10 mM borate, 150 mM NaCl, 1 mM MgSO$_4$, pH 7.0) at 2–8° C. for at least four hours. The buffer was changed at least twice prior to use of the AP. When the AP was removed from dialysis and brought to room temperature, the concentration was determined by absorbance at 280 nm using an absorbance of 0.77 for a 1 mg/mL solution. The AP was diluted to 5 mg/mL with column buffer. The reaction of AP and succinimidyl 4-(N-maleimidomethyl) cyclohexane-1-carboxylate (SMCC, Pierce Chemical Co., Rockford, Ill.) was carried out using a 20:1 ratio of SMCC:AP. SMCC was dissolved in acetonitrile at 20 mg/mL and diluted by a factor of 84 when added to AP while vortexing or rapidly stirring. The solution was allowed to stand at room temperature for 90 minutes before the unreacted SMCC and low molecular weight reaction products were separated from the AP using gel filtration chromatography (G50 Fine, Pharmacia Biotech, Piscataway, N.J.) in a column equilibrated with column buffer.

Antibodies were dialyzed in a minimum of 100 volumes of PBS and diluted to 2 mg/mL in PBS. A solution containing 40 mM N-succinimidyl S-acetylthiopropionate (SATP, Pierce Chemical Co., Rockford, Ill.) was prepared in dimethylsulfoxide, diluted to a final concentration of 0.32 mM in the antibody solution, and incubated for 90 minutes at room temperature. Aminoethanesulfonic acid was added to a final concentration of 20 mM and incubated for 5 minutes to stop the reaction. The modified antibody was dialyzed using a minimum of 100 volumes of 50 mM potassium phosphate, 10 mM borate, 150 mM NaCl, pH 7.0, for a minimum of 4 hours before the dialysis buffer was changed and dialysis continued for at least four hours. The antibody concentration was determined using the absorbance at 280 nm with an absorbance of 1.6 corresponding to a 1 mg/mL solution. Hydroxylamine was dissolved to a concentration of 0.5 M in 0.1 M potassium phosphate, 10 mM ethylenediaminetetraacetic acid, pH 7.2. This solution was diluted into the antibody solution to achieve a final concentration of hydroxylamine of 50 mM and incubated for 2 hours at room temperature. Modified antibody was mixed with SMCC-AP in equimolar amounts and incubated for one hour at room temperature before adding β-mercaptoethanol to a final concentration of 1 mM, incubating for 5 minutes, adding N-ethylmaleimide to a final concentration of 2 mM and incubating for 5 minutes. Antibody-enzyme conjugates were separated from unconjugated antibody by gel filtration chromatography using SEPHACRYL™ S-200 (Pharmacia Biotech, Piscataway, N.J.) in column buffer. Conjugates were diluted into block solution for use in immunoassays.

EXAMPLE 27

Epitope Mapping of Human Monoclonal Antibodies to IL-8

A BIACORE® 3000 instrument (Biacore AB, Uppsala, Sweden) was used to measure the epitope binding. Goat anti-human kappa antibody (Fisher Scientific, Pittsburgh, Pa.) was immobilized onto a CM5 sensor chip (Biacore AB, Uppsala, Sweden) as described in Biacore Application note 101 (Biacore AB, Uppsala, Sweden), except goat anti-human kappa antibody was diluted into 10 mM sodium acetate, pH 4.0.

Fourteen human monoclonal antibodies (Example 15) were used to map the epitopes of IL-8 using a two-site assay (Johne et al., Journal of Immunological Methods, 160 (1993) 191–198). Each antibody was diluted to 100 µg/mL and the IL-8 was diluted to 1 µM in 10 mM N-2-hydroxyethylpiperazine-N'-2-ethane-sulfonic acid, 150 mM sodium chloride, 3 mM EDTA, 0.005% polysorbate 20, pH7.4 (HBS-EP, Biacore AB, Uppsala, Sweden). The primary antibody (M1-10) was bound to the goat anti-human kappa antibody on the CM5 chip by injecting 20 µL of antibody over all 4 channels. IL-8 (10 µL) was then bound to the primary antibody in all 4 channels. One secondary antibody (10 µL) was passed through one channel each. The resonance units of the secondary antibodies were measured 20 seconds after the injection was over. Blank resonance unit values for each primary/secondary antibody combination were obtained by injecting HBS-EP instead of IL-8 and these were subtracted from the resonance units measured for the corresponding primary/secondary antibody pairing that was contacted with IL-8. Blocking antibody injections were not done. The high levels of resonance units for all antibody combinations except M1-10 with itself indicate that all of the antibodies listed except M1-10 bind to an epitope that is different from the epitope bound by M1-10 and that the binding of these antibodies is largely unaffected by the binding of M1-10 to IL-8. Data not shown indicate that the binding to IL-8 of all antibodies listed other than M1-10 is substantially affected by the prior binding of any one of them to IL-8.

| Secondary Monoclonal Antibody | Resonance Units |
|---|---|
| M1-3 | 839 |
| M1-4 | 911 |
| M1-5 | 820 |
| M1-8 | 888 |
| M1-10 | −17 |
| M1-21 | 706 |
| M1-23 | 796 |
| M1-25 | 925 |
| M2-11 | 798 |
| M2-12 | 794 |
| M2-16 | 818 |
| M2-18 | 754 |
| M2-20 | 848 |
| M2-34 | 799 |

EXAMPLE 28

Experimental Procedures

A sequential sandwich enzyme-linked immunosorbent assay (ELISA) was performed to create a standard curve of response versus concentration and to determine the assay sensitivity for each antibody set. All assays were performed in 384-well black polystyrene streptavidin-coated microplates (Pierce Chemical Co., Rockford, Ill.) with an average binding capacity of approximately 50 femtomoles biotin/well. Alkaline phosphatase (AP)-labeled antibodies were used to bind antigen captured by antibody on the solid phase, and the binding was detected using AttoPhos substrate (JBL Scientific, San Luis Obispo, Calif.). The antibody sets that were analyzed were polyclonal murine antibody-biotin/polyclonal murine antibody-AP, polyclonal human antibody-biotin/polyclonal human antibody-AP, and monoclonal human antibodyM1-10-biotin/monoclonal human antibody M1-25-AP. Both polyclonal human and polyclonal murine antibodies were selected to bind IL-8 using a lower affinity cutoff of $10^9$ $M^{-1}$. Both monoclonal antibodies were selected from the polyclonal human library. The polyclonal mouse antibody library was obtained as described in PCT 98/06704, filed, Apr. 3, 1998 using multiple rounds of selection with biotinylated IL-8 at 1 nM. Reagent pipetting was performed using a TECAN Genesis RSP 200/8 robotic sample processor (TECAN U.S., Inc., Research Triangle Park, N.C.). Individual microplate wells were washed by a TECAN Columbus 384-well strip washer, and kinetic fluorescence in each microplate well was determined by a TECAN SpectraFluor Plus microplate reader using an excitation wavelength of 430 nm and an emission wavelength of 570 nm. All pipetting methods were programmed using TECAN Gemini 3.0 liquid handling software. All TECAN robotic resources were controlled using the TECAN multi-scheduler software FACTS 4.5.

Samples to be analyzed were diluted 1:4.5 in conjugate diluent (CD8; 10 mM Tris, 150 mM sodium chloride, 1 mM magnesium chloride, 0.1 mM zinc chloride, 0.1% polyvinyl alcohol, 1% bovine serum albumin, 0.1% sodium azide, at pH 8.15). Standard curves were created using samples of either conjugate diluent or pooled normal plasma with various concentrations of interleukin-8 (IL-8) added. 40 μl of 2 μg/ml biotinylated polyclonal murine antibody, polyclonal human antibody or monoclonal human antibody M1-10 in CD8 were pipetted into individual microplate wells. The microplate was incubated for 1 hour at 25° C. and individual wells were washed three times with wash buffer (20 mM borate, 150 mM sodium chloride, 0.02% polyoxyethylene 20-sorbitan monolaurate, 0.1% sodium azide, at pH 8.2) in overflow mode. 40 μl of the sample to be analyzed was pipetted into individual microplate wells, and the plate was incubated for 1 hour at 25° C. Individual microplate wells were washed three times with wash buffer, and 40 μl of 5 μg/ml alkaline phosphatase-labeled antibody in CD8 was pipetted into individual microplate wells. Polyclonal murine antibody-AP, polyclonal human antibody-AP, and monoclonal human antibody M1-25-AP were paired with polyclonal murine antibody-biotin, polyclonal human antibody-biotin, and monoclonal human antibody M1-10-biotin, respectively. The microplate was incubated for 1 hour at 25° C. and individual wells were washed six times with wash buffer. 40 μl of 1 mM AttoPhos substrate in 2.4 M diethanolamine, 0.057 mM magnesium chloride, 0.005% sodium azide at pH 10.0 was pipetted into each microplate well, and the kinetic fluorescence was read for 20 minutes. Samples known to contain human-anti-mouse antibodies (HAMA) or heterophilic antibodies were purchased (Scantibodies, Inc., Santee, Calif.). All HAMA-positive and standard curve samples were analyzed in quadruplicate.

All statistical calculations and graphs used for data analysis were prepared using Microsoft Excel 97. The kinetic fluorescence of each well was quantified by calculating the slope of the response, in units of 0.1×milli-relative fluorescent units per second (0.1×mRFU/sec). A standard curve was created for each antibody set by plotting blank-corrected slope (0.1×mRFU/sec; y-axis) versus concentration (x-axis). The correlation coefficient for the linear portion of the curve was determined. Assay sensitivity was calculated from the standard curve and is defined as the analyte concentration corresponding to a slope equal to the slope plus two standard deviations of the assay blank (negative control; no analyte present). Slope (0.1×mRFU/sec) was converted to concentration (pM) for all HAMA-positive samples using the standard curve created from plasma samples with various concentrations of IL-8 added.

The sensitivity of the polyclonal murine antibody, polyclonal human antibody for detecting the IL-8 concentration in human plasma samples using a sequential sandwich ELISA was calculated to be 65.2 pM, 30.7 pM, and 1.3 pM, respectively. The correlation coefficients for the blank-corrected linear portion of the standard curve of the polyclonal murine antibody, polyclonal human antibody for detecting the IL-8 concentration in human plasma samples using a sequential sandwich ELISA was calculated to be 0.912, 0.993, and 0.998, respectively.

The data provided in the Table show a dramatic reduction in the values for IL-8 concentration as a result of using human antibodies. Because both human antibody-based assays are substantially more sensitive than the murine antibody-based assay, these results indicate that the apparent IL-8 concentrations determined in these samples using the polyclonal murine antibody-based assay that are above the sensitivity limit of that assay are falsely elevated due to HAMA or heterophilic antibodies in the samples.

TABLE 5

| | SLOPE (0.1 × mRFU/sec), BLANK CORRECTED | | | [IL-8] (pM) | | |
|---|---|---|---|---|---|---|
| SAMPLE ID | POLY-CLONAL MURINE ANTIBODY | POLY-CLONAL HUMAN ANTIBODY | MONOCLONAL HUMAN ANTIBODIES M1 10/M1–25 | POLYCLONAL MURINE ANTIBODY | POLYCLONAL HUMAN ANTIBODY | MONOCLONAL HUMAN ANTIBODIES M1 10/M1–25 |
| HAMA-POSITIVE HUMAN PLASMA | | | | | | |
| 11882-201 | 0.2671 | 0.5830 | 0.6530 | 31.42 | 1.27 | 1.30 |
| 11879-966 | 0.4351 | 0.2260 | 0.1397 | 51.19 | 0.49 | 0.28 |
| 2172-51 | 4.3512 | 3.9161 | 3.7688 | 511.91 | 8.55 | 7.49 |
| 11658-332 | 16.0843 | 0.9385 | 1.7111 | 1892.27 | 2.05 | 3.40 |
| 11879-857 | 46.8286 | 0.8811 | 0.3661 | 5509.25 | 1.92 | 0.73 |
| 2161-17 | 20.1484 | 0.7397 | 0.9231 | 2370.40 | 1.61 | 1.84 |
| 11707-22 | 7.4092 | 1.7971 | 2.5912 | 871.67 | 3.92 | 5.15 |
| 11707-31 | 16.0596 | 0.1015 | 2.4966 | 1889.36 | 0.22 | 4.96 |
| 11879-819 | 5.1529 | 0.3544 | 0.5127 | 606.22 | 0.77 | 1.02 |
| 11658-88 | 2.3892 | 0.6264 | 0.7798 | 281.08 | 1.37 | 1.55 |
| 2160-52 | 0.8846 | 0.6428 | 1.0283 | 104.07 | 1.40 | 2.04 |
| 2154-7 | 25.5515 | 0.8860 | 2.7664 | 3006.06 | 1.93 | 5.50 |
| 10132-523 | 54.9596 | 0.6422 | 0.6183 | 6465.83 | 1.40 | 1.23 |
| 9881-276 | 6.9326 | 1.6051 | 2.2132 | 815.60 | 3.50 | 4.40 |
| 11906-47 | 5.5530 | 0.2734 | 0.7166 | 653.29 | 0.60 | 1.43 |
| 11879-210 | 50.7084 | 0.7032 | 0.5550 | 5965.69 | 1.54 | 1.10 |
| HETEROPHILIC HUMAN PLASMA | | | | | | |
| 10049-320 | 8.4718 | 0.3944 | −0.1345 | 996.68 | 0.86 | −0.27 |
| 2217-1 | 0.1872 | 0.1965 | 0.1952 | 22.03 | 0.43 | 0.39 |
| 10049-114 | 0.5470 | 0.5707 | 0.1850 | 64.36 | 1.25 | 0.37 |
| 10060-285 | 0.4577 | 0.2119 | 0.0569 | 53.84 | 0.46 | 0.11 |

What is claimed is:

1. A method of detecting an analyte in a human sample containing human antibodies that specifically bind to antibodies from a nonhuman species, comprising:

contacting the sample with a human antibody, wherein the human antibody specifically binds to the analyte without specifically binding to the human antibodies that specifically bind to antibodies from a nonhuman species, and detecting the binding between the human antibody and the analyte to indicate presence of the analyte.

2. The method of claim 1, wherein the human sample contains human anti-mouse antibodies.

3. The method of claim 2, wherein the human anti-mouse antibodies are anti-mouse idiotype antibodies.

4. The method of claim 1, wherein the human sample contains heterophilic antibodies.

5. The method of claim 1, wherein the sample is contacted with a first human antibody that is immobilized on a support and a second human antibody in solution wherein the first and second human antibodies bind to different epitopes on the analyte; and the detecting step detects binding between the first and second human antibody to the analyte.

6. The method of claim 5, wherein the detecting step detects binding between the second human antibody and the analyte.

7. The method of claim 6, wherein the second human antibody is labelled.

8. The method of claim 6, wherein the sample is contacted with a first population of human antibodies immobilized to a support and a second population of human antibodies in solution, wherein members from the first and second populations bind to different epitopes on the analyte.

9. The method of claim 8, wherein the second population of human antibodies is labelled.

10. The method of claim 5, wherein the first and second human antibodies each have affinities of at least $10^9$ $M^{-1}$ for their respective epitopes on the analyte.

11. The method of claim 5, wherein the first and second human antibodies are produced by subcloning nucleic acids encoding the first and second human antibodies from a transgenic mouse expressing human immunoglobulin genes into a phage display vector, and screening phage displaying the first human antibodies and phage displaying the second human antibodies for desired binding specificities.

12. The method of claim 1, wherein the human antibody has an affinity of at least $10^8$ $M^{-1}$ for the analyte.

13. The method of claim 1, wherein the human antibody has an affinity of at least $10^9$ $M^{-1}$ for the analyte.

14. The method of claim 1, wherein the human antibody has an affinity of at least $10^{10}$ $M^{-1}$ for the analyte.

15. The method of claim 1, wherein the human antibody has an affinity of a least $10^{11} M^{-1}$ for the analyte.

16. The method of claim 1, wherein binding of the human antibody to the analyte reaches equilibrium within an hour.

17. The method of claim 1, wherein the antibody was produced by expression by expression of a recombinant construct in *E. coli*.

18. The method of claim 17, wherein at least 90% of molecules of the antibody are immunoreactive with the analyte.

19. A method of detecting an analyte in a sample, comprising contacting the sample with a first human antibody immobilized to a solid phase, and a second human antibody in solution, wherein the first and second antibodies bind to different epitopes of the analyte if present in the sample detecting binding of the analyte to the first and second antibodies, binding indicating presence of the analyte in the sample wherein the first and second human antibodies are produced by subcloning nucleic acids encoding the first and second human antibodies from a transgenic mouse expressing human immunoglobulin genes into a phage display vector, and screening phage displaying the first human antibodies and phage displaying the second human antibodies for desired binding specificities.

20. The method of claim 19, wherein the second antibody is labelled and the detecting detects binding of second antibody to the analyte.

21. The method of claim 20, wherein the sample is contacted with a first population of human antibodies immobilized to the solid phase and a second population of human antibodies in solution, wherein members from the first and second populations bind to different epitopes on the analyte.

22. The method of claim 21, wherein the second population of human antibodies is labelled.

23. The method of claim 19, wherein the first and second human antibodies each have an affinity of at least $10^9$ $M^{-1}$ for their respective epitopes on the analyte.

24. The method of claim 19, wherein the first and second human antibodies each have an affinity of at least $10^{10}$ $M^{-1}$ for the analyte.

25. The method of claim 19, wherein the first and second human antibodies have an affinity of a least $10^{11} M^{-1}$ for the analyte.

26. The method of claim 19, wherein binding of the first and second human antibodies to the analyte reaches equilibrium within an hour.

27. The method of claim 19, wherein the first and second human antibodies were produced by expression by expression of recombinant constructs in *E. coli*.

28. The method of claim 27, wherein at least 90% of molecules of the first and second antibody are immunoreactive with the analyte.

* * * * *